United States Patent
Gray et al.

(10) Patent No.: US 9,879,028 B2
(45) Date of Patent: Jan. 30, 2018

(54) COMPOUNDS THAT MODULATE EGFR ACTIVITY AND METHODS FOR TREATING OR PREVENTING CONDITIONS THEREWITH

(71) Applicant: Gatekeeper Pharmaceuticals, Inc., Milbrae, CA (US)

(72) Inventors: Nathanael S. Gray, Boston, MA (US); Wenjun Zhou, Eugene, OR (US)

(73) Assignee: GATEKEEPER PHARMACEUTICALS, INC., Milbrae, CA (US)

(*) Notice: Subject to any disclaimer, the term of this patent is extended or adjusted under 35 U.S.C. 154(b) by 0 days.

(21) Appl. No.: 14/023,681

(22) Filed: Sep. 11, 2013

(65) Prior Publication Data

US 2014/0011810 A1 Jan. 9, 2014

Related U.S. Application Data

(63) Continuation of application No. 12/976,980, filed on Dec. 22, 2010, now abandoned.

(60) Provisional application No. 61/331,488, filed on May 5, 2010, provisional application No. 61/289,798, filed on Dec. 23, 2009.

(51) Int. Cl.
| | |
|---|---|
| C07D 401/12 | (2006.01) |
| C07D 401/14 | (2006.01) |
| C07D 403/12 | (2006.01) |
| C07D 403/14 | (2006.01) |
| C07D 413/12 | (2006.01) |
| C07D 413/14 | (2006.01) |
| A61K 31/433 | (2006.01) |
| A61K 31/4535 | (2006.01) |
| A61K 31/5375 | (2006.01) |
| A61K 31/495 | (2006.01) |
| A61P 35/00 | (2006.01) |
| C07D 285/135 | (2006.01) |
| C07D 495/04 | (2006.01) |
| C07D 417/12 | (2006.01) |
| C07D 487/04 | (2006.01) |
| C07D 239/95 | (2006.01) |
| C07D 471/04 | (2006.01) |
| C07D 473/18 | (2006.01) |

(52) U.S. Cl.
CPC ......... *C07D 495/04* (2013.01); *C07D 239/95* (2013.01); *C07D 285/135* (2013.01); *C07D 401/12* (2013.01); *C07D 401/14* (2013.01); *C07D 403/12* (2013.01); *C07D 417/12* (2013.01); *C07D 471/04* (2013.01); *C07D 473/18* (2013.01); *C07D 487/04* (2013.01)

(58) Field of Classification Search
CPC ............ C07D 271/107; C07D 271/113; C07D 285/12; C07D 285/125; C07D 249/12; C07D 249/14; A61K 31/4196; A61K 31/433; A61K 31/4245
USPC ..... 548/136, 143, 262.2, 142; 514/363, 365, 514/383, 385, 341; 546/268.7
See application file for complete search history.

(56) References Cited

U.S. PATENT DOCUMENTS

| | | |
|---|---|---|
| 6,391,874 B1 | 5/2002 | Cockerill et al. |
| 2006/0106019 A1 | 5/2006 | Bernard |
| 2007/0032495 A1 | 2/2007 | Guzi et al. |
| 2007/0161645 A1 | 7/2007 | Noronha et al. |
| 2009/0202989 A1 | 8/2009 | Hillan |
| 2009/0306087 A1 | 12/2009 | Ibrahim et al. |
| 2009/0318405 A1 | 12/2009 | Li et al. |
| 2010/0087482 A1 | 4/2010 | Haber et al. |
| 2010/0173285 A1 | 7/2010 | Varmus et al. |
| 2011/0207736 A1 | 8/2011 | Gray et al. |

FOREIGN PATENT DOCUMENTS

WO    WO-2009/062258    5/2009

OTHER PUBLICATIONS

Pyne et al. Cancer Res 2011;71:6576-6582.*
Wolff Manfred E. "Burger's Medicinal Chemistry, 5ed, Part 1", John Wiley & Sons, 1995, pp. 975-977.*
Banker, G.S. et al, "Modern Pharmaceutics, 3ed.", Marcel Dekker, New York. 1996, pp. 451 and 596.*
Zhang X., Expert Opin. Pharmacother. (2014) 15(9):1277-1288.*
Feldinger K., Breast Cancer: Targets and Therapy 2015:7 147-162.*
Cecil Textbook of Medicine, edited by Bennet, J.C., and Plum F., 20th edition, vol. 1, 1004-1010, 1996.
Cohen (1999) Current Opinion in Chemical Biology 3:459-465 "The development and therapeutic potential of protein kinase inhibitors".
Dermer (1994) Bio/Technology vol. 12:320 "Another Anniversary for the War on Cancer".
Fabbro et al. (2002) Pharmacology & Therapeutics 93:79-98 "Protein kinases as targets for anticancer agents: from inhibitors to useful drugs".
Ferrara (2005) Oncology 69(suppl 3):11-16 "VEGF as a Therapeutic Target in Cancer".
Freshney (1983) Culture of Animal Cells, A Manual of Basic Technique, Alan R. Liss, Inc., 1983, New York, p. 4.
Gautschi et al. (2008) Clin. Cancer Res. 14(6):1639-1648 "Aurora Kinases as Anticancer Drug Targets".
Golub et al. (1999) Science 286:531-537 "Molecular Classification of Cancer: Class Discovry and Class Prediction by Gene Expression Monitoring".
Int'l Search Report & Written Opinion dated Mar. 11, 2011 in PCT/US10/61927.
IPRP dated Jun. 26, 2012 in PCT/US10/61927.
Jain et al. (2006) Nature Clinical Practice Oncology 3(1):24-40 "Lessons from phase III clinical trials on anti-VEGF therapy for cancer".
Mass (2004) Int. J. Radiation Oncology Biol. Phys. 58(3):932-940 "The HER Receptor Family: A Rich Target for Therapeutic Development".

(Continued)

*Primary Examiner* — Venkataraman Balasubramanian
(74) *Attorney, Agent, or Firm* — Swanson & Bratschun, L.L.C.

(57) ABSTRACT

Provided are compounds and methods for treating or preventing kinase-mediated disorders therewith.

11 Claims, 1 Drawing Sheet

(56) References Cited

OTHER PUBLICATIONS

Mountzios et al. (2008) Cancer Treatment Reviews 34:175-182, "Aurora kinases as targets for cancer therapy".
Qui et al. (2000) Oncogen 19:5651-5661 "Signaling network of the Btk family kinases".
Snyder et al. (2000) J. Med. Liban. 48(4):208-214 "Common bacteria whose susceptibility to antimicrobials is no longer predictable".
Sugar et al. (1995) Diagn. Microbiol. Infect. Dis. 21:129-133 "Comparison of Three Methods of Antifungal Susceptibility Testing with the Proposed NCCLS Standard Broth Macrodilution Assay: Lack of Effect of Phenol Red".
Turner et al. (1996) Current Pharmaceutical Design. 2:209-224 "Recent Advances in the Medicinal Chemistry of Antifungal Agents".
Yee (2012) J. Natl. Cancer Inst. 104(13):975-981 "Insulin-like Growth Factor Receptor Inhibitors: Baby or the Bathwater?".
Zhang et al. (2009) Nature Reviews—Cancer 9:28-39 "Targeting cancer with small molecule kinase inhibitors".

\* cited by examiner

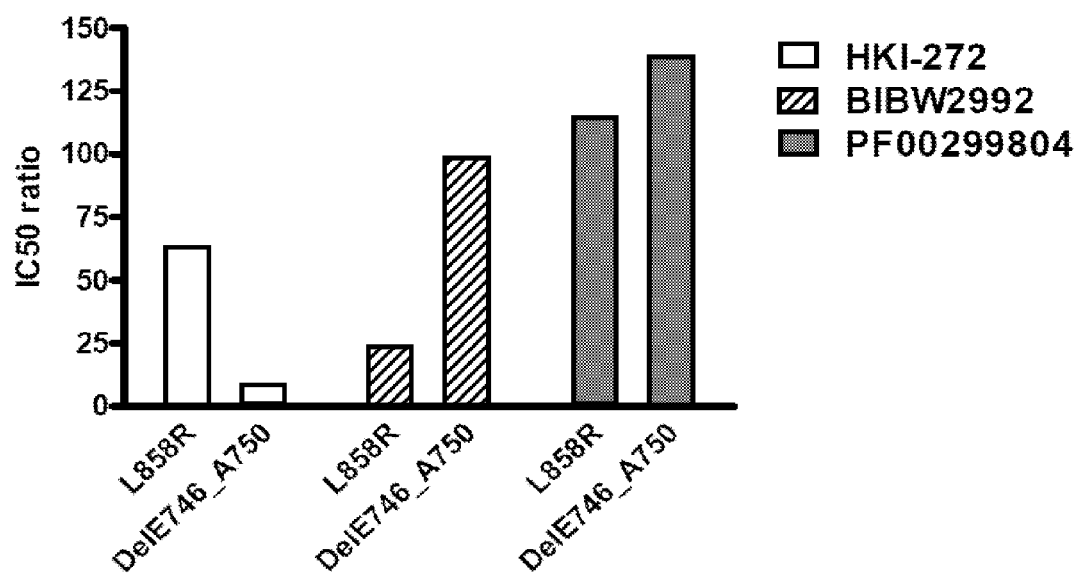

COMPOUNDS THAT MODULATE EGFR ACTIVITY AND METHODS FOR TREATING OR PREVENTING CONDITIONS THEREWITH

CROSS-REFERENCE TO RELATED APPLICATIONS

This application is a continuation of U.S. application Ser. No. 12/976,980, filed Dec. 22, 2010, entitled "Compounds that Modulate EGFR Activity and Methods for Treating or Preventing Conditions Therewith". U.S. application Ser. No. 12/976,980 claims the benefit of U.S. provisional application Ser. Nos. 61/289,798, filed Dec. 23, 2009, and 61/331,488, filed May 5, 2010. The contents of each of the above-referenced applications are herein incorporated by reference in their entirety.

BACKGROUND OF THE INVENTION

The epidermal growth factor receptor (EGFR, Erb-B1) belongs to a family of proteins involved in the proliferation of normal and malignant cells. Overexpression of EGFR is found in over 70% of human cancers including without limitation non-small cell lung carcinomas (NSCLC), breast cancers, gliomas, squamous cell carcinoma of the head and neck, and prostate cancer. The EGFR tyrosine kinase (EGFR-TK) reversible inhibitor erlotinib (Tarceva®) is approved by the United States Food and Drug Administration (FDA) for the treatment of NSCLC and advanced pancreatic cancer. Other FDA approved anti-EGFR targeted molecules include gefitinib (Iressa®) and lapatinib.

The response rate of lung cancer tumor shrinkage to erlotinib or gefitinib is about 8-10% and the median time to tumor progression is approximately 2 months. However, lung cancers with somatic mutations in EGFR can be associated with dramatic clinical responses following treatment with geftinib and erlotinib. Somatic mutations identified to date include point mutations in which a single amino acid residue is altered in the expressed protein (e.g. L858R, G719S, G719C, G719A, L861Q), as well as small in frame deletions in exon 19 or insertions in exon 20. Prospective clinical trials treating chemotherapy naïve patients with EGFR mutations with gefitinib or erlotinib have found radiographic response rates ranging from 60-82% and median times to progression of 9.4 to 13.3 months. See Inoue, A. et al., Prospective phase II study of gefitinib for chemotherapy-naive patients with advanced non-small-cell lung cancer with epidermal growth factor receptor gene mutations. *J Clin Oncol* 24, 3340-3346 (2006); Sequist, L. V. et al., First-line gefitinib in patients with advanced non-small-cell lung cancer harboring somatic EGFR mutations. *J Clin Oncol* 26, 2442-2449 (2008). These outcomes are 3- to 4-fold greater than that observed with platin-based chemotherapy (20-30% and 3-4 months, respectively) for advanced NSCLC. Conversely, NSCLC patients with wild type EGFR may have a worse outcome when they received gefitinib compared to chemotherapy as their initial treatment for advanced NSCLC. Thus EGFR mutations can be used to select NSCLC patients for therapy with EGFR TKIs over conventional chemotherapy.

Despite the initial clinical benefits of gefitinib/erlotinib in NSCLC patients harboring EGFR mutations, most if not all patients ultimately develop progressive cancer while receiving therapy on these agents. A secondary EGFR mutation, T790M, can render gefitinib and erlotinib ineffective inhibitors of EGFR kinase activity. The EGFR T790M mutation is found in approximately 50% of tumors (24/48) from patients that acquire resistance to gefitinib or erlotinib. This secondary genetic alteration occurs in the "gatekeeper" residue and in an analogous position to other secondary resistance alleles in diseases treated with kinase inhibitors, e.g., T315I in ABL in imatinib resistant chronic myeloid leukemia (CML).

Another major limitation of current EGFR inhibitors is the development of toxicity in normal tissues. Because ATP affinity of EGFR T790M is similar to wild type EGFR, the concentration of an irreversible EGFR inhibitor required to inhibit EGFR T790M may also effectively inhibit wild type EGFR. The class-specific toxicities of current EGFR kinase inhibitors, e.g., skin rash and diarrhea, are a result of inhibiting wild type EGFR in non-cancer tissues. These toxicities preclude dose escalation of current agents to plasma levels that can effectively inhibit EGFR T790M.

The present invention provides mutant specific EGFR inhibitors that are less effective against wild type EGFR.

SUMMARY OF THE INVENTION

In one embodiment, the invention encompasses a compound of Formula I, Ia, Ib, II, IIa, IIb, III, IIIa, IIIb, IV, IVa, IVb, V, VI, VIa, VIb, VII, VIIa, VIIb, VIII, VIIIa, VIIIb, IX, IXa, IXb, Xb, XI, XIa, XIb, XII, XIIa, or XIIb, as described below.

In another embodiment, the invention encompasses pharmaceutical compositions comprising a compound of Formula I, Ia, Ib, II, IIa, IIb, III, IIIa, IIIb, IV, IVa, IVb, V, VI, VIa, VIb, VII, VIIa, VIIb, VIII, VIIIa, VIIIb, IX, IXa, IXb, Xb, XI, XIa, XIb, XII, XIIa, or XIIb, and a pharmaceutically acceptable excipient.

In another embodiment, the invention encompasses methods for inhibiting a kinase, comprising contacting the kinase with an effective amount of a compound of Formula I, Ia, Ib, II, IIa, IIb, III, IIIa, IIIb, IV, IVa, IVb, V, VI, VIa, VIb, VII, VIIa, VIIb, VIII, VIIIa, VIIIb, IX, IXa, IXb, Xb, XI, XIa, XIb, XII, XIIa, or XIIb.

In another embodiment, the invention encompasses methods for inhibiting EGFR in a subject in need thereof, comprising administering to the subject an effective amount of a compound of Formula I, Ia, Ib, II, IIa, IIb, III, IIIa, IIIb, IV, IVa, IVb, V, VI, VIa, VIb, VII, VIIa, VIIb, VIII, VIIIa, VIIIb, IX, IXa, IXb, Xb, XI, XIa, XIb, XII, XIIa, or XIIb.

In another embodiment, the invention encompasses methods for treating or preventing a disease that is mediated by a kinase comprising administering an effective amount of a compound of Formula I, Ia, Ib, II, IIa, IIb, III, IIIa, IIIb, IV, IVa, IVb, V, VI, VIa, VIb, VII, VIIa, VIIb, VIII, VIIIa, VIIIb, IX, IXa, IXb, Xb, XI, XIa, XIb, XII, XIIa, or XIIb to a subject in need thereof.

In another embodiment, the invention encompasses methods for treating or preventing a disease resistant to an EGFR targeted therapy in a subject in need thereof, comprising administering to the subject an effective amount of a compound of Formula I, Ia, Ib, II, IIa, IIb, III, IIIa, IIIb, IV, IVa, IVb, V, VI, VIa, VIb, VII, VIIa, VIIb, VIII, VIIIa, VIIIb, IX, IXa, IXb, Xb, XI, XIa, XIb, XII, XIIa, or XIIb.

In another embodiment, the invention encompasses methods for treating or preventing an EGFR activated disease in a subject in need thereof, comprising administering to the subject an effective amount of a compound of Formula I, Ia, Ib, II, IIa, IIb, III, IIIa, IIIb, IV, IVa, IVb, V, VI, VIa, VIb, VII, VIIa, VIIb, VIII, VIIIa, VIIIb, IX, IXa, IXb, Xb, XI, XIa, XIb, XII, XIIa, or XIIb.

In another embodiment, the invention encompasses methods for treating or preventing an ERBB2 activated disease in a subject in need thereof, comprising administering to the subject an effective amount of a compound of Formula I, Ia, Ib, II, IIa, IIb, III, IIIa, IIIb, IV, IVa, IVb, V, VI, VIa, VIb, VII, VIIa, VIIb, VIII, VIIIa, VIIIb, IX, IXa, IXb, Xb, XI, XIa, XIb, XII, XIIa, or XIIb.

In another embodiment, the invention encompasses methods for preventing resistance to gefitinib or erlotinib in a subject in need thereof, comprising administering to the subject an effective amount of a compound of Formula I, Ia, Ib, II, IIa, IIb, III, IIIa, IIIb, IV, IVa, IVb, V, VI, VIa, VIb, VII, VIIa, VIIb, VIII, VIIIa, VIIIb, IX, IXa, IXb, Xb, XI, XIa, XIb, XII, XIIa, or XIIb.

In another embodiment, the invention encompasses kits comprising a compound of Formula I, Ia, Ib, II, IIa, IIb, III, IIIa, IIIb, IV, IVa, IVb, V, VI, VIa, VIb, VII, VIIa, VIIb, VIII, VIIIa, VIIIb, IX, IXa, IXb, Xb, XI, XIa, XIb, XII, XIIa, or XIIb, and instructions for use of the compound in treating a disease or disorder in a subject in need thereof.

INCORPORATION BY REFERENCE

All publications, patents, and patent applications mentioned in this specification are herein incorporated by reference in their entirety.

BRIEF DESCRIPTION OF THE DRAWINGS

FIG. 1 illustrates $IC_{50}$ ratios of irreversible EGFR inhibitors currently under clinical development. For each drug, the $IC_{50}$ ratio, defined as the $IC_{50}$ in Ba/F3 cells with an EGFR activating mutation and T790M to the $IC_{50}$ in Ba/F3 cells with the EGFR activating mutation alone for a given genotype (e.g. (L858R/T790M)/L858R)) is calculated. The data are obtained from Engelman, J. A. et al., PF00299804, an irreversible pan-ERBB inhibitor, is effective in lung cancer models with EGFR and ERBB2 mutations that are resistant to gefitinib. *Cancer Res* 67, 11924-11932 (2007); Yuza, Y. et al., Allele-Dependent Variation in the Relative Cellular Potency of Distinct EGFR Inhibitors. *Cancer Biol Ther* 6 (2007); Li, D. et al., BIBW2992, an irreversible EGFR/HER2 inhibitor highly effective in preclinical lung cancer models. *Oncogene* (2008); Wong, K. K., Searching for a magic bullet in NSCLC: the role of epidermal growth factor receptor mutations and tyrosine kinase inhibitors. *Lung Cancer* 60 Suppl 2, S10-18 (2008).

DETAILED DESCRIPTION OF THE INVENTION

The present invention provides compounds that are able to modulate the activity of epidermal growth factor receptor (EGFR), including EGFR kinase activity and human epidermal growth factor receptor kinase (Her-kinases). The invention further provides the use of these compounds in the treatment of various Conditions.

The EGFR kinase inhibitors, gefitinib and erlotinib, are clinical therapies for non-small cell lung cancers (NSCLC) that harbor activating mutations in the EGFR kinase domain. EGFR activating mutations can be located in exons 18-21 of the EGFR kinase domain and can lead to constitutive activation of EGFR kinase activity and oncogenic transformation. At least two of these activating mutations (the L858R point mutation and an exon 19 deletion mutation) impart an increased affinity for gefitinib and a decreased affinity for ATP relative to wild type (WT) EGFR. Together, these two effects yield as much as a 100-fold more potent inhibition of mutant EGFR compared to WT EGFR by gefitinib. However, the clinical efficacy of EGFR kinase inhibitors is limited by the development of drug resistance in all patients. Secondary mutations in the gatekeeper T790 residue (T790M) have been detected in 50% of EGFR mutant NSCLC patients that have developed acquired resistance to gefitinib or erlotinib. EGFR T790M only modestly affects gefitinib binding but more importantly leads to a higher affinity for ATP similar to that of wild type EGFR. The T790M mutation does not preclude binding of irreversible inhibitors but can confer resistance to reversible inhibitors in part by increasing the affinity of the enzyme for ATP. Irreversible inhibitors can overcome this mechanism of resistance because they are no longer in competition with ATP after they are covalently bound.

The majority of EGFR inhibitors that are currently approved or under clinical evaluation were initially identified and developed as ATP-competitive inhibitors of wild-type EGFR. Currently approved EGFR inhibitors include three reversible EGFR kinase inhibitors (gefitinib, erlotinib and lapatinib) which are all based on a 4-anilinoquinazoline core scaffold. Previously developed irreversible EGFR kinase inhibitors that can inhibit EGFR are also based upon a 4-anilinoquinazoline or the closely related 4-anilinoquinoline-3-carbonitrile scaffolds but contain an electrophilic functionality which undergoes a Michael addition reaction with a conserved, solvent exposed cysteine residue present in certain kinases such as EGFR (Cys 797) and ERBB2 (Cys 805). The covalent nature of these compounds allows them to achieve greater occupancy of the ATP-site relative to the reversible inhibitors providing the ability to inhibit EGFR T790M, despite increased ATP affinity conferred by this secondary mutation. However, current irreversible inhibitors are 10-140 fold worse at inhibiting the growth of models harboring EGFR T790M compared to those with just an EGFR activating mutation. See FIG. 1. Furthermore as the ATP affinity of EGFR T790M is similar to WT EGFR, the concentration of an irreversible EGFR inhibitor required to inhibit EGFR T790M can also effectively inhibit WT EGFR. The class-specific toxicities of current EGFR kinase inhibitors, e.g., skin rash and diarrhea, are a result of inhibiting WT EGFR in non-cancer tissues. To date, the clinical efficacy of the irreversible EGFR kinase inhibitors EKB-569, CI-1033 (also known as canertinib), HKI-272 (also known as neratinib) and PF00299804 has been limited, especially in gefitinib/erlotinib resistant NSCLC patients, and the dose limiting toxicity for this class of agents includes diarrhea and skin rash.

The present invention provides compounds that are up to 100-fold more potent than current irreversible EGFR kinase inhibitors against drug resistant EGFR in vivo. Moreover, they are up to 100-fold less potent than current irreversible EGFR kinase inhibitors against wild type EGFR. In some embodiments, the compounds of the invention are about 2-, 3-, 4-, 5-, 6-, 7-, 8-, 9-, 10-, 15-, 20-, 25-, 30-, 40-, 50-, 60-, 70-, 80-, 90- or 100-fold more selective for EGFR activating and the T790M resistance mutation relative to wild-type EGFR.

I. Definitions

As used herein, unless otherwise defined, the term "$C_1$-$C_6$ alkyl" refers to a straight chain or branched non-cyclic hydrocarbon having from 1 to 6 carbon atoms, wherein one of the hydrocarbon's hydrogen atoms has been replaced by a single bond. Representative straight chain $C_1$-$C_6$ alkyls include -methyl, -ethyl, -n-propyl, -n-butyl, -n-pentyl, and n-hexyl. Representative branched $C_1$-$C_6$ alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl, and 1,2-dimethylpropyl.

As used herein, unless otherwise defined, the term "$C_1$-$C_6$ haloalkyl" refers to a "$C_1$-$C_6$ alkyl" as defined above, wherein at least one of the hydrogen atoms has been replaced by a halogen ("Hal"). Representative straight chain $C_1$-$C_6$ haloalkyls include —C(Hal)H$_2$, —C(Hal)$_2$H, —C(Hal)$_3$, —CH$_2$C(Hal)H$_2$, —CH$_2$C(Hal)$_2$H, and —CH$_2$C(Hal)$_3$. Representative branched $C_1$-$C_6$ haloalkyls include —CH$_2$CH(CH(Hal)$_2$)CH$_3$ and —CH$_2$C(C(Hal)$_3$)$_2$CH$_2$CH$_3$.

As used herein, unless otherwise defined, the term "$C_1$-$C_6$ alkoxy" refers to a "$C_1$-$C_6$ alkyl" as defined above, wherein at least one of the hydrogen atoms has been replaced by an oxygen. Representative straight chain $C_1$-$C_6$ alkoxys include -methoxy, -ethoxy, -n-propoxy, -n-butoxy, -n-pentoxy, and n-hexoxy. Representative branched $C_1$-$C_6$ alkoxys include -isopropoxy, -sec-butoxy, -isobutoxy, -tert-butoxy, -isopentoxy, -neopentoxy, 1-methylbutoxy, 2-methylbutoxy, 3-methylbutoxy, 1,1-dimethylpropoxy, and 1,2-dimethylpropoxy.

As used herein, unless otherwise defined, the term "$C_1$-$C_6$ haloalkoxy" refers to a "$C_1$-$C_6$ alkoxy" as defined above, wherein at least one of the hydrogen atoms has been replaced by a halogen.

As used herein, unless otherwise defined, the term "$C_3$-$C_6$ cycloalkyl" refers to a cyclic hydrocarbon having from 3 to 6 carbon atoms, wherein one of the hydrocarbon's hydrogen atoms has been replaced by a single bond. Representative $C_3$-$C_6$ cycloalkyls include cyclopropyl, cyclobutyl, cyclopentyl, and cyclohexyl.

As used herein, unless otherwise defined, the term "halogen" or "halo" or "hal" refers to —F, —Cl, —Br or —I.

As used herein, unless otherwise defined, the term "$C_2$-$C_6$ alkenyl" refers to a straight chain or branched non-cyclic hydrocarbon having from 2 to 6 carbon atoms and having at least one carbon-carbon double bond, wherein one of the hydrocarbon's hydrogen atoms has been replaced by a single bond. Representative straight chain $C_2$-$C_6$ alkenyls include ethenyl, 1-propenyl, 1-butenyl, 2-butenyl, 1-pentenyl, 2-pentenyl, 1-hexenyl, 2-hexenyl, and 3-hexenyl. Representative branched $C_2$-$C_6$ alkenyls include -isobutenyl, 1,1-dimethylpropenyl, and -isopentenyl.

As used herein, unless otherwise defined, the term "$C_2$-$C_6$ alkynyl" refers to a straight chain or branched non-cyclic hydrocarbon having from 2 to 6 carbon atoms and having at least one carbon-carbon triple bond, wherein one of the hydrocarbon's hydrogen atoms has been replaced by a single bond. Representative straight chain $C_2$-$C_6$ alkynyls include ethynyl, 1-propynyl, 1-butynyl, 2-butynyl, 1-pentynyl, 2-pentynyl, 1-hexynyl, 2-hexynyl, and 3-hexynyl. Representative branched $C_2$-$C_6$ alkynyls include -isobutynyl, 1,1-dimethylpropynyl, and -isopentynyl.

As used herein, unless otherwise defined, the term "$C_4$-$C_9$ heterocycloalkenyl" refers to a cyclic hydrocarbon having from 4 to 6 carbon atoms and having at least one carbon-carbon double bond, wherein at least one of the carbon atoms has been replaced by a nitrogen, oxygen, or sulfur atom and wherein one of the hydrocarbon's hydrogen atoms has been replaced by a single bond. Representative $C_4$-$C_9$ heterocycloalkenyls include

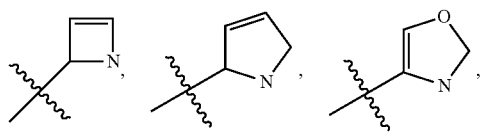

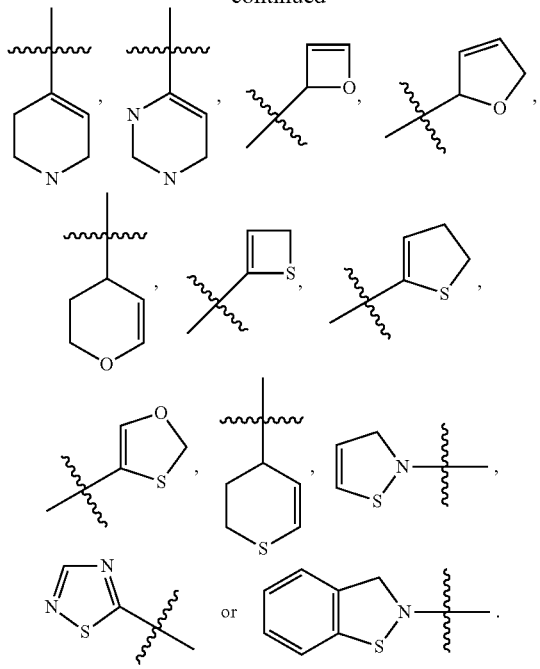

As used herein, unless otherwise defined, the term "$C_3$-$C_6$ heterocycle" refers to a cyclic hydrocarbon having from 3 to 6 carbon atoms, wherein at least one of the carbon atoms has been replaced by a nitrogen, oxygen, or sulfur atom and wherein one of the hydrocarbon's hydrogen atoms has been replaced by a single bond. Representative $C_3$-$C_6$ heterocycles include

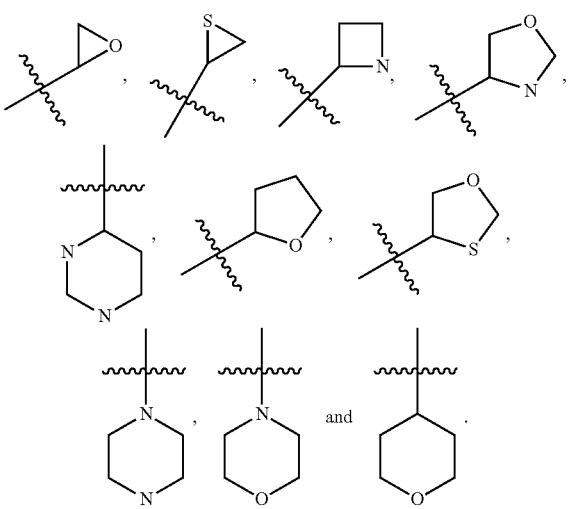

As used herein, unless otherwise defined, the term "pharmaceutically acceptable salt" refers to a salt of an acidic or basic group on the compounds of the invention. Illustrative salts of a basic group include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, and pamoate (i.e., 1,1'-methylene-bis-(2-hydroxy-3-naphthoate)) salts. The term "pharmaceutically acceptable salt" also refers to a salt of a compound of the invention having an acidic functional group, such as a carboxylic acid, phenolic, or enolic functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like. Additional suitable pharmaceutically acceptable salts are described, for example, by S. M. Berge, et al., *J. Pharmaceutical Sciences*, 66: 1-19 (1977).

As used herein, unless otherwise defined, the term "pharmaceutically acceptable ester" refers to esters of the compounds of the invention. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

As used herein, unless otherwise defined, the term "pharmaceutically acceptable prodrug" refers to precursors of the compounds of the invention that metabolize to a compound of the invention in vivo after administration to a subject. Various forms of prodrugs are known in the art, for example, as discussed in Design of Prodrugs, (Bundgaard, ed., Elsevier, 1985); Methods in Enzymology, Vol. 4 (Widder, et al., eds., Academic Press, 1985); Design and Application of Prodrugs, Textbook of Drug Design and Development, Chapter 5, 113-191 (Krogsgaard-Larsen, et al., eds., 1991); Prodrugs as Novel Drug Delivery Systems, (Higuchi and Stella, eds., American Chemical Society, 1975); Bundgaard, et al., *J. Drug Delivery Rev.*, 8:1-38 (1992); Bundgaard, *J. Pharm. Sci.*, 77:285 et seq. (1988); and B. Testa & J. Mayer, Hydrolysis In Drug And Prodrug Metabolism: Chemistry, Biochemistry And Enzymology, (John Wiley and Sons, Ltd. 2002). Prodrugs include compounds wherein an amino acid residue, or a polypeptide chain of two or more (e.g., two, three or four) amino acid residues is covalently joined through an amide or ester bond to a free amino, hydroxy or carboxylic acid group of a compound of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in *Advanced Drug Delivery Reviews*, 19(1):15 (1996). Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.*, 39: 10 (1996). Free amines can also be derivatized as amides, sulfonamides or phosphonamides. All of these prodrug moieties may incorporate groups including but not limited to ether, amine and carboxylic acid functionalities.

As used herein, unless otherwise defined, the term "effective amount," when used in connection with a compound of the invention, is an amount that is effective for treating or preventing a Condition.

As used herein, unless otherwise defined, the term "subject," refers to a mammal. Examples of mammals include a human, mouse, rat, guinea pig, dog, cat, horse, cow, pig, or non-human primate, such as a monkey, chimpanzee, or baboon. In one embodiment, the mammal is a human.

As used herein, unless otherwise defined, the term "pharmaceutically acceptable excipient" means a non-toxic, inert solid, semi-solid or liquid filler, diluent, encapsulating material or formulation auxiliary of any type.

II. Compounds of the Invention

In one embodiment, the invention encompasses compounds of the following Formula I:

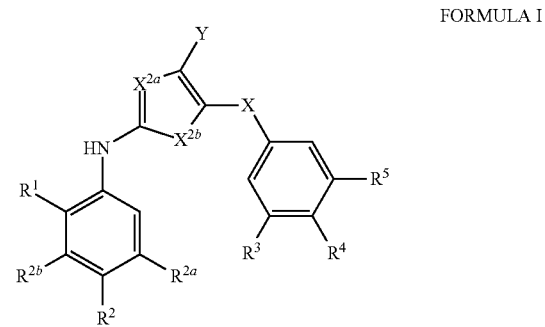

FORMULA I and pharmaceutically acceptable salts, esters, and prodrugs thereof, wherein:

X is oxygen, sulfur, carbonyl, —NR$^6$, C$_1$-C$_6$ alkyl, or C$_1$-C$_6$ haloalkyl;

X$^{2a}$ is nitrogen, CH, or CR$^{30}$;

X$^{2b}$ is oxygen, sulfur, NH, or NR$^9$;

Y is hydrogen, halogen, or C$_1$-C$_6$ alkyl;

each R$^1$ is independently C$_1$-C$_6$ alkyl, C$_1$-C$_6$ alkoxy, C$_1$-C$_6$ haloalkyl, or C$_1$-C$_6$ haloalkoxy;

(i) one of R$^2$, R$^{2a}$, and R$^{2b}$ is piperidine, pyrrolidine, piperazine, or morpholine that is optionally substituted with C$_1$-C$_6$ alkyl; or C$_3$-C$_6$ alkyl or C$_3$-C$_6$ cycloalkyl containing at least one nitrogen; and the other two of R$^2$, R$^{2a}$, and R$^{2b}$ are hydrogen or C$_1$-C$_6$ alkyl; or (ii) R$^2$ and one of R$^{2a}$ and R$^{2b}$ join to form a piperidine, pyrrolidine, or morpholine that is optionally substituted with C$_1$-C$_6$ alkyl; or C$_3$-C$_6$ cycloalkyl containing at least one nitrogen; and the other of R$^{2a}$ and R$^{2b}$ is hydrogen or C$_1$-C$_6$ alkyl;

one of R$^3$, R$^4$, and R$^5$ is Z, and the other two of R$^3$, R$^4$, and R$^5$ are hydrogen;

each $R^6$ is independently hydrogen or $C_1$-$C_6$ alkyl;

$R^7$ is hydrogen, $C_1$-$C_6$ alkyl, or $C_2$-$C_6$ alkenyl;

$R^8$ is $C_1$-$C_6$ alkyl that is substituted with halogen, cyano, —C(O)$R^9$, or —OC(O)$R^9$; $C_2$-$C_6$ alkenyl that is optionally substituted with halogen or —N$R^9_2$; $C_2$-$C_6$ alkynyl; $C_3$-$C_6$ cycloalkyl that is substituted with cyano or —C(O)$R^9$; $C_4$-$C_6$ cycloalkenyl that is optionally substituted with halogen; or $C_4$-$C_9$ heterocycloalkenyl that is optionally substituted with halogen, $C_1$-$C_6$ alkyl, or carbonyl;

each $R^9$ is independently $C_1$-$C_6$ alkyl;

$R^{10}$ is hydrogen or $C_1$-$C_6$ alkyl;

$R^{11}$ is $C_2$-$C_6$ alkenyl;

$R^{12}$ is $C_2$-$C_6$ alkenyl substituted with cyano or —C(O)O$R^9$;

$R^{30}$ is halogen or $C_1$-$C_6$ alkyl;

Z is $C_2$-$C_6$ alkenyl, $C_2$-$C_6$ alkynyl, $C_3$-$C_6$ cycloalkyl that is substituted with cyano or acetyl, —(CH$_2$)$_n$N$R^7$C(O)$R^8$, —(CH$_2$)$_n$—C(O)(CH$_2$)$_n$$R^8$, —(CH$_2$)$_n$OC(O)$R^8$,

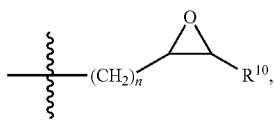

(NH)$_m$(SO$_2$)$R^{11}$,
—CH$R^{11}$OC(O)$R^{11}$, —O$R^{12}$, —(CH$_2$)$_n$C(OH)$R^{12}$,

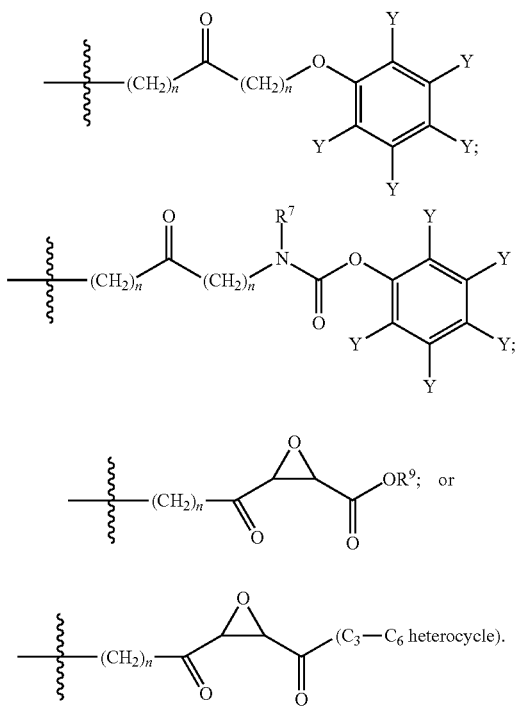

n is an integer from 0 to 6; and m is 0 or 1.

In some embodiments, $X^{2a}$ is nitrogen and $X^{2b}$ is sulfur and the compound of Formula I is:

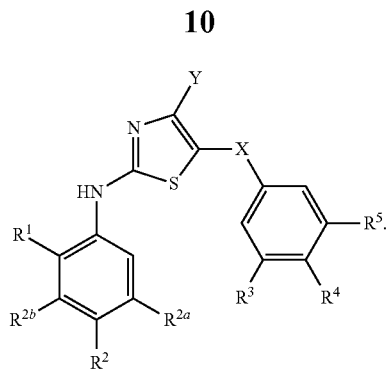

In other embodiments, $X^{2a}$ is nitrogen and $X^{2b}$ is oxygen and the compound of Formula I is:

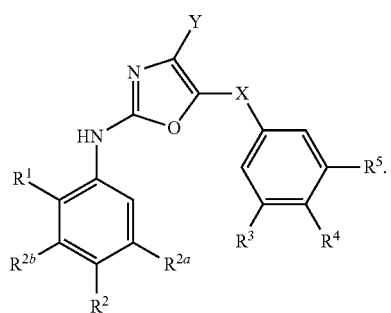

In other embodiments, $X^{2a}$ is CH and $X^{2b}$ is oxygen and the compound of Formula I is:

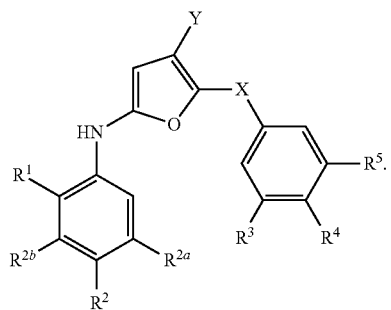

In some embodiments, X is oxygen, sulfur, carbonyl, NH, NCH$_3$, CH$_2$, CF$_2$, or CH(CH$_3$). In other embodiments, Y is hydrogen, fluorine, chlorine, or methyl. In other embodiments, $R^1$ is —CH$_3$, —CH$_2$CH$_3$, —OCH$_3$, —OCH$_2$CH$_3$, or —OCH$_2$(CH$_3$)$_2$.

In some embodiments, Z is

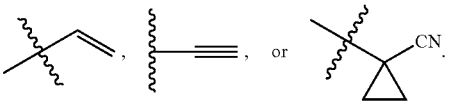

In other embodiments, Z is
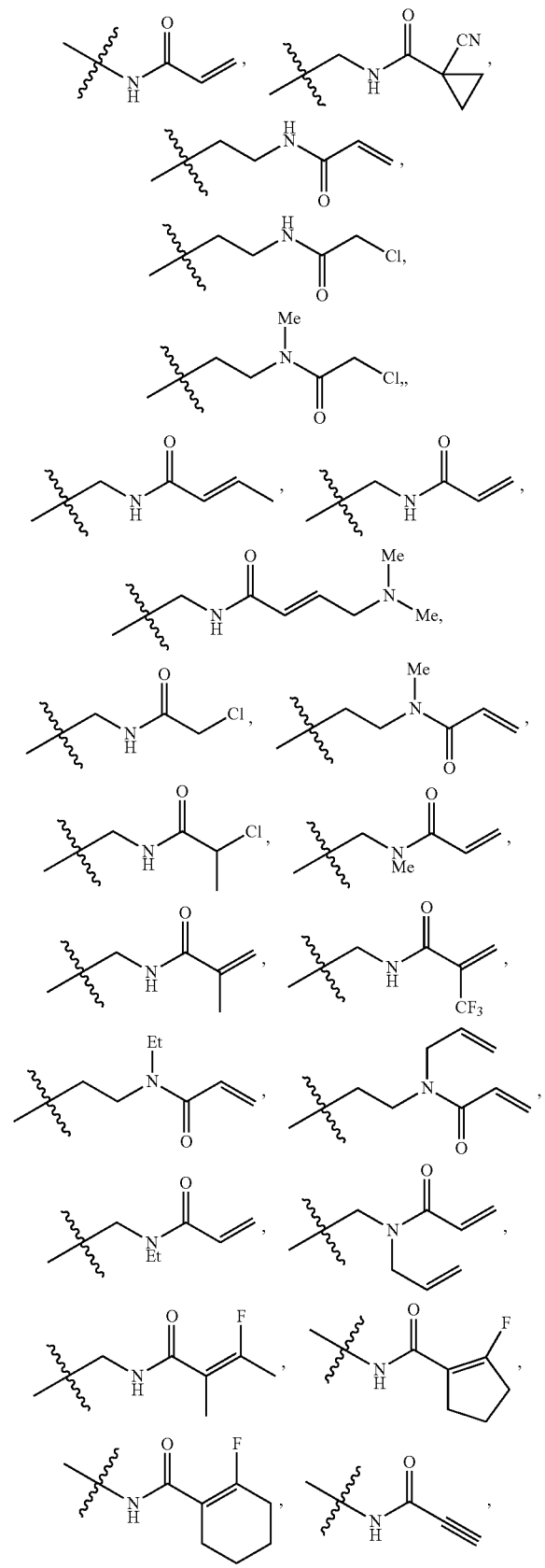
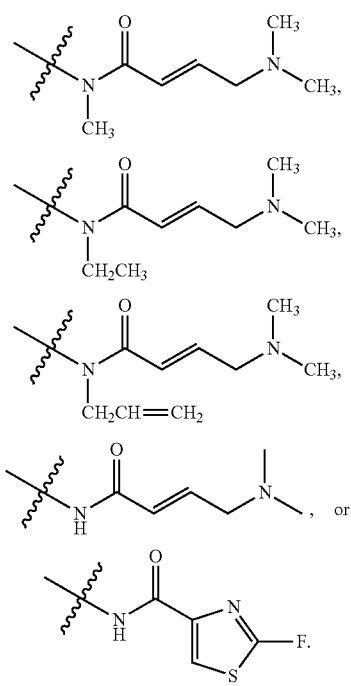
In other embodiments, Z is —(CH$_2$)$_n$NR$^7$C(O)R$^8$. In other embodiments, Z is —(CH$_2$)$_n$NR$^7$C(O)R$^8$, wherein R$^7$ is hydrogen and R$^8$ is C$_2$-C$_6$ alkenyl. In other embodiments, Z is
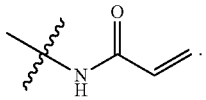 [SMILES: *NC(=O)C=C]
In other embodiments, Z is
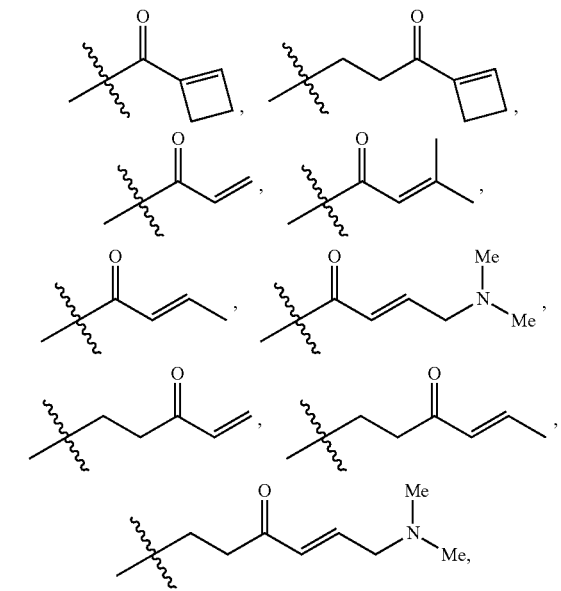

-continued
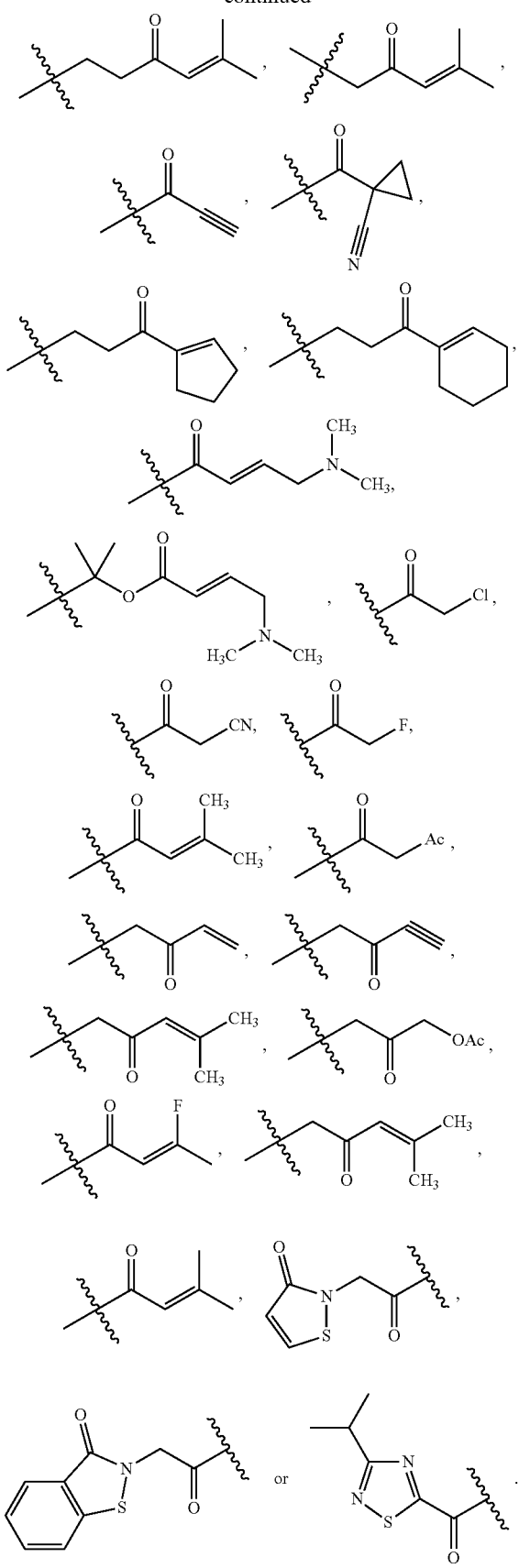
In other embodiments, Z is
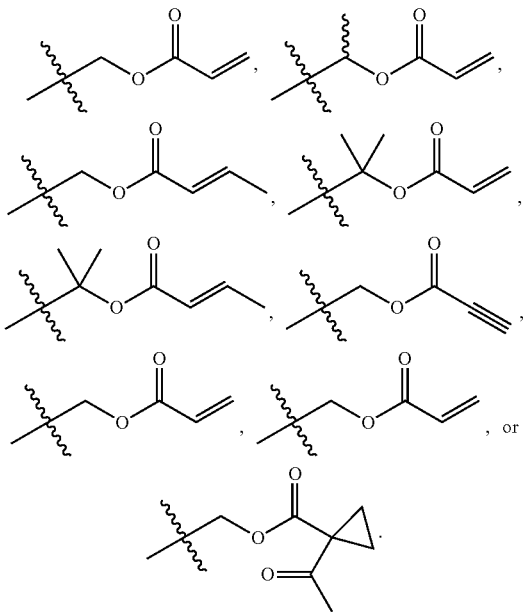
In other embodiments, Z is
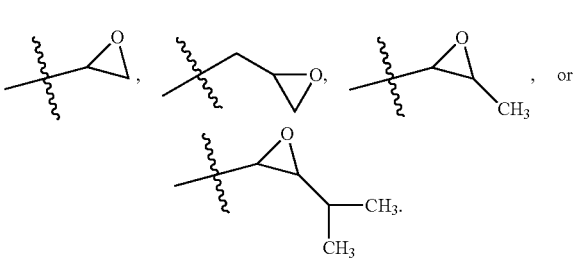
In other embodiments, Z is
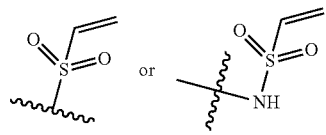
In other embodiments, Z is
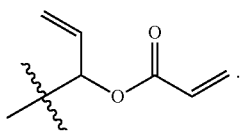 [SMILES: *C(C=C)OC(=O)C=C]
In other embodiments, Z is
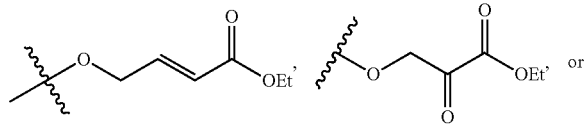

-continued

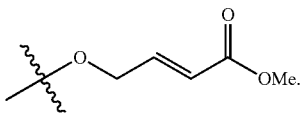

In other embodiments, Z is

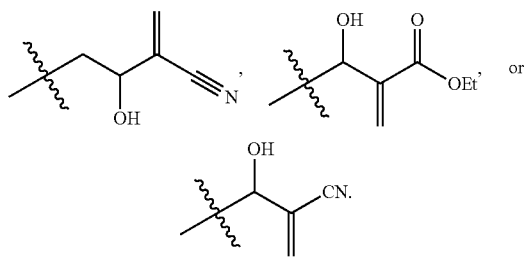

In other embodiments, Z is

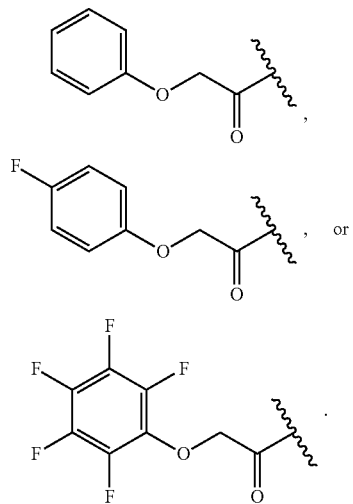

In other embodiments, Z is

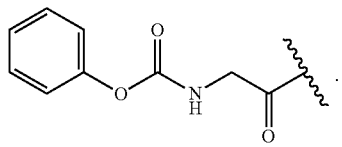 [SMILES: *C(=O)CNC(=O)Oc1ccccc1]

In other embodiments, Z is

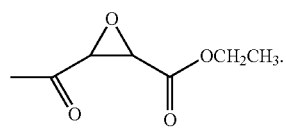

In other embodiments, Z is

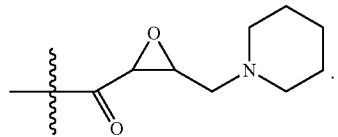 [SMILES: *C(=O)C1OC1CN1CCCCC1]

In one embodiment, the invention encompasses compounds of Formula I, wherein: X is oxygen; Y is halogen; $R^1$ is $C_1$-$C_6$ alkoxy; $R^2$ is piperidine that is substituted at the N position with $C_1$-$C_6$ alkyl or piperazine that is substituted at the N position with $C_1$-$C_6$ alkyl; $R^{2a}$ and $R^{2b}$ are hydrogen; one of $R^3$, $R^4$, and $R^5$ is Z, and the other two of $R^3$, $R^4$, and $R^5$ are hydrogen; $R^7$ is hydrogen or $C_1$-$C_6$ alkyl; $R^8$ is $C_2$-$C_6$ alkenyl; and Z is —$(CH_2)_nNR^7C(O)R^8$.

In some embodiments, the compound of Formula I is one of the following compounds or a pharmaceutically acceptable salt, ester, or prodrug thereof.

Compound I-1

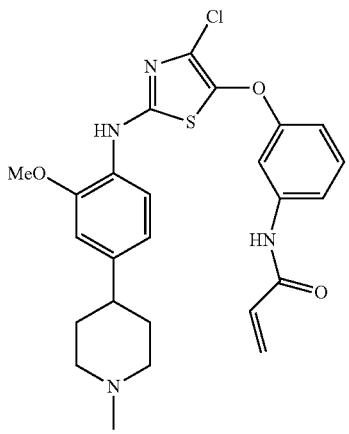

Compound I-2

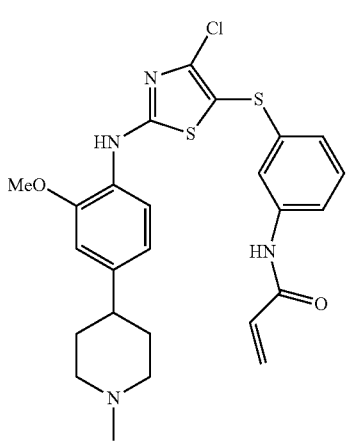

Compound I-3
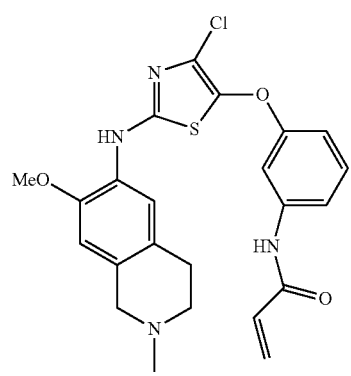
Compound I-4
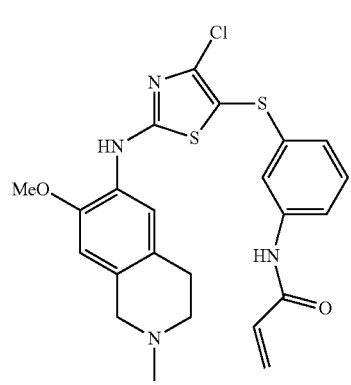
Compound I-5
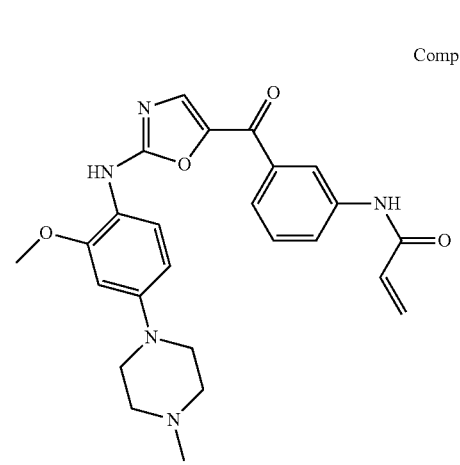
Compound I-6
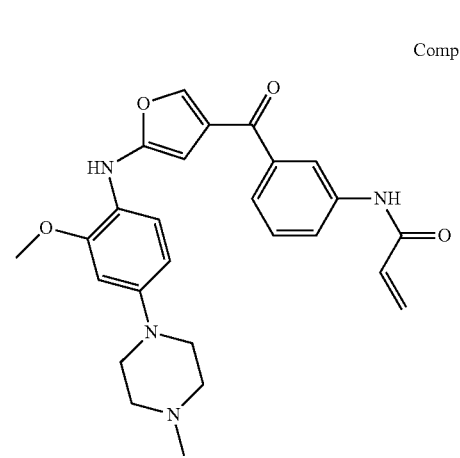
Compound I-7
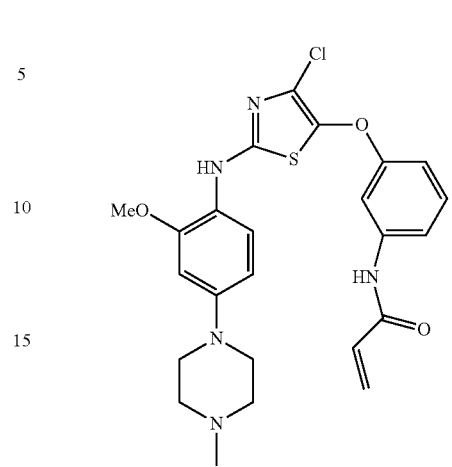
Compound I-8
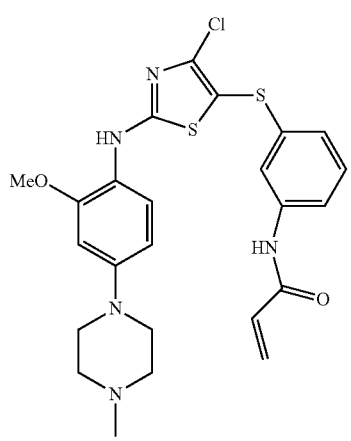
In another embodiment, the invention encompasses compounds of the following Formula Ia:
FORMULA Ia
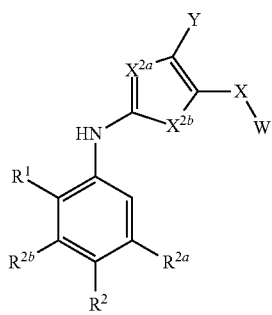
and pharmaceutically acceptable salts, esters, and prodrugs thereof, wherein:
$X$, $X^{2a}$, $X^{2b}$, $Y$, $R^1$, $R^2$, $R^{2a}$, $R^{2b}$, and $R^6$, and $R^{30}$ are as defined above for the compounds of Formula I;

W is

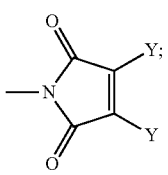

a benzene ring substituted with at least one of halogen, —NO$_2$, or cyano; a pyridine, pyrimidine, oxazole, isoxazole, thiazole, or isothiazole ring that is substituted with at least one of C$_2$-C$_6$ alkenyl, C$_2$-C$_6$ alkynyl, halogen, or cyano; an imidazole or pyrazole ring that is C-substituted with at least one of C$_2$-C$_6$ alkenyl, C$_2$-C$_6$ alkynyl, halogen, or cyano and that is optionally N-substituted with C$_1$-C$_6$ alkyl; a 3-oxobenzisothiazole that is optionally substituted with halogen or C$_1$-C$_6$ alkyl; a pyrrolidine that is N-substituted with acrylate or cyano;

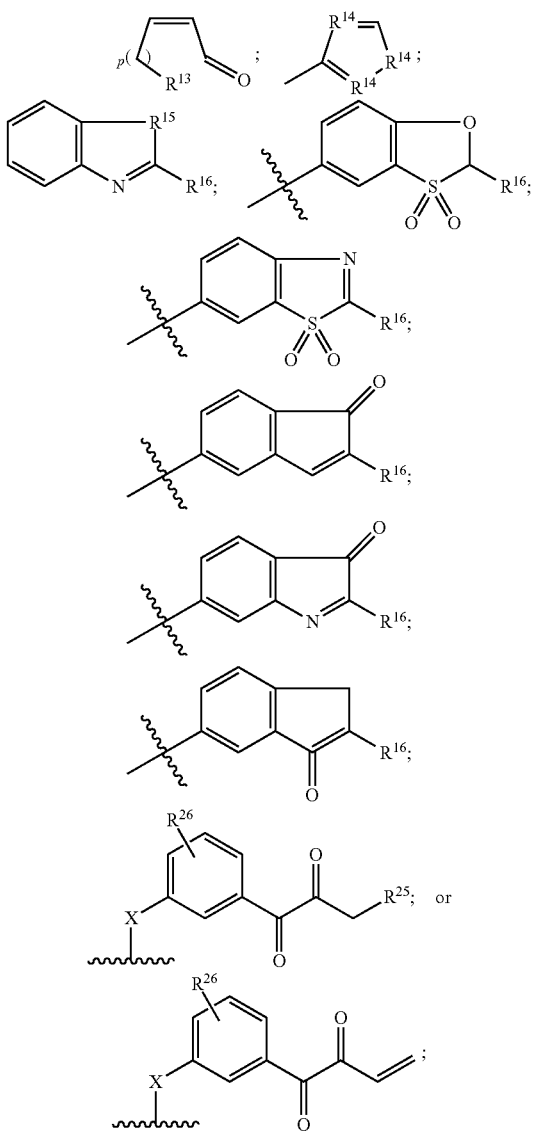

R$^{13}$ is carbon, nitrogen, or oxygen;
each R$^{14}$ is independently sulfur, nitrogen, or oxygen;

R$^{15}$ is oxygen or sulfur;
R$^{16}$ is C$_2$-C$_6$ alkenyl that is optionally substituted with NR$^6_2$ or C$_2$-C$_6$ alkynyl;
R$^{25}$ is halogen;
R$^{26}$ is halogen, C$_1$-C$_6$ alkyl, or C$_1$-C$_6$ haloalkyl; and
p is 1 or 2.

In some embodiments, X$^{2a}$ is nitrogen and X$^{2b}$ is sulfur and the compound of Formula Ia is:

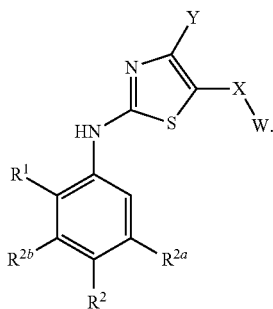

In other embodiments, X$^{2a}$ is nitrogen and X$^{2b}$ is oxygen and the compound of Formula Ia is:

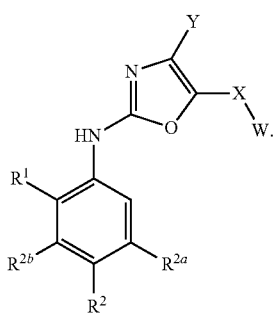

In other embodiments, X$^{2a}$ is CH and X$^{2b}$ is oxygen and the compound of Formula Ia is:

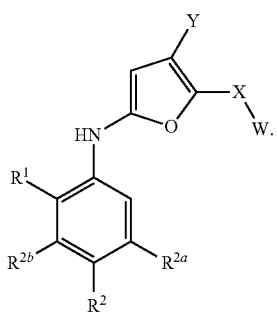

In some embodiments, W is

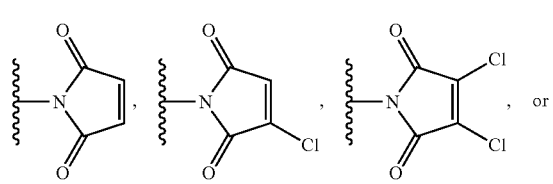

-continued
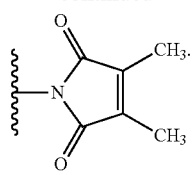
In other embodiments, W is
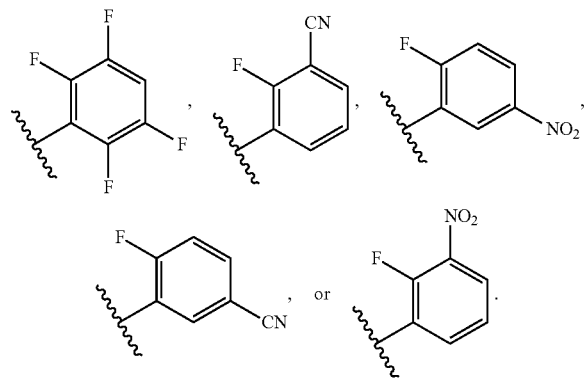
In other embodiments, W is
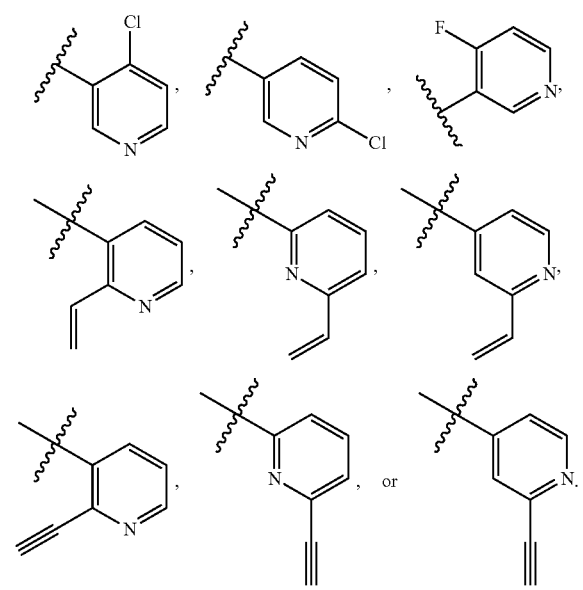
In other embodiments, W is
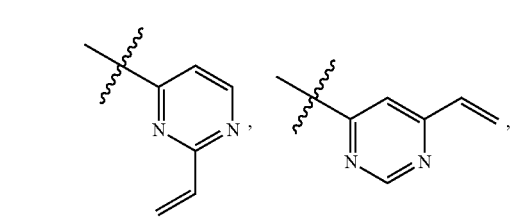
-continued
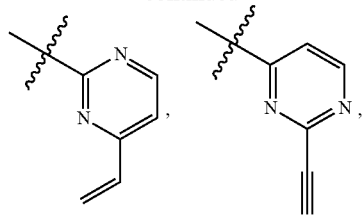,
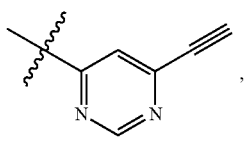,
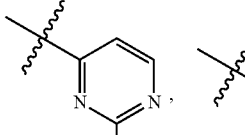,
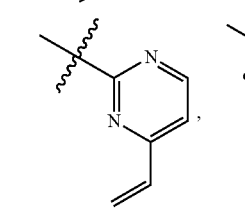,
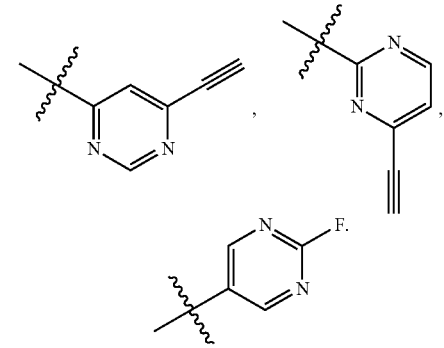, or
In other embodiments, W is
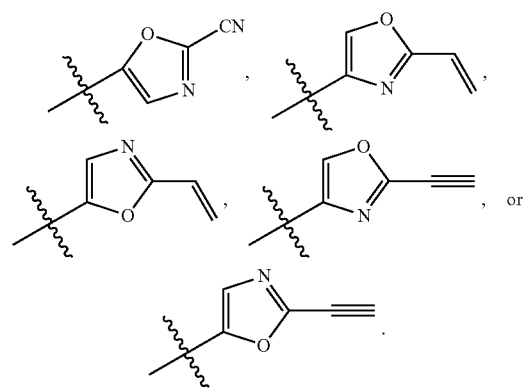.

In other embodiments, W is
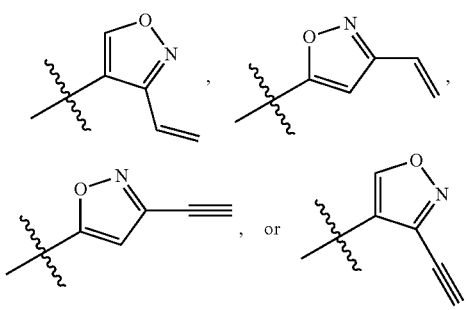
In other embodiments, W is
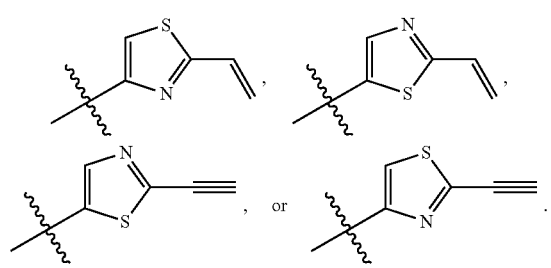
In other embodiments, W is
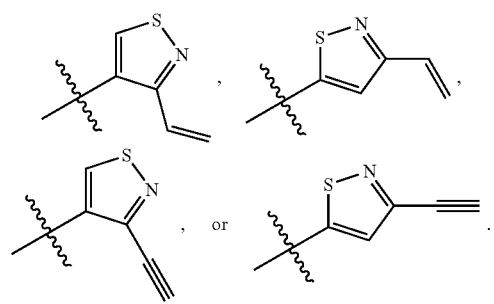
In other embodiments, W is
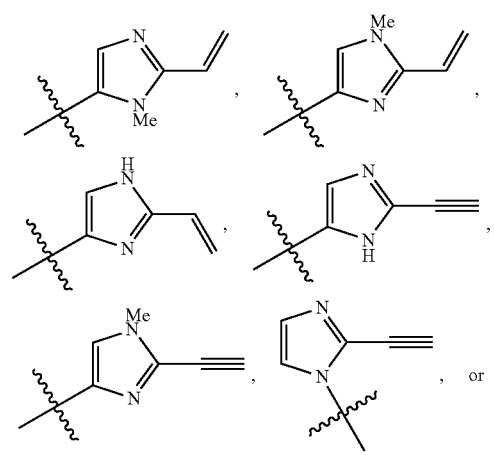
-continued
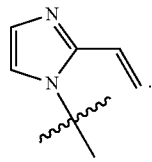
In other embodiments, W is
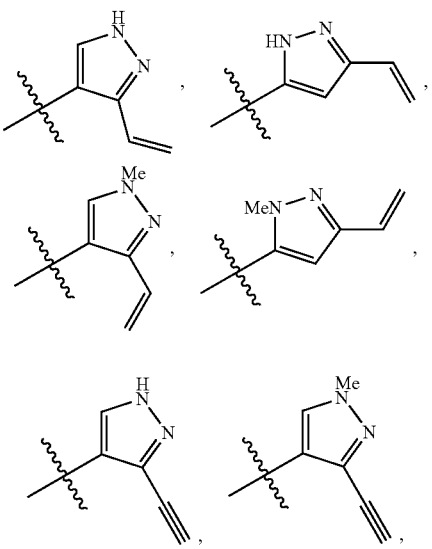
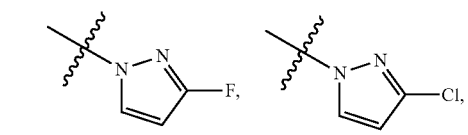
or. In other embodiments, W is
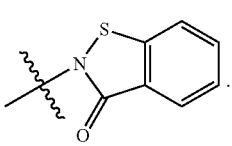 [SMILES: *n1sc2ccccc2c1=O]

In other embodiments, W is

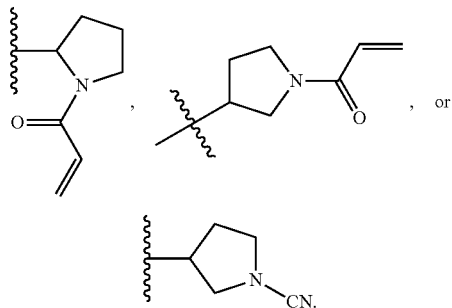

In other embodiments, W is

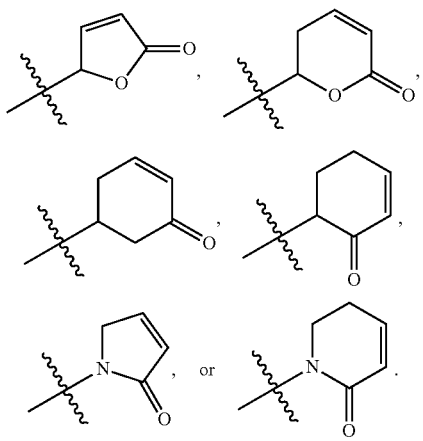

In other embodiments, W is

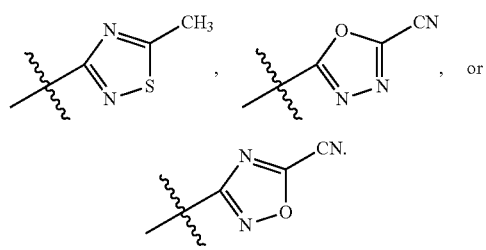

In other embodiments, W is

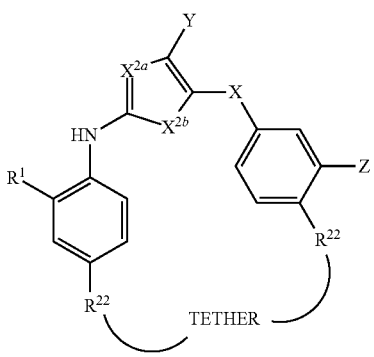

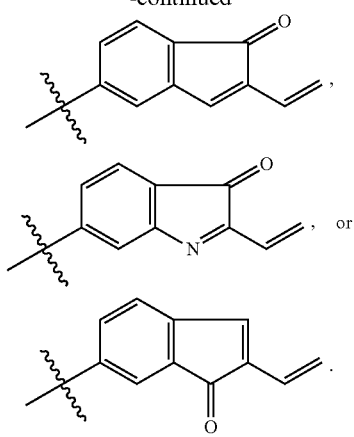

In another embodiment, the invention encompasses compounds of the following Formula Ib:

FORMULA Ib and pharmaceutically acceptable salts, esters, and prodrugs thereof, wherein:

X, $X^{2a}$, $X^{2b}$, Y Z, n, m, and $R^1$ and $R^6$ to $R^{12}$, and $R^{30}$ are as defined above for the compounds of Formula I;

each $R^{22}$ is independently $CH_2$, $CHR^1$, $CR^1_2$, sulfur, oxygen, carbonyl, or $NR^6$; and TETHER is a group having 3-10 atoms selected from carbon, nitrogen, sulfur and oxygen.

In one embodiment, the $R^{22}$-TETHER-$R^{22}$ moiety in the compounds of Formula Ib is:

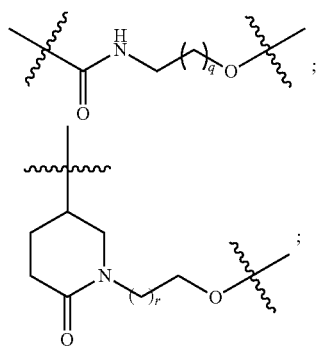

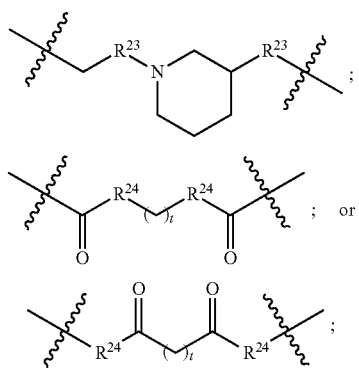

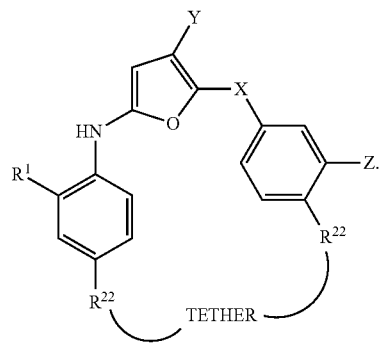

wherein:

q is 0, 1, 2, 3, or 4;

r is 1, 2, 3, or 4;

t is 2, 3, or 4;

each $R^{23}$ is independently oxygen, sulfur, $NR^6$, or $CR^1_2$; and each $R^{24}$ is independently oxygen, sulfur, or $NR^6$.

In some embodiments, $X^{2a}$ is nitrogen and $X^{2b}$ is sulfur and the compound of Formula Ib is:

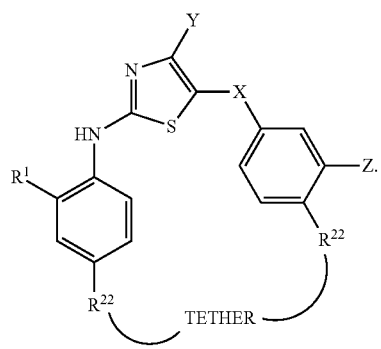

In other embodiments, $X^{2a}$ is nitrogen and $X^{2b}$ is oxygen and the compound of Formula Ib is:

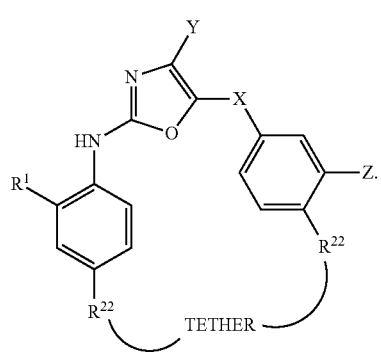

In other embodiments, $X^{2a}$ is CH and $X^{2b}$ is oxygen and the compound of Formula Ib is:

In one embodiment, the invention encompasses pyrazole compounds of the following Formula II:

FORMULA II

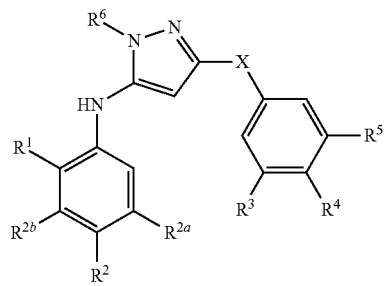

and pharmaceutically acceptable salts, esters, and prodrugs thereof, wherein X, Y, Z, n, m, and $R^1$ to $R^{12}$, and $R^{30}$ are as defined above for the compounds of Formula I.

In one embodiment, the compound of Formula II is:

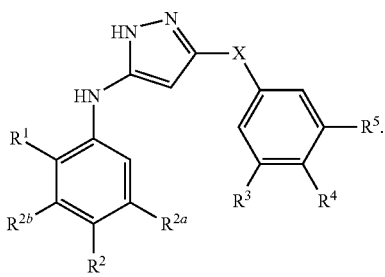

In one embodiment, the invention encompasses compounds of Formula II, wherein: X is oxygen; $R^1$ is $C_1$-$C_6$ alkoxy; $R^2$ is piperidine that is substituted at the N position with $C_1$-$C_6$ alkyl or piperazine that is substituted at the N position with $C_1$-$C_6$ alkyl; $R^{2a}$ and $R^{2b}$ are hydrogen; one of $R^3$, $R^4$, and $R^5$ is Z, and the other two of $R^3$, $R^4$, and $R^5$ are hydrogen; $R^7$ is hydrogen or $C_1$-$C_6$ alkyl; $R^8$ is $C_2$-$C_6$ alkenyl; and Z is —$(CH_2)_n NR^7 C(O)R^8$.

In some embodiments, the compound of Formula II is one of the following compounds or a pharmaceutically acceptable salt, ester, or prodrug thereof.

Compound II-1
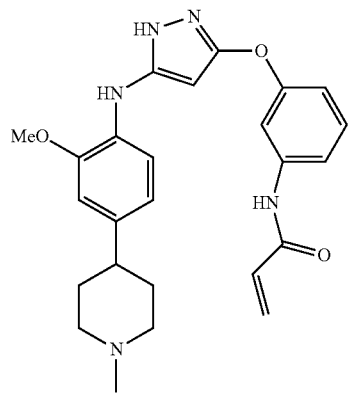

Compound II-2
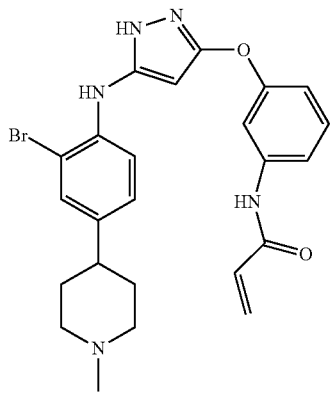

Compound II-3
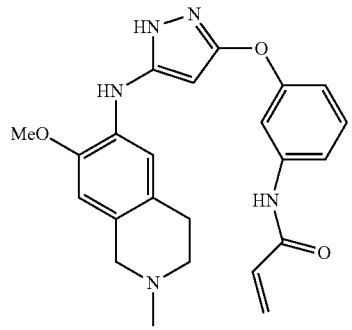

Compound II-4
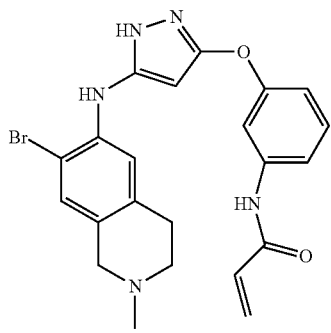

Compound II-5
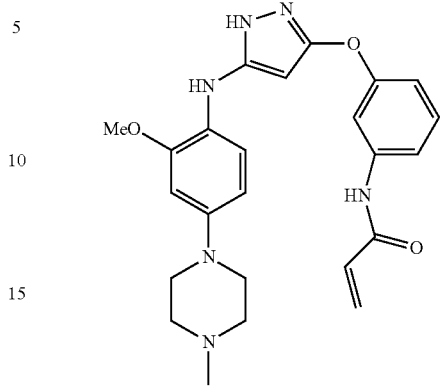

Compound II-6
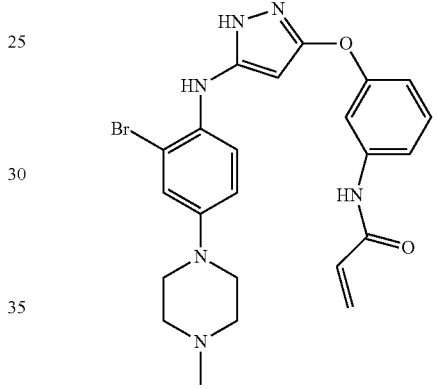

In another embodiment, the invention encompasses pyrazole compounds of the following Formula IIa:

FORMULA IIa
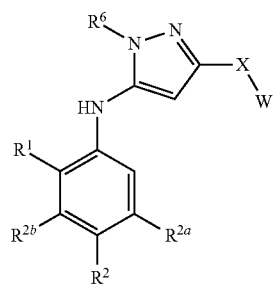

and pharmaceutically acceptable salts, esters, and prodrugs thereof, wherein W, X, Y, $R^1$, $R^2$, $R^{2a}$, $R^{2b}$, $R^6$, $R^{13}$, $R^{14}$, $R^{15}$, $R^{16}$, $R^{25}$, $R^{26}$, and p are as defined above for the compounds of Formula Ia.

In one embodiment, the compound of Formula IIa is:

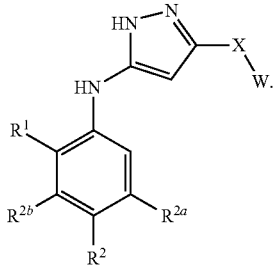

In another embodiment, the invention encompasses compounds of the following Formula IIb:

FORMULA IIb

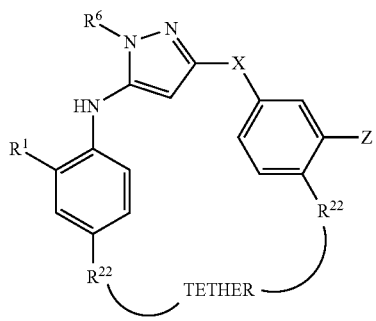

and pharmaceutically acceptable salts, esters, and prodrugs thereof, wherein X, Z, n, m, and $R^1$ and $R^6$ to $R^{12}$, $R^{22}$, and TETHER are as defined above for the compounds of Formula Ib.

In one embodiment, the compound of Formula IIb is:

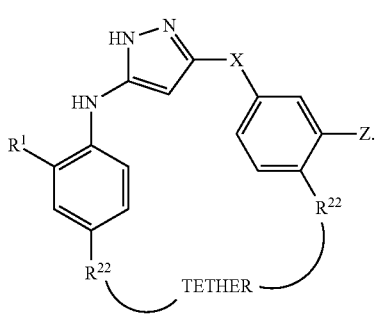

In one embodiment, the invention encompasses cyclic urea compounds of the following Formula III:

FORMULA III

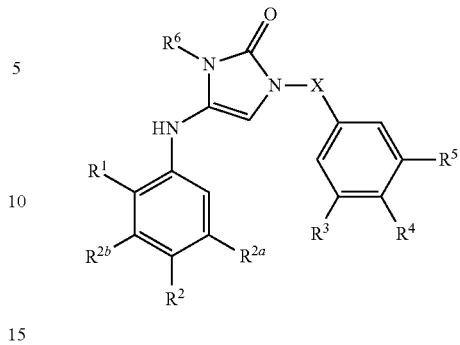

and pharmaceutically acceptable salts, esters, and prodrugs thereof, wherein X, Y, Z, n, m, and $R^1$ to $R^{12}$ are as defined above for the compounds of Formula I.

In one embodiment, the compound of Formula III is:

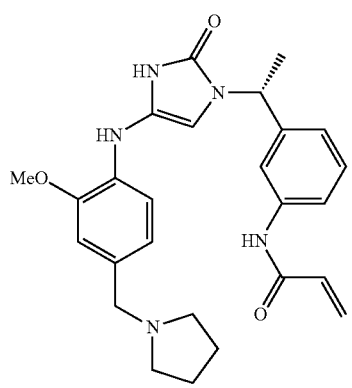

In one embodiment, the invention encompasses compounds of Formula III, wherein: X is $C_1$-$C_6$ alkyl; $R^1$ is $C_1$-$C_6$ alkoxy; $R^2$ is pyrrolidine that is substituted at the N position with $C_1$-$C_6$ alkyl; $R^{2a}$ and $R^{2b}$ are hydrogen; one of $R^3$, $R^4$, and $R^5$ is Z, and the other two of $R^3$, $R^4$, and $R^5$ are hydrogen; $R^7$ is hydrogen or $C_1$-$C_6$ alkyl; $R^8$ is $C_2$-$C_6$ alkenyl; and Z is —$(CH_2)_n NR^7 C(O)R^8$.

In some embodiments, the compound of Formula III is one of the following compounds or a pharmaceutically acceptable salt, ester, or prodrug thereof.

Compound III-1

Compound III-2

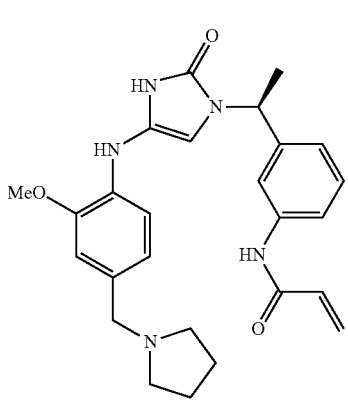

In another embodiment, the invention encompasses cyclic urea compounds of the following Formula IIIa:

FORMULA IIIa

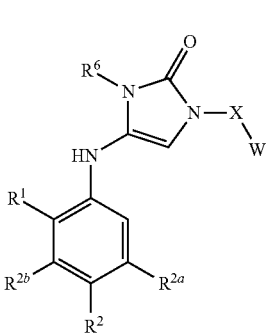

and pharmaceutically acceptable salts, esters, and prodrugs thereof, wherein W, X, Y, $R^2$, $R^{2a}$, $R^{2b}$, $R^6$, $R^{13}$, $R^{14}$, $R^{15}$, $R^{16}$, $R^{25}$, $R^{26}$, and p are as defined above for the compounds of Formula Ia.

In one embodiment, the compound of Formula IIIa is:

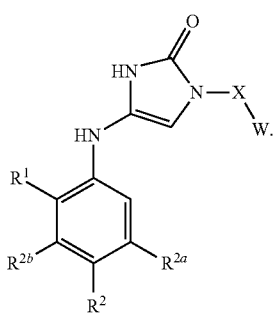

In another embodiment, the invention encompasses compounds of the following Formula IIIb:

FORMULA IIIb

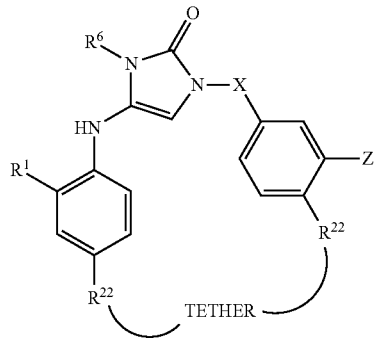

and pharmaceutically acceptable salts, esters, and prodrugs thereof, wherein X, Y, Z, n, m, and $R^1$ and $R^6$ to $R^{12}$, $R^{22}$, and TETHER are as defined above for the compounds of Formula Ib.

In one embodiment, the compound of Formula IIIb is:

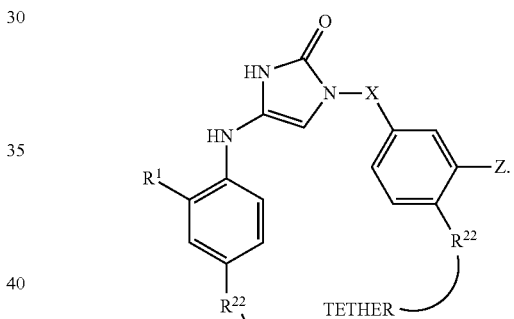

In one embodiment, the invention encompasses compounds of the following Formula IV:

FORMULA IV

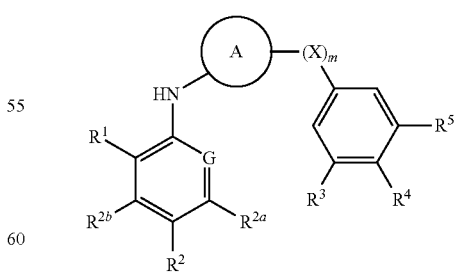

and pharmaceutically acceptable salts, esters, and prodrugs thereof, wherein:

X, $X^{2b}$, Z, n, m, $R^1$ to $R^{12}$, and $R^{30}$ are as defined above for the compounds of Formula I;

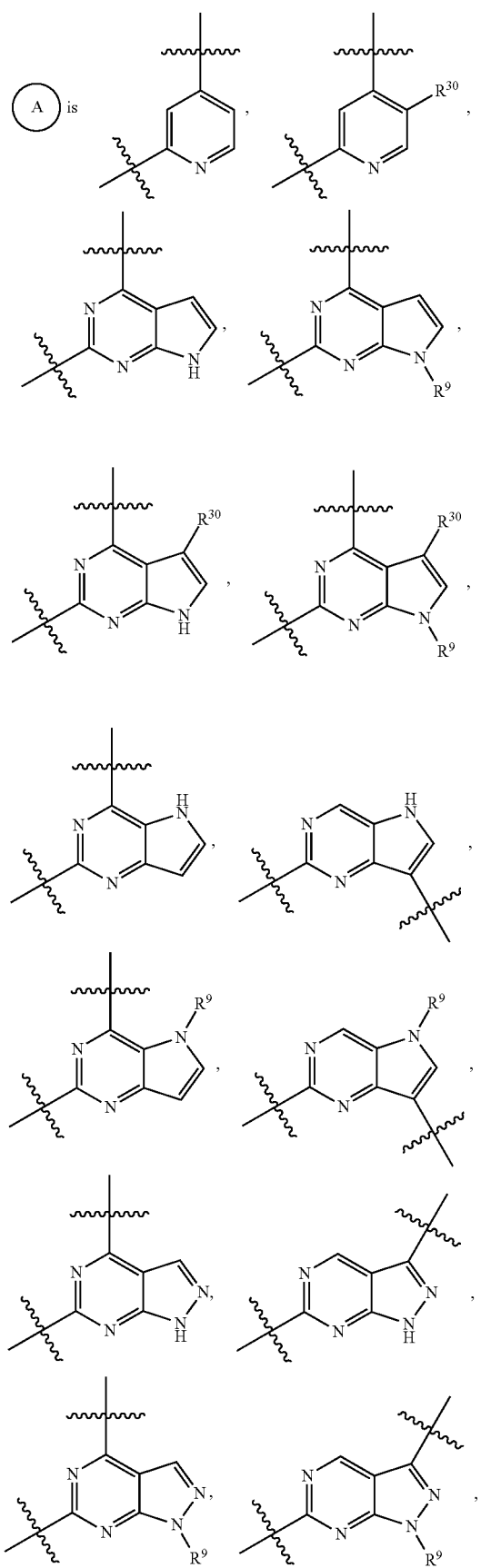
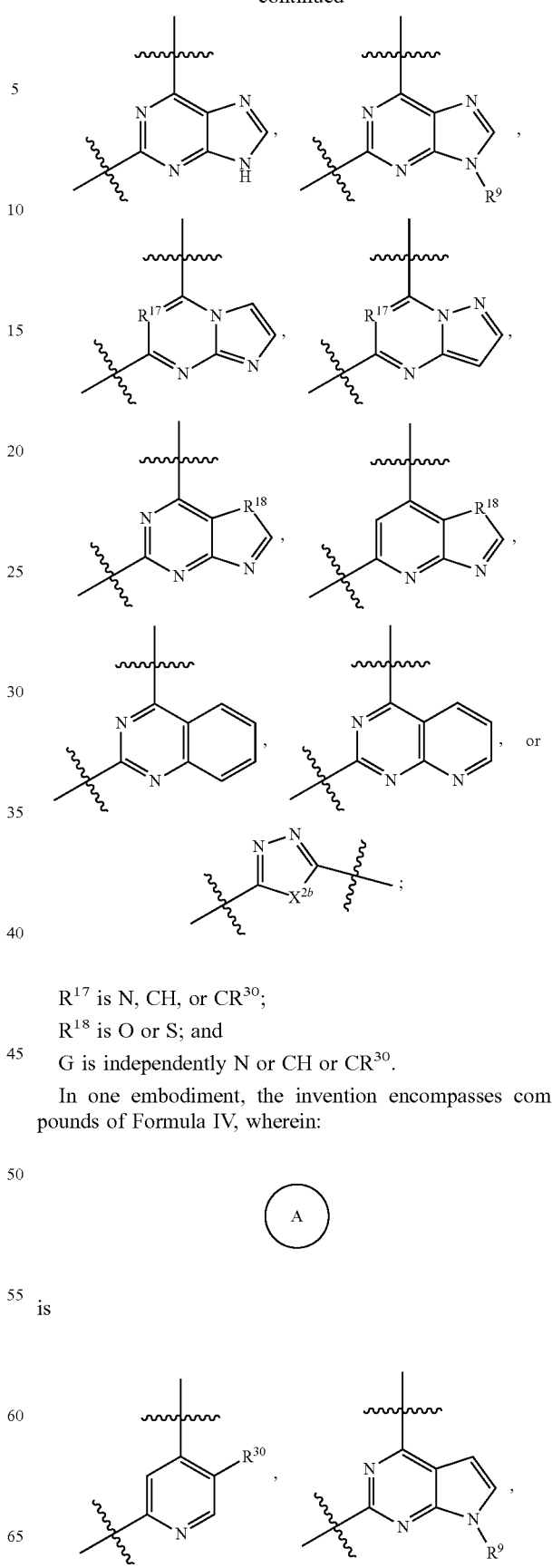
$R^{17}$ is N, CH, or $CR^{30}$;
$R^{18}$ is O or S; and
G is independently N or CH or $CR^{30}$.
In one embodiment, the invention encompasses compounds of Formula IV, wherein:

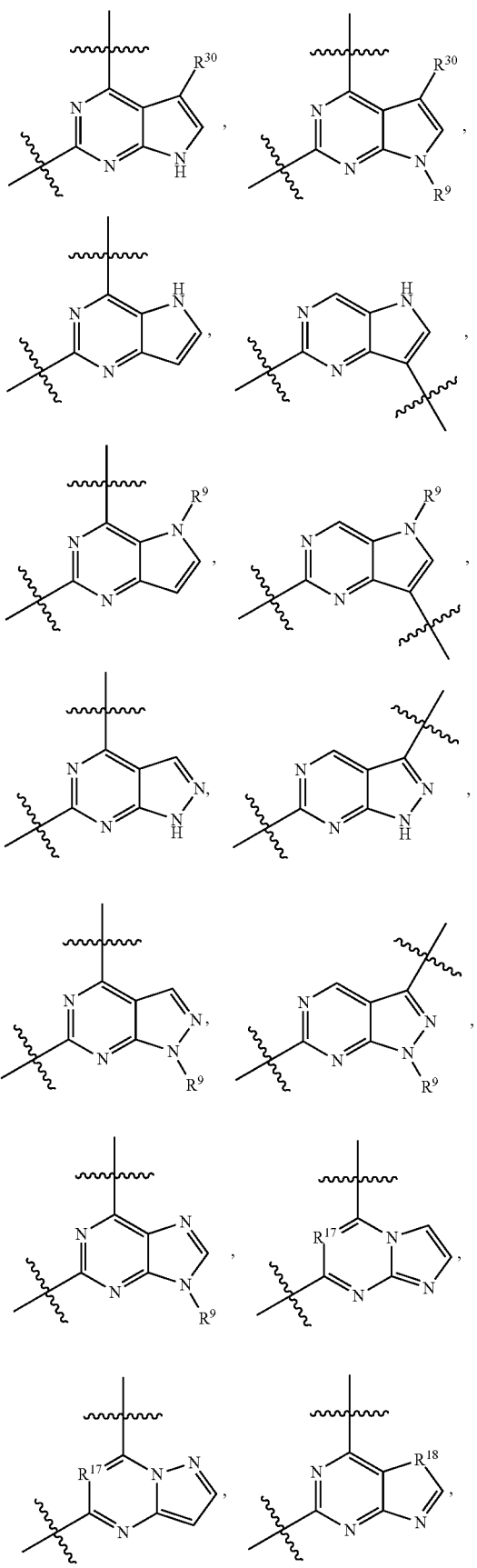
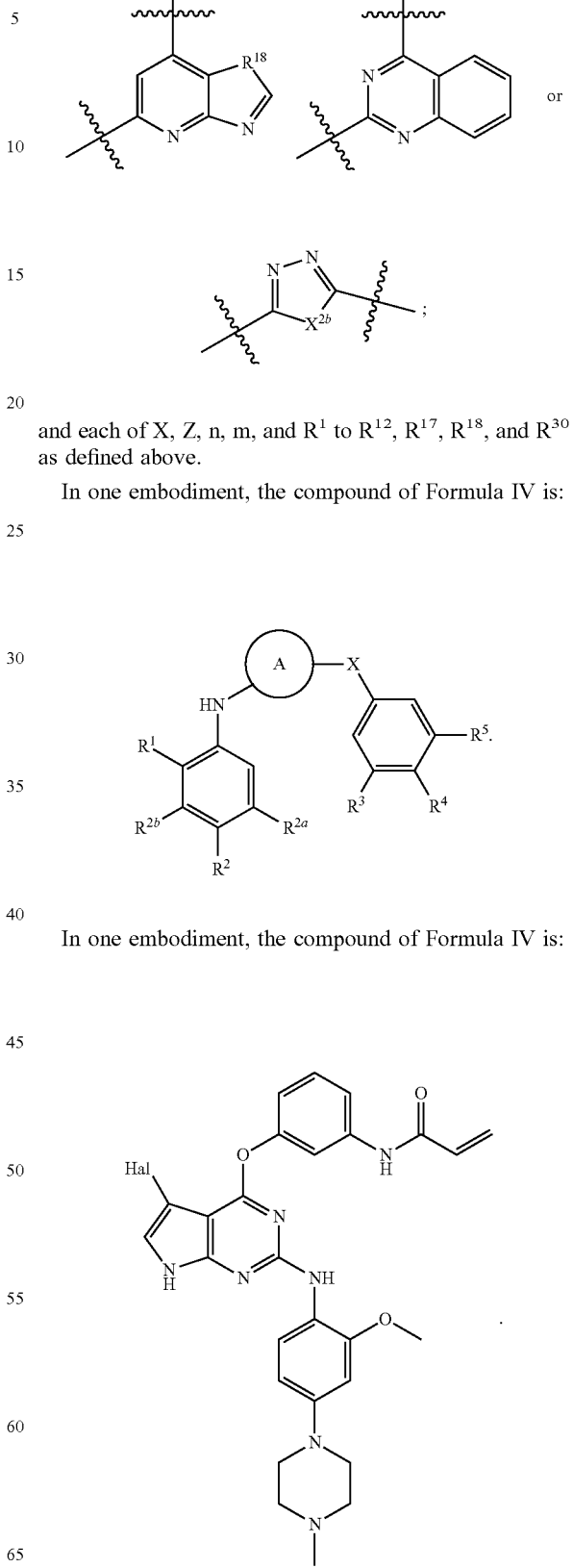
and each of X, Z, n, m, and $R^1$ to $R^{12}$, $R^{17}$, $R^{18}$, and $R^{30}$ is as defined above.
In one embodiment, the compound of Formula IV is:
In one embodiment, the compound of Formula IV is:

In one embodiment, the compound of Formula IV is:

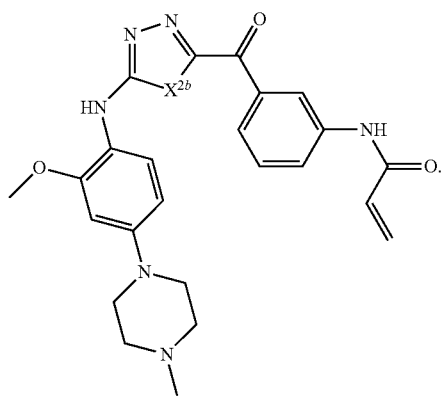

In one embodiment, the invention encompasses compounds of Formula IV, wherein: X is oxygen; $R^1$ is $C_1$-$C_6$ alkoxy; $R^2$ is piperidine that is substituted at the N position with $C_1$-$C_6$ alkyl or piperazine that is substituted at the N position with $C_1$-$C_6$ alkyl; $R^{2a}$ and $R^{2b}$ are hydrogen; one of $R^3$, $R^4$, and $R^5$ is Z, and the other two of $R^3$, $R^4$, and $R^5$ are hydrogen; $R^7$ is hydrogen or $C_1$-$C_6$ alkyl; $R^8$ is $C_2$-$C_6$ alkenyl; and Z is $-(CH_2)_n NR^7 C(O)R^8$.

In some embodiments, the compound of Formula IV is one of the following compounds or a pharmaceutically acceptable salt, ester, or prodrug thereof.

Compound IV-1

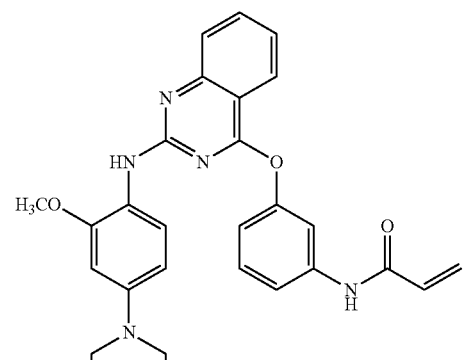

Compound IV-2

Compound IV-3

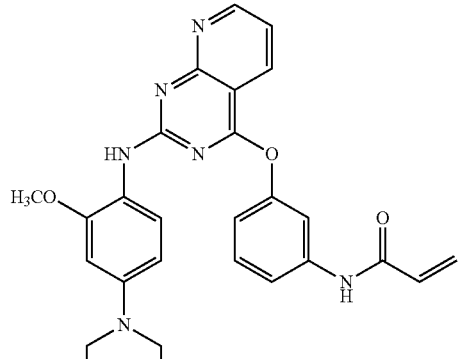

Compound IV-4

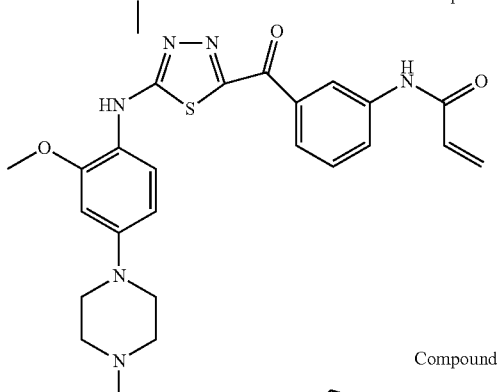

Compound IV-5

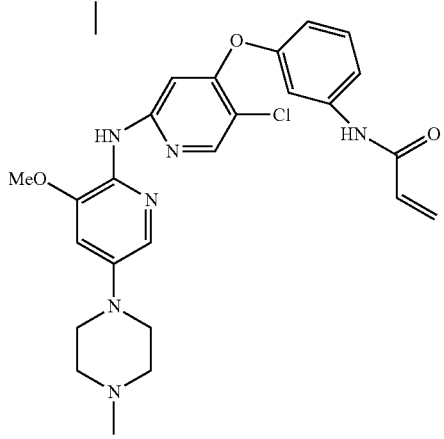

Compound IV-6

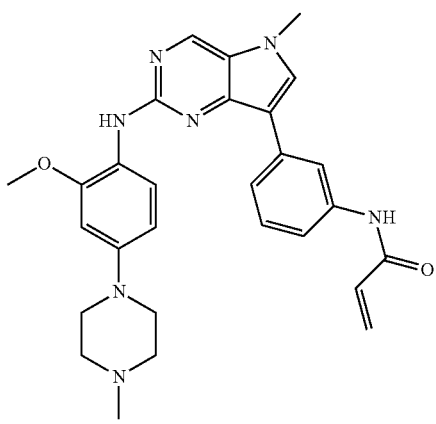

-continued

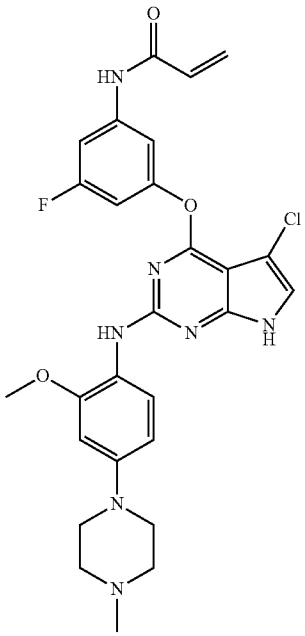

Compound IV-7

In one embodiment, the invention encompasses compounds of the following Formula IVa:

FORMULA IVa

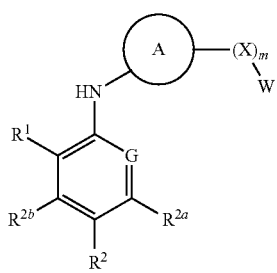

and pharmaceutically acceptable salts, esters, and prodrugs thereof, wherein:

W, X, Y, $R^1$, $R^2$, $R^{2a}$, $R^{2b}$, $R^6$, $R^9$, $R^{13}$, $R^{14}$, $R^{15}$, $R^{16}$, $R^{25}$, $R^{26}$, and p are as defined above for the compounds of Formula Ia; and

$R^{17}$, and $R^{18}$ are as defined above for the compounds of Formula IV.

In one embodiment, the compound of Formula IVa is:

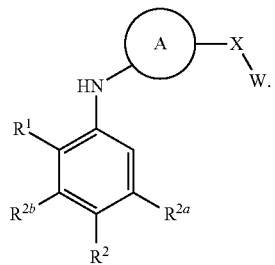

In another embodiment, the invention encompasses compounds of the following Formula IVb:

FORMULA IVb

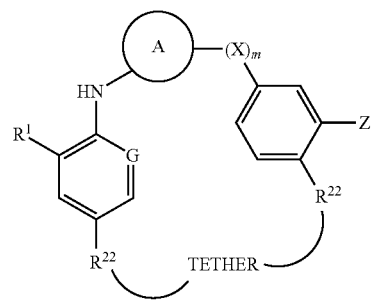

and pharmaceutically acceptable salts, esters, and prodrugs thereof, wherein:

X, Z, n, m, and $R^1$, $R^6$ to $R^{12}$, $R^{22}$, and TETHER are as defined above for the compounds of Formula Ib; and

$R^{17}$, and $R^{18}$ are as defined above for the compounds of Formula IV.

In one embodiment, the compound of Formula IVb is:

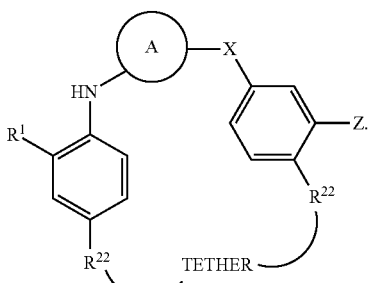

In one embodiment, the invention encompasses compounds of the following Formula V:

FORMULA V

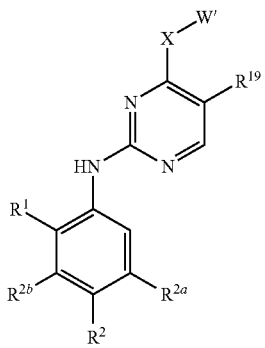

and pharmaceutically acceptable salts, esters, and prodrugs thereof, wherein:

X, $R^1$, $R^2$, $R^{2a}$, $R^{2b}$, and $R^6$ are as defined above for the compounds of Formula I;

$R^{14}$, $R^{15}$, $R^{16}$, $R^{25}$ and $R^{26}$ are as defined above for the compounds of Formula Ia;

W' is

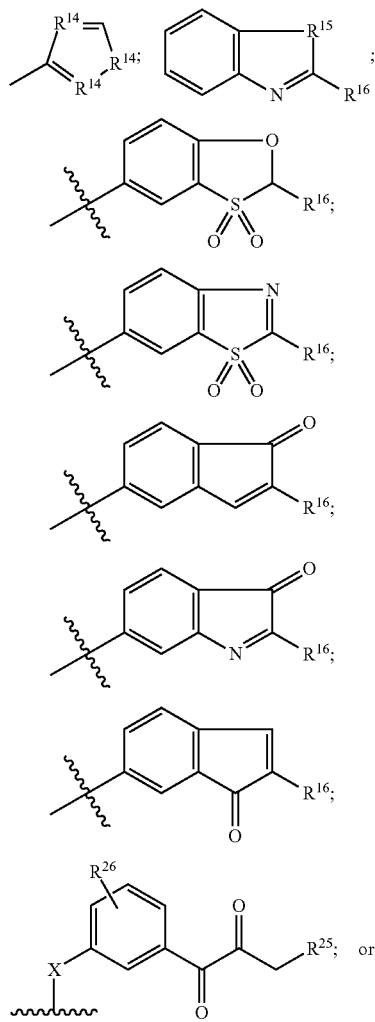

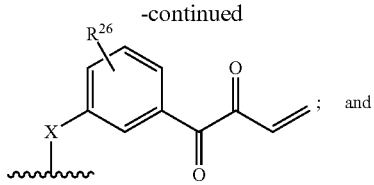

$R^{19}$ is hydrogen, halogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, OH, $NR^6{}_2$, CN, $N_3$, or $NO_2$.

In one embodiment, the invention encompasses compounds of Formula V, wherein: X is carbonyl; $R^1$ is $C_1$-$C_6$ alkoxy; $R^2$ is piperidine that is substituted at the N position with $C_1$-$C_6$ alkyl or piperazine that is substituted at the N position with $C_1$-$C_6$ alkyl; $R^{2a}$ and $R^{2b}$ are hydrogen; and $R^{19}$ is halogen.

In another embodiment, the compound of Formula V is one of the following compounds or a pharmaceutically acceptable salt, ester, or prodrug thereof:

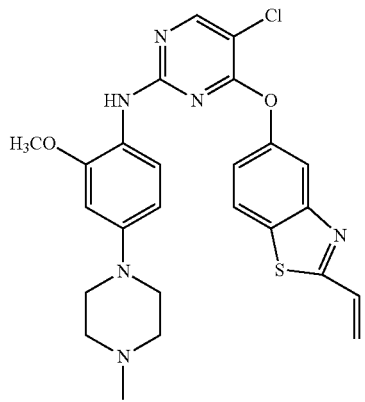

Compound V-1

In one embodiment, the invention encompasses compounds of the following Formula VI:

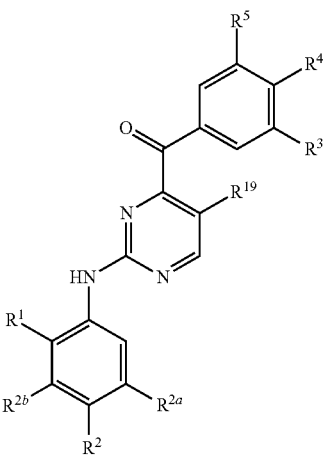

FORMULA VI and pharmaceutically acceptable salts, esters, and prodrugs thereof, wherein:

Z, n, m, and $R^1$ to $R^{12}$ are as defined above for the compounds of Formula I; and $R^{19}$ is as defined above for the compounds of Formula V.

In one embodiment, the invention encompasses compounds of Formula VI, wherein: $R^1$ is $C_1$-$C_6$ alkoxy; $R^2$ is piperidine that is substituted at the N position with $C_1$-$C_6$ alkyl or piperazine that is substituted at the N position with $C_1$-$C_6$ alkyl; $R^{2a}$ and $R^{2b}$ are hydrogen; $R^{19}$ is halogen; one of $R^3$, $R^4$, and $R^5$ is Z, and the other two of $R^3$, $R^4$, and $R^5$ are hydrogen; $R^7$ is hydrogen or $C_1$-$C_6$ alkyl; $R^8$ is $C_2$-$C_6$ alkenyl; and Z is —$(CH_2)_n NR^7C(O)R^8$.

In another embodiment, the compound of Formula V is one of the following compounds or a pharmaceutically acceptable salt, ester, or prodrug thereof:

Compound VI-1

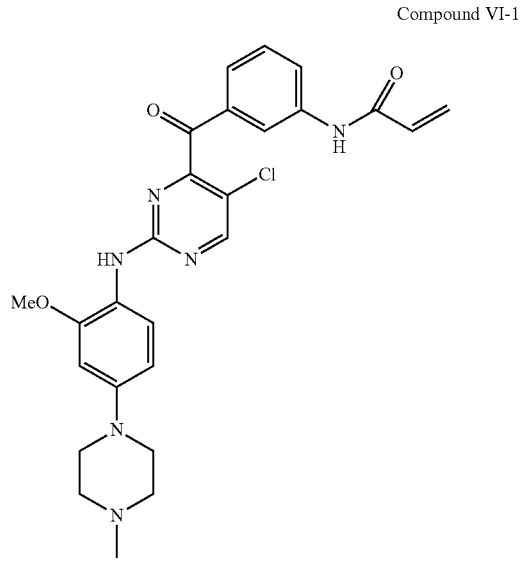 [SMILES: C=CC(=O)Nc1cccc(C(=O)c2nc(Nc3ccc(N4CCN(C)CC4)cc3OC)ncc2Cl)c1]

In one embodiment, the invention encompasses compounds of Formula VIa:

FORMULA VIa

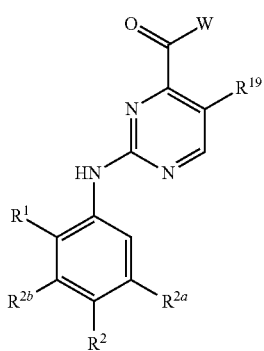

and pharmaceutically acceptable salts, esters, and prodrugs thereof, wherein:

W, X, Y, $R^1$, $R^2$, $R^{2a}$, $R^{2b}$, $R^3$, $R^4$, $R^5$, $R^6$, $R^{13}$, $R^{14}$, $R^{15}$, $R^{16}$, $R^{25}$, $R^{26}$, and p are as defined above for the compounds of Formula Ia; and $R^{19}$ is as defined above for the compounds of Formula V.

In another embodiment, the invention encompasses compounds of the following Formula VIb:

FORMULA VIb

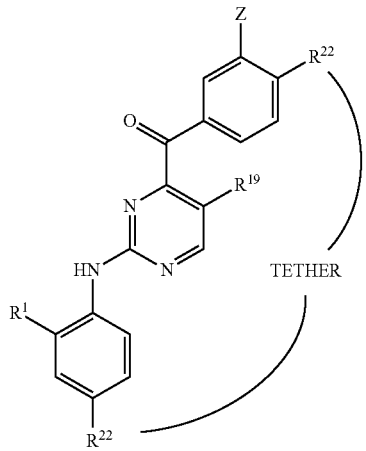

and pharmaceutically acceptable salts, esters, and prodrugs thereof, wherein:

X, Z, n, m, and $R^1$, $R^6$ to $R^{12}$, $R^{22}$, and TETHER are as defined above for the compounds of Formula Ib; and $R^{19}$ is as defined above for the compounds of Formula V.

In one embodiment, the invention encompasses compounds of the following Formula VII

FORMULA VII

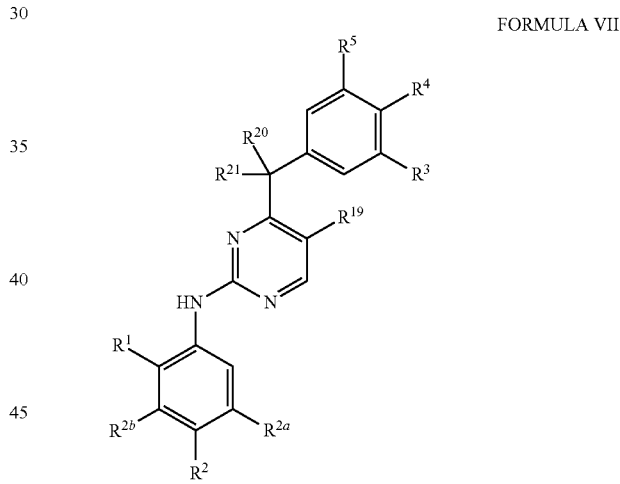

and pharmaceutically acceptable salts, esters, and prodrugs thereof, wherein:

Z, n, m, and $R^1$ to $R^{12}$ are as defined above for the compounds of Formula I;

$R^{19}$ is as defined above for the compounds of Formula V; and $R^{20}$ and $R^{21}$ are each independently hydrogen, halogen, $C_1$-$C_6$ alkyl, or $C_1$-$C_6$ haloalkyl, or $R^{20}$ and $R^{21}$ together form a $C_3$-$C_6$ cycloalkyl that is optionally substituted with halogen or $C_1$-$C_6$ alkyl, a $C_3$-$C_6$ cycloalkenyl that is optionally substituted with halogen or $C_1$-$C_6$ alkyl, or a $C_3$-$C_6$ heterocycle that is optionally substituted with halogen or $C_1$-$C_6$ alkyl.

In some embodiments, the invention encompasses compounds of Formula VII wherein: $R^1$ is $C_1$-$C_6$ alkoxy; $R^2$ is piperidine that is substituted at the N position with $C_1$-$C_6$ alkyl or piperazine that is substituted at the N position with $C_1$-$C_6$ alkyl; $R^{2a}$ and $R^{2b}$ are hydrogen; $R^{19}$ is halogen; one of $R^3$, $R^4$, and $R^5$ is Z, and the other two of $R^3$, $R^4$, and $R^5$ are hydrogen; $R^7$ is hydrogen or $C_1$-$C_6$ alkyl; $R^8$ is $C_2$-$C_6$ alkenyl; and Z is —$(CH_2)_nNR^7C(O)R^8$, and $R^{20}$ and $R^{21}$ together form a $C_3$-$C_6$ cycloalkyl or $C_3$-$C_6$ cycloalkenyl.

In another embodiment, the compound of Formula VII is one of the following compounds or a pharmaceutically acceptable salt, ester, or prodrug thereof:

Compound VII-1

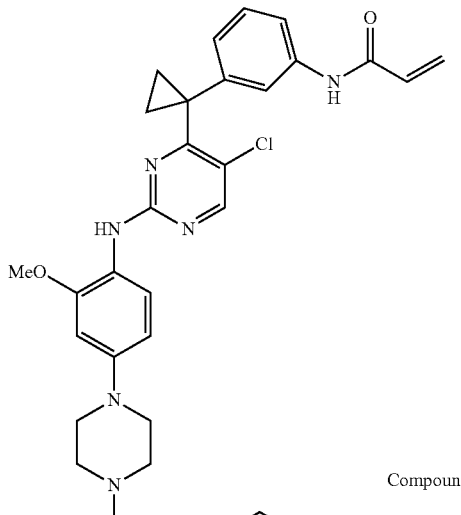

Compound VII-2

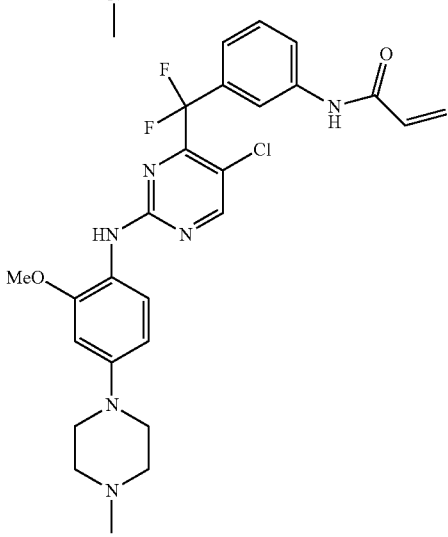

In one embodiment, the invention encompasses compounds of the following Formula VIIa FORMULA VIIa

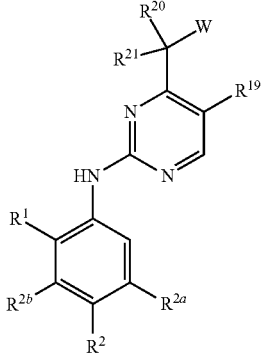

and pharmaceutically acceptable salts, esters, and prodrugs thereof, wherein:

W, X, Y, $R^1$, $R^2$, $R^{2a}$, $R^{2b}$, $R^3$, $R^4$, $R^5$, $R^6$, $R^{13}$, $R^{14}$, $R^{15}$, $R^{16}$, $R^{25}$, $R^{26}$, and p are as defined above for the compounds of Formula Ia;

$R^{19}$ is as defined above for the compounds of Formula V; and $R^{20}$ and $R^{21}$ are as defined above for the compounds of Formula VII.

In another embodiment, the invention encompasses compounds of the following Formula VIIb:

FORMULA VIIb

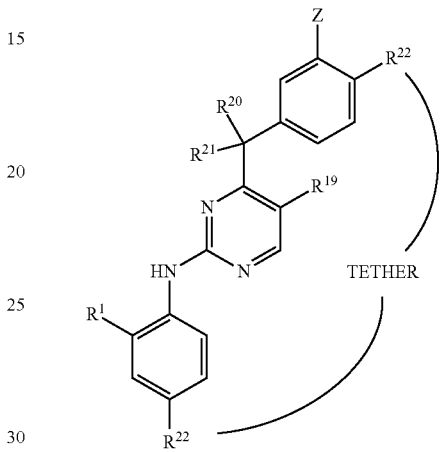

and pharmaceutically acceptable salts, esters, and prodrugs thereof, wherein:

X, Z, n, m, $R^1$, $R^6$ to $R^{12}$, $R^{22}$, and TETHER are as defined above for the compounds of Formula Ib;

$R^{19}$ is as defined above for the compounds of Formula V; and $R^{20}$ and $R^{21}$ are as defined above for the compounds of Formula VII.

In one embodiment, the invention encompasses thienopyrimidine compounds of the following Formula VIII

FORMULA VIII

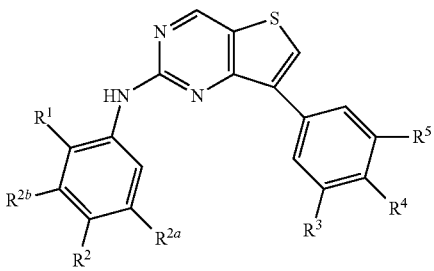

and pharmaceutically acceptable salts, esters, and prodrugs thereof, wherein Z, n, m, and $R^1$ to $R^{12}$ are as defined above for the compounds of Formula I.

In one embodiment, the invention encompasses compounds of Formula VIII, wherein: $R^1$ is $C_1$-$C_6$ alkoxy; $R^2$ is piperidine that is substituted at the N position with $C_1$-$C_6$ alkyl or piperazine that is substituted at the N position with $C_1$-$C_6$ alkyl; $R^{2a}$ and $R^{2b}$ are hydrogen; one of $R^3$, $R^4$, and $R^5$ is Z, and the other two of $R^3$, $R^4$, and $R^5$ are hydrogen; $R^7$ is hydrogen or $C_1$-$C_6$ alkyl; $R^8$ is $C_2$-$C_6$ alkenyl; and Z is —$(CH_2)_nNR^7C(O)R^8$.

In another embodiment, the compound of Formula VIII is one of the following compounds or a pharmaceutically acceptable salt, ester, or prodrug thereof:

Compound VIII-1

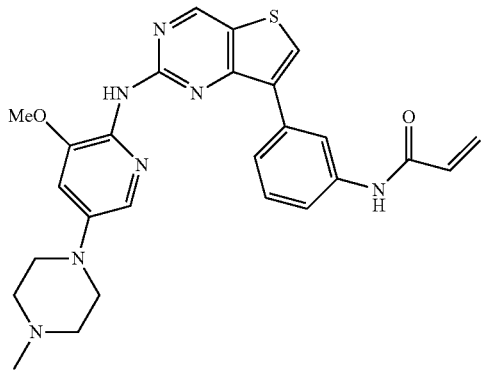

In another embodiment, the invention encompasses thienopyrimidine compounds of the following Formula VIIIa FORMULA VIIIa

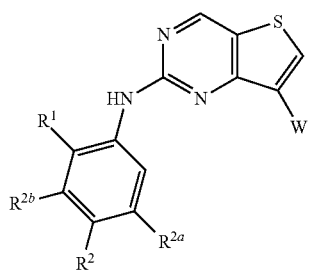

and pharmaceutically acceptable salts, esters, and prodrugs thereof, wherein W, X, Y, $R^1$, $R^2$, $R^{2a}$, $R^{2b}$, $R^6$, $R^{13}$, $R^{14}$, $R^{16}$, $R^{25}$, $R^{26}$, and p are as defined above for the compounds of Formula Ia.

In another embodiment, the invention encompasses thienopyrimidine compounds of the following Formula VIIIb FORMULA VIIIb

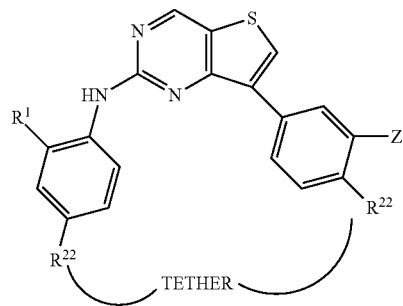

and pharmaceutically acceptable salts, esters, and prodrugs thereof, wherein X, Z, n, m, $R^1$, $R^6$ to $R^{12}$, $R^{22}$, and TETHER are as defined above for the compounds of Formula Ib.

In one embodiment, the invention encompasses thienopyridine compounds of the following Formula IX

FORMULA IX

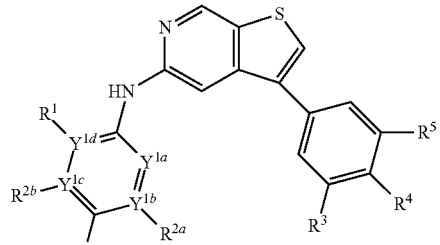

and pharmaceutically acceptable salts, esters, and prodrugs thereof, wherein:

Z, n, m, and $R^1$ to $R^{12}$ are as defined above for the compounds of Formula I; and each of $Y^{1a}$, $Y^{1b}$, $Y^{1c}$, and $Y^{1d}$ is independently carbon or nitrogen, wherein at least one of $Y^{1a}$, $Y^{1b}$, $Y^{1c}$, and $Y^{1d}$ is nitrogen.

In one embodiment, the invention encompasses compounds of Formula IX, wherein: $R^1$ is $C_1$-$C_6$ alkoxy; $R^2$ is piperidine that is substituted at the N position with $C_1$-$C_6$ alkyl or piperazine that is substituted at the N position with $C_1$-$C_6$ alkyl; $R^{2a}$ and $R^{2b}$ are hydrogen; one of $R^3$, $R^4$, and $R^5$ is Z, and the other two of $R^3$, $R^4$, and $R^5$ are hydrogen; $R^7$ is hydrogen or $C_1$-$C_6$ alkyl; $R^8$ is $C_2$-$C_6$ alkenyl; Z is —(CH$_2$)$_n$NR$^7$C(O)R$^8$; one of $Y^{1a}$ and $Y^{1d}$ is nitrogen; and $Y^{1b}$, $Y^{1c}$, and the other of $Y^{1a}$ and $Y^{1d}$ are carbon.

In another embodiment, the compound of Formula IX is one of the following compounds or a pharmaceutically acceptable salt, ester, or prodrug thereof:

Compound IX-1

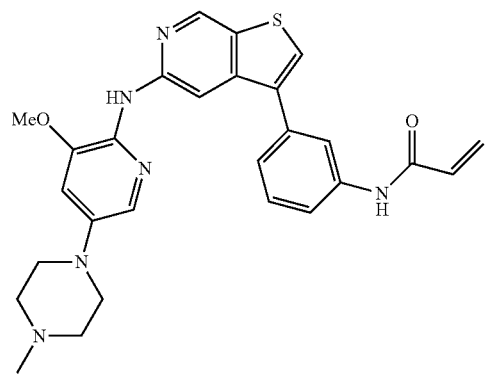

In another embodiment, the invention encompasses thienopyridine compounds of the following Formula IXa FORMULA IXa

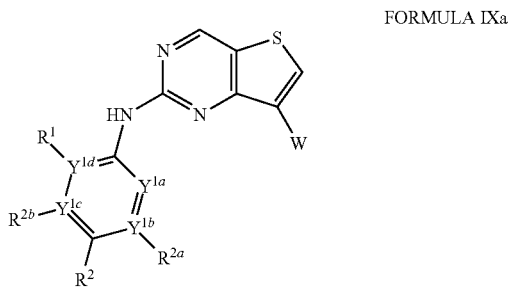

and pharmaceutically acceptable salts, esters, and prodrugs thereof, wherein:

W, X, Y, $R^1$, $R^2$, $R^{2a}$, $R^{2b}$, $R^6$, $R^{13}$, $R^{14}$, $R^{15}$, $R^{16}$, $R^{25}$, $R^{26}$, and p are as defined above for the compounds of Formula Ia; and each of $Y^{1a}$, $Y^{1b}$, $Y^{1c}$, and $Y^{1d}$ is independently carbon or nitrogen, wherein at least one of $Y^{1a}$, $Y^{1b}$, $Y^{1c}$, and $Y^{1d}$ is nitrogen.

In another embodiment, the invention encompasses thienopyridine compounds of the following Formula IXb

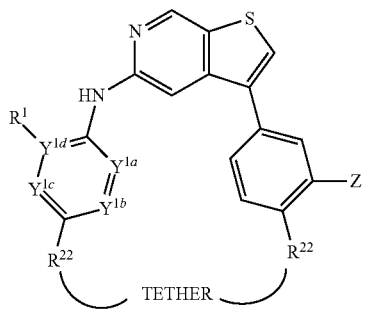

FORMULA IXb and pharmaceutically acceptable salts, esters, and prodrugs thereof, wherein:

X, Z, n, m, $R^1$, $R^6$ to $R^{12}$, $R^{22}$, and TETHER are as defined above for the compounds of Formula Ib; and each of $Y^{1a}$, $Y^{1b}$, $Y^{1c}$, and $Y^{1d}$ is independently carbon or nitrogen, wherein at least one of $Y^{1a}$, $Y^{1b}$, $Y^{1c}$, and $Y^{1d}$ is nitrogen.

In another embodiment, the invention encompasses compounds of the following Formula Xb

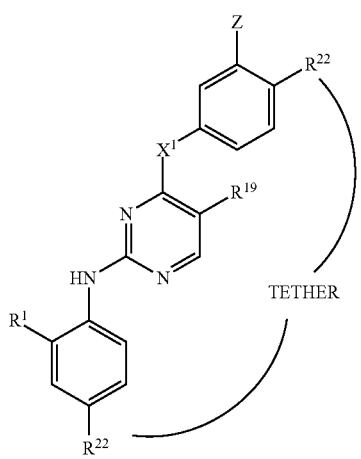

FORMULA Xb and pharmaceutically acceptable salts, esters, and prodrugs thereof, wherein:

Z, n, m, $R^1$, $R^6$ to $R^{12}$, $R^{22}$, and TETHER are as defined above for the compounds of Formula Ib; and $X^1$ is oxygen, sulfur, or —$NR^6$.

In one embodiment, the invention encompasses compounds of Formula Xb, wherein: $R^1$ is $C_1$-$C_6$ alkoxy; $R^7$ is hydrogen or $C_1$-$C_6$ alkyl; $R^8$ is $C_2$-$C_6$ alkenyl; Z is —$(CH_2)_nNR^7C(O)R^8$; and the $R^{22}$-TETHER-R22 moiety is —(CO)—NH—($C_2$-$C_4$ alkyl)-NH—(CO)—. In another embodiment, the compound of Formula Xb is:

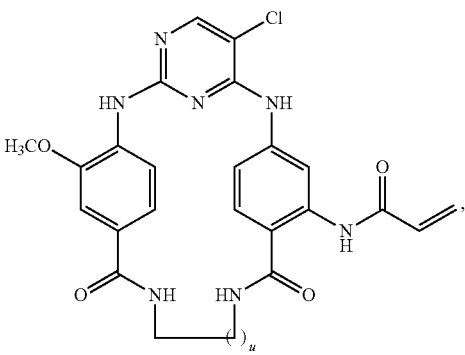

where u is 1, 2, or 3.

In one embodiment, the invention encompasses compounds of the following Formula XI:

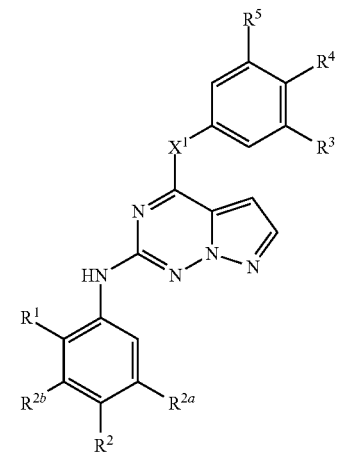

FORMULA XI and pharmaceutically acceptable salts, esters, and prodrugs thereof, wherein:

$R^1$, $R^2$, $R^{2a}$, and $R^{2b}$, $R^3$ to $R^{12}$, Z, n, and m are as defined above for the compounds of Formula I; and $X^1$ is oxygen, sulfur, or —$NR^6$.

In one embodiment, the invention encompasses compounds of Formula XI, wherein: $X^1$ is oxygen, sulfur, or —NH; $R^2$ is piperidine that is substituted at the N position with $C_1$-$C_6$ alkyl or piperazine that is substituted at the N position with $C_1$-$C_6$ alkyl; $R^{2a}$ and $R^{2b}$ are hydrogen or $C_1$-$C_6$ alkyl; one of $R^3$, $R^4$, and $R^5$ is Z, and the other two of $R^3$, $R^4$, and $R^5$ are hydrogen; $R^7$ is hydrogen or $C_1$-$C_6$ alkyl; $R^8$ is $C_2$-$C_6$ alkenyl; and Z is —$(CH_2)_nNR^7C(O)R^8$.

In another embodiment, the compound of Formula XI is one of the following compounds or a pharmaceutically acceptable salt, ester, or prodrug thereof:

Compound XI-1
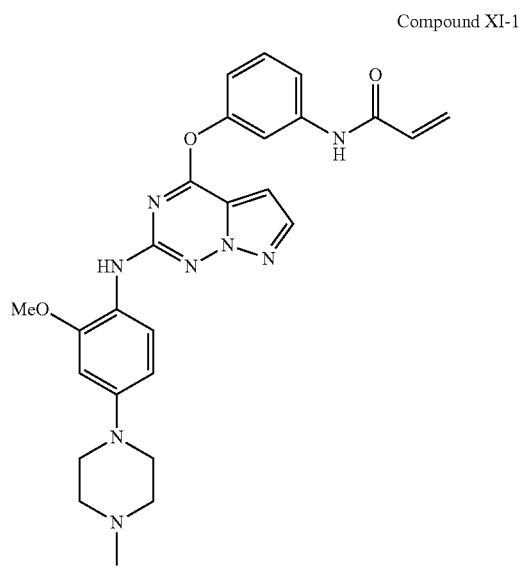
Compound XI-4
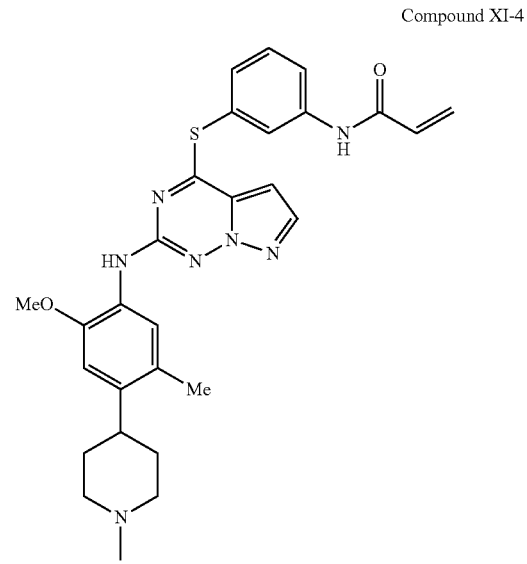
Compound XI-2
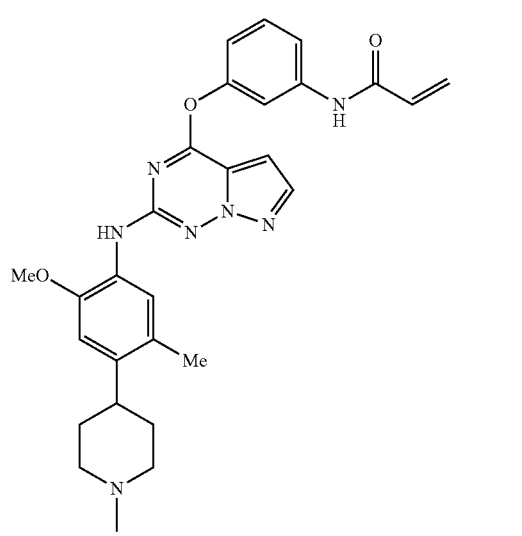
Compound XI-5
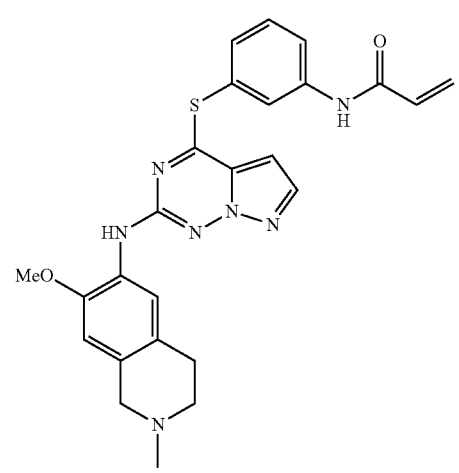
Compound XI-3
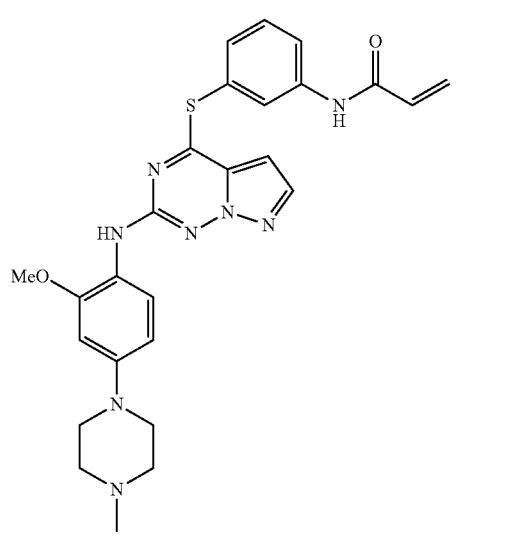
Compound XI-6
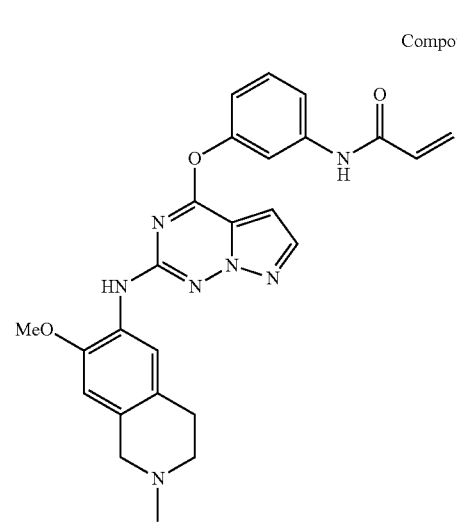

In another embodiment, the invention encompasses compounds of the following Formula XIa:

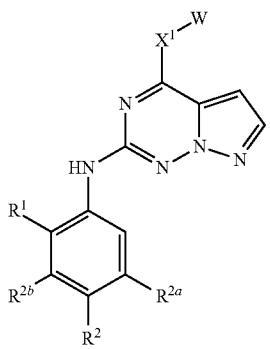

FORMULA XIa and pharmaceutically acceptable salts, esters, and prodrugs thereof, wherein:

W, $R^1$, $R^2$, $R^{2a}$, and $R^{2b}$, $R^6$, $R^{13}$, $R^{14}$, $R^{15}$, $R^{16}$, $R^{25}$, $R^{26}$, and p are as defined above for the compounds of Formula Ia; and $X^1$ is oxygen, sulfur, or —$NR^6$.

In another embodiment, the invention encompasses compounds of the following Formula XIb:

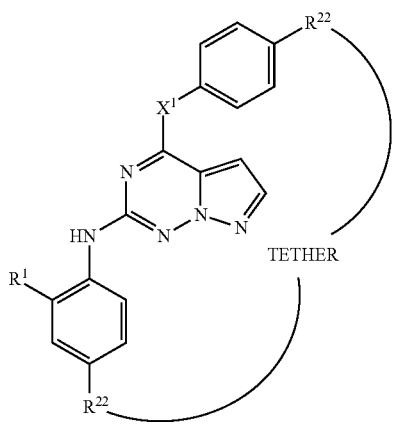

FORMULA XIb and pharmaceutically acceptable salts, esters, and prodrugs thereof, wherein:

Z, n, m, and $R^1$ and $R^6$ to $R^{12}$, $R^{22}$, and TETHER are as defined above for the compounds of Formula Ib; and $X^1$ is oxygen, sulfur, or —$NR^6$.

In one embodiment, the invention encompasses compounds of the following Formula XII:

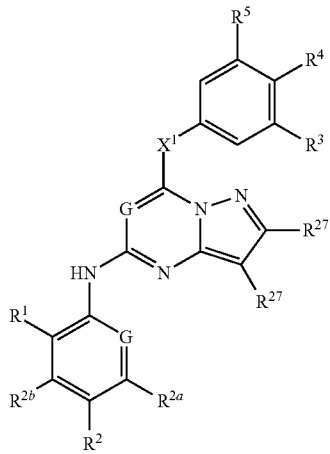

FORMULA XII and pharmaceutically acceptable salts, esters, and prodrugs thereof, wherein:

$R^1$, $R^2$, $R^{2a}$, and $R^{2b}$, $R^3$ to $R^{12}$, $R^{30}$, Z, n, and m are as defined above for the compounds of Formula I;

$X^1$ is oxygen, sulfur, or —$NR^6$;

each G is independently N or CH or $CR^{30}$; and each $R^{27}$ is independently hydrogen, halogen, $C_1$-$C_3$ alkyl, or $C_1$-$C_3$ alkoxy.

In one embodiment of the compound of Formula XII, at least one G is N.

In one embodiment, the invention encompasses compounds of Formula XII, wherein: $X^1$ is oxygen, sulfur, or —NH; $R^2$ is piperidine that is substituted at the N position with $C_1$-$C_6$ alkyl or piperazine that is substituted at the N position with $C_1$-$C_6$ alkyl; $R^{2a}$ and $R^{2b}$ are hydrogen or $C_1$-$C_6$ alkyl; one of $R^3$, $R^4$, and $R^5$ is Z, and the other two of $R^3$, $R^4$, and $R^5$ are hydrogen; $R^7$ is hydrogen or $C_1$-$C_6$ alkyl; $R^8$ is $C_2$-$C_6$ alkenyl; and Z is —$(CH_2)_n NR^7 C(O)R^8$.

In another embodiment, the compound of Formula XII is one of the following compounds or a pharmaceutically acceptable salt, ester, or prodrug thereof:

Compound XII-1

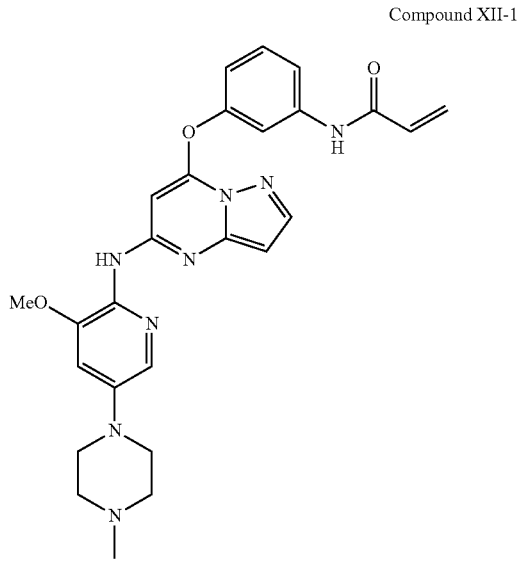

Compound XII-2
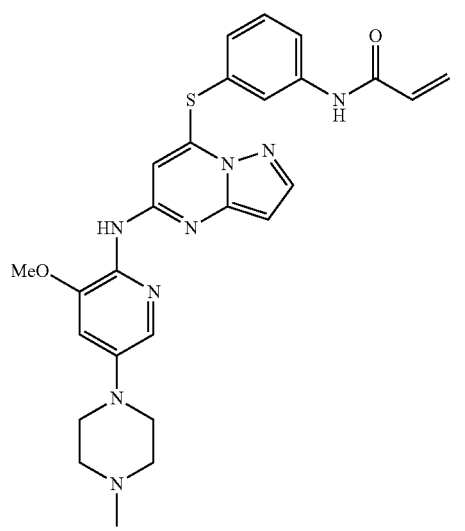
Compound XII-5
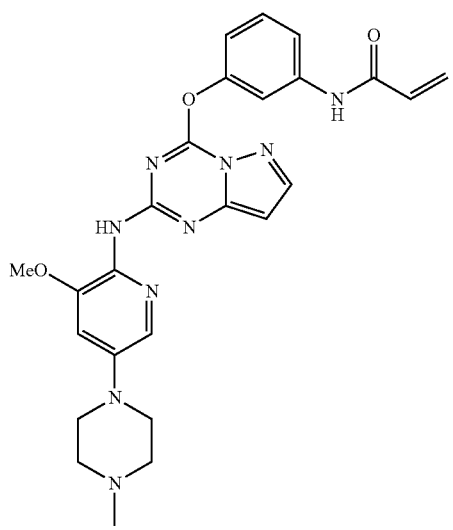
Compound XII-3
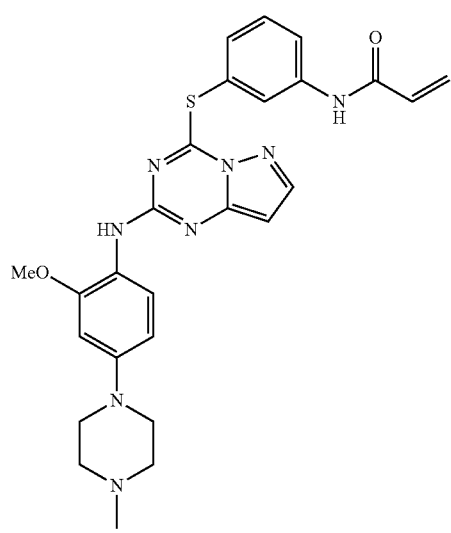
Compound XII-6
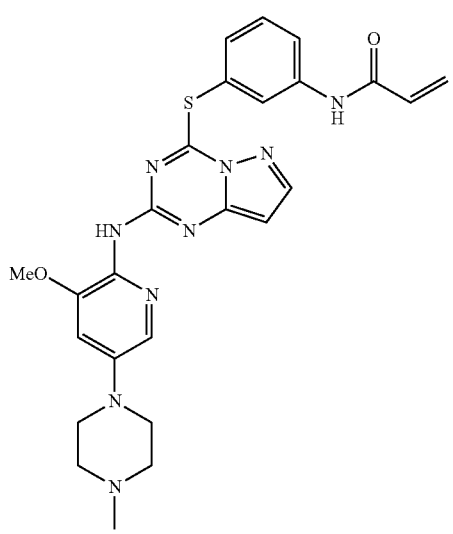
Compound XII-4
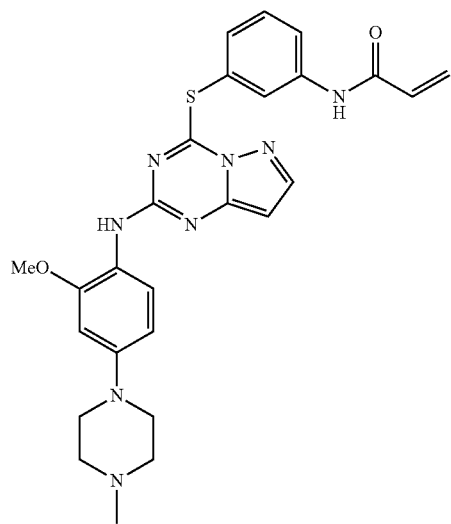
Compound XII-7

Compound XII-8
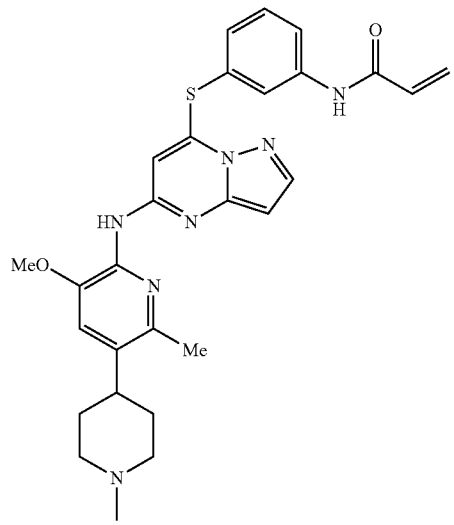
Compound XII-9
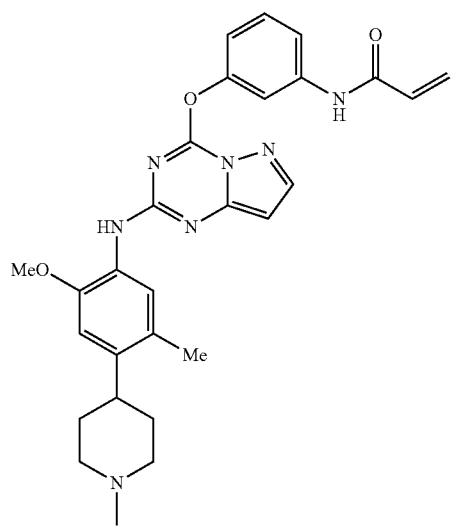
Compound XII-10
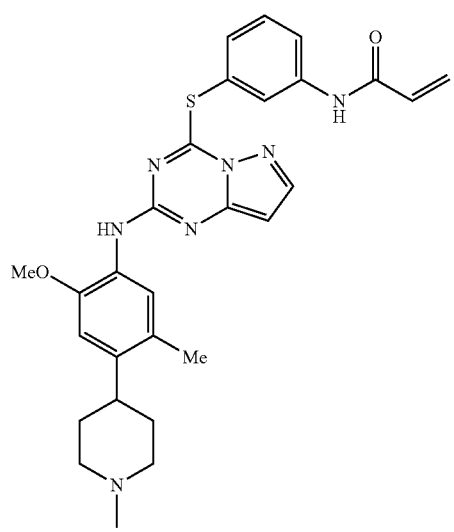
Compound XII-11
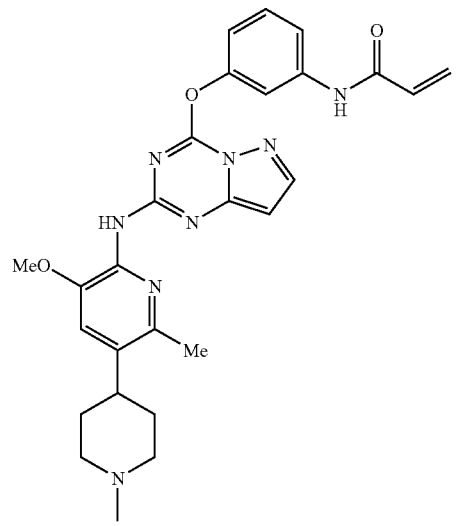
Compound XII-12
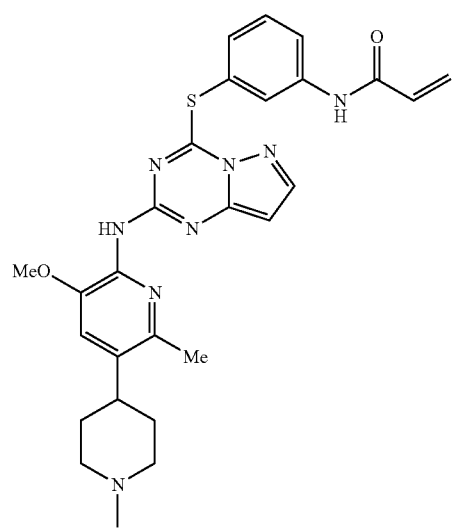
Compound XII-13
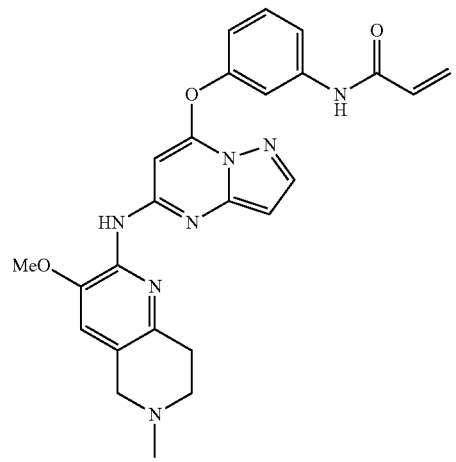

-continued

Compound XII-14
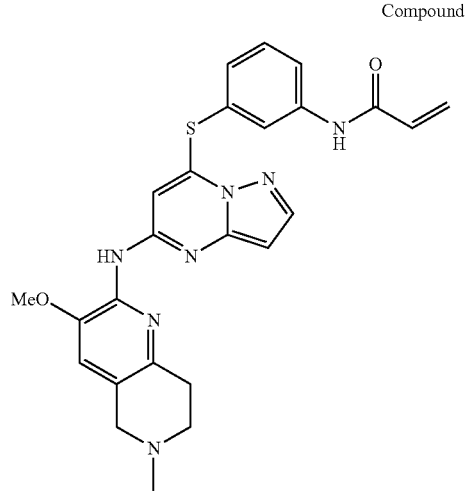

Compound XII-15
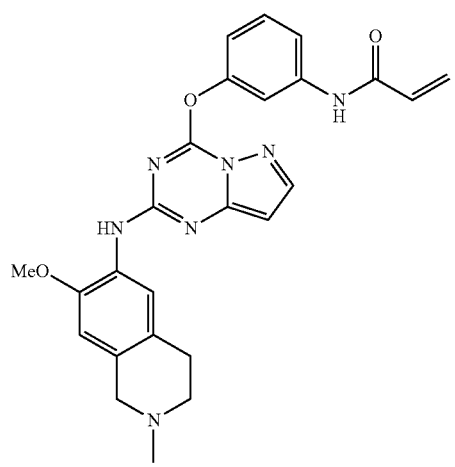

Compound XII-16
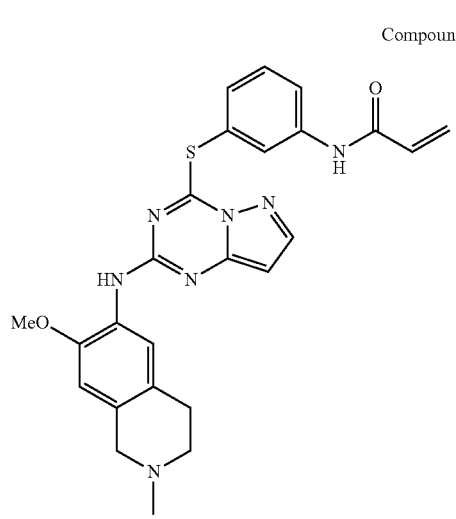

-continued

Compound XII-17
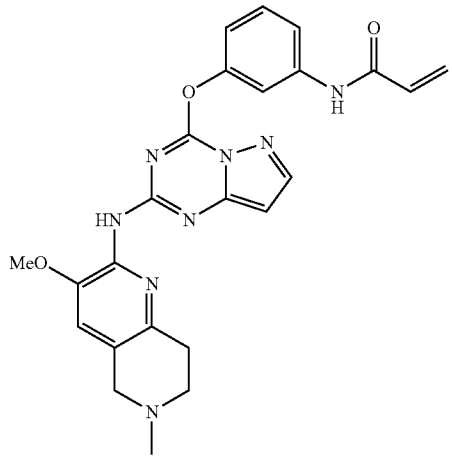

Compound XII-18
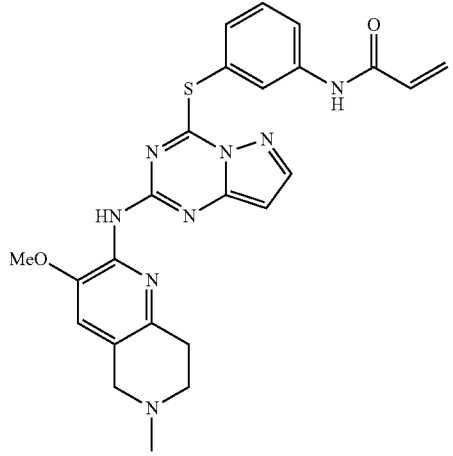

In another embodiment, the invention encompasses compounds of the following Formula XIIa:

FORMULA XIIa
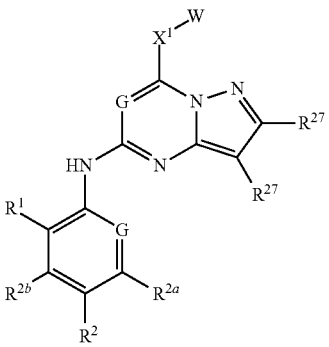

and pharmaceutically acceptable salts, esters, and prodrugs thereof, wherein:

W, $R^1$, $R^2$, $R^{2a}$, and $R^{2b}$, $R^6$, $R^{13}$, $R^{14}$, $R^{15}$, $R^{16}$, $R^{25}$, $R^{26}$, $R^{30}$, and p are as defined above for the compounds of Formula Ia;

$X^1$ is oxygen, sulfur, or —$NR^6$;

each G is independently N or CH or $CR^{30}$; and each $R^{27}$ is independently hydrogen, halogen, $C_1$-$C_3$ alkyl, or $C_1$-$C_3$ alkoxy.

In another embodiment, the invention encompasses compounds of the following Formula XIIb:

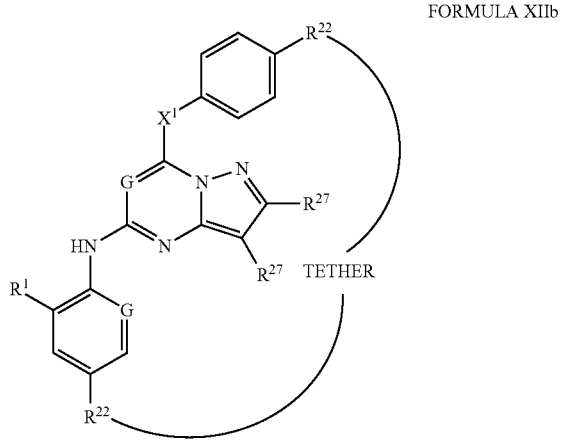

FORMULA XIIb and pharmaceutically acceptable salts, esters, and prodrugs thereof, wherein:

Z, n, m, and $R^1$ and $R^6$ to $R^{12}$, $R^{22}$, $R^{30}$, and TETHER are as defined above for the compounds of Formula Ib;

$X^1$ is oxygen, sulfur, or —$NR^6$;

each G is independently N or CH or $CR^{30}$; and each $R^{27}$ is independently hydrogen, halogen, $C_1$-$C_3$ alkyl, or $C_1$-$C_3$ alkoxy.

In one embodiment, the invention encompasses an isotopically labeled compound of Formula I, Ia, Ib, II, IIa, IIb, III, IIa, IIIb, IV, IVa, IVb, V, VI, VIa, VIb, VI, VIa, VIb, VIII, VIIIa, VIIIb, IX, IXa, IXb, Xb, XI, XIa, XIb, XII, XIIa, or XIIb. Such compounds have one or more isotope atoms which may or may not be radioactive (e.g., $^3$H, $^2$H, $^{14}$C, $^{13}$C, $^{35}$S, $^{32}$P, $^{125}$I and $^{131}$I) introduced into the compound. Such compounds are useful for drug metabolism studies and diagnostics, as well as therapeutic applications.

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamoylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Hydrates of compounds of the present invention can be conveniently prepared by recrystallization from an aqueous/organic solvent mixture, using organic solvents such as dioxin, tetrahydrofuran or methanol.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present invention. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present invention. All crystal forms of the compounds described herein are expressly included in the present invention.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

III. Synthesis of the Compounds of the Invention

Compounds of Formula I, where X is oxygen or sulfur and Y is halogen, can be synthesized, for example, by the procedure set forth in the following Scheme 1.

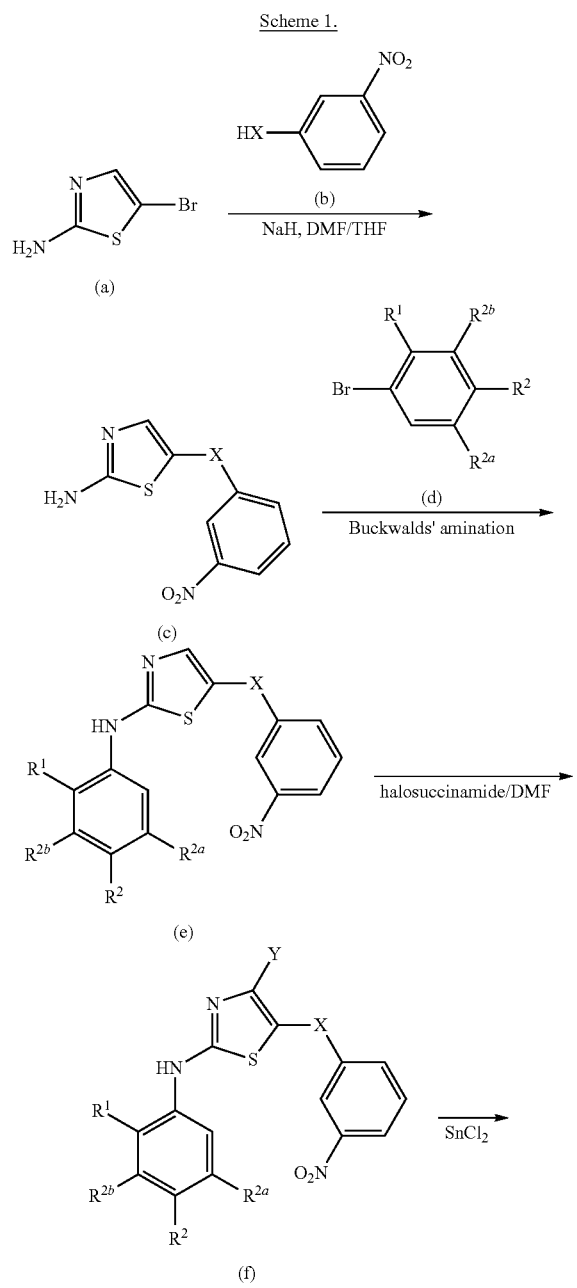

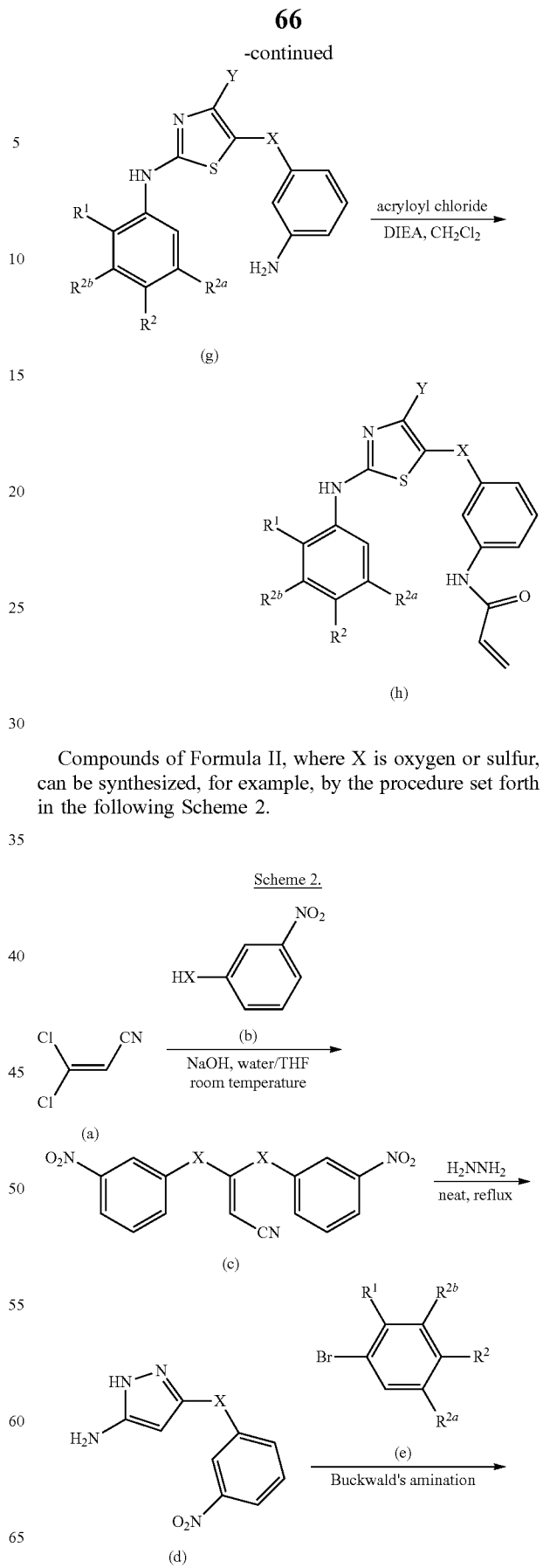

Compounds of Formula II, where X is oxygen or sulfur, can be synthesized, for example, by the procedure set forth in the following Scheme 2.

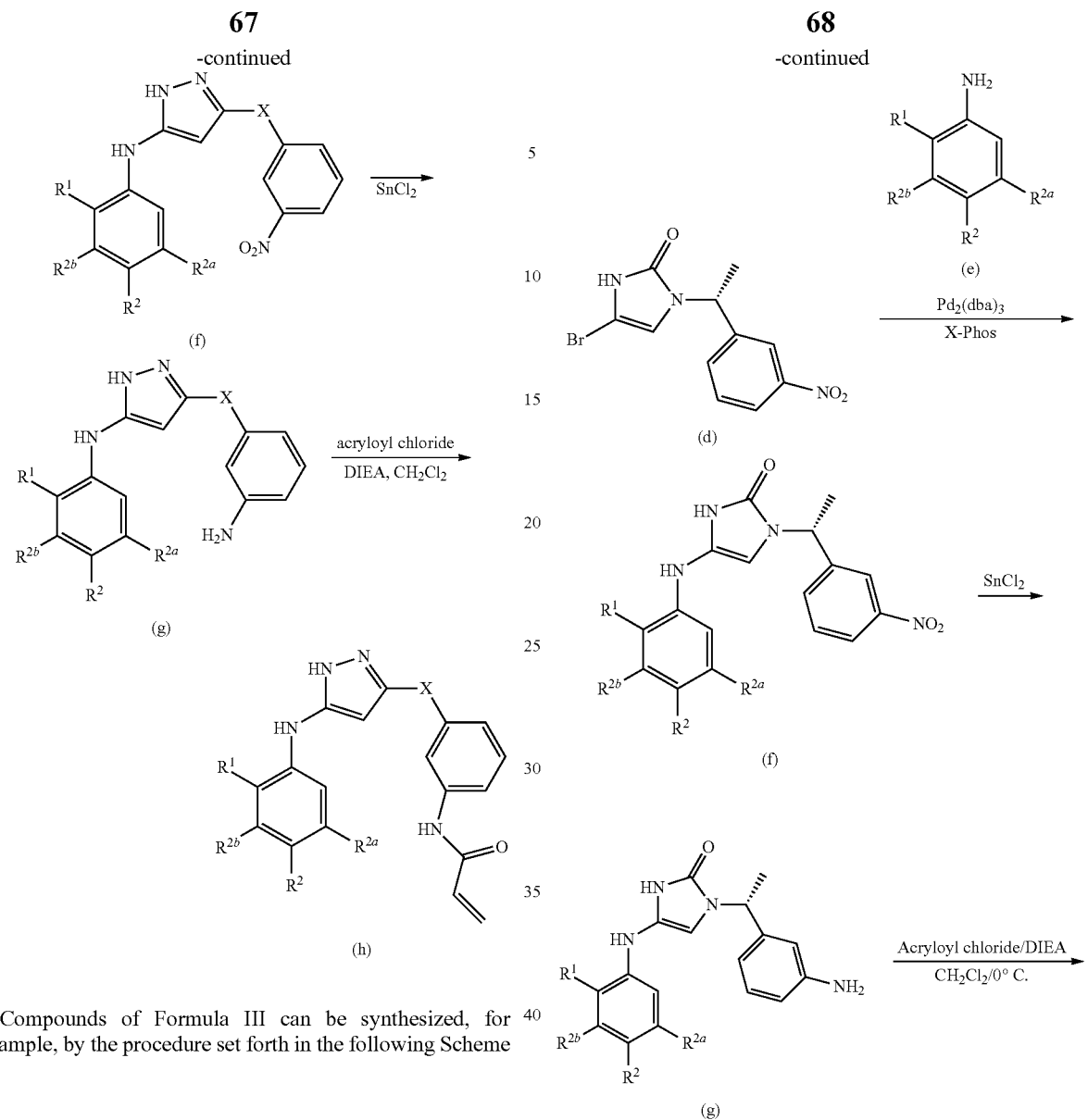
Compounds of Formula III can be synthesized, for example, by the procedure set forth in the following Scheme 3.
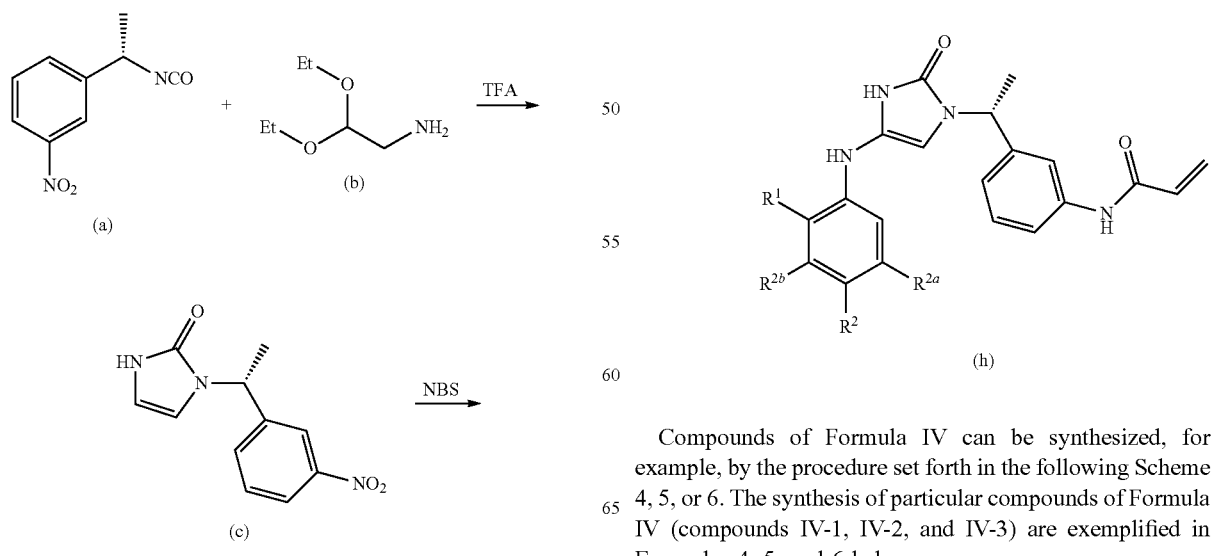
Compounds of Formula IV can be synthesized, for example, by the procedure set forth in the following Scheme 4, 5, or 6. The synthesis of particular compounds of Formula IV (compounds IV-1, IV-2, and IV-3) are exemplified in Examples 4, 5, and 6 below.

Scheme 4.
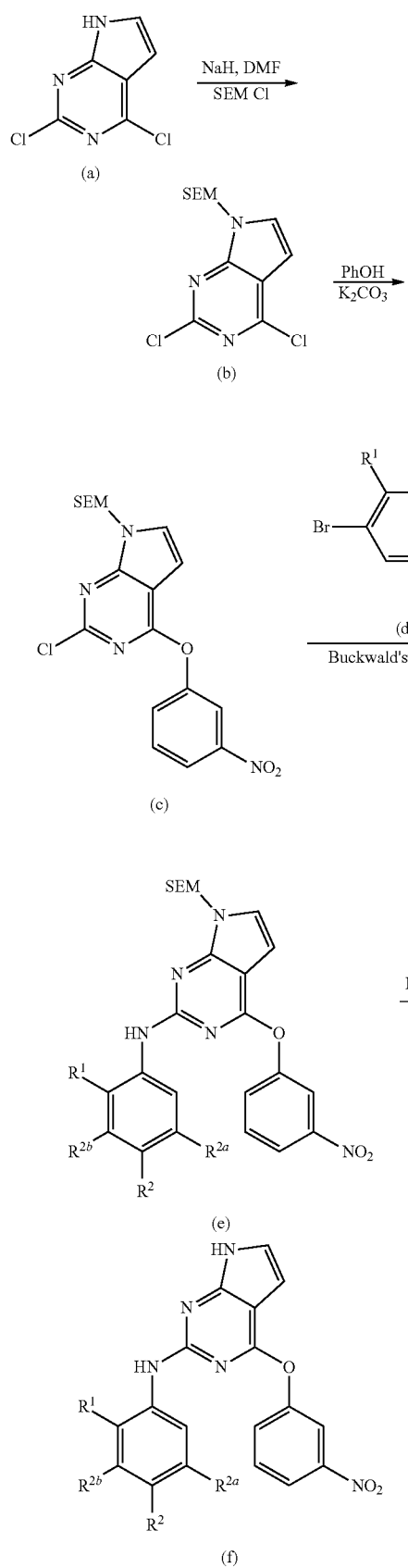
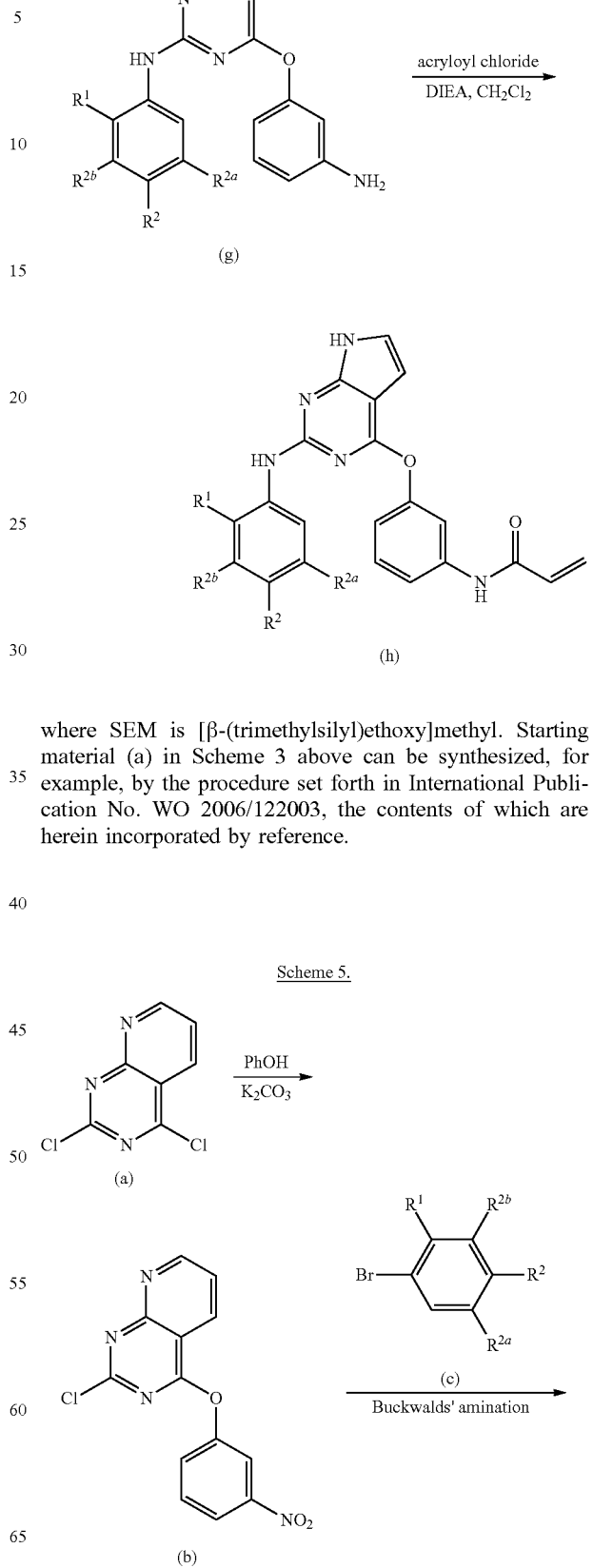
where SEM is [β-(trimethylsilyl)ethoxy]methyl. Starting material (a) in Scheme 3 above can be synthesized, for example, by the procedure set forth in International Publication No. WO 2006/122003, the contents of which are herein incorporated by reference.

71
-continued
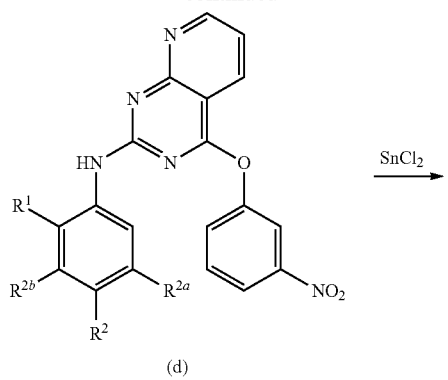
(d)
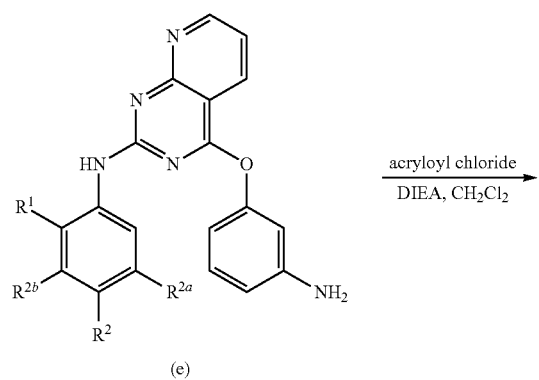
(e)
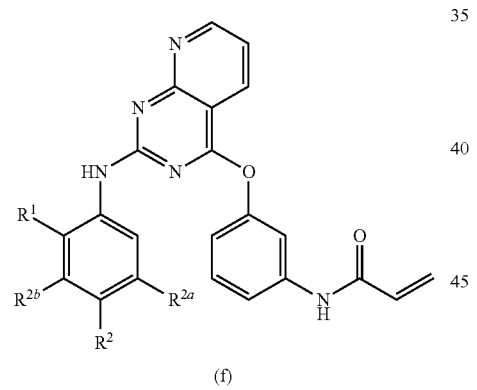
(f)
Starting material (a) in Scheme 4 above can be synthesized, for example, by the procedure set forth in International Publication No. WO 2006/090167, the contents of which are herein incorporated by reference.
Scheme 6.
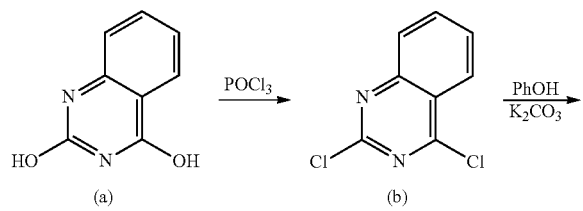
72
-continued
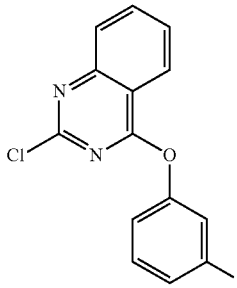 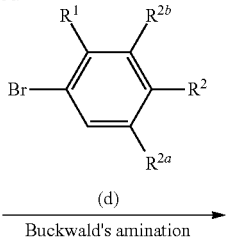
(c)
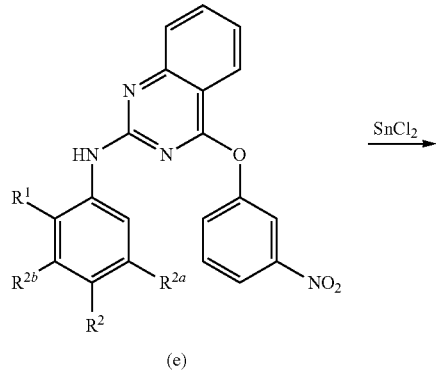
(e)
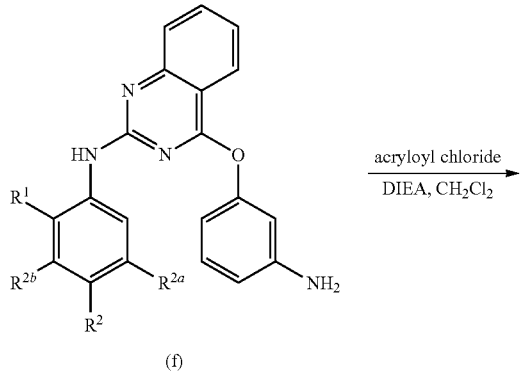
(f)
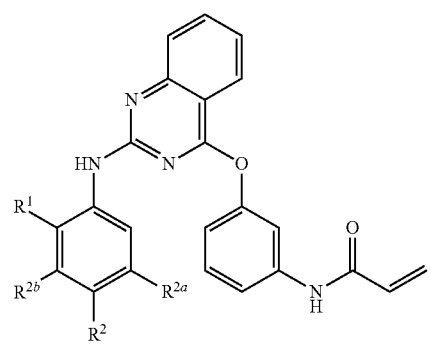
(g)
Compounds of Formula V can be synthesized, for example by the procedure set forth in the following Scheme 7 or 8.

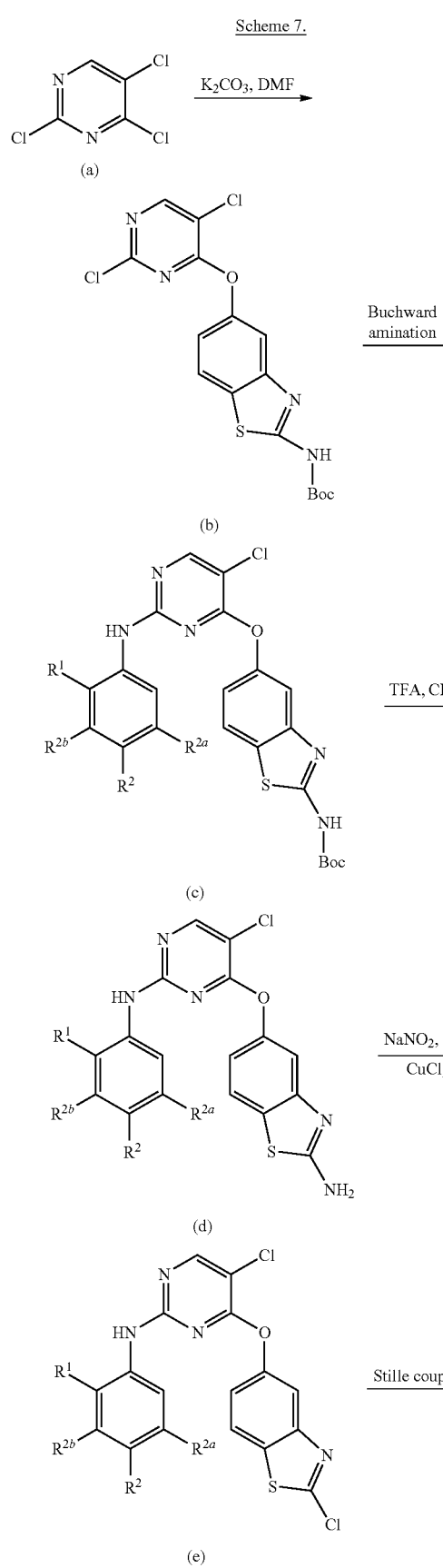
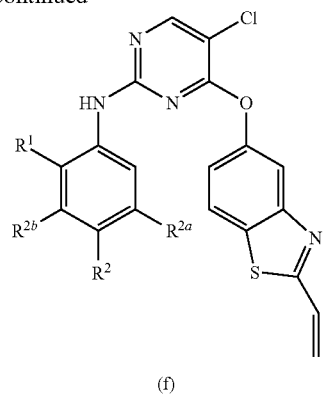
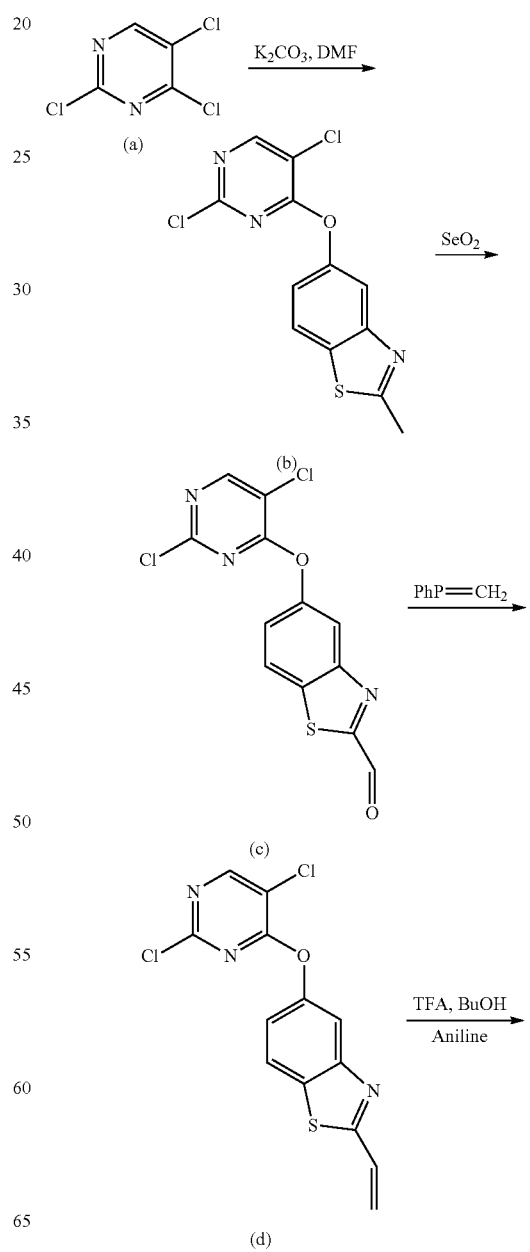

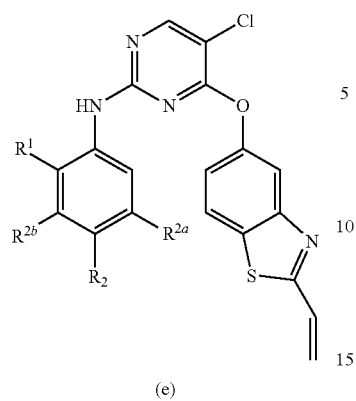
(e)
Compounds of Formula VI can be synthesized, for example, by the procedure set forth in the following Scheme 9.
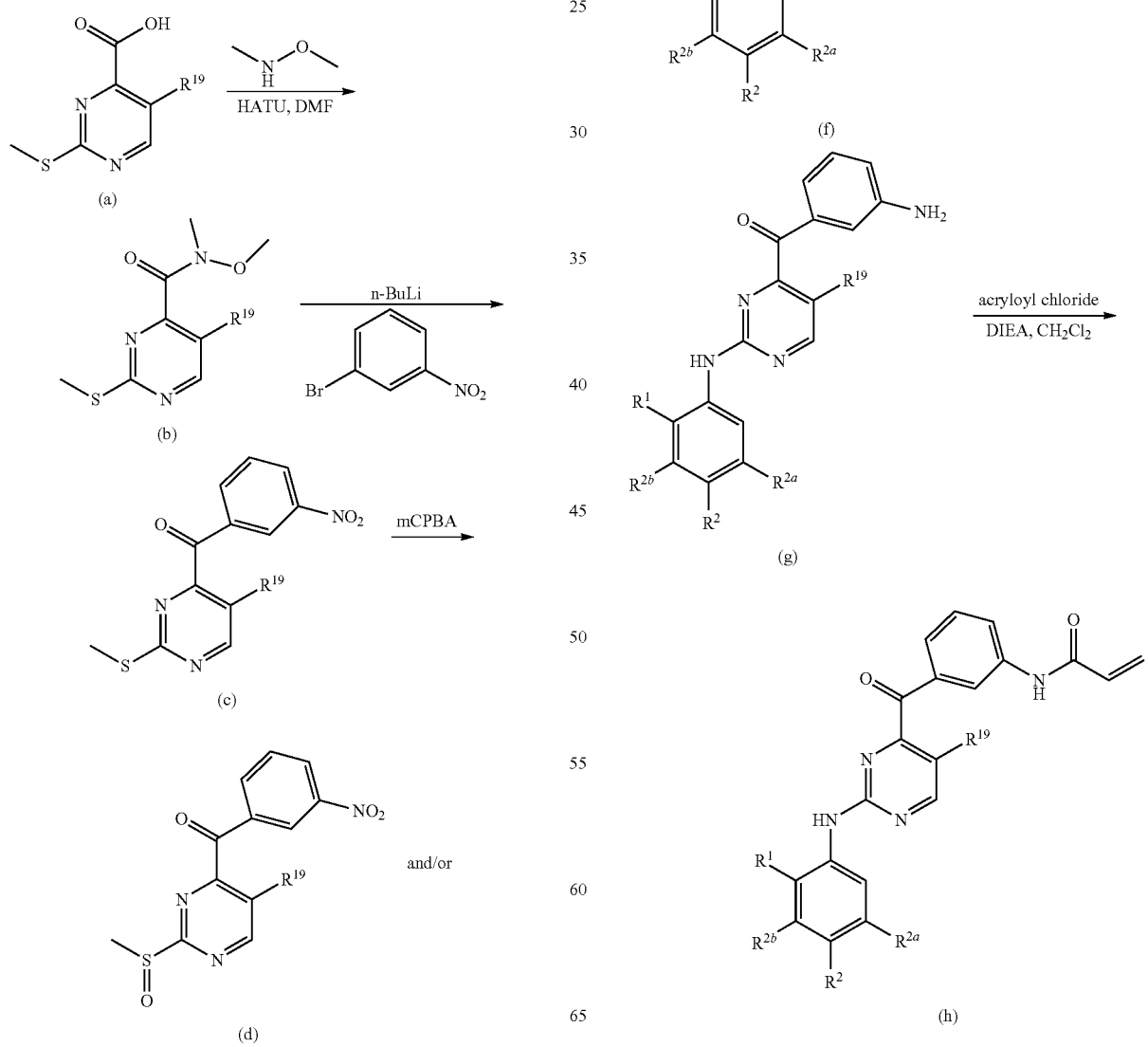

Compounds of Formula VII can be synthesized, for example, by the procedure set forth in the following Scheme 10 or 11.

Scheme 10.

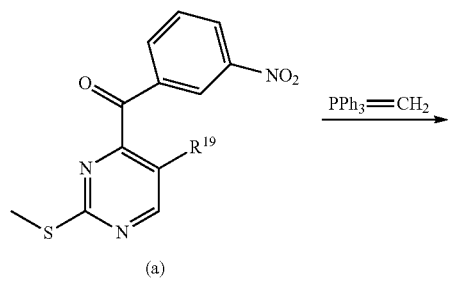

(a)

PPh₃=CH₂ →

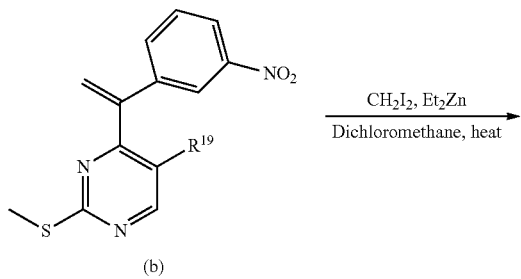

(b)

CH₂I₂, Et₂Zn
───────────
Dichloromethane, heat →

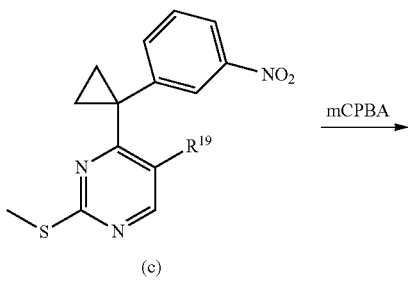

(c)

mCPBA →

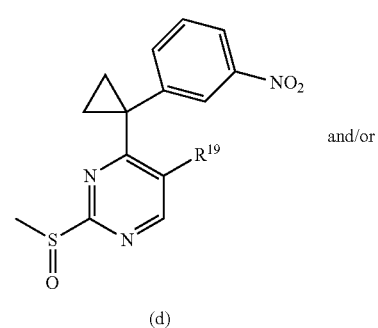

(d)

and/or

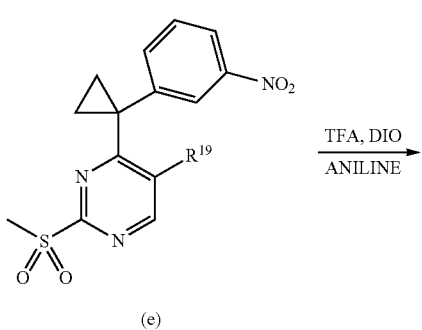

(e)

TFA, DIO
────────
ANILINE →

-continued

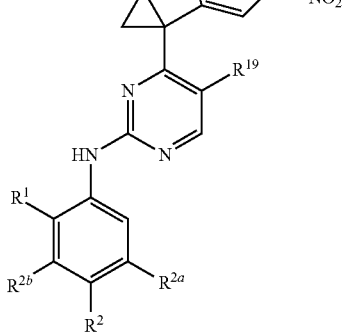

(f)

SnCl₂ →

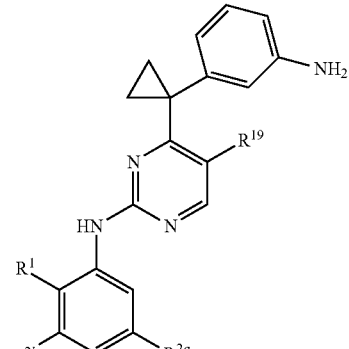

(g)

acryloyl chloride
─────────────
DIEA, CH₂Cl₂ →

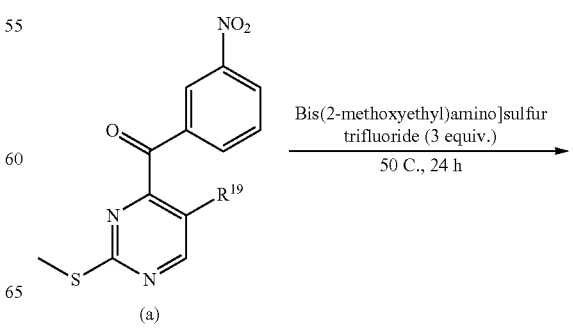

(h)

Scheme 11.

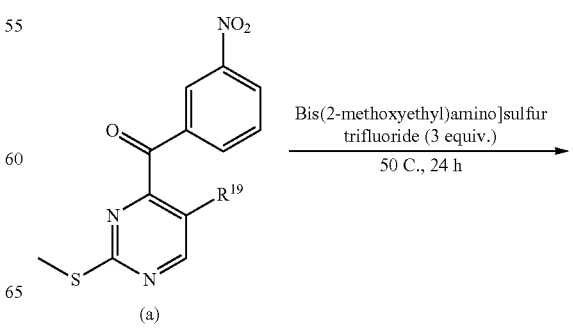

(a)

Bis(2-methoxyethyl)amino]sulfur trifluoride (3 equiv.)
───────────────
50 C., 24 h →

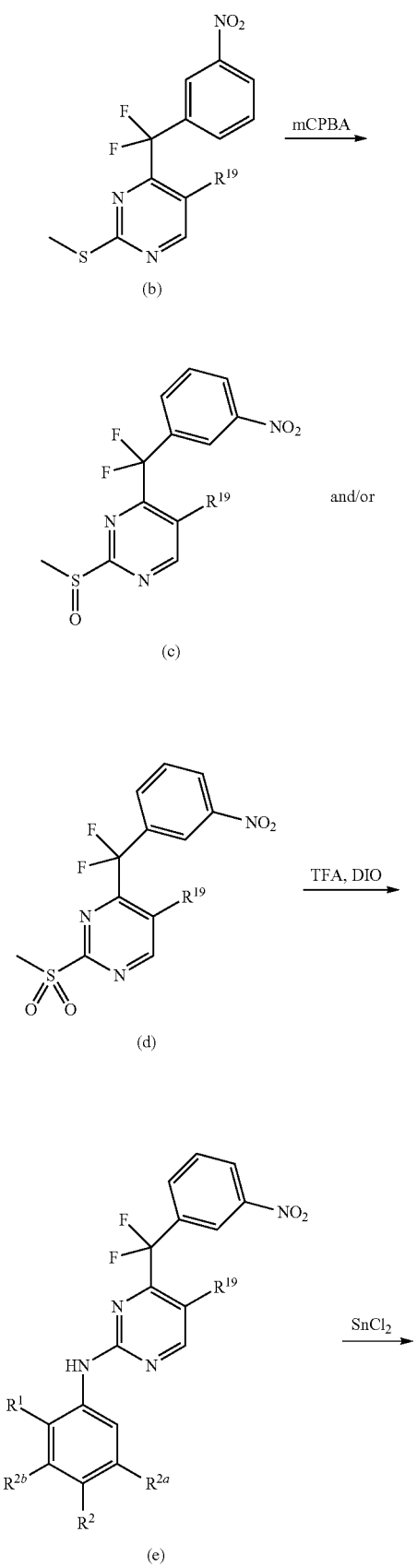
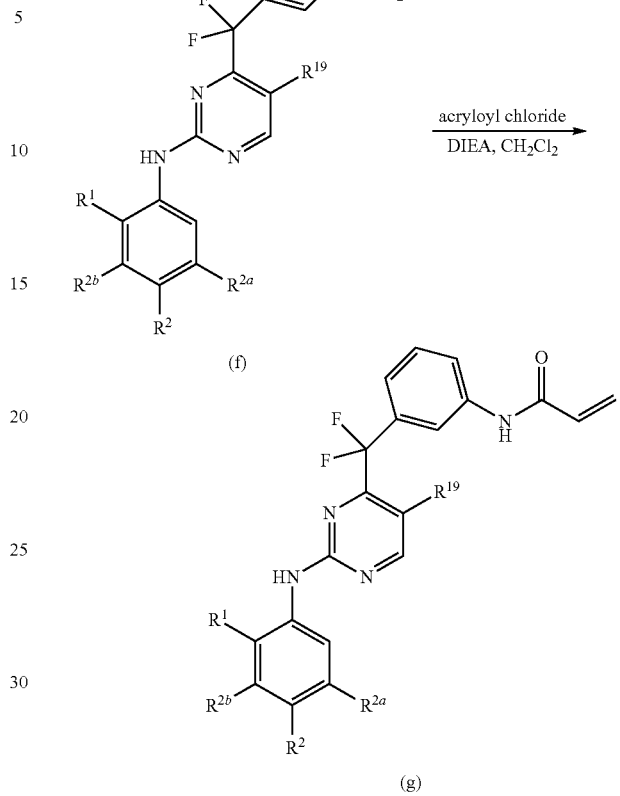
Compounds of Formula VIII can be synthesized, for example, by the procedure set forth in the following Scheme 12. The synthesis of a particular compound of Formula VIII (compound VIII-1) is exemplified in Example 3 below.
Scheme 12.
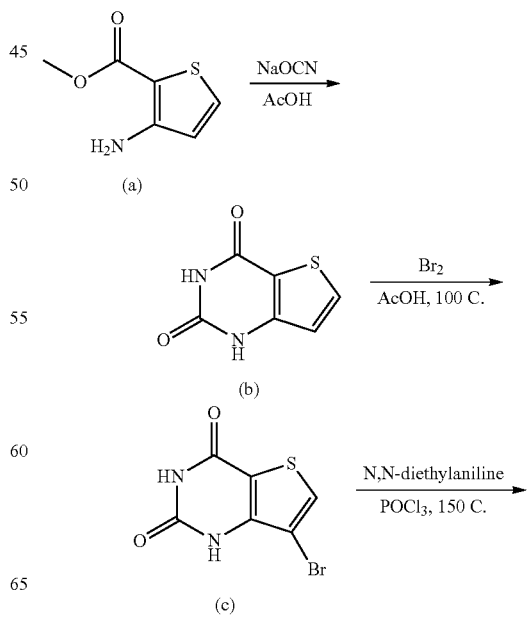

Scheme 13.
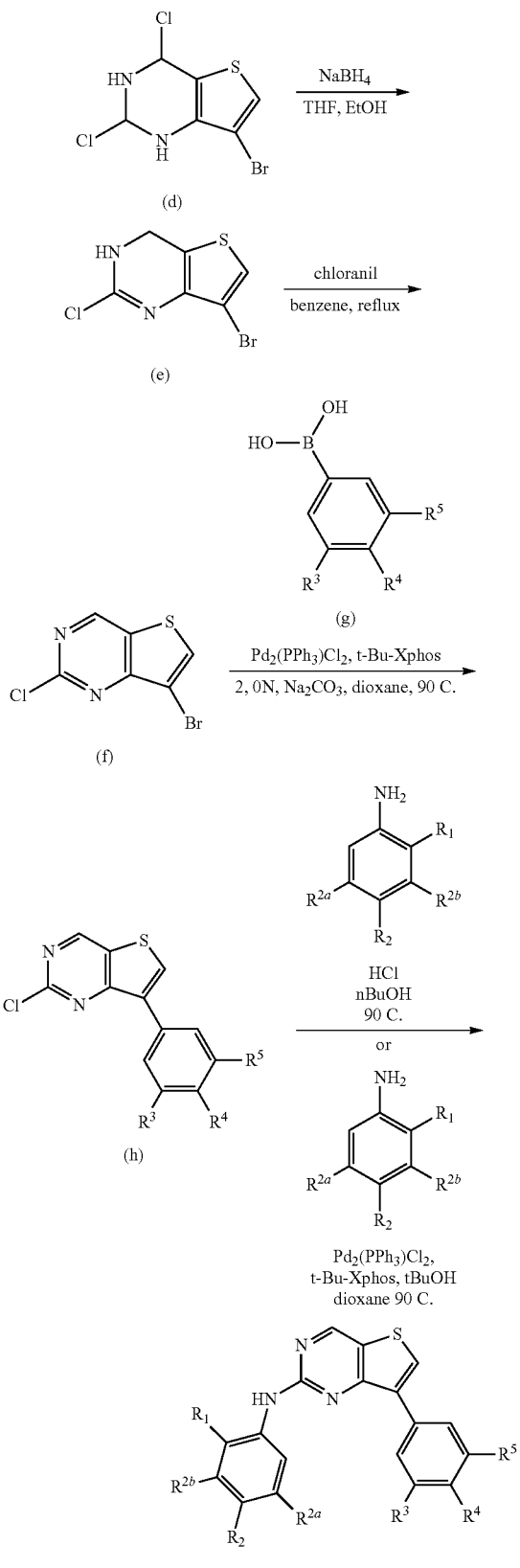
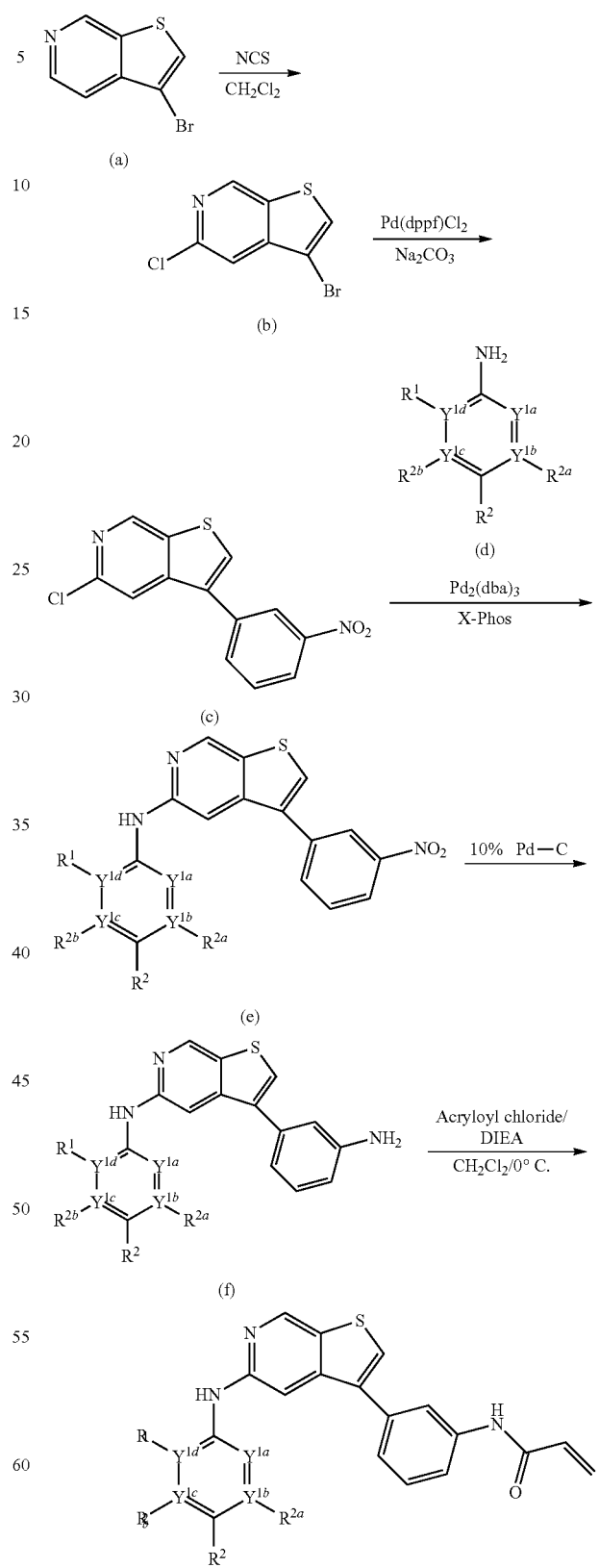
Compounds of Formula IX can be synthesized, for example, by the procedure set forth in the following Scheme 13.

Compounds of Formula Xb can be synthesized, for example, by the procedure set forth in the following Scheme 14 or 15.
Scheme 14.
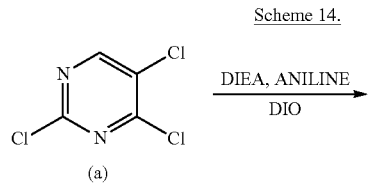
(a)
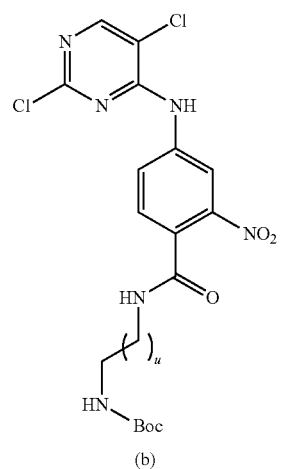
(b)
1. TFA, CH$_2$Cl$_2$
2. Acid, HATU, DMF
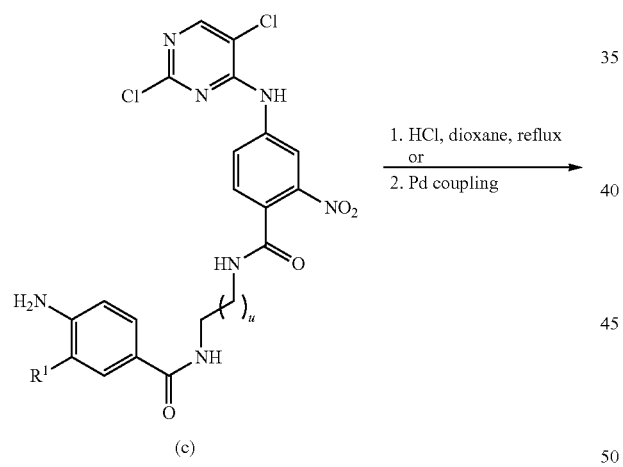
(c)
1. HCl, dioxane, reflux
or
2. Pd coupling
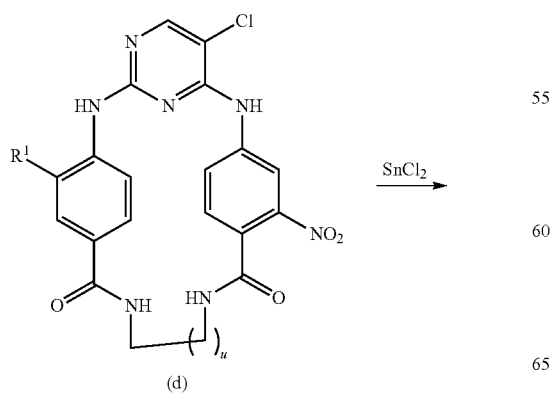
(d)
DIEA, ANILINE
DIO
SnCl$_2$
-continued
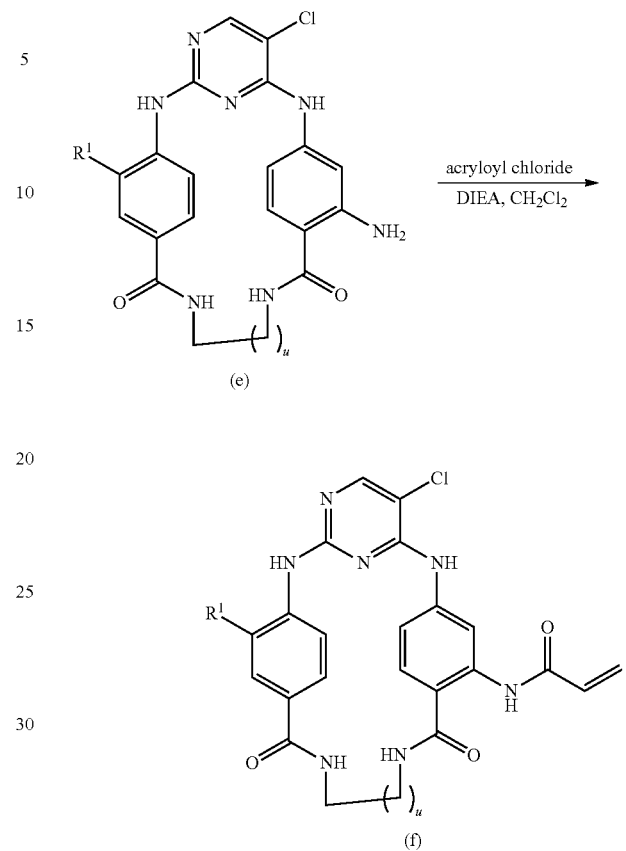
(e)
acryloyl chloride
DIEA, CH$_2$Cl$_2$
(f)
wherein u is 1, 2, or 3.
Scheme 15.
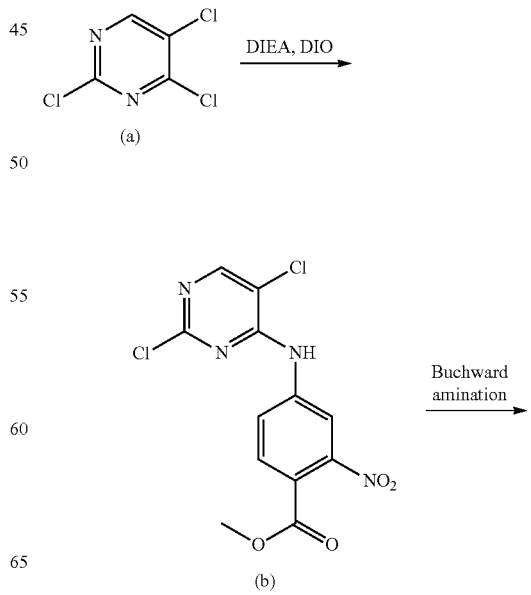
(a)
DIEA, DIO
(b)
Buchward amination 85
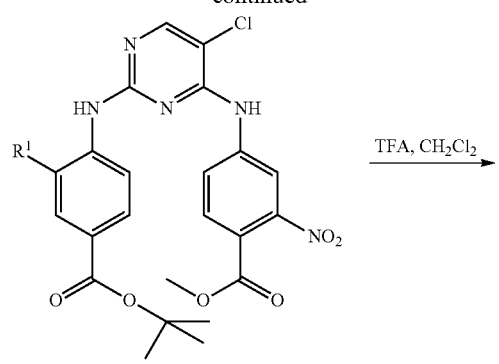
(c)
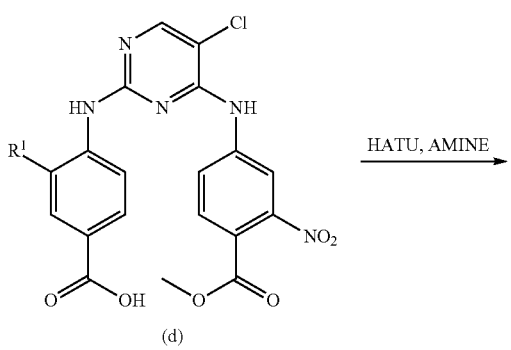
(d)
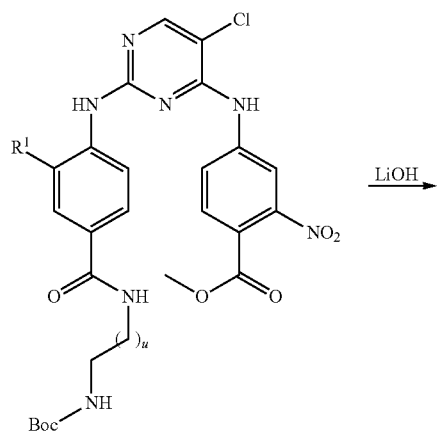
(e)
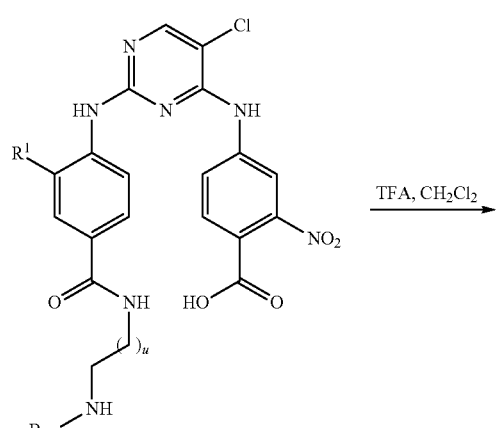
(f)
86
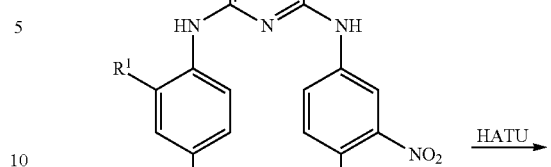
TFA, CH₂Cl₂
HATU
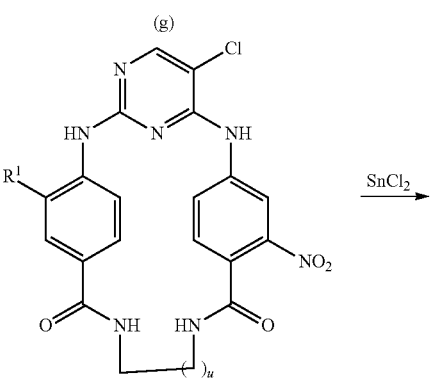
(g)
SnCl₂
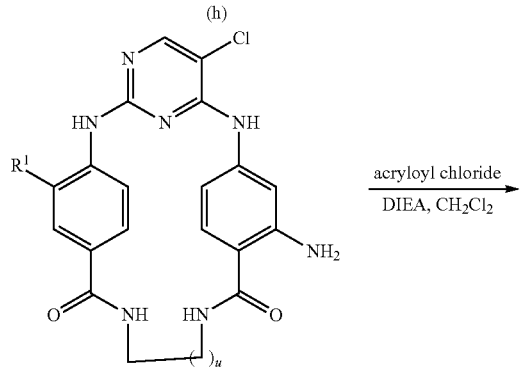
(h)
acryloyl chloride
DIEA, CH₂Cl₂
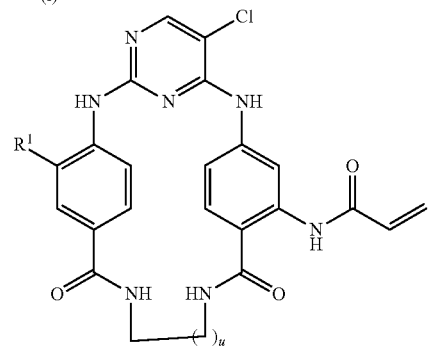
(j)
wherein u is 1, 2, or 3.
Compounds of Formula XI, where $X^1$ is O, can be synthesized, for example, by the procedure set forth in the following Scheme 16.

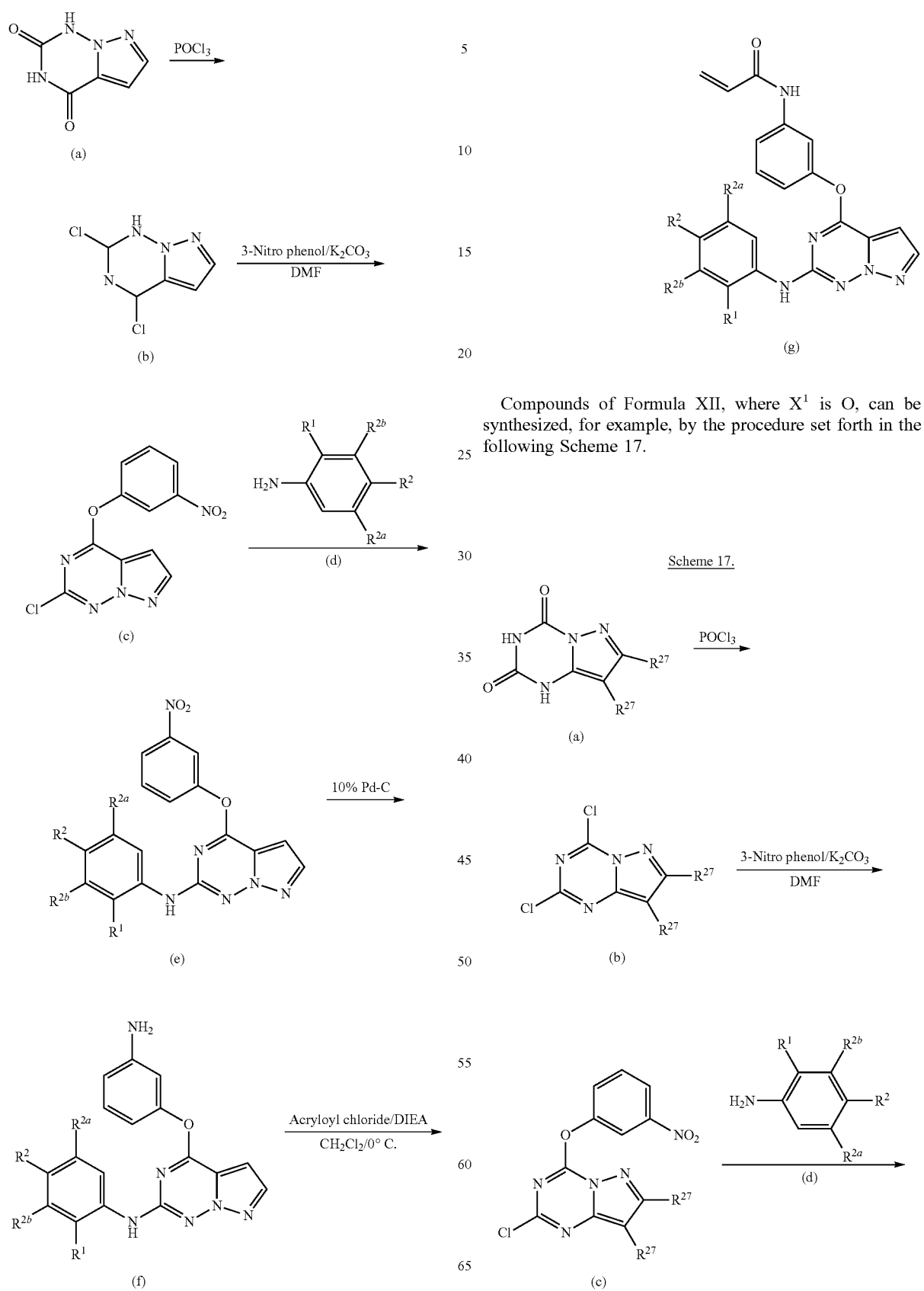
Compounds of Formula XII, where $X^1$ is O, can be synthesized, for example, by the procedure set forth in the following Scheme 17.

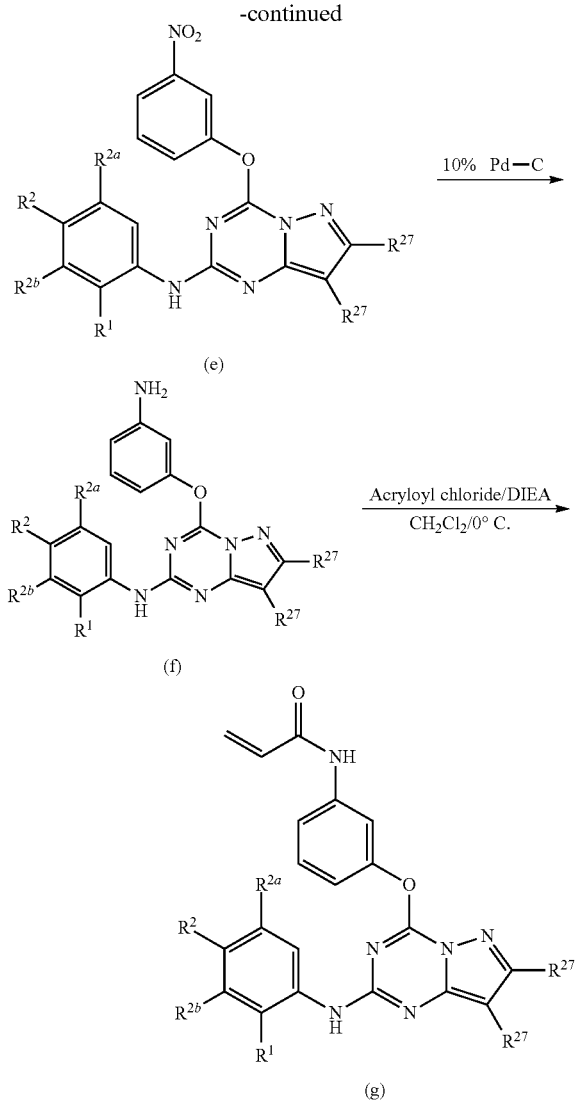

IV. Pharmaceutical Compositions of the Invention

In another aspect, the invention provides pharmaceutical compositions comprising a compound of Formula I, Ia, Ib, II, IIa, IIb, III, IIIa, IIIb, IV, IVa, IVb, V, VI, VIa, VIb, VI, VIa, VIb, VIII, VIIIa, VIIIb, IX, IXa, IXb, Xb, XI, XIa, XIb, XII, XIIa, or XIIb, or a pharmaceutically acceptable ester, salt, or prodrug thereof, and a pharmaceutically acceptable excipient.

The pharmaceutical compositions can be formulated for intradermal, intramuscular, intraperitoneal, intravenous, subcutaneous, intranasal, epidural, oral, sublingual, intracerebral, intravaginal, intraventricular, intrathecal, epidural, transdermal, rectal, by inhalation, or topical administration. In one embodiment, the pharmaceutical composition is formulated for oral administration. The pharmaceutical compositions can take the form of solutions, suspensions, emulsions, tablets, pills, pellets, capsules, capsules containing liquids, powders, suppositories, emulsions, aerosols, sprays, suspensions, or any other form suitable for use.

The compositions can be formulated for immediate release, sustained release, or controlled release of the compounds of the invention.

Suitable pharmaceutical excipients include, for example, a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners.

Additional suitable pharmaceutical excipients can be liquids, such as water and oils, including those of petroleum, animal, vegetable, or synthetic origin, such as peanut oil, soybean oil, mineral oil, sesame oil and the like. The pharmaceutical excipients can be saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when the compound of the invention is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

Additional suitable pharmaceutical excipients include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Compositions for oral delivery can be in the form of tablets, lozenges, aqueous or oily suspensions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving a compound of the invention are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

In another embodiment, the compositions can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In another embodiment, the compositions can be formulated for intranasal form via use of suitable intranasal vehicles, or via transdermal routes, using those forms of transdermal skin patches well known to those of ordinary skill in that art. To be administered in the form of a transdermal delivery system, the dosage administration can be continuous rather than intermittent throughout the dosage regimen. Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

In another embodiment, the compositions can be formulated for rectal or vaginal administration. Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound. Solid compositions of a similar type may also be employed as fillers in soft and hard-filled gelatin capsules using such excipients as lactose or milk sugar as well as high molecular weight polyethylene glycols and the like.

Compositions can be prepared according to conventional mixing, granulating or coating methods, respectively, and the present compositions can contain, in one embodiment, from about 0.1% to about 99%; and in another embodiment from about 1% to about 70% of the compound of the invention by weight or volume.

In certain embodiments, these compositions further comprise one or more additional therapeutic agents. For example, chemotherapeutic agents or other antiproliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the compounds of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-I RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anticonvulsants, ion channel blockers, riluzole, and antiparkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, antileukemic agents, and growth factors; and agents for treating immunodeficiency disorders such as gamma globulin.

V. Methods for Treating or Preventing a Condition

As inhibitors of Her kinases, the compounds and compositions of this invention are particularly useful for treating, lessening the severity of, or preventing a disease that is mediated by a kinase (hereinafter a "Condition").

In one embodiment, the invention encompasses methods for treating or preventing a Condition in a subject, comprising administering to the subject an effective amount of a compound of Formula I, Ia, Ib, II, IIa, IIb, III, IIIa, IIIb, IV, IVa, IVb, V, VI, VIa, VIb, VI, VIa, VIb, VIII, VIIIa, VIIIb, IX, IXa, IXb, Xb, XI, XIa, XIb, XII, XIIa, or XIIb, or a pharmaceutically acceptable salt, ester, or prodrug thereof.

In one embodiment, the Condition is a disease that is mediated by a kinase. In one embodiment, the kinase comprises a cysteine residue. In a further embodiment, the cysteine residue is located in or near the position equivalent to Cys 797 in epidermal growth factor receptor ("EGFR"), including Jak3, Blk, Bmx, Btk, HER2 (ErbB2), HER4 (ErbB4), Itk, Tec, and Txk.

In one embodiment, the Condition is a disease that is mediated by EGFR. In a further embodiment, the EGFR is a Her-kinase. In a further embodiment, the disease is mediated by HER1, HER2, or HER4.

In one embodiment, the Condition is an EGFR-tyrosine kinase ("EGFR-TK") related disease. An EGFR-TK related disease is a disease that involves inappropriate EGFR-TK activity or over-activity of the EGFR-TK. Inappropriate activity refers to either; (i) EGFR-TK expression in cells which normally do not express EGFR-TKs; (ii) increased EGFR-TK expression leading to unwanted cell proliferation, differentiation and/or growth; or, (iii) decreased EGFR-TK expression leading to unwanted reductions in cell proliferation, differentiation and/or growth. Over-activity of EGFR-TKs refers to either amplification of the gene encoding a particular EGFR-TK or production of a level of EGFR-TK activity which can correlate with a cell proliferation, differentiation and/or growth disorder (that is, as the level of the EGFR-TK increases, the severity of one or more of the symptoms of the cellular disorder increases). Over activity can also be the result of ligand independent or constitutive activation as a result of mutations such as deletions of a fragment of a EGFR-TK responsible for ligand binding. In some embodiments, the EGFR-TK related diseases and disorders comprise proliferative disorders, e.g., cancers.

In one embodiment, the Condition is a disease that is resistant to EGFR targeted therapy. In one embodiment, the EGFR targeted therapy comprises treatment with gefitinib, erlotinib, lapatinib, XL-647, HKI-272, BIBW2992, AV-412, CI-1033, PF00299804, BMS 690514, cetuximab, panitumumab, or matuzumab.

In some embodiments, the Condition is an autoimmune disease, inflammatory disease, proliferative or hyperproliferative disease, immunologically-mediated disease, bone disease, metabolic disease, neurological or neurodegenerative disease, cardiovascular disease, hormone related disease, allergy, or asthma.

In one embodiment, the Condition is a proliferative disease. In some embodiments, the compounds of the invention are used to inhibit cell proliferative disease such as hyperplasias, dysplasias and pre-cancerous lesions. Dysplasia is the earliest form of pre-cancerous lesion recognizable in a biopsy by a pathologist. Examples of pre-cancerous lesions may occur in skin, esophageal tissue, breast and cervical intra-epithelial tissue. Inhibition may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition is observed, and may be referred to as prevention or chemoprevention.

In one embodiment, the Condition is a cancer. Cancers that can be treated with the methods of the invention include without limitation the following cancers: epidermoid, Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, liporna and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. A cancerous cell includes a cell afflicted by any one of the above-identified conditions.

Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

In a further embodiment, the Condition is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemia, lymphoma, myeloma, or a solid tumor.

In one embodiment, the cancer comprises EGFR activated tumors. In certain embodiments, the EGFR activation is selected from mutation of EGFR, amplification of EGFR, expression of EGFR, and ligand mediated activation of EGFR. In a further embodiment, the mutation of EGFR is located at G719S, G719C, G719A, L858R, L861Q, an exon 19 deletion mutation or an exon 20 insertion mutation.

In another embodiment, the cancer comprises $ERBB_2$ activated tumors. In certain embodiments, the $ERBB_2$ activation is selected from mutation of $ERBB_2$, expression of $ERBB_2$ and amplification of ERBB2. In a further embodiment, the mutation is a mutation in exon 20 of ERBB2.

In other embodiments, the Condition is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, angiogenesis including neoplasia, metastasis, a central nervous system disorder, a central nervous system disorder having an inflammatory or apoptotic component, Alzheimer's disease, Parkinson's disease, Huntington's disease, amyotrophic lateral sclerosis, spinal cord injury, and peripheral neuropathy, or Canine B-Cell Lymphoma.

In a further embodiment, the Condition is inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, dermatitis, pain, pulmonary disorders, lung inflammation, adult respiratory distress syndrome, pulmonary sarcoisosis, asthma, chronic pulmonary inflammatory disease, and chronic obstructive pulmonary disease (COPD), cardiovascular disease, arteriosclerosis, myocardial infarction (including post-myocardial infarction indications), congestive heart failure, cardiac reperfusion injury, inflammatory bowel disease, Crohn's disease, gastritis, irritable bowel syndrome, leukemia, or lymphoma.

In one embodiment, the Condition is a neurodegenerative disease. Examples of neurodegenerative diseases include, without limitation, Adrenoleukodystrophy (ALD), Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Familial fatal insomnia, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), Multiple System Atrophy, Multiple sclerosis, Narcolepsy, Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Subacute combined degeneration of spinal cord secondary to Pernicious Anaemia, Spielmeyer-Vogt-Sjogren-Batten disease (also known as Batten disease), Spinocerebellar ataxia (multiple types with varying characteristics), Spinal muscular atrophy, Steele-Richardson-Olszewski disease, Tabes dorsalis, and Toxic encephalopathy.

In another aspect, the invention provides a method of inhibiting a kinase in a subject, comprising administering to the subject an effective amount of a compound of Formula I, Ia, Ib, II, IIa, IIb, III, IIa, IIIb, IV, IVa, IVb, V, VI, VIa, VIb, VI, VIa, VIb, VIII, VIIIa, VIIIb, IX, IXa, IXb, Xb, XI, XIa, XIb, XII, XIIa, or XIIb, or a pharmaceutically acceptable salt, ester, or prodrug thereof. In one embodiment, the kinase comprises a cysteine residue. In a further embodiment, the cysteine residue is located in or near the position equivalent to Cys 797 in EGFR, including Jak3, Blk, Bmx, Btk, HER2 (ErbB2), HER4 (ErbB4), Itk, Tec, and Txk.

In another aspect, the invention provides a method of inhibiting epidermal growth factor receptor (EGFR) in a subject, comprising administering to the subject an effective amount of a compound of Formula I, Ia, Ib, II, IIa, IIb, III, IIIa, IIIb, IV, IVa, IVb, V, VI, VIa, VIb, VI, VIa, VIb, VIII, VIIIa, VIIIb, IX, IXa, IXb, Xb, XI, XIa, XIb, XII, XIIa, or XIIb, or a pharmaceutically acceptable salt, ester, or prodrug thereof. In one embodiment, the EGFR is a Her-kinase.

The invention also provides a method of preventing resistance to gefitinib or erlotinib in a disease, comprising administering to a subject an effective amount of a compound of Formula I, Ia, Ib, II, IIa, IIb, III, IIIa, IIIb, IV, IVa, IVb, V, VI, VIa, VIb, VI, VIa, VIb, VIII, VIIIa, VIIIb, IX, IXa, IXb, Xb, XI, XIa, XIb, XII, XIIa, or XIIb, or a pharmaceutically acceptable salt, ester, or prodrug thereof.

The amount of the compounds of the invention that is effective in the treatment or prevention of a Condition can be determined by standard clinical techniques. In addition, in vitro or in vivo assays can optionally be employed to help identify optimal dosage ranges. The precise dose to be employed can also depend on the route of administration, and the seriousness of the condition being treated and can be decided according to the judgment of the practitioner and each subject's circumstances in view of, e.g., published clinical studies.

In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

In certain embodiments, a therapeutic amount or dose of the compounds of the present invention may range from about 0.1 mg/kg to about 500 mg/kg, alternatively from about 1 to about 50 mg/kg. In general, treatment regimens according to the present invention comprise administration to a patient in need of such treatment from about 10 mg to about 1000 mg of the compound(s) of this invention per day in single or multiple doses (such as two, three, or four times daily). Therapeutic amounts or doses will also vary depending on route of administration, as well as the possibility of co-usage with other agents.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In certain embodiments, a compound of the invention is administered to a human that has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In some embodiments, a compound of the invention is administered to a human infant. In other embodiments, a compound of the invention is administered to a human toddler. In other embodiments, a compound of the invention is administered to a human child. In other embodiments, a compound of the invention is administered to a human adult. In yet other embodiments, a compound of the invention is administered to an elderly human.

In some embodiments, the methods further comprise administering an additional therapeutic agent to the subject. In other embodiments, the compound and the additional therapeutic agent are administered simultaneously or sequentially.

For example, synergistic effects can occur with other anti-proliferative, anti-cancer, immunomodulatory or anti-inflammatory substances. Where the compounds of the invention are administered in conjunction with other therapies, dosages of the co-administered compounds will of course vary depending on the type of co-drug employed, on the specific drug employed, on the condition being treated and so forth.

Combination therapy includes the administration of the compounds of the invention in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect of the invention, the compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g. HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g, MET, RON, SEA, SEX); insulin receptor (e.g. IGFI-R); Eph (e.g. CEK5, CEK8, EBK, ECK, EEK, EHK-1, EHK-2, ELK, EPH, ERK, HEK, MDK2, MDK5, SEK); Axl (e.g. Mer/Nyk, Rse); RET; and platelet-derived growth factor receptor (PDGFR) (e.g. PDGF.alpha.-R, PDG.beta.-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g. p43, ARG); BTK (e.g. ITK/EMT, TEC); CSK, FAK, FPS, JAK, SRC, BMX, FER, CDK and SYK.

In another aspect of the invention, the compounds of the invention may be administered in combination with one or more agents that modulate non-kinase biological targets or processes. Such targets include histone deacetylases (HDAC), DNA methyltransferase (DNMT), heat shock proteins (e.g. HSP90), and proteosomes.

In a preferred embodiment, compounds of the invention may be combined with antineoplastic agents (e.g. small molecules, monoclonal antibodies, antisense RNA, and fusion proteins) that inhibit one or more biological targets such as vorinostat, erlotinib, gefitinib, lapatinib, imatinib, sunitinib, dasatinib, sorafenib, CNF2024, RG108, BMS387032, Isis-3521, bevacizumab, trastuzumab, cetuximab, AG24322, PD325901, ZD6474, PD184322, Obatodax, ABT737 and AEE788. Such combinations may enhance therapeutic efficacy over efficacy achieved by any of the agents alone and may prevent or delay the appearance of resistant mutational variants.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplastics such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA).

In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, the compounds of the invention are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that compounds of the invention can be used in combination with an immunotherapeutic agent, such as agents used to transfer the immunity of an immune donor, e.g., another person or an animal, to a host by inoculation. The term embraces the use of serum or gamma globulin containing performed antibodies produced by another individual or an animal; nonspecific systemic stimulation; adjuvants; active specific immunotherapy; and adoptive immunotherapy. Adoptive immunotherapy refers to the treatment of a disease by therapy or agents that include host inoculation of sensitized lymphocytes, transfer factor, immune RNA, or antibodies in serum or gamma globulin.

One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol. 121:487). In U.S. Pat. No. 5,484,596, Hanna Jr. et al. claim a method for treating a respectable carcinoma to prevent recurrence or metastases, comprising surgically removing the tumor, dispersing the cells with collagenase, irradiating the cells, and vaccinating the patient with at least three consecutive doses of about $10^7$ cells. The compounds of the invention can be used in conjunction with such techniques.

It will be appreciated that the compounds of the invention may advantageously be used in conjunction with one or more adjunctive therapeutic agents. Examples of suitable agents for adjunctive therapy include a $5HT_1$ agonist, such as a triptan (e.g. sumatriptan or naratriptan); an adenosine A1 agonist; an EP ligand; an NMDA modulator, such as a glycine antagonist; a sodium channel blocker (e.g. lamotrigine); a substance P antagonist (e.g. an $NK_1$ antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neurone stabilising antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor a; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an $H_2$-antagonist (e.g. ranitidine); a proton pump inhibitor (e.g. omeprazole); an antacid (e.g. aluminium or magnesium hydroxide; an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine.

In another aspect, the invention provides a kit comprising a compound of Formula I, Ia, Ib, II, IIa, IIb, III, IIa, IIIb, IV, IVa, IVb, V, VI, VIa, VIb, VII, VIIa, VIIb, VIII, VIIIa, VIM, IX, IXa, IXb, Xb, XI, XIa, XIb, XII, XIIa, or XIIb, and instructions for use in treating a Condition, e.g., a cancer. In one embodiment, the kit further comprises an additional therapeutic agent.

VI. Other Uses

As inhibitors of Her kinases, the compounds and compositions of this invention are also useful in biological samples. One aspect of the invention relates to inhibiting protein kinase activity in a biological sample, which method comprises contacting said biological sample with a compound of the invention or a composition comprising said compound. The term "biological sample," as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof. Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this invention relates to the study of Her kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as Her kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands.

EXAMPLES

The compounds and methods of the present invention will be better understood in connection with the following examples, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1: In Vitro Assays (a) Materials
(1) Cell Culture and Reagents

The EGFR mutant NSCLC cell lines HCC827 (del E746_A750), H3255 (L858R), HCC827 GR (del E746_A750/MET amplified), H1975 (L858R/T790M) and PC9 (del E746_A750) have been previously characterized (Amann, J. et al. Cancer Res 65, 226-35 (2005); Engelman, J. A. et al. Science 316, 1039-43 (2007); Ono, M. et al. Mol Cancer Ther 3, 465-72 (2004); Ogino, A. et al. Cancer Res 67, 7807-14 (2007)). The PC9 GR (del E746_A750/T790M) cells are generated and verified to contain del E746_A750 in cis with T790M. The ERBB2 amplified (Calu-3 and H1819) and mutant (H1781) are obtained from ATCC. All cell lines are maintained in RPMI 1640 (Celigro; Mediatech Inc., Herndon, Calif.) supplemented with 10% FBS 100 units/mL penicillin, 100 units/mL streptomycin, and 2 mM glutamine. H3255 are maintained in ACL-4 media (Invitrogen, Carlsbad, Calif.) supplemented with 5% FBS, 100 units/mL penicillin, 100 units/mL streptomycin, and 2 mM glutamine.

The EGFR and iERBB2 mutant Ba/F3 cells and the NIH-3T3 cells have been previously characterized (Engelman, J. A. et al. Cancer Res 67, 11924-32 (2007); Yuza, Y. et al. Cancer Biol Ther 6 (2007)). The EGFR C797S and the ERBB2 T798I mutations are introduced using site directed mutagenesis using the Quick Change Site-Directed Mutagenesis kit (Stratagene; La Jolla, Calif.) according to the manufacturer's instructions (Mukohara, T. et al. J Natl Cancer Inst 97, 1185-94 (2005)). The oligonucleotide sequences are available upon request. All constructs are confirmed by DNA sequencing. The constructs are shuttled into the retroviral vector JP1540 using the BD Creator™ System (BD Biosciences). Ba/F3 of NIH-3T3 cells are infected with retrovirus according to standard protocols, as described previously (Engelman, J. A. et al. Proc Natl Acad Sci USA 102, 3788-93 (2005); Zhao, J. J. et al. Cancer Cell 3, 483-95 (2003)). Stable populations are obtained by selection in puromycin (2 μg/ml).

(2) Kinase Inhibitors

Gefitinib is obtained from commercial sources and is purified through an ethyl acetate extraction. The resulting product is verified by liquid chromatography-electrospray mass spectrometry (LC-MS). CL-387,785 was obtained from EMD (Gibbstown, N.J.). HKI-272 is obtained from Medicilon Inc. (Shanghai, China). The structure of HKI-272 is confirmed LC-MS and $^1$H and $^{13}$C nuclear magnetic resonance (NMR). HKI-272 is determined to be >95% pure by LC-MS. Stock solutions of all drugs were prepared in DMSO and stored at −20° C.

(3) Antibodies and Western Blotting

Cells grown under the previously specified conditions are lysed in the following lysis buffer: 20 mM Tris, pH 7.4/150 mM NaCL/1% Nonidet P-40/10% glycerol/1 mM EDTA/1 mM EGTA/5 mM sodium pyrophosphate/50 mM NaF/10 nM β-glycerophosphate/1 mM sodium vanadate/0.5 mM DTT/4 µg/ml leupeptin/4 µg/ml pepstatin/4 µg/ml apoprotein/1 mM PMSF. After cell lysis, lysates are centrifuged at 16,000×g for 5 min at 4° C. The supernatant is used for subsequent procedures. Western blot analyses are conducted after separation by SDS/PAGE electrophoresis and transfer to nitrocellulose membranes. Immunoblotting is performed according to the antibody manufacturers' recommendations. Antibody binding is detected using an enhanced chemiluminescence system (New England Nuclear Life Science Products Inc.). Anti-phospho-Akt (Ser-473), anti-total Akt, and anti-EGFR antibodies are obtained from Cell Signaling Technology. The phospho-specific EGFR (pY1068), total ERK1/2, phospho-ERK1/2 (pT185/pY187) antibodies are purchased from Biosource International Inc.

(b) Cell Proliferation and Growth Assays

Growth and inhibition of growth is assessed by MTS assay. This assay, a colorimetric method for determining the number of viable cells, is based on the bioreduction of 3-(4,5-dimethylthiazol-2-yl)-5-(3-carboxymethoxyphenyl)-2-(4-sulfophenyl)-2H-tetrazolium (MTS) by cells to a formazan product that is soluble in cell culture medium, can be detected spectrophotometrically and was performed according to previously established methods (Mukohara, T. et al. J Natl Cancer Inst 97, 1185-94 (2005); Paez, J. G. et al. Science 304, 1497 500 (2004); Engelman, J. A. et al. J Clin Invest 116, 2695-2706 (2006). NSCLC or Ba/F3 cells are exposed to treatment for 72 hours and the number of cells used per experiment determined empirically and has been previously established. All experimental points are set up in six to twelve wells and all experiments are repeated at least three times. The data is graphically displayed using Graph-Pad Prism version 5.0 for Windows, (GraphPad Software; www.graphpad.com). The curves are fitted using a non-linear regression model with a sigmoidal dose response.

(c) Mass Spectrometry

For intact protein mass spectral analysis, the proteins T790M alone and with small molecules bound are injected onto a POROS 20 R$^2$ protein trap and desalted with 0.05% trifluoroacetic acid (TFA) at a flow rate of 100 µL/min. The proteins are eluted into the mass spectrometer using a linear 15%-75% (v/v) acetonitrile gradient over 4 min at 50 µL/min using a Shimadzu HPLC system (LC-10ADvp). Intact protein analyses are performed on an LCT-Premier instrument (Waters Corp., Milford, Mass., USA) equipped with a standard electrospray source. The capillary voltage is 3.2 kV and the cone voltage of 35 V. Nitrogen is used as desolvation gas. A source temperature of 175° C. and a desolvation temperature of 80° C. are applied. The instrument is calibrated by infusing a solution of 500 fmol/µL myoglobin and the mass accuracy is less than 10 ppm.

(d) Pepsin Digestion and Peptide Analysis

For the elucidation of the modification site, all three proteins (50 pmol each) are digested offline with pepsin in an enzyme: substrate ratio of 1:1. The pepsin digestion is performed in a potassium phosphate buffer (75 mM KH$_2$PO$_4$/75 mM K$_2$HPO$_4$) pH 2.5. The reaction is carried out for 5 minutes on ice. The resulting peptides are injected into a Waters nanoAcquity UPLC system (Waters, Milford, Mass.) and trapped and desalted for 3 min at 100 µL/min and then separated in 60 min by an 8%-40% acetonitrile:water gradient at 40 µL/min. The separation column is a 1.0×100.0 mm ACQUITY UPLC C18 BEH (Waters) containing 1.7 µm particles.

Mass spectra are obtained with a Waters QTOF Premier equipped with standard ESI source (Waters Corp., Milford, Mass., USA). The instrument configuration is the following: capillary was 3.5 kV, trap collision energy at 6V, sampling cone at 37 V, source temperature of 100° C. and desolvation temperature of 250° C. Mass spectra are acquired over an m/z range of 100 to 2000. Mass accuracy was ensured by calibration with 100 fmol/µL GFP, and is less than 10 ppm throughout all experiments. Identification of the peptic fragments is accomplished through a combination of exact mass analysis and MS$^{E12}$ using custom Identity Software from the Waters Corporation. MS$^E$ is performed by a series of low-high collision energies ramping from 5-25 V, therefore ensuring proper fragmentation of all the peptic peptides eluting from the LC system.

(e) In-Vitro Inhibitory Enzyme Kinetic Assays

The assays are carried out in triplicate using the ATP/NADH coupled assay system in a 96-well format as previously described. Yun, C. H. et al., Cancer Cell 11, 217-227 (2007). The final reaction mixture contains 0.5 mg/mL Bovine Serum Albumin (BSA), 2 mM MnCl$_2$, 1 mM phospho(enol) pyruvic acid (PEP, Sigma-Aldrich, Cat. P7002), 1 mM TCEP, 0.1M Hepes 7.4, 2.5 mM poly-[Glu$_4$Tyr$_1$] peptide (Sigma-Aldrich, Cat. P7244), 1/50 of the final reaction mixture volume of pyruvate kinase/lactic dehydrogenase enzymes from rabbit muscle (Sigma-Aldrich; catalogue no. P-0294), 0.5 mM NADH, 0.5 µM EGFR kinase, 100 µM ATP and varied amount of inhibitors. Inhibitors and ATP are mixed and made separate stock from the mixture with all other ingredients and added last to the latter to start the reaction. Steady state initial velocity data are drawn from the slopes of the A340 curves.

An additional EGFR kinase assay is performed using a GST-kinase fusion protein according to the manufacturer's recommended conditions (catalogue number 7908; Cell Signaling Technology, Beverly, Mass.). The final reaction mixture contains 60 mM HEPES pH 7.5, 5 mM MgCl$_2$, 5 mM MnCl$_2$, 3 mM Na$_3$VO$_4$, 1.25 mM DTT, 20 µM ATP, 1.5 µM PTP1B (Tyr66) biotinylated peptide and 50 ng of EGFR kinase. A phospho-tyrosine mab (pTyr100) is used to detect phosphorylation of the EGFR substrate peptide in the presence of a compound of the invention, gefitinib or HKI-272 (concentration ranges 0-10 µM for all drugs) followed a fluorescent Anti-mouse IgG secondary antibody. Fluorescence emission is detected at 615 nm.

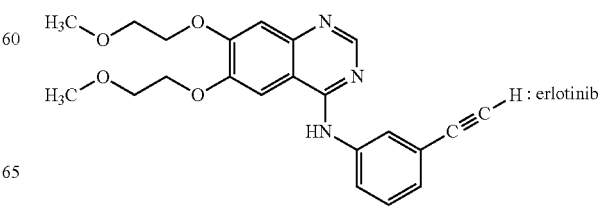

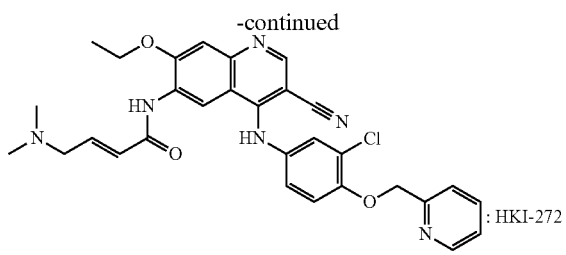
: HKI-272

(f) Equilibrium Binding Assay

Dissociation constants for binding of a compound of the invention to WT or mutant EGFR kinases are measured using the equilibrium fluorescence quenching method as previously described, Yun, C. H. et al., Proc Natl Acad Sci USA 105, 2070-2075 (2008), except that inhibitor stock solutions are prepared in degassed water at concentrations of 500 μM (for wild-type EGFR), 250 μM (for T790M and L858R mutants), or 125 μM (for L858R/T790M mutant).

(g) ENU Mutagenesis Assay

N-ethyl-N-nitrosourea (ENU) mutagenesis is carried out as previously described. Bradeen, H. A. et al., Blood 108, 2332-2338 (2006). Briefly, L858R or DelE746_A750 Ba/F3 cells (1×10$^6$ cells/ml) are exposed to ENU (50 μg/ml) for 24 hours. Cells are then washed 3 times with RPMI, and expanded in growth media for 5-7 days. Cells are subsequently cultured in 96-well plates (1×10$^4$ cells/well; total 5×10$^5$ cells per inhibitor) in the presence of 100 nM of a compound of the invention, 200 nM HKI-272 or 1 μM gefitnib. Wells are observed for growth by visual inspection and resistant wells were expanded in the presence of the corresponding inhibitor. Total RNA is isolated from the resistant cell lines using Trizol™ (Invitrogen, Carlsbad, Calif.) and purified using RNeasy™ minielute cleanup kit (Qiagen, Valencia, Calif.). cDNA is transcribed from 2 μg of total RNA with Superscript II Reverse Transcriptase (Invitrogen Life technologies, Carlsbad, Calif.). The cDNA is used as template for subsequent sequencing of the EGFR tyrosine kinase domain (exons 18-21).

Example 2: In Vivo Assays (a) Generation of Mouse Cohorts and Treatment with a Compound of the Invention EGFR-TL (T790M/L858R) mice are generated as previously described (Li, D. et al. Cancer Cell 12, 81-93 (2007)). EGFR exon 19 Deletion-T790M (TD) inducible bitransgenic mice are similarly generated and characterized. Briefly, exon 19 deletion is introduced in the human EGFR gene through site directed mutagenesis in the pTRE2-hyg-EGFR-T790M. The constructs are then digested with XhoI to release the entire allele containing Tet-op-EGFR TD-beta-globin PolyA. Transgenic mice are then generated by injection of the construct into FVB/N fertilized eggs. Progeny are genotyped through PCR exactly the same as reported. Founders are crossed with CCSP-rtTA mice and inducible bitransgenic mice with high and inducible expression of the mutant hEGFR transgene were identified and expanded for subsequent analyses and experiments. All mice are housed in a pathogen-free environment at the Harvard School of Public Health and are handled in strict accordance with Good Animal Practice as defined by the Office of Laboratory Animal Welfare, and all animal work is done with Dana-Farber Cancer Institute IACUC approval.

Cohorts of EGFR TL/CCSP-rtTA and EGFR TD/CCSP-rtTA are put on doxycycline diet at 5 weeks of age to induce the expression of mutant EGFR. These mice undergo MRI after 6 to 8 weeks of doxycycline diet to document and quantify the lung cancer burden before being assigned to various treatment study cohorts. There is a minimum of 3 mice per treatment group. Mice are then treated either with vehicle (NMP (10% 1-methyl-2-pyrrolidinone: 90% PEG-300) alone or WZ4002 at 25 mg/kg gavage daily. After 2 weeks of treatment, these mice undergo a second round of MRI to document their response to the treatment. MRIs and tumor burden measurement are performed as described previously (Li, D. et al. Cancer Cell 12, 81-93 (2007); Ji, H. et al. Cancer Cell 9, 485-95 (2006)).

(b) MRI Scanning and Tumor Volume Measurement

Mice are anesthetized with 1% isoflurane in an oxygen/air mixture. The respiratory and cardiac rates of anesthetized mice are monitored using Biotrig Software. The animals are imaged with a rapid acquisition with relaxation enhancement (RARE) sequence (TR=2000 ms, TE effect=25 ms) in the coronal and axial planes with a 1 mm slice thickness and with sufficient number of slices to cover the entire lung. Matrix size of 128×128 and a field of view (FOV) of 2.5 cm×2.5 cm$^2$ are used for all imaging. With same geometry and described above, the mice are also imaged with a gradient echo fast imaging (GEFI) sequence (TR=180 ms, TE effect=2.2 ms) with respiratory and cardiac gating, in both coronal and axial planes. The detailed procedure for MRI scanning has been previously described (Li, D. et al. Cancer Cell 12, 81-93 (2007); Ji, H. et al. Cancer Cell 9, 485-95 (2006)).

(c) Immunohistochemical Analyses

Hematoxylin and eosin (H&E) staining of tumor sections is performed at the Department of Pathology at the Brigham and Women's Hospital. Immunohistochemistry is performed on formal fixed paraffin embedded tumor sections. The antibodies used are: total EGFR and phospho-EGFR Y1068 (Cell Signaling Technology) and Ki67. Apoptosis is measured by counting nuclear bodies in H&E stained sections and by a terminal deoxynucleotidyl-transferase mediated dUTP-biotin nick end labeling (TUNEL) assay.

(d) Pharmacokinetic Analyses

Healthy male C57BL/6 Mice (8-12 weeks old) weighing between 25 and 30 g are procured from RCC Laboratories Private Limited, Hyderabad, India. A maximum of three animals are housed in each cage. All procedures of the present study are in accordance with the guidelines provided by the Committee for the Purpose of Control and Supervision of Experiments on Animals (CPCSEA). Prior approval of the Institutional Animal Ethics Committee (IAEC) is obtained before initiation of the study (IAEC Protocol No. IAEC/PRT/004-09).

Dose administration: All mice are weighed before dose administration and randomized. For intravenous administration, freshly prepared solution of a compound of the invention is administered at a dose level of 1 mg/kg via tail vein at a slow and steady rate. The dosing volume for intravenous administration is 5 mL/kg. For oral administration, freshly prepared solution of a compound of the invention is administered at an oral dose of 10 mg/kg, by stomach intubation using a 16 gauge oral feeding needle. The dosing volume for oral dose group is 10 mL/kg.

Blood samples: Blood samples (0.06 mL) are collected from saphenous vein of each mouse at regular intervals. During each sampling point, blood samples are collected in labeled micro-tubes containing K2EDTA as an anticoagulant. Samples are centrifuged at 4000 rpm for 10 min at 4±2° C. (Centrifuge Model: Kubota 3500). The recovered quantity of plasma from each sample is transferred to labeled micro-tubes. The plasma samples are stored at −70° C. until bioanalysis.

Bioanalysis of samples: Bioanalytical method for the determination of a compound of the invention in mouse plasma is developed using LC-MS/MS equipment. The method is partially validated prior to sample analysis.

Pharmacokinetic analysis: The pharmacokinetic parameters of a compound of the invention such as $T_{max}$, $C_{max}$, AUC, CL, $V_d$, $T_{1/2}$ A and bioavailability in mouse plasma are determined from the concentration-time data using non-compartmental analysis (WinNonlin Enterprise version 5.2, Pharsight Corporation, USA).

(e) Serum Creatinine and White Blood Cell Count Analyses

Blood is collected from vehicle and mice treated with a compound of the invention into appropriate tubes and analyzed at the clinical laboratory at the Boston Children's Hospital.

(f) Statistical Analyses

Statistical analyses are performed using an unpaired two tailed Student's t-test. A p value of less than 0.05 is considered significant.

Example 3: Synthesis of Compound VIII-1

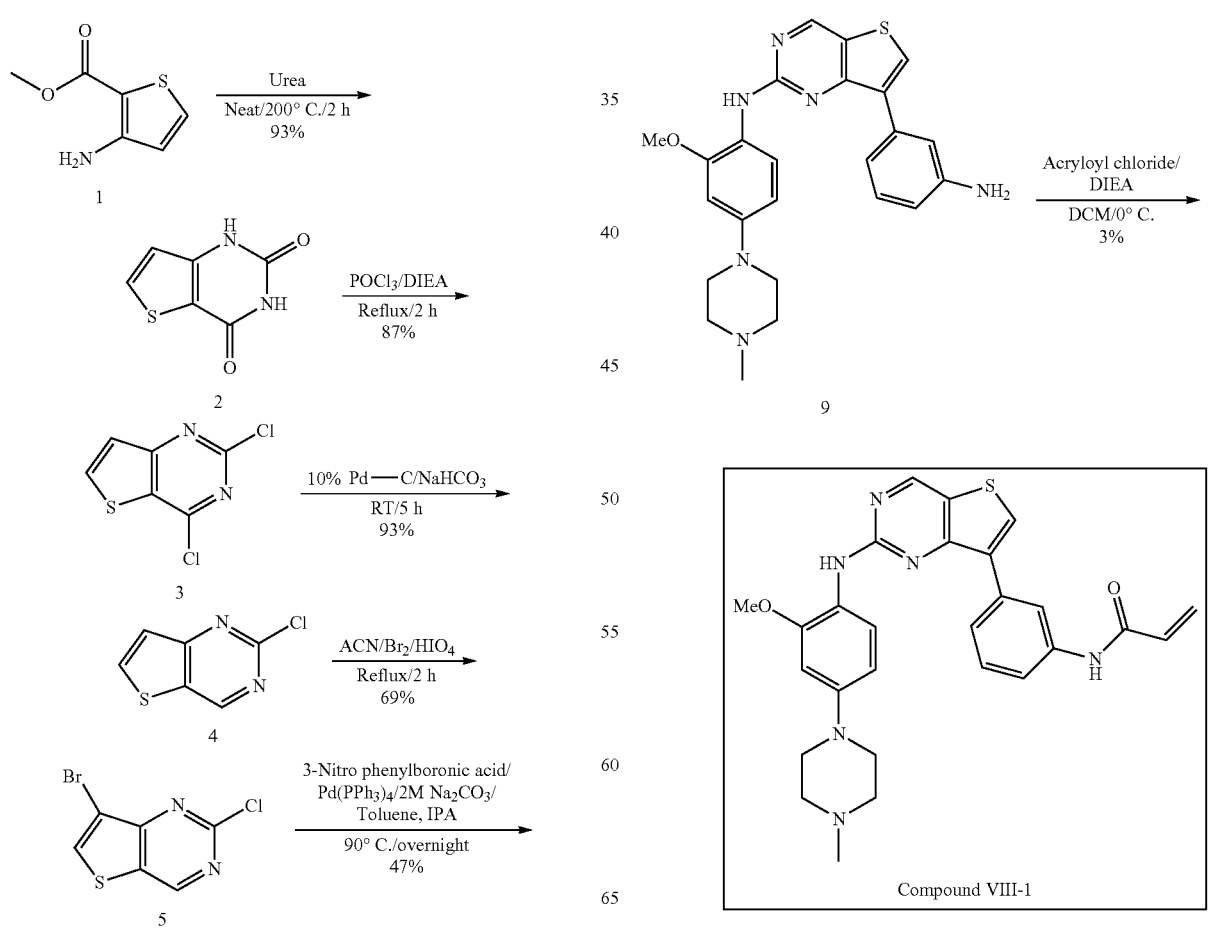

Step 1: Preparation of thieno[3,2-d]pyrimidine-2,4(1H,3H)-dione (2)

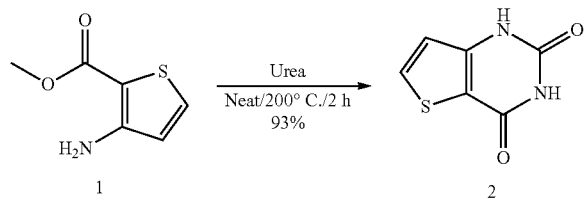

Methy 3-aminothiophene-2-carboxylate (1, 1 g, 6.36 mmol) and urea (2.19 g, 36.62 mmol) were mixed together and heated at 200° C. for 2 h. The solid obtained was dissolved in 5% aq. NaOH and filtered. The filtrate was acidified to pH 5.5 by dropwise addition of 2M HCl, resulting in a precipitate. The resultant precipitate was filtered and dried to afford cream white solid of thieno[3,2-d]pyrimidine-2,4(1H,3H)-dione (2, 1.07 g, 93.45%). $^1$HNMR (DMSO-$d_6$): 11.55 (bs, 1H), 11.20 (bs, 1H), 8.05 (d, 1H), 6.95 (d, 1H).

Step 2: Preparation of 2,4-dichlorothieno[3,2-d]pyrimidine (3)

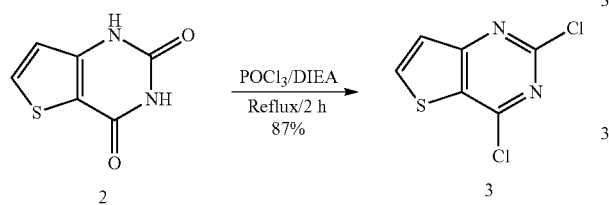

Thieno[3,2-d]pyrimidine-2,4(1H,3H)-dione (2, 5 g, 29 mmol) was taken up in POCl$_3$ (41 mL) to form a mixture. N,N-diisopropylethylamine (DIEA) (13 mL, 74 mmol) was added to the mixture and the mixture was heated to reflux for 2 h, after which product (3) was detected in the mixture by LCMS. The POCl$_3$ and DIEA were then removed from the mixture under vacuum. Water was added to the resultant residue, and the obtained aqueous layer was extracted with dichloromethane (DCM). The aqueous layer was made basic by the addition of 5N NaOH and extracted with DCM. The combined DCM extracts were then dried over Na$_2$SO$_4$ and concentrated to obtain a brown solid of 2,4-dichlorothieno[3,2-d]pyrimidine (3, 6.07 g, 87.30%). $^1$HNMR (CDCl$_3$): 8.15 (d, 1H), 7.66 (d, 1H).

Step 3: Preparation of 2-chlorothieno[3,2-d]pyrimidine (4)

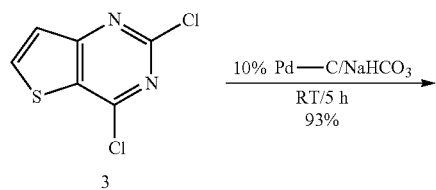

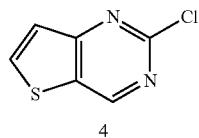

2,4-dichlorothieno[3,2-d]pyrimidine (3, 1.19 g, 5.8 mmol) was taken up in ethanol (25 mL) and ethyl acetate (25 mL) to form a mixture. NaHCO$_3$ (1.1 g, 13.1 mmol), followed by 10% Pd—C (0.206 g) were added to the mixture, and the mixture was stirred under hydrogen balloon for 5 h, after which product (4) was detected in the mixture by liquid chromatography-mass spectrometry (LCMS). The reaction mixture was then filtered through celite and concentrated to obtain an off white solid of 2-chlorothieno[3,2-d]pyrimidine (4, 0.990 g, quantitative). $^1$HNMR (CDCl$_3$): 9.17 (s, 1H), 8.16-8.12 (d, 1H), 7.55-7.51 (d, 1H).

Step 4: Preparation of 7-bromo-2-chlorothieno[3,2-d]pyrimidine (5)

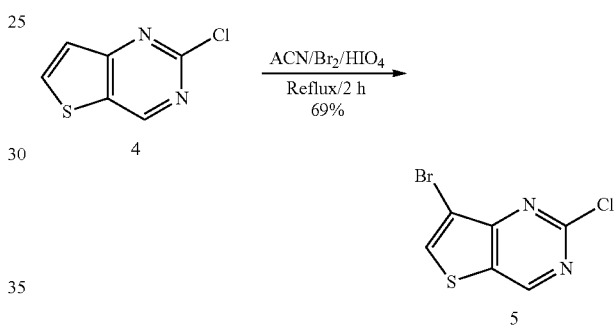

2-chlorothieno[3,2-d]pyrimidine (4, 0.9 g, 5 mmol) was taken up in acetonitrile (10 mL) to form a mixture. Bromine (0.450 mL, 8 mmol), followed by HIO$_4$ (0.558 g, 2 mmol) were added to the mixture and the mixture was refluxed for 2 h. Thin layer chromatography (TLC) of the reaction mixture showed complete conversion of compound 4 to compound 5. The reaction mixture was then cooled and poured in ethyl acetate to form a mixture. Water, followed by saturated sodium thiosulfate were added to the mixture to form a biphasic mixture having an organic layer and an aqueous layer. The organic layer was separated from the aqueous layer, washed successively with bicarbonate and brine, dried over Na$_2$SO$_4$ and concentrated to obtain 7-bromo-2-chlorothieno[3,2-d]pyrimidine (5, 1 g, 68.96%). $^1$HNMR (CDCl$_3$): 9.18 (s, 1H), 8.10 (s, 1H).

Step 5: Preparation of 2-chloro-7-(3-nitrophenyl)thieno[3,2-d]pyrimidine (6)

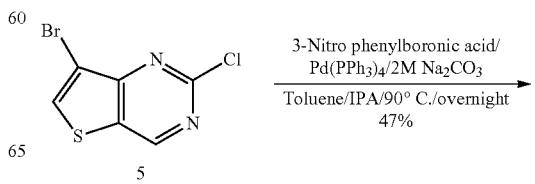

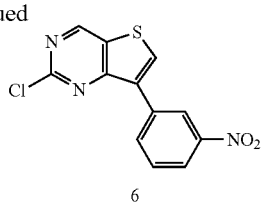

7-bromo-2-chlorothieno[3,2-d]pyrimidine (5, 0.8 g, 3.22 mmol) was taken up in a toluene (20 mL):IPA (3 mL) mixture along with 3-Nitro phenylboronic acid (0.646 g, 3.87 mmol), Pd(PPh₃)₄ (0.373 g, 0.33 mmol), and 2 M Na₂CO₃ (3.6 mL) to form a mixture. The mixture was heated at 90° C. overnight (16 h). TLC of the reaction mixture showed complete conversion of compound 5 to compound 6. The reaction mixture was cooled to room temperature, diluted with ethyl acetate, washed with 10% aq. NaHCO₃ solution, dried over Na₂SO₄ and concentrated. The concentrate was purified by column chromatography (Silica gel 20-30% ethyl acetate in hexane) to obtain a white solid of 2-chloro-7-(3-nitrophenyl)thieno[3,2-d]pyrimidine (6, 0.44 g, 46.9%). ¹HNMR (CDCl₃): 9.23 (s, 1H), 8.78 (s, 1H), 8.42-8.40 (d, 1H), 8.37 (s, 1H), 8.30-8.27 (d, 1H), 7.73-7.70 (t, 1H).

Step 6: Preparation of
2-methoxy-4-(4-methylpiperazin-1-yl)aniline (7)

Step i:
1-(3-methoxy-4-nitrophenyl)-4-methylpiperazine (12)

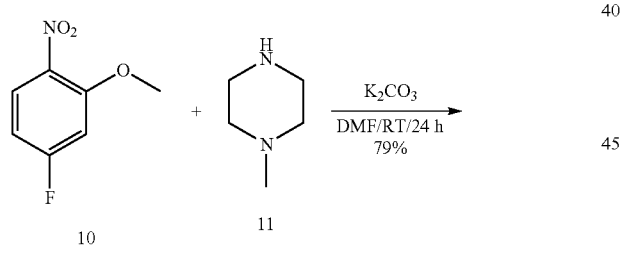

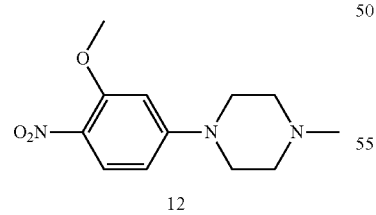

To a solution of 1-methyl-4-piperazine (11, 7.8 mL, 70) in DMF (100 mL) was added K₂CO₃ (9.68 g, 70 mmol) followed by the addition of 4-fluoro-2-methoxy-1-nitrobenzene (10, 10 g, 58 mmol) to form a mixture. The resultant mixture was stirred at room temperature overnight. The reaction mixture was then diluted with water and extracted with ethyl acetate. The organic extract was washed with brine, dried over anhydrous sodium sulfate and evaporated to dryness to afford a thick oily compound, and was triturated with diethyl ether. The obtained solid was filtered and dried to afford 1-(3-methoxy-4-nitrophenyl)-4-methylpiperazine (12, 11.5 g, 79%) as yellow solid. ¹H NMR (CDCl₃): 8.03-7.99 (d, 1H), 6.46-6.41 (d, 1H), 6.33 (s, 1H), 3.96 (s, 3H) 3.43-3.37 (m, 4H), 2.60-2.55 (m, 4H), 2.37 (s, 3H).

Step ii:
2-methoxy-4-(4-methylpiperazin-1-yl)aniline (7)

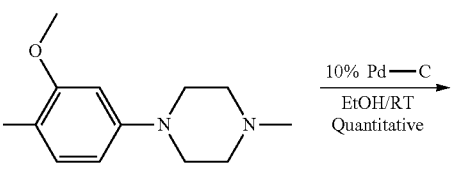

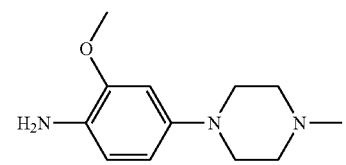

1-(3-methoxy-4-nitrophenyl)-4-methylpiperazine (12, 0.5 g, 1.99 mmol) was taken up in ethanol (10 mL) to form a mixture. 10% Pd—C was added to the mixture and the mixture was stirred under hydrogen balloon for 2 h. TLC of the reaction mixture showed complete conversion of compound 12 to compound 7. The reaction mixture was then filtered through celite and concentrated to afford 2-methoxy-4-(4-methylpiperazin-1-yl)aniline (7, 0.44 g, quantitative). ¹H NMR (CDCl₃): 6.67-6.64 (d, 1H), 6.52 (s, 1H), 6.44-6.40 (d, 1H), 3.85 (d, 1H), 3.10-3.05 (m, 4H), 2.62-2.58 (m, 4H), 2.38 (s, 3H).

Step 7: Preparation of N-(2-methoxy-4-(4-methylpiperazin-1-yl)phenyl)-7-(3-nitrophenyl)thieno[3,2-d]pyrimidin-2-amine (8)

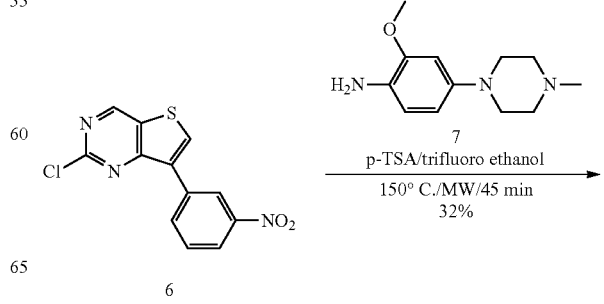

-continued

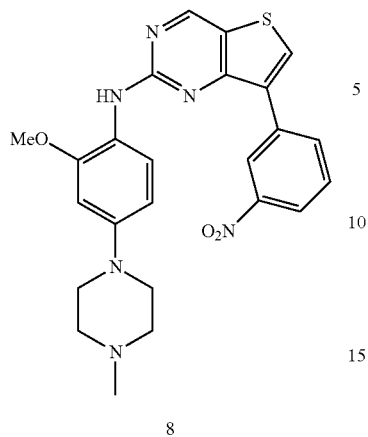

8

2-chloro-7-(3-nitrophenyl)thieno[3,2-d]pyrimidine (6, 0.5 g, 1.7 mmol) and 2-methoxy-4-(4-methylpiperazin-1-yl) aniline (7, 0.34 g, 1.5 mmol) were taken up in 2,2,2 trifluoroethanol (5 mL) along with p-toluenesulfonic acid (p-TSA) (0.980 g, 5.1 mmol) to form a mixture. The mixture was heated at 150° C. for 45 min in a microwave. The production of product 8 in the reaction mixture was monitored using LCMS. The reaction mixture was then basified with 0.5M NaOH (in CH$_3$OH) and concentrated. Water was added to the resultant concentrate and the mixture was extracted in ethyl acetate, dried over Na$_2$SO$_4$ and concentrated. The resultant concentrate was purified by column chromatography (Silica gel 10% CH$_3$OH in DCM) to obtain a yellow solid of N-(2-methoxy-4-(4-methylpiperazin-1-yl) phenyl)-7-(3-nitrophenyl)thieno[3,2-d]pyrimidin-2-amine (8, 0.265 g, 32%). $^1$HNMR (CDCl$_3$): 8.58-8.55 (d, 2H), 8.43-8.35 (dd, 2H), 8.30-8.25 (d, 1H), 8.10 (s, 1H), 7.70-7.63 (m, 2H), 6.58 (s, 1H), 6.58 (s, 1H), 3.90 (s, 3H), 3.24-3.18 (m, 4H), 2.72-2.65 (m, 4H), 2.40 (s, 3H).

Step 8: Preparation of 7-(3-aminophenyl)-N-(2-methoxy-4-(4-methylpiperazin-1-yl)phenyl)thieno[3,2-d]pyrimidin-2-amine (9)

-continued

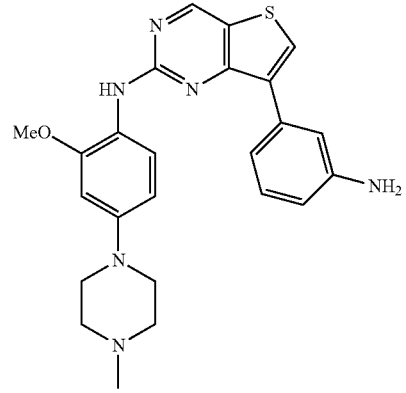

9

N-(2-methoxy-4-(4-methylpiperazin-1-yl)phenyl)-7-(3-nitrophenyl)thieno[3,2-d]pyrimidin-2-amine (8, 0.55 g, 1.1 mmol) was taken up in methanol (10 mL) to form a mixture. 10% Pd—C (0.055 g, 10 mol %) was added to the mixture and the mixture was stirred under hydrogen balloon for 1 h. TLC of the reaction mixture showed complete conversion of compound 8 to compound 9. The reaction mixture was then filtered through celite and the filtrate was concentrated to obtain 7-(3-aminophenyl)-N-(2-methoxy-4-(4-methylpiperazin-1-yl)phenyl)thieno[3,2-d]pyrimidin-2-amine (9, 0.41 g, 79.61%). $^1$HNMR (CDCl$_3$): 8.90 (s, 1H), 8.60-8.57 (d, 1H), 7.92 (s, 1H), 7.68-7.60 (d, 1H), 7.37-7.22 (m, 3H), 6.77-6.70 (d, 1H), 6.61 (s, 1H), 6.60 (s, 1H), 3.90 (s, 3H), 3.80 (bs, 2H) 3.20-3.15 (m, 4H), 2.62-2.57 (m, 4H), 2.38 (s, 3H).

Step 9: Preparation of N-(3-(2-((2-methoxy-4-(4-methylpiperazin-1-yl)phenyl)amino)thieno[3,2-d]pyrimidin-7-yl)phenyl)acrylamide (Compound VIII-1)

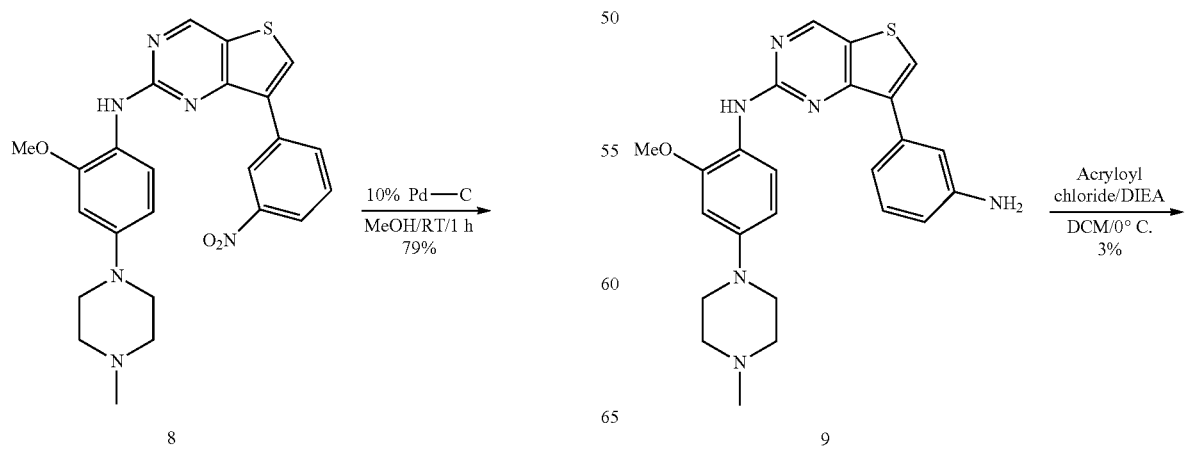

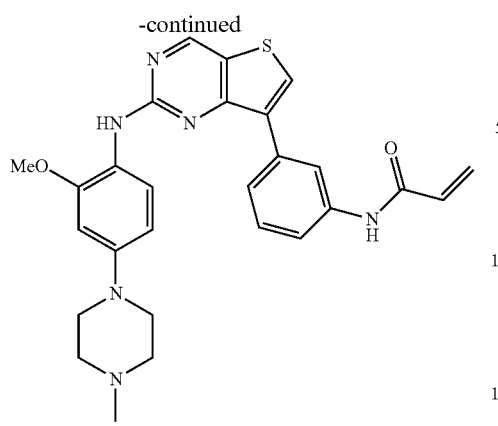

Compound VIII-1

7-(3-aminophenyl)-N-(2-methoxy-4-(4-methylpiperazin-1-yl)phenyl)thieno[3,2-d]pyrimidin-2-amine (9, 0.2 g, 0.448 mmol) was taken up in DCM (10 mL) to form a mixture and the mixture was cooled to 0° C. DIEA (0.116 g, 0.896 mmol) was added to the mixture and the mixture was stirred for 5 min. Acryloyl chloride (0.041 g, 0.0.448 mmol) solution in DCM (1 mL) was added dropwise to the mixture and quenched immediately after one minute. The mixture was extracted in DCM, dried over sodium sulfate and concentrated. The resultant concentrate was purified twice by preparative silica gel TLC Plate (5% CH$_3$OH in DCM) to obtain N-(3-(2-((2-methoxy-4-(4-methylpiperazin-1-yl)phenyl)amino)thieno[3,2-d]pyrimidin-7-yl)phenyl)acrylamide (Compound VIII-1, 0.008 g, 3.57%). $^1$HNMR (CDCl$_3$): 8.90 (s, 1H), 8.53-8.50 (d, 1H), 8.30 (s, 1H), 8.04 (s, 1H), 8.02-7.96 (m, 1H), 7.73-7.70 (s, 1H), 7.66 (s, 1H), 7.50-7.45 (t, 1H), 7.33 (s, 1H), 6.60-6.45 (m, 3H), 6.33-6.26 (m, 1H), 5.83-5.80 (d, 1H), 3.92 (s, 3H), 3.20-3.15 (m, 4H), 2.62-2.57 (m, 4H), 2.38 (s, 3H).

Example 4: Synthesis of Compound IV-1

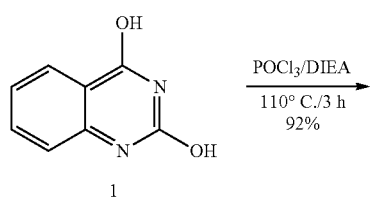

1

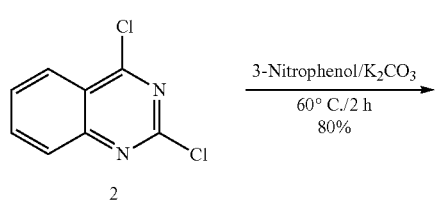

2

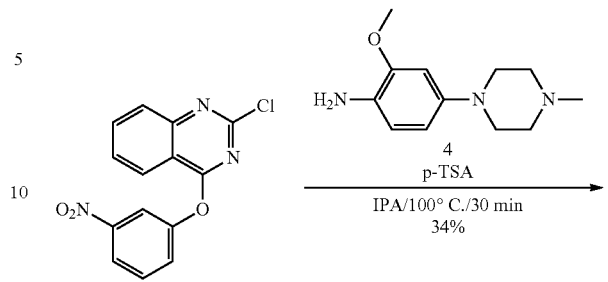

3

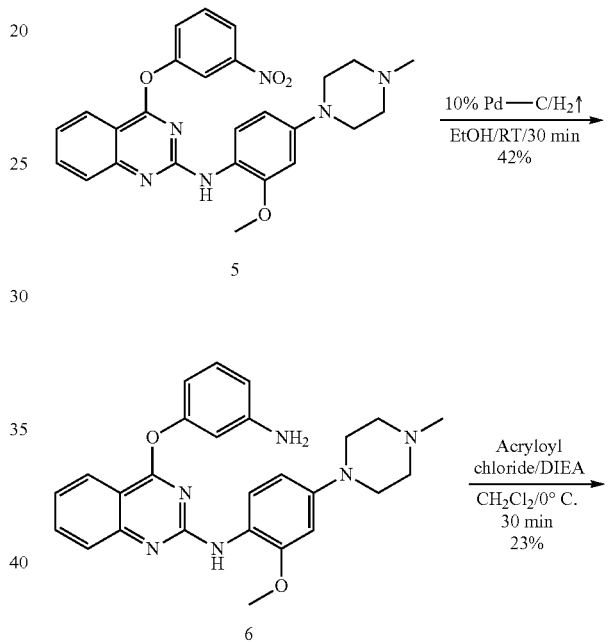

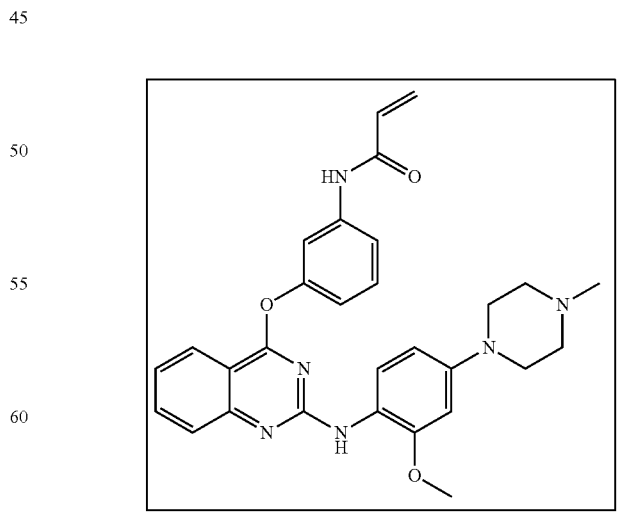

Compound IV-1

Step 1: Preparation of 2,4-Dichloroquinazoline (2)

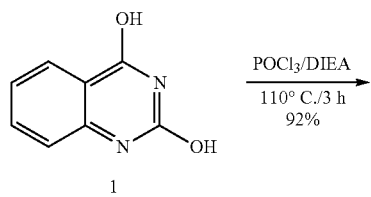

To a stirred suspension of quinazoline-2,4-diol (1, 5 g, 30.86 mmol) and DIEA (12.3 mL, 70.9 mmol), POCl₃ (25 mL. 270 mmol) was added and the suspension was stirred at 110° C. for 3 h. The reaction mixture was concentrated to dryness, basified with aqueous NaHCO₃ solution, and extracted with ethyl acetate. The organic extract was dried over anhydrous sodium sulfate and evaporated to dryness to afford 2,4-Dichloroquinazoline as yellow solid (2, 6 g, 98.4%). ¹H NMR (CDCl₃): δ 8.30-8.20 (d, 1H), 8.10-8.00 (m, 2H), 7.80-7.70 (d, 1H).

Step 2: Preparation of 2-Chloro-4-(3-nitrophenoxy)quinazoline (3)

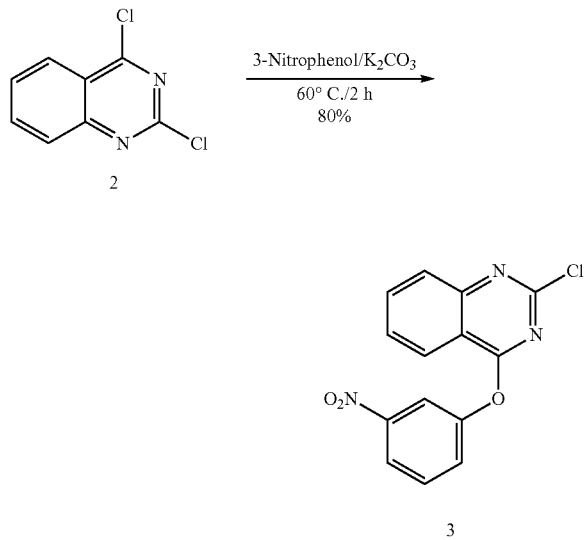

To a solution of 3-nitro phenol (3.77 g, 27.1 mmol) in dimethyl formamide (DMF) (90 mL) was added K₂CO₃ (7.5 g, 54.2 mmol) followed by the addition of 2,4-Dichloroquinazoline (2, 5.4 g, 27.1 mmol) to form a mixture. The mixture was then stirred at 60° C. for 2 h. The reaction mixture was filtered, and the filtrate was diluted with ethyl acetate and washed with water to form a biphasic mixture. The organic layer of the biphasic mixture was separated and washed with brine, dried over anhydrous sodium sulfate and evaporated to dryness to afford 2-Chloro-4-(3-nitrophenoxy) quinazoline as a yellow solid (3, 7 g, 86%). ¹H NMR (CDCl₃): δ 8.40-8.30 (d, 1H), 8.30-8.20 (m, 2H), 8.00-7.90 (m, 2H), 7.80-7.60 (m, 3H).

Step 3: Preparation of N-(2-methoxy-4-(4-methyl-piperazin-1-yl)phenyl)-4-(3-nitrophenoxy)quinazolin-2-amine (5)

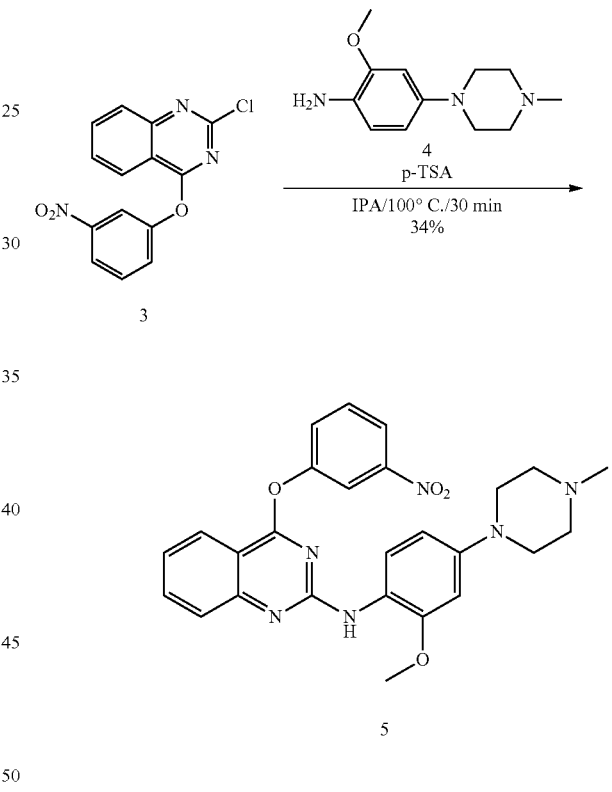

To a solution of 2-Chloro-4-(3-nitrophenoxy)quinazoline (3, 500 mg, 1.66 mmol) in isopropanol (IPA) (20 mL) was added p-TSA (315 mg, 1.66 mmol) and compound 4 (367 mg, 1.66 mmol). The solution was then stirred at 100° C. for 30 min. The reaction was monitored by TLC. After completion of the reaction, the reaction mixture was concentrated to dryness, diluted with water, and extracted with ethyl acetate. The organic extract was dried over anhydrous sodium sulfate and evaporated under reduced pressure. The resultant crude product was purified by column chromatography using 2-5% CH₃OH-DCM to afford N-(2-methoxy-4-(4-methylpiperazin-1-yl)phenyl)-4-(3-nitrophenoxy)quinazolin-2-amine as yellow solid (5, 0.28 g, 34.6%). ¹H NMR (CDCl₃): δ 8.30-8.10 (m, 3H), 7.80-7.60 (m, 4H), 7.40-7.20 (m, 2H), 6.50 (s, 1H), 6.40 (bs, 1H), 3.80 (s, 3H), 3.20-3.00 (m, 4H), 2.70-2.60 (m, 4H), 2.40 (s, 3H).

Step 4: Preparation of 4-(3-aminophenoxy)-N-(2-methoxy-4-(4-methylpiperazin-1-yl)phenyl)quinazolin-2-amine (6)

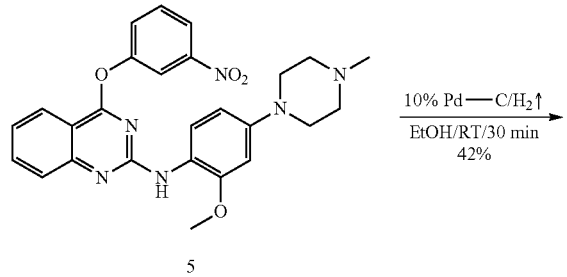

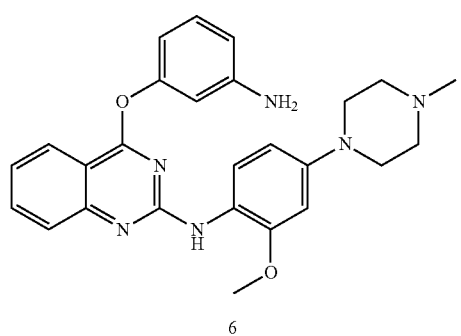

To a solution of N-(2-methoxy-4-(4-methylpiperazin-1-yl)phenyl)-4-(3-nitrophenoxy)quinazolin-2-amine (5, 0.3 g, 0.61 mmol) in ethanol (20 mL) was added 10% Pd—C (50 mg) and the solution was stirred under hydrogen atmosphere for 30 min. After completion of the reaction, the reaction mixture was filtered through celite, washed with ethanol, and concentrated to dryness to afford 4-(3-aminophenoxy)-N-(2-methoxy-4-(4-methylpiperazin-1-yl)phenyl)quinazolin-2-amine (6, 0.12 g, 42.7%). $^1$H NMR (CDCl$_3$): δ 8.20-8.10 (d, 2H), 7.80-7.70 (d, 1H), 7.70-7.60 (m, 2H), 7.40-7.00 (m, 2H), 6.70-6.60 (m, 2H), 6.50-6.40 (m, 2H), 3.80 (s, 3H), 3.30-3.10 (m, 4H), 2.80-2.70 (m, 4H), 2.50 (s, 3H).

Step 5: Preparation of N-(3-((2-((2-methoxy-4-(4-methylpiperazin-1-yl)phenyl)amino)quinazolin-4-yl)oxy)phenyl)acrylamide (Compound IV-1)

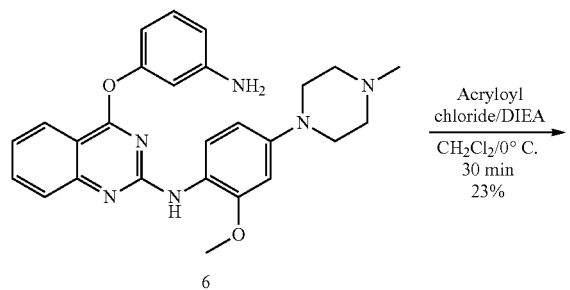

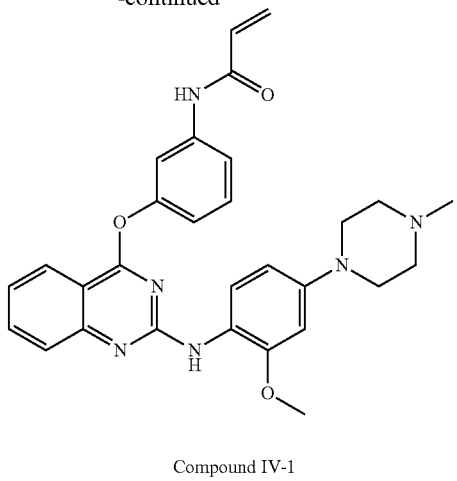

4-(3-Aminophenoxy)-N-(2-methoxy-4-(4-methylpiperazin-1-yl)phenyl)quinazolin-2-amine (6, 430 mg, 0.94 mmol) was taken up in DCM (30 mL) to form a mixture. DIEA (0.163 mL, 0.94 mmol) was then added slowly to the mixture and the mixture was cooled to 0° C. Acryloyl chloride (76 μL, 0.94 mmol) was then added slowly to the mixture and the mixture was stirred at 0° C. for 30 min. The reaction was monitored using TLC. After completion of the reaction, the reaction mixture was quenched with NaHCO$_3$ solution and extracted with dichloromethane. The organic extract was then evaporated under reduced pressure to obtain a crude product. The resultant crude product was purified by preparative TLC using 5% CH$_3$OH-DCM to afford 110 mg (84.1% by HPLC) of Compound IV-1 as a yellow solid. 35 mg of Compound IV-1 was further purified by preparative TLC to afford 5 mg (97.4% by HPLC) of N-(3-((2-((2-methoxy-4-(4-methylpiperazin-1-yl)phenyl)amino)quinazolin-4-yl)oxy)phenyl)acrylamide (Compound IV-1) as a pale yellow solid (110 mg, 22.9%). $^1$H NMR (CDCl$_3$): δ 8.20-8.10 (d, 2H), 7.80-7.60 (m, 3H), 7.60-7.40 (m, 2H), 7.30-7.20 (m, 2H), 7.10-7.00 (d, 1H), 6.50-6.40 (m, 1H), 6.50-6.40 (m, 1H), 6.30-6.20 (m, 1H), 5.80-5.70 (d, 1H), 3.80 (s, 3H), 3.20 (s, 4H), 2.60 (s, 4H), 2.40 (s, 3H).

Example 5: Synthesis of Compound IV-2

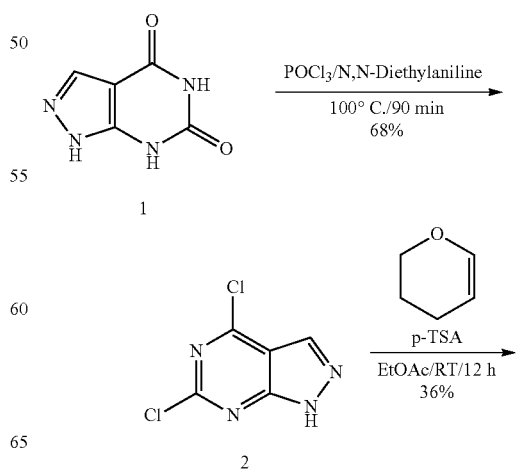

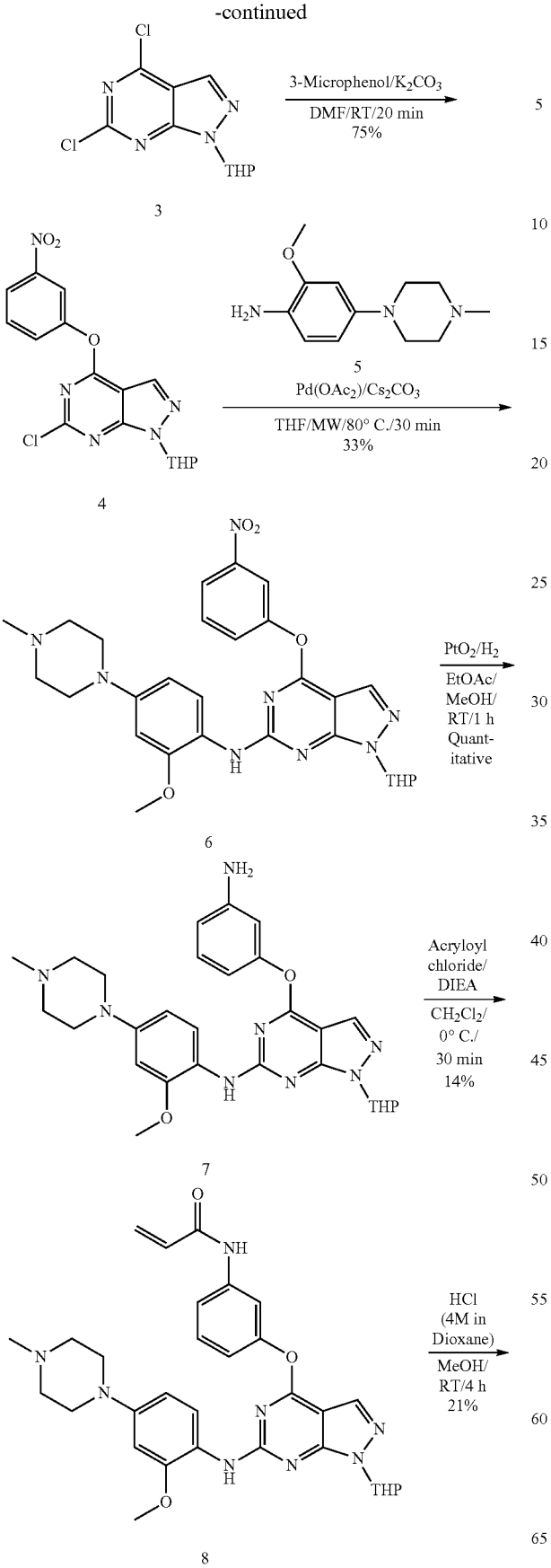

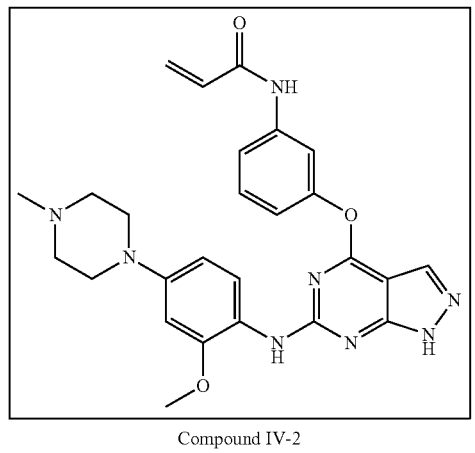

Compound IV-2

Step 1: Synthesis of 4,6-dichloro-1H-pyrazolo[3,4-d]pyrimidine (1)

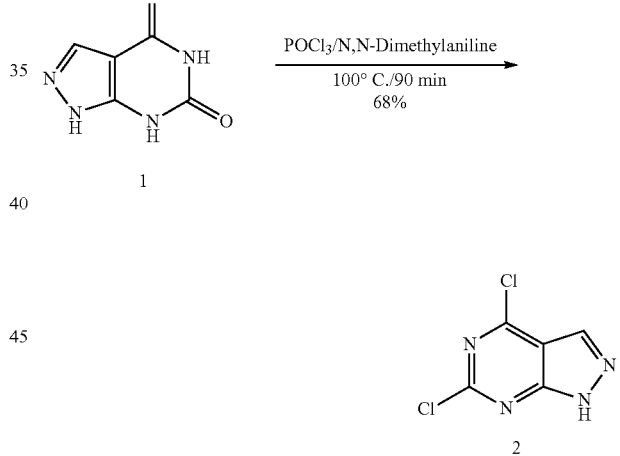

POCl₃ (1 mL, re distilled) and N,N-diethyl aniline (0.5 mL) were added sequentially to 1H-pyrazolo[3,4-d]pyrimidine-4,6(5H,7H)-dione (1, 0.5 g, 3.2 mmol) to form a slurry. The resulting slurry was then heated from room temperature to 100° C. for 90 min. The reaction mixture was the cooled to room temperature and concentrated under vacuum. The resulting concentrate was then poured onto ice while stirring to form a mixture. The mixture was slowly filtered through celite (green impurities were removed), and the resulting crude product was extracted with diethyl ether (aqueous layer is pink). The combined organic extracts were concentrated to afford a light yellow product, which was used as such for the next step. (2, 0.42, 68%). ¹H NMR (400 MHz, CDCl₃): δ 8.30 (s, 1H).

Step 2: Synthesis of 4,6-dichloro-1-(tetrahydro-2H-pyran-2-yl)-1H-pyrazolo[3,4-d]pyrimidine (2)

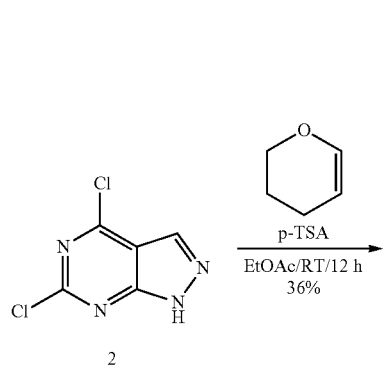

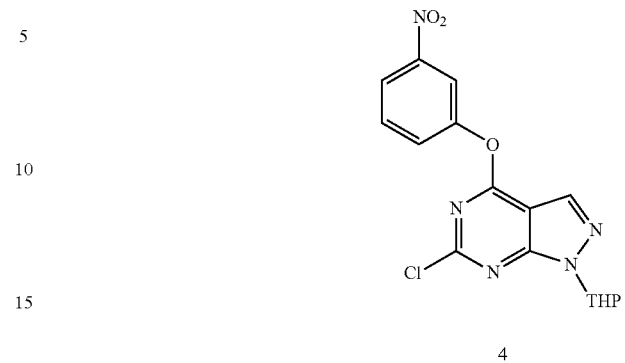

4,6-dichloro-1H-pyrazolo[3,4-d]pyrimidine (2, 0.21 g, 1.1 mmol), dihydropyran (DHP) (0.3 mL) and p-TSA (7 mg) were taken up in ethyl acetate (5 mL) to form a mixture and the mixture was stirred at room temperature for 12 h. The progress of the reaction was monitored by TLC. After completion of the reaction, the reaction mixture was diluted with ethyl acetate, washed with water, dried over anhydrous sodium sulfate and evaporated to dryness to obtain a crude product. The crude product was purified by column chromatography using 20% EtOAc-hexane to afford 4,6-dichloro-1-(tetrahydro-2H-pyran-2-yl)-1H-pyrazolo[3,4-d]pyrimidine (3, 0.11 g, 36%). $^1$H NMR (400 MHz, CDCl$_3$): δ 8.25 (s, 1H), 6.04-6.00 (d, 1H), 4.18-4.13 (m, 1H), 3.85-3.80 (t, 1H), 2.60-2.58 (m, 1H), 2.17-2.15 (m, 1H), 1.99-1.96 (d, 1H), 1.84-1.82 (t, 2H), 1.77-1.76 (d, 1H).

Step 3: Synthesis of 6-chloro-4-(3-nitrophenoxy)-1-(tetrahydro-2H-pyran-2-yl)-1H-pyrazolo[3,4-d]pyrimidine (4)

4,6-dichloro-1-(tetrahydro-2H-pyran-2-yl)-1H-pyrazolo[3,4-d]pyrimidine (3, 0.3 g, 1 mmol) and potassium carbonate (0.151 g, 1 mmol) in 4 mL of DMF were combined to form a mixture and 3-nitro phenol (0.152 g, 1 mmol) was added to the mixture, and the mixture was stirred at room temperature for 30 min. The progress of the reaction was monitored by TLC and liquid chromatography-mass spectrometry (LC-MS). After completion of the reaction, water was added to the reaction mixture and the reaction mixture was extracted with ethyl acetate. The resulting organic extract was washed with brine, dried over anhydrous sodium sulfate and evaporated to dryness to obtain a crude product. The crude product was purified on silica gel using 20% EtOAc-hexane to afford 6-chloro-4-(3-nitrophenoxy)-1-(tetrahydro-2H-pyran-2-yl)-1H-pyrazolo[3,4-d]pyrimidine (4, 0.31 g, 75%). $^1$H NMR (400 MHz, CDCl$_3$): δ 8.24-8.22 (d, 2H), 8.17 (s, 1H), 7.70-7.62 (m, 2H), 6.05-6.00 (d, 1H), 4.18-4.13 (m, 1H), 3.86-3.80 (t, 1H), 2.60-2.58 (m, 1H), 2.17-2.16 (m, 1H), 1.99-1.96 (d, 1H), 1.84-1.82 (m, 2H), 1.77-1.76 (d, 1H).

Step 4: Synthesis of N-(2-methoxy-4-(4-methylpiperazin-1-yl)phenyl)-4-(3-nitrophenoxy)-1-(tetrahydro-2H-pyran-2-yl)-1H-pyrazolo[3,4-d]pyrimidin-6-amine (6)

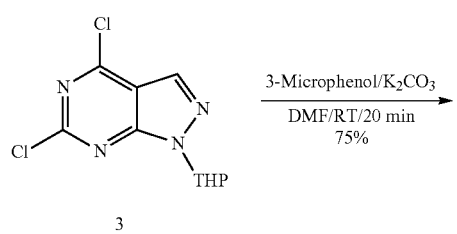

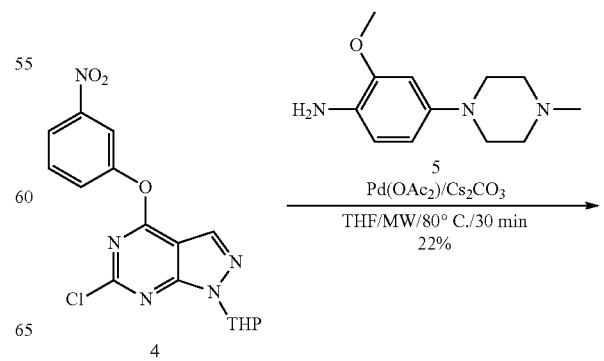

125 -continued

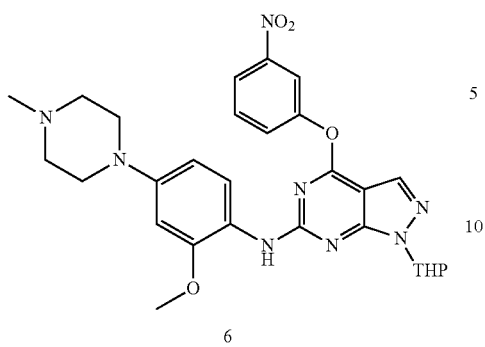

6

6-chloro-4-(3-nitrophenoxy)-1-(tetrahydro-2H-pyran-2-yl)-1H-pyrazolo[3,4-d]pyrimidine (4, 0.15 g, 0.4 mmol), 2-methoxy-4-(4-methylpiperazin-1-yl)aniline (5, 88 mg, 0.4 mmol), Pd(OAc)$_2$ (5 mg, 0.02 mmol), X-phos (23 mg, 0.04 mmol) and Cs$_2$CO$_3$ (390 mg, 1.2 mmol) were taken up in tetrahydrofuran (THF) (2 mL) to form a mixture and the mixture was placed under microwave irradiation at 85° C. for 45 min. The progress of the reaction was monitored by TLC. After completion of the reaction, the reaction mixture was concentrated, and water was added. The resulting mixture was then extracted with ethyl acetate and the organic extract was dried over anhydrous sodium sulfate and evaporated to dryness to form a crud product. The crude product was purified by column chromatography using 3% MeOH-DCM to afford N-(2-methoxy-4-(4-methyl piperazin-1-yl)phenyl)-4-(3-nitrophenoxy)-1-(tetrahydro-2H-pyran-2-yl)-1H-pyrazolo[3,4-d]pyrimidin-6-amine (6, 49 mg, 22%). $^1$H NMR (400 MHz, CDCl$_3$): δ 8.30-8.22 (m, 2H), 7.95 (s, 1H), 7.68-7.60 (m, 3H), 7.40 (s, 1H), 6.55 (s, 1H), 5.90-5.85 (d, 1H), 4.19-4.10 (d, 1H), 3.85 (s, 3H), 3.80-3.79 (m, 1H), 3.18 (bs, 4H), 2.65-2.60 (m, 5H), 2.36 (s, 3H), 2.19-2.18 (m, 1H), 1.95-1.90 (d, 1H), 1.80-1.78 (m, 2H), 1.65-1.60 (d, 1H).

Step 5: Synthesis of 4-(3-aminophenoxy)-N-(2-methoxy-4-(4-methylpiperazin-1-yl)phenyl)-1-(tetrahydro-2H-pyran-2-yl)-1H-pyrazolo[3,4-d]pyrimidin-6-amine (7)

126 -continued

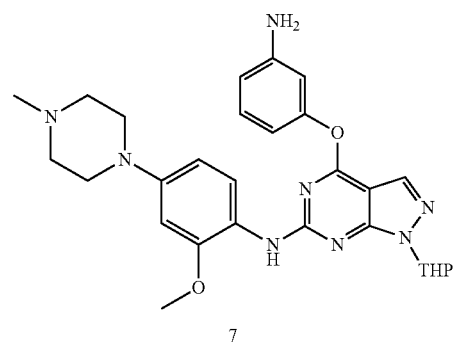

7

N-(2-methoxy-4-(4-methylpiperazin-1-yl)phenyl)-4-(3-nitrophenoxy)-1-(tetrahydro-2H-pyran-2-yl)-1H-pyrazolo[3,4-d]pyrimidin-6-amine (6, 200 mg, 0.35 mmol) was taken up in mixture of EtOAC:CH$_3$OH (5 mL:15 mL) to form a mixture, and PtO$_2$ (11 mg) was added to the mixture. The mixture was then stirred at room temperature for 1 h under hydrogen atmosphere. The progress of the reaction was monitored by TLC. After completion of the reaction, the reaction mixture was filtered through celite, washed with ethyl acetate and evaporated under reduced pressure to afford 4-(3-aminophenoxy)-N-(2-methoxy-4-(4-methylpiperazin-1-yl)phenyl)-1-(tetrahydro-2H-pyran-2-yl)-1H-pyrazolo[3,4-d]pyrimidin-6-amine as off white solid (7, 0.189 g, quantitative). $^1$H NMR (400 MHz, CDCl$_3$): δ 8.30-8.20 (m, 1H), 7.60-7.50 (m, 1H), 7.50-7.30 (m, 1H), 6.90-6.85 (m, 2H), 6.85-6.80 (d, 1H), 6.70-6.60 (d, 1H), 6.60-6.40 (m, 1H), 5.90-5.80 (d, 1H), 4.20-4.10 (d, 1H), 3.90 (s, 3H), 3.85-3.80 (d, 1H), 3.20 (bs, 4H), 2.60 (bs, 4H), 2.60-2.50 (m, 1H), 2.40 (s, 3H), 2.20-2.10 (m, 1H), 2.00-1.90 (d, 1H), 1.80-1.70 (m, 3H).

Step 6: Synthesis of N-(3-((6-((2-methoxy-4-(4-methylpiperazin-1-yl)phenyl)amino)-1-(tetrahydro-2H-pyran-2-yl)-1H-pyrazolo[3,4-d]pyrimidin-4-yl)oxy)phenyl)acrylamide (8)

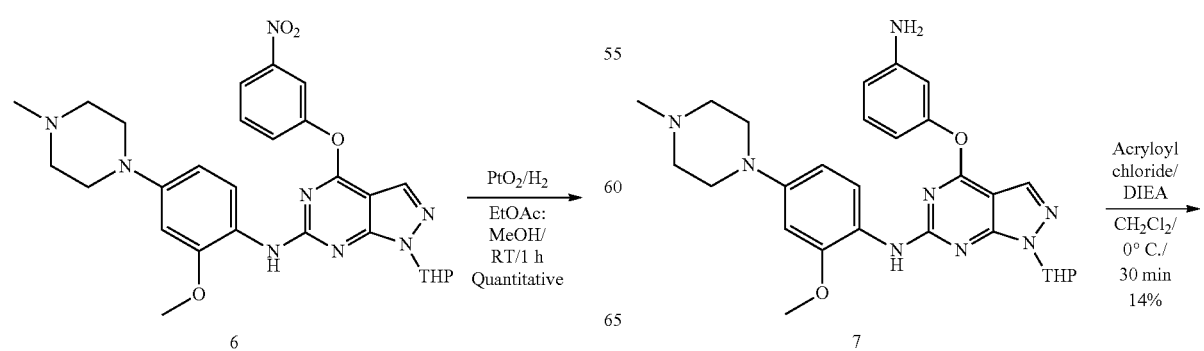

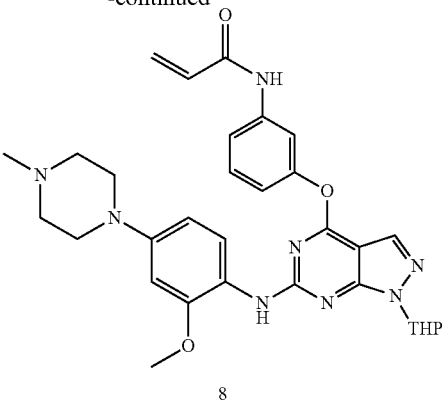

8

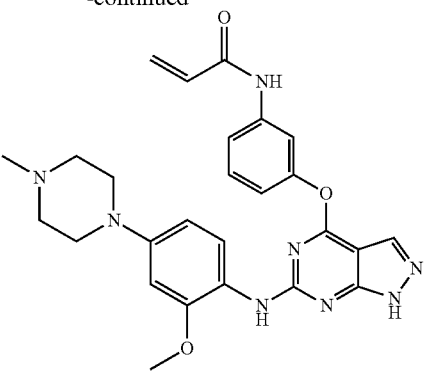

Compound IV-2

To a solution of 4-(3-aminophenoxy)-N-(2-methoxy-4-(4-methylpiperazin-1-yl)phenyl)-1-(tetrahydro-2H-pyran-2-yl)-1H-pyrazolo[3,4-d]pyrimidin-6-amine (7, 200 mg, 0.37 mmol) in dry DCM (10 mL), was added N,N,-diisopropylethylamine (DIEA) (0.06 mL, 0.37 mmol) to form a mixture. The mixture was then stirred at room temperature for 10 min. The mixture was then cooled to 0° C., acryloyl chloride (0.03 mL dissolved in 0.5 mL of dry DCM, 0.37 mmol) was added to the mixture, and the mixture was stirred at 0° C. for 30 min. The progress of the reaction was monitored by TLC. After completion of the reaction, the reaction mixture was quenched with saturated sodium bicarbonate solution and extracted with dichloromethane. The resulting organic extract was dried over anhydrous sodium sulfate, concentrated under reduced pressure and purified using preparative TLC (5% MeOH-DCM) to afford N-(3-((6-((2-methoxy-4-(4-methylpiperazin-1-yl)phenyl)amino)-1-(tetrahydro-2H-pyran-2-yl)-1H-pyrazolo[3,4-d]pyrimidin-4-yl)oxy)phenyl)acrylamide as off-white solid. (8, 31 mg, 14%). $^1$H NMR (400 MHz, DMSO): δ 7.80 (s, 1H), 7.70 (s, 1H), 7.70-7.58 (d, 1H), 7.50-7.40 (t, 1H), 7.10-7.00 (d, 1H), 6.60 (s, 1H), 6.50-6.40 (m, 1H), 6.30 (s, 1H), 6.00-5.90 (m, 1H), 5.90-5.80 (m, 1H), 5.80-5.78 (d, 1H), 5.70-5.60 (d, 1H), 4.00-3.90 (d, 1H), 3.80 (s, 3H), 3.70-3.60 (m, 1H), 3.10 (bs, 4H), 2.40 (bs, 4H), 2.20 (s, 3H), 2.00-1.90 (d, 1H), 1.90-1.80 (d, 1H), 1.80-1.60 (m, 2H), 1.60-1.50 (m, 2H).

Step 7: Synthesis of N-(3-((6-((2-methoxy-4-(4-methylpiperazin-1-yl)phenyl)amino)-1H-pyrazolo[3,4-d]pyrimidin-4-yl)oxy)phenyl)acrylamide (Compound IV-2)

To a solution of N-(3-((6-((2-methoxy-4-(4-methylpiperazin-1-yl)phenyl)amino)-1-(tetrahydro-2H-pyran-2-yl)-1H-pyrazolo[3,4-d]pyrimidin-4-yl)oxy)phenyl)acrylamide (8, 23 mg, 0.039 mmol) in methanol (2 mL) was added 4M HCl in dioxane (0.1 mL) to form a mixture and the mixture was stirred at room temperature for 4 h. The progress of the reaction was monitored by LC-MS. After completion of the reaction, the reaction mixture was concentrated to dryness and triturated with diethyl ether to afford 20 mg of N-(3-((6-((2-methoxy-4-(4-methylpiperazin-1-yl)phenyl)amino)-1H-pyrazolo[3,4-d]pyrimidin-4-yl)oxy)phenyl)acrylamide as HCl salt. The salt was converted to free base with an ammonia solution (25% aqueous). The resulting crude product was purified by preparative high performance liquid chromatograph (HPLC) using neutral conditions (without TFA in mobile phase) to afford 4 mg of Compound IV-2 as free base (4 mg, 21%). $^1$H NMR (400 MHz, CD$_3$OD): δ 8.00-7.90 (m, 1H), 7.80 (s, 1H), 7.70-7.60 (d, 1H), 7.60-7.50 (m, 1H), 7.50-7.40 (t, 1H), 7.10-7.00 (d, 1H), 6.60 (s, 1H), 6.40-6.30 (m, 3H), 5.80-5.70 (d, 1H), 3.80 (s, 3H), 3.40-3.30 (m, 8H), 2.90 (s, 3H).

Example 6: Synthesis of Compound IV-3

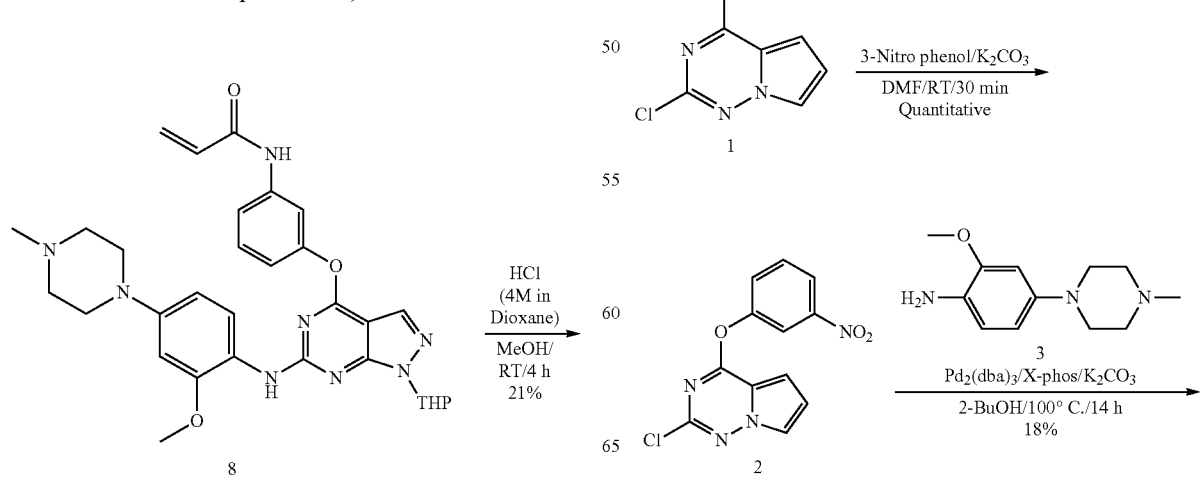

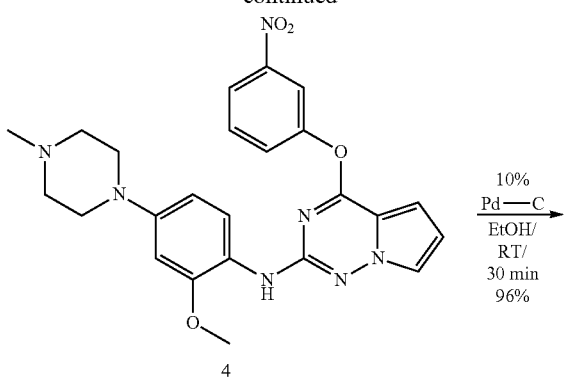

4

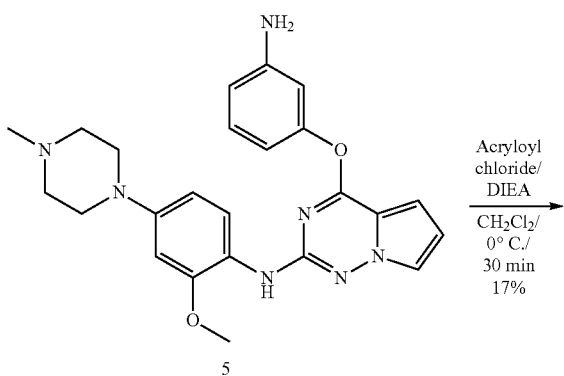

5

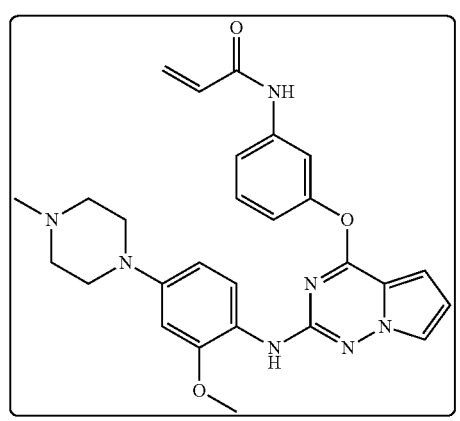

Compound IV-3

Step 1: Synthesis of 2-chloro-4-(3-nitrophenoxy)pyrrolo[2,1-f][1,2,4]triazine (2)

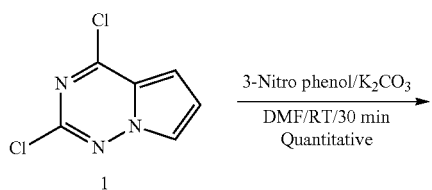

2,4-dichloropyrrolo[2,1-f][1,2,4]triazine (1, 2 g, 10.6 mmol) was taken up in DMF (40 mL) to form a mixture, and K$_2$CO$_3$ (1.46 g, 10.6 mmol) and 3-nitro phenol (1.47 g, 10.6 mmol) were added to the mixture and the mixture was stirred at room temperature for 30 min. The progress of the reaction was monitored by TLC. After completion of the reaction, ice was added to the reaction mixture and the obtained solid was filtered and dried to afford 2-chloro-4-(3-nitrophenoxy)pyrrolo[2,1-f][1,2,4]triazine as white solid (2, 3 g, quantitative). $^1$H NMR (400 MHz, CDCl$_3$): δ 8.30-8.20 (m, 2H), 7.80 (s, 1H), 7.70-7.60 (m, 2H), 7.15-7.10 (d, 1H), 6.95-6.90 (d, 1H).

Step 2: Synthesis of N-(2-methoxy-4-(4-methylpiperazin-1-yl)phenyl)-4-(3-nitro phenoxy)pyrrolo[2,1-f][1,2,4]triazin-2-amine (4)

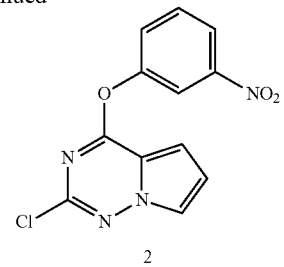

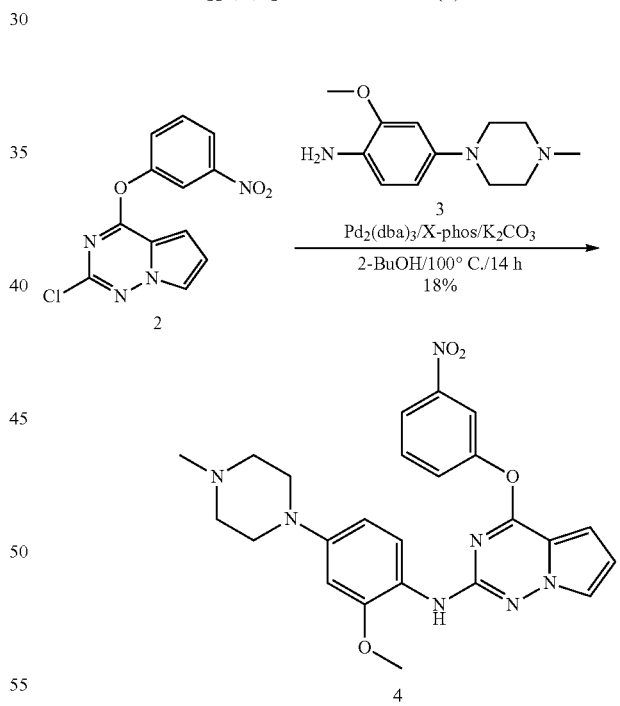

To a solution of 2-chloro-4-(3-nitrophenoxy)pyrrolo[2,1-f][1,2,4]triazine (2, 2 g, 6.89 mmol) in 2-BuOH (50 mL) was added 2-methoxy-4-(4-methylpiperazin-1-yl)aniline (3, 1.52 g, 6.89 mmol), Pd$_2$(dba)$_3$ (71 mg, 0.068 mmol), X-phos (98 mg, 0.2 mmol), and K$_2$CO$_3$ (1.9 g, 13.78 mmol). The resulting mixture was then stirred at 100° C. for 14 h. The progress of the reaction was monitored by TLC. After completion of the reaction, the reaction mixture was concentrated, diluted with water, and extracted with ethyl acetate. The resulting organic extract was dried over anhydrous sodium sulfate and evaporated to dryness to obtain a crude product. The crude product was purified by column chromatography using ethyl acetate to afford N-(2-methoxy-4-(4-methylpiperazin-1-yl)phenyl)-4-(3-nitrophenoxy)pyrrolo[2,1-f][1,2,4]triazin-2-amine as brown solid (4, 0.6 g, 18%). $^1$H NMR (400 MHz, CDCl$_3$): δ 8.30-8.10 (m, 3H), 7.70-7.60 (m, 3H), 6.95-6.90 (d, 1H), 6.80 (s, 1H), 6.70-6.60 (d, 1H), 6.50-6.40 (t, 1H), 3.80 (s, 3H), 3.20-3.10 (m, 4H), 2.70-2.50 (m, 4H), 2.40 (s, 3H).

Step 3: 4-(3-aminophenoxy)-N-(2-methoxy-4-(4-methylpiperazin-1-yl)phenyl)pyrrolo[2,1-f][1,2,4]triazin-2-amine (5)

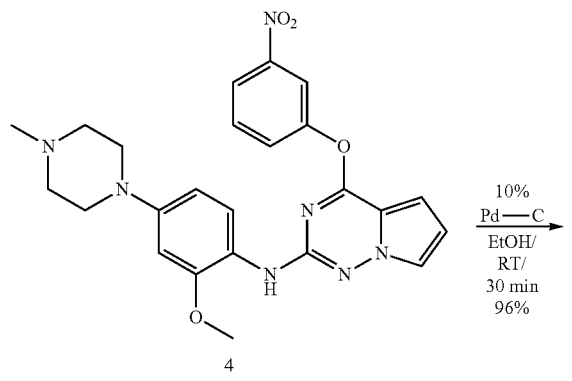

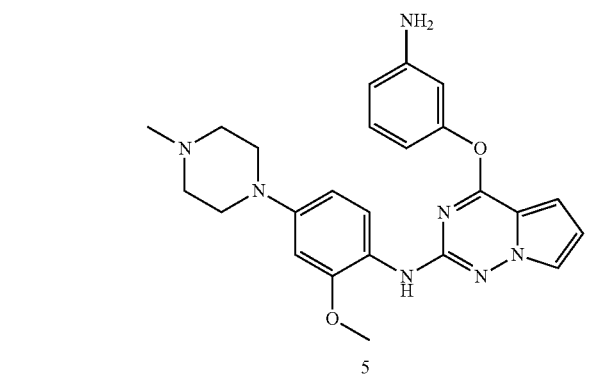

To a solution of N-(2-methoxy-4-(4-methylpiperazin-1-yl)phenyl)-4-(3-nitrophenoxy)pyrrolo[2,1-f][1,2,4]triazin-2-amine (4, 0.2 g, 0.42 mmol) in ethanol (10 mL) was added 10% Pd—C (20 mg). The resulting mixture was stirred at room temperature under hydrogen atmosphere for 30 min. The progress of the reaction was monitored by TLC. After completion of the reaction, the reaction mixture was filtered through celite and washed with ethanol. The ethanol was then evaporated under reduced pressure to afford 4-(3-aminophenoxy)-N-(2-methoxy-4-(4-methylpiperazin-1-yl) phenyl)pyrrolo[2,1-f][1,2,4]triazin-2-amine as a light yellow solid (5, 0.18 g, 96%). $^1$H NMR (400 MHz, CDCl$_3$): δ 8.30-8.20 (d, 1H), 7.60 (s, 1H), 7.22-7.20 (t, 1H), 6.90 (s, 1H), 6.80-6.78 (d, 1H), 6.70-6.50 (m, 5H), 3.80 (s, 3H), 3.30-3.10 (m, 4H), 2.70-2.60 (m, 4H), 2.40 (s, 3H).

Step 4: N-(3-((2-((2-methoxy-4-(4-methylpiperazin-1-yl)phenyl)amino)pyrrolo[2,1-f][1,2,4]triazin-4-yl)oxy)phenyl)acrylamide (Compound IV-3)

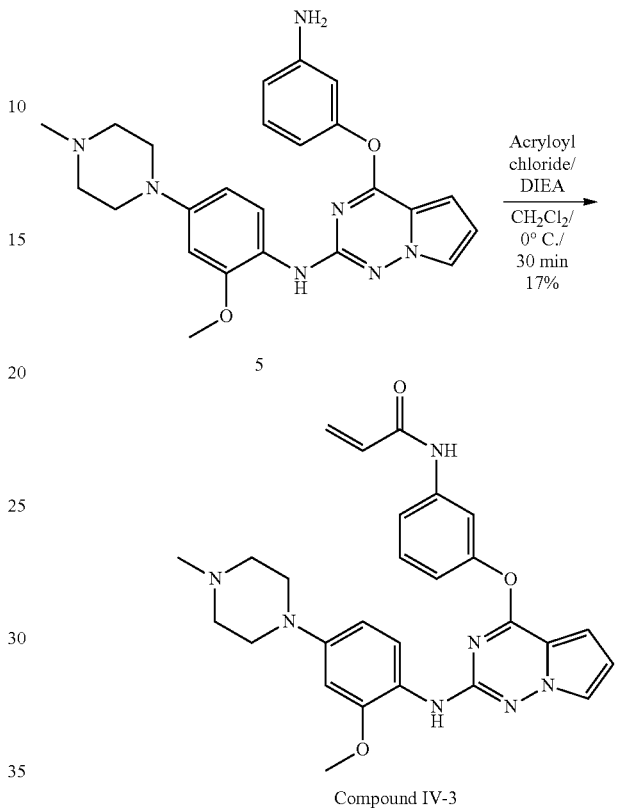

To a solution of 4-(3-aminophenoxy)-N-(2-methoxy-4-(4-methylpiperazin-1-yl)phenyl)pyrrolo[2,1-f][1,2,4]triazin-2-amine (5, 180 mg, 0.4 mmol) in dry DCM (5 mL), DIEA (0.07 mL, 0.4 mmol) was added. The resulting mixture was then stirred at room temperature for 10 min. The mixture was then cooled to 0° C., acryloyl chloride (0.032 mL dissolved in 0.5 mL of dry DCM, 0.4 mmol) was added to the mixture, and the mixture was stirred at 0° C. for 30 min. The progress of the reaction was monitored by TLC. After completion of the reaction, the reaction mixture was diluted with saturated sodium bicarbonate solution and extracted with dichloromethane. The organic extract was dried over anhydrous sodium sulfate, concentrated and purified using preparative TLC (5% MeOH-DCM, 3 runs) to afford Compound IV-3 as a light yellow solid (37 mg, 17%). $^1$H NMR (400 MHz, CD$_3$OD): δ 8.10-8.00 (d, 1H), 7.70 (s, 1H), 7.70-7.60 (m, 2H), 7.50-7.40 (t, 1H), 7.10-7.00 (d, 1H), 6.88-6.85 (d, 1H), 6.70-6.60 (m, 2H), 6.50-6.40 (m, 3H), 6.20-6.00 (m, 1H), 5.80-5.70 (d, 1H), 5.55-5.50 (d, 1H), 4.80 (s, 3H), 3.20-3.18 (m, 4H), 2.70-2.60 (m, 4H), 2.40 (s, 3H).

Example 7: Synthesis of Compound IV-4

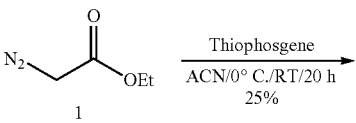

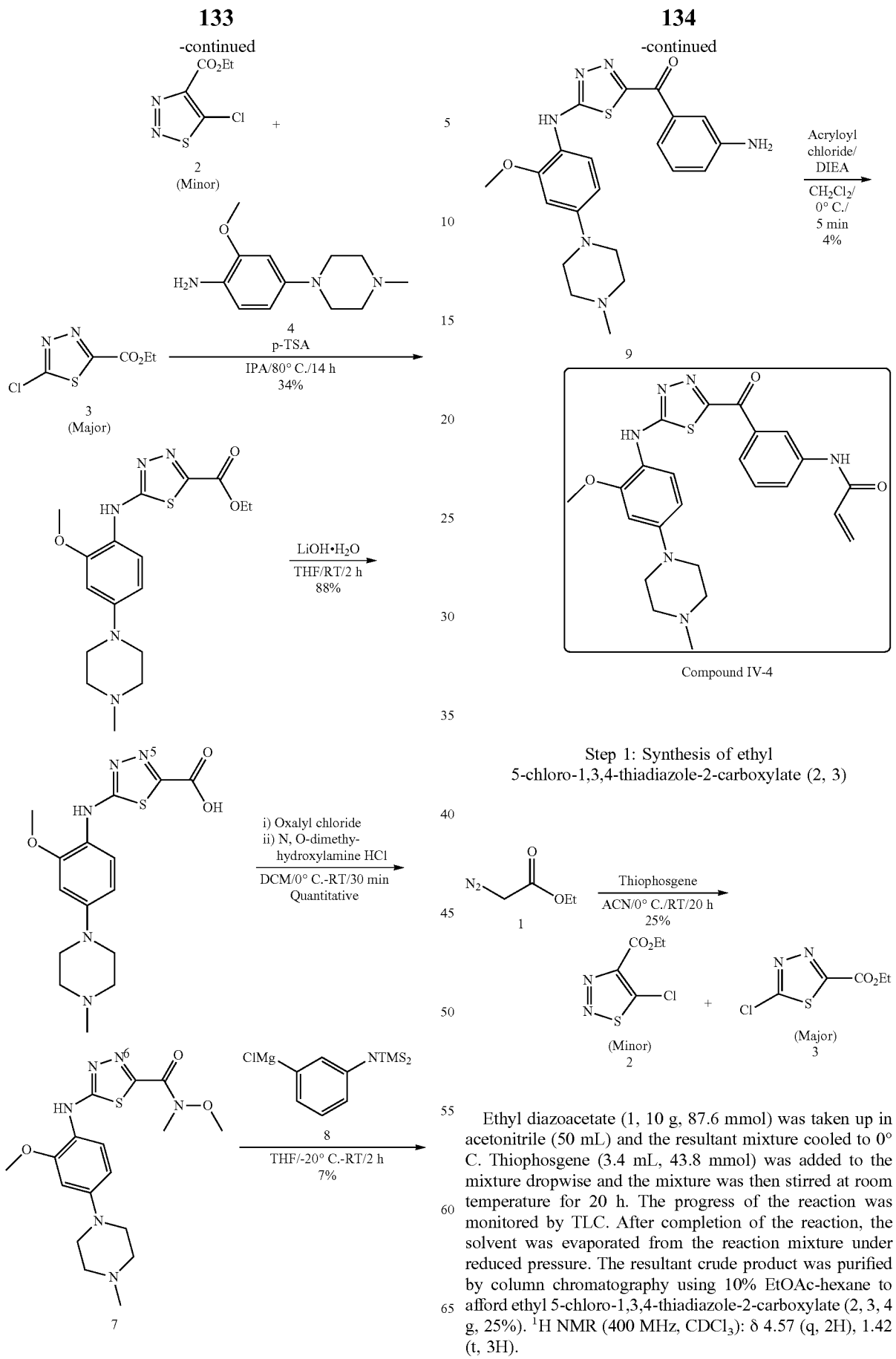

Step 1: Synthesis of ethyl 5-chloro-1,3,4-thiadiazole-2-carboxylate (2, 3)

Ethyl diazoacetate (1, 10 g, 87.6 mmol) was taken up in acetonitrile (50 mL) and the resultant mixture cooled to 0° C. Thiophosgene (3.4 mL, 43.8 mmol) was added to the mixture dropwise and the mixture was then stirred at room temperature for 20 h. The progress of the reaction was monitored by TLC. After completion of the reaction, the solvent was evaporated from the reaction mixture under reduced pressure. The resultant crude product was purified by column chromatography using 10% EtOAc-hexane to afford ethyl 5-chloro-1,3,4-thiadiazole-2-carboxylate (2, 3, 4 g, 25%). $^1$H NMR (400 MHz, CDCl$_3$): δ 4.57 (q, 2H), 1.42 (t, 3H).

Step 2: Synthesis of ethyl 5-((2-methoxy-4-(4-methylpiperazin-1-yl)phenyl)amino)-1,3,4-thiadiazole-2-carboxylate (5)

Step 3: Synthesis of 5-((2-methoxy-4-(4-methylpiperazin-1-yl)phenyl)amino)-1,3,4-thiadiazole-2-carboxylic acid (6)

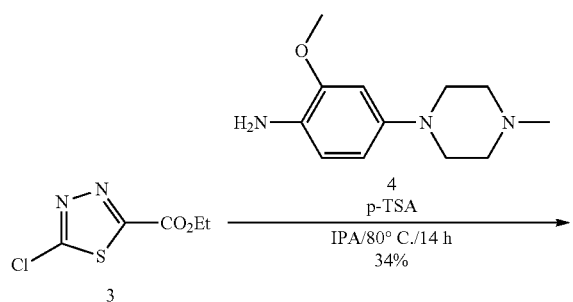

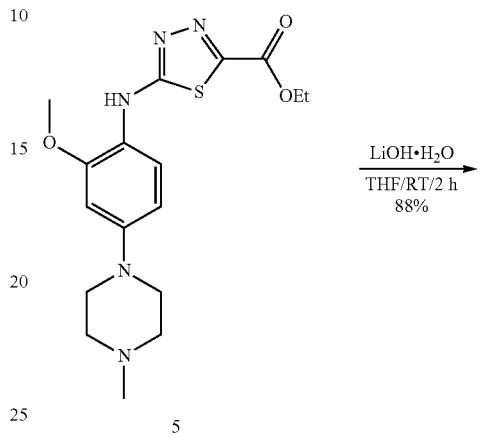

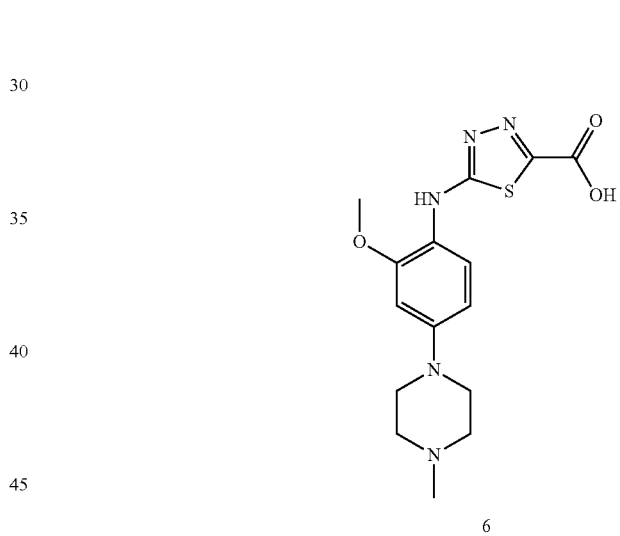

Ethyl 5-chloro-1,3,4-thiadiazole-2-carboxylate (3, 3 g, 15.7 mmol), 2-methoxy-4-(4-methyl piperazin-1-yl)aniline (4, 3.4 g, 15.7 mmol) and p-TSA (3 g, 15.7 mmol) were taken up in IPA (25 mL) and the resultant mixture was stirred at 80° C. overnight. The progress of the reaction was monitored by TLC. After completion of the reaction, the solvent was evaporated from the reaction mixture under reduced pressure, and the resultant residue was basified using aq. NaHCO$_3$ solution and extracted with ethyl acetate. The organic extract was dried over anhydrous sodium sulfate and evaporated under reduced pressure. The resultant crude product was purified by column chromatography using 5% MeOH-DCM to afford ethyl 5-((2-methoxy-4-(4-methylpiperazin-1-yl)phenyl)amino)-1,3,4-thiadiazole-2-carboxylate (5, 1.5 g, 25%). $^1$H NMR (400 MHz, CDCl$_3$): δ 7.90 (bs, 1H), 7.43 (d, 1H), 6.59-6.55 (m, 2H), 4.50 (q, 2H), 3.90 (s, 3H), 3.25-3.22 (m, 4H), 2.65-1.60 (m, 4H), 2.40 (s, 3H), 1.42 (t, 3H).

Ethyl 5-((2-methoxy-4-(4-methylpiperazin-1-yl)phenyl) amino)-1,3,4-thiadiazole-2-carboxylate (5, 2 g, 5.3 mmol) was taken up in THF (20 mL) to form a mixture. LiOH.H$_2$O (0.66 g, 15.9 mmol) in 5 mL of water was then added to the mixture and the mixture was stirred at room temperature for 2 h. The progress of the reaction was monitored by TLC. After completion of the reaction, the solvent was evaporated from the reaction mixture under reduced pressure. The resultant reside was taken up in water and acidified using 1N HCl. The resultant white solid was filtered and dried to afford 5-((2-methoxy-4-(4-methylpiperazin-1-yl)phenyl) amino)-1,3,4-thiadiazole-2-carboxylic acid (6, 1.6 g, 88%). $^1$H NMR (400 MHz, DMSO): δ 9.25 (bs, 1H), 7.82 (d, 1H), 6.63 (s, 1H), 6.50 (d, 1H), 3.82 (s, 3H), 3.25-3.18 (m, 4H), 2.72-2.60 (m, 4H), 2.40 (s, 3H).

Step 4: Synthesis of N-methoxy-5-((2-methoxy-4-(4-methylpiperazin-1-yl)phenyl)amino)-N-methyl-1,3,4-thiadiazole-2-carboxamide (7)

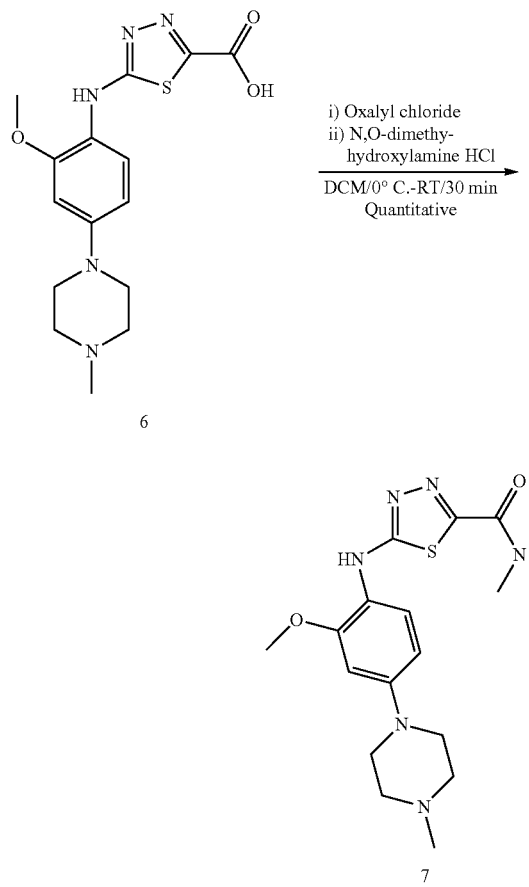

5-((2-methoxy-4-(4-methylpiperazin-1-yl)phenyl) amino)-1,3,4-thiadiazole-2-carboxylic acid (6, 1.6 g, 4.58 mmol) was taken up in dry DCM (10 mL) to form a mixture. Oxalyl chloride (0.6 mL, 6.87 mmol) was added dropwise to the mixture and the mixture was stirred at room temperature for 15 min. A catalytic amount of DMF was then added to the mixture and the mixture was stirred at room temperature for 1 h.

In a separate vessel, N,O-dimethyl hydroxylamine hydrochloride (0.536 g, 5.49 mmol) was taken up in DCM to form a mixture, the mixture was cooled to 0° C., and triethylamine (2 mL, 13.7 mmol) was added to the mixture and stirred at 0° C. for 15 min. Excess oxalyl chloride was then evaporated from the mixture under reduced pressure. The resultant acid chloride was taken up in DCM (5 mL) and added to the above vessel containing Weinrib amide at 0° C. and stirred at room temperature for 30 min.

The progress of the reaction was monitored by TLC. After completion of reaction, the reaction mixture was quenched by adding ice water and extracted with DCM. The organic extract was dried over anhydrous sodium sulfate and evaporated under reduced pressure to afford N-methoxy-5-((2-methoxy-4-(4-methylpiperazin-1-yl)phenyl)amino)-N-methyl-1,3,4-thiadiazole-2-carboxamide as a crude product (7, 2 g, Quantitative). $^1$H NMR (400 MHz, CDCl$_3$): δ 7.23 (d, 1H), 6.52-6.45 (m, 2H), 3.84 (s, 3H), 3.39-3.35 (m, 4H), 2.96 (s, 3H), 2.62-2.59 (m, 4H), 2.40 (s, 3H).

Step 5: Synthesis of (3-aminophenyl)(5-((2-methoxy-4-(4-methylpiperazin-1-yl)phenyl)amino)-1,3,4-thiadiazol-2-yl)methanone (9)

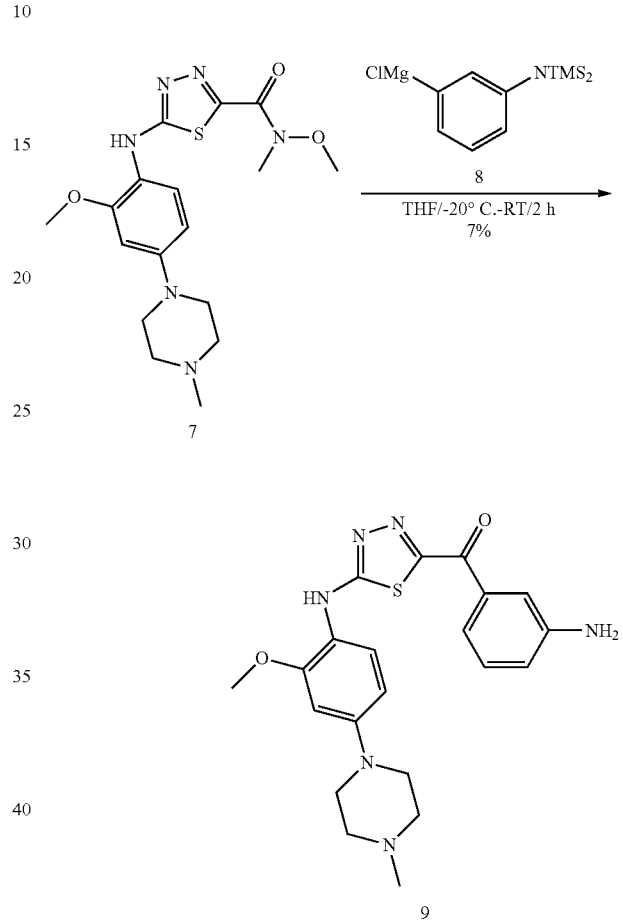

N-methoxy-5-((2-methoxy-4-(4-methylpiperazin-1-yl) phenyl)amino)-N-methyl-1,3,4-thiadiazole-2-carboxamide (7, 2 g, 5.11 mmol) was taken up in THF (15 mL) to form a mixture and the mixture cooled to −20° C. (3-(bis(trimethylsilyl)amino)phenyl)magnesium chloride (8, 6 mL, 6.13 mmol) was added dropwise to the mixture and the mixture was stirred at room temperature for 2 h. The progress of the reaction was monitored by TLC and LCMS. After completion of reaction, the reaction mixture was quenched by adding ice water and extracted with ethyl acetate. The organic extract was dried over anhydrous sodium sulfate and evaporated under reduced pressure. The resultant crude product was purified by preparative TLC to afford (3-aminophenyl)(5-((2-methoxy-4-(4-methylpiperazin-1-yl)phenyl) amino)-1,3,4-thiadiazol-2-yl)methanone (9, 0.14 g, 7%) $^1$H NMR (400 MHz, CDCl$_3$): δ 7.98-7.90 (m, 1H), 7.80 (s, 1H), 7.60 (d, 1H), 7.25 (d, 1H), 6.90 (d, 1H), 6.60-6.53 (m, 2H), 3.90 (s, 3H), 3.24-3.20 (m, 4H), 2.62-2.56 (m, 4H), 2.40 (s, 3H).

Step 6: Synthesis of N-(3-(5-((2-methoxy-4-(4-methylpiperazin-1-yl)phenyl)amino)-1,3,4-thiadiazole-2-carbonyl)phenyl)acrylamide (Compound IV-4)

Example 8: Synthesis of Compound IV-7

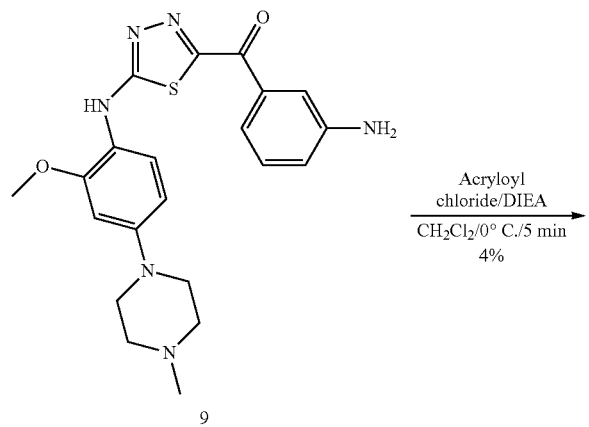

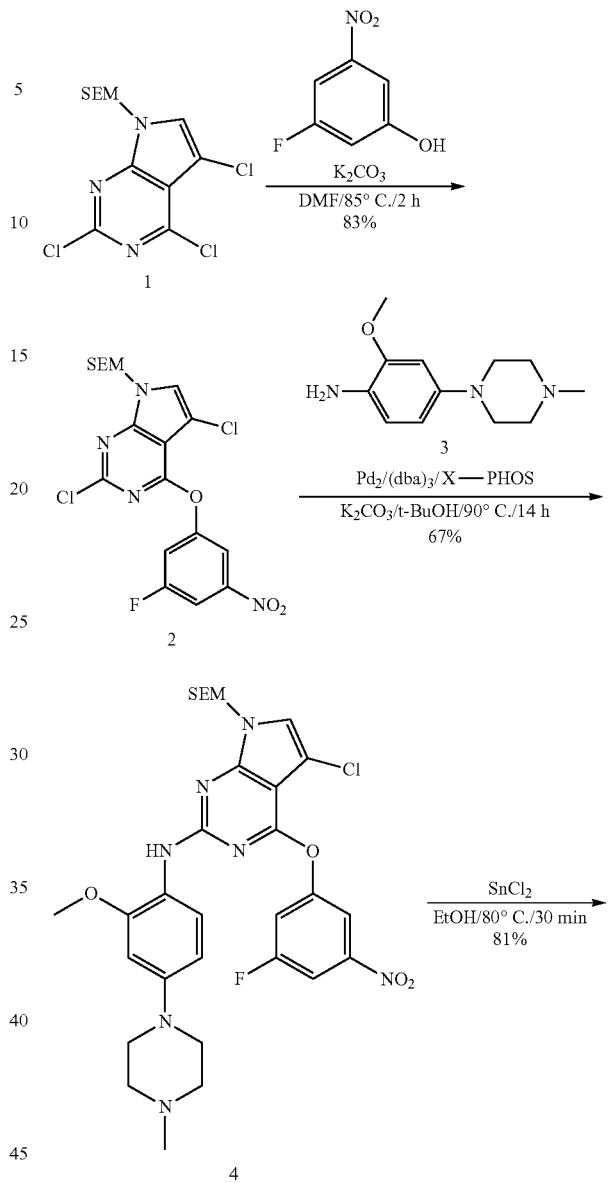

(3-aminophenyl) (5-((2-methoxy-4-(4-methylpiperazin-1-yl)phenyl)amino)-1,3,4-thiadiazol-2-yl)methanone (9, 70 mg, 0.165 mmol) was taken up in DCM (5 mL) to form a mixture. DIEA (23 mg, 0.18 mmol) was then added slowly to the mixture and the mixture was cooled to 0° C. Acryloyl chloride (14 mg, 0.165 mmol) was then added slowly to the mixture and the mixture was stirred at 0° C. for 5 min. The progress of the reaction was monitored by TLC. After completion of reaction, the reaction mixture was quenched by adding water and extracted with dichloromethane. The organic extract was dried over anhydrous sodium sulfate and evaporated under reduced pressure. The resultant crude product was purified by preparative TLC using 5% MeOH-DCM to afford Compound IV-4 (3.5 mg, 4%). $^1$H NMR (400 MHz, CDCl$_3$): δ 8.42 (s, 1H), 8.30 (d, 1H), 8.20 (d, 1H), 7.62 (d, 1H), 7.58-7.50 (m, 2H), 6.62-6.58 (m, 2H), 6.50 (d, 1H), 6.30 (q, 1H), 5.83 (d, 1H), 3.92 (s, 3H), 3.25-3.20 (m, 4H), 2.61-2.58 (m, 4H), 2.38 (s, 3H).

-continued

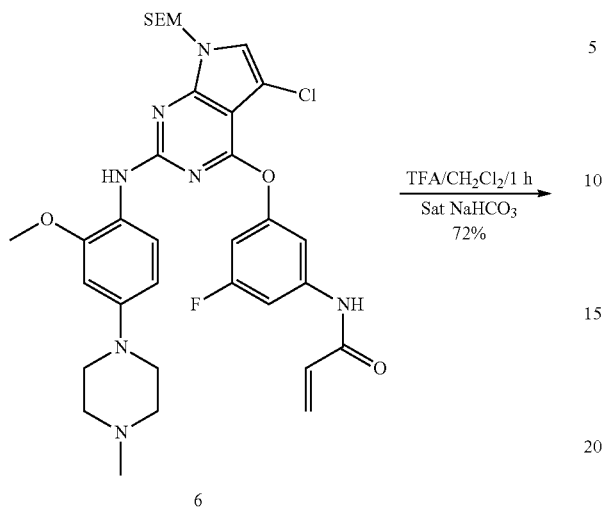

6

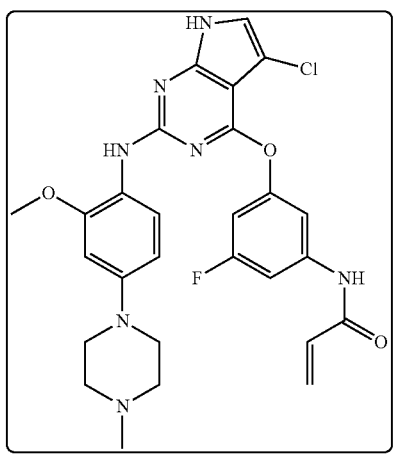

Compound IV-7

Step 1: Synthesis of 2,5-dichloro-4-(3-fluoro-5-nitrophenoxy)-7-((2-(trimethylsilyl)ethoxy)methyl)-7H-pyrrolo[2,3-d]pyrimidine -continued

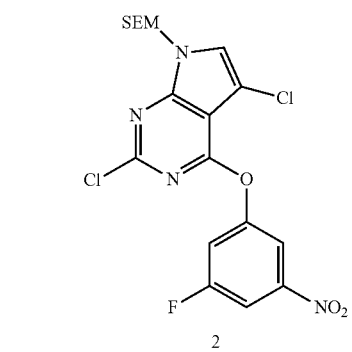

2

To a stirred solution of 2,4,5-trichloro-7-((2-(trimethylsilyl)ethoxy)methyl)-7H-pyrrolo[2,3-d]pyrimidine (1, 0.9 g, 2.54 mmol) in DMF (5 mL) was added 3-fluoro-5-nitro phenol (0.4 g, 2.54 mmol), potassium carbonate (0.352 g, 2.54 mmol) and stirred at 85° C. for 2 h. Reaction was monitored by TLC. After completion of the reaction, water was added, extracted with ethyl acetate. Organic layer was washed with brine, dried over anhydrous sodium sulfate and evaporated to dryness. Crude product was purified by column chromatography using 4% EtOAc-hexane to afford 2,5-dichloro-4-(3-fluoro-5-nitrophenoxy)-7-((2-(trimethylsilyl)ethoxy)methyl)-7H-pyrrolo[2,3-d]pyrimidine (2, 1 g, 83%) as white solid. $^1$H NMR (400 MHz, CDCl$_3$): δ 8.00 (s, 1H), 7.90-7.80 (d, 1H), 7.50-7.40 (d, 1H), 7.20 (s, 1H), 5.59 (s, 2H), 3.60-3.50 (t, 2H), 1.00-0.90 (t, 2H), 0.2 (s, 9H).

Step 2: Synthesis of 5-chloro-4-(3-fluoro-5-nitrophenoxy)-N-(2-methoxy-4-(4-methyl piperazin-1-yl) phenyl)-7-((2-(trimethylsilyl)ethoxy)methyl)-7H-pyrrolo[2,3-d]pyrimidin-2-amine

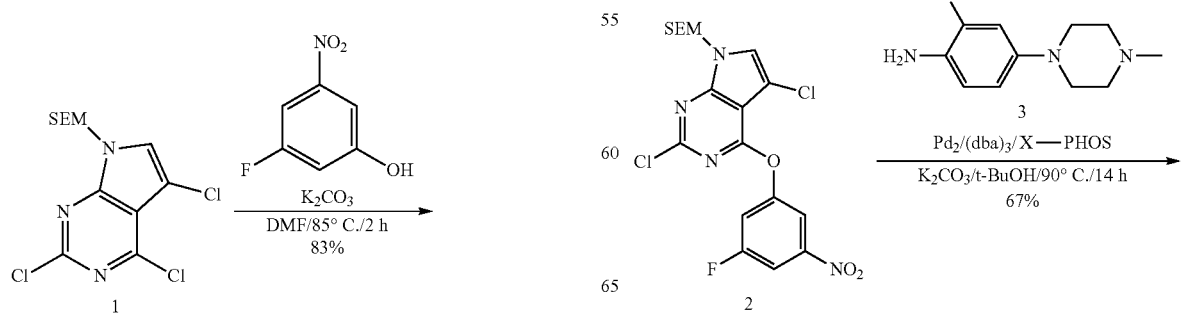

143
-continued

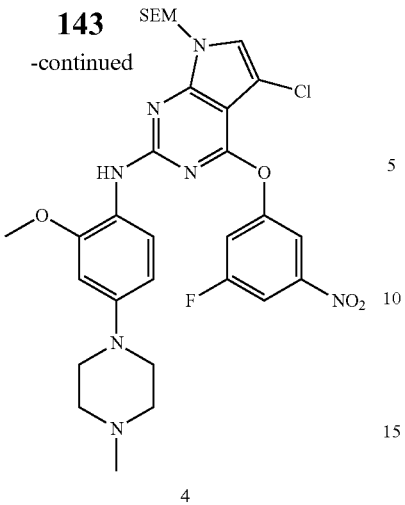

4

144
-continued

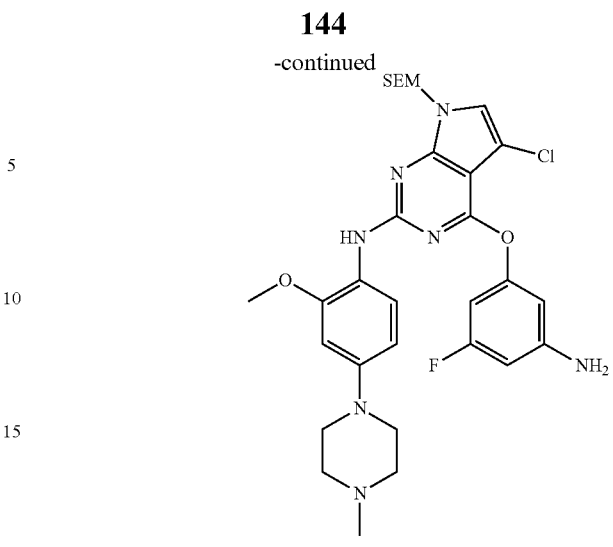

5

To a stirred solution of 2,5-dichloro-4-(3-fluoro-5-nitrophenoxy)-7-((2-(trimethylsilyl)ethoxy)methyl)-7H-pyrrolo[2,3-d]pyrimidine (2, 0.25 g, 0.5 mmol) in t-BuOH (10 mL), 2-methoxy-4-(4-methylpiperazin-1-yl)aniline (3, 0.116 g, 0.5 mmol), Pd$_2$(dba)$_3$ (13 mg, 0.01 mmol), X-PHOS (12 mg, 0.02 mmol), K$_2$CO$_3$ (0.145 g, 1.0 mmol) were added and stirred at 90° C. for 14 h. Reaction was monitored by TLC and LCMS. After completion of the reaction, reaction mixture was concentrated under reduced pressure, water was added, extracted with ethyl acetate. Organic layer was washed with brine, dried over anhydrous sodium sulfate and evaporated to dryness. Crude product was purified by column chromatography using 4% MeOH-DCM to afford 5-chloro-4-(3-fluoro-5-nitrophenoxy)-N-(2-methoxy-4-(4-methylpiperazin-1-yl)phenyl)-7-((2-(trimethylsilyl)ethoxy)methyl)-7H-pyrrolo[2,3-d]pyrimidin-2-amine (4, 0.233 g, 67%). $^1$H NMR (400 MHz, CDCl$_3$): δ 8.10 (s, 1H), 7.90-7.80 (d, 1H), 7.42-7.40 (d, 1H), 7.30 (s, 1H), 6.90 (s, 1H), 6.50 (s, 1H), 6.40-6.30 (d, 1H), 5.50 (s, 2H), 3.80 (s, 3H), 3.60-3.50 (t, 2H), 3.20-3.10 (m, 4H), 2.70-2.60 (m, 4H), 2.40 (s, 3H), 1.00-0.95 (t, 2H), 0.2 (s, 9H).

Step 3: Synthesis of 4-(3-amino-5-fluorophenoxy)-5-chloro-N-(2-methoxy-4-(4-methyl piperazin-1-yl)phenyl)-7-((2-(trimethylsilyl)ethoxy)methyl)-7H-pyrrolo[2,3-d]pyrimidin-2-amine To a stirred solution of 5-chloro-4-(3-fluoro-5-nitrophenoxy)-N-(2-methoxy-4-(4-methyl piperazin-1-yl)phenyl)-7-((2-(trimethylsilyl)ethoxy)methyl)-7H-pyrrolo[2,3-d]pyrimidin-2-amine (4, 0.233 g, 0.35 mmol) in ethanol (10 mL) was added SnCl$_2$ (0.159 g, 0.7 mmol) and stirred at 80° C. for 30 min. Reaction was monitored by TLC. After completion of the reaction, reaction mixture was concentrated to dryness, basified with aq. sodium bicarbonate solution, extracted with ethyl acetate. Organic layer was dried over anhydrous sodium sulfate and evaporated under reduced pressure to afford 4-(3-amino-5-fluorophenoxy)-5-chloro-N-(2-methoxy-4-(4-methyl piperazin-1-yl)phenyl)-7-((2-(trimethylsilyl)ethoxy)methyl)-7H-pyrrolo[2,3-d]pyrimidin-2-amine (5, 0.18 g, 81%). $^1$H NMR (400 MHz, CDCl$_3$): δ 7.40 (s, 1H), 6.90 (s, 1H), 6.60-6.30 (m, 5H), 5.50 (s, 2H), 3.80 (s, 3H), 3.60-3.50 (t, 2H), 3.30-3.10 (m, 4H), 2.80-2.65 (m, 4H), 2.40 (s, 3H), 1.00-0.95 (t, 2H), 0.2 (s, 9H).

Step 4: Synthesis of N-(3-((5-chloro-2-((2-methoxy-4-(4-methylpiperazin-1-yl)phenyl)amino)-7-((2-(trimethylsilyl)ethoxy)methyl)-7H-pyrrolo[2,3-d]pyrimidin-4-yl)oxy)-5-fluoro phenyl)acrylamide

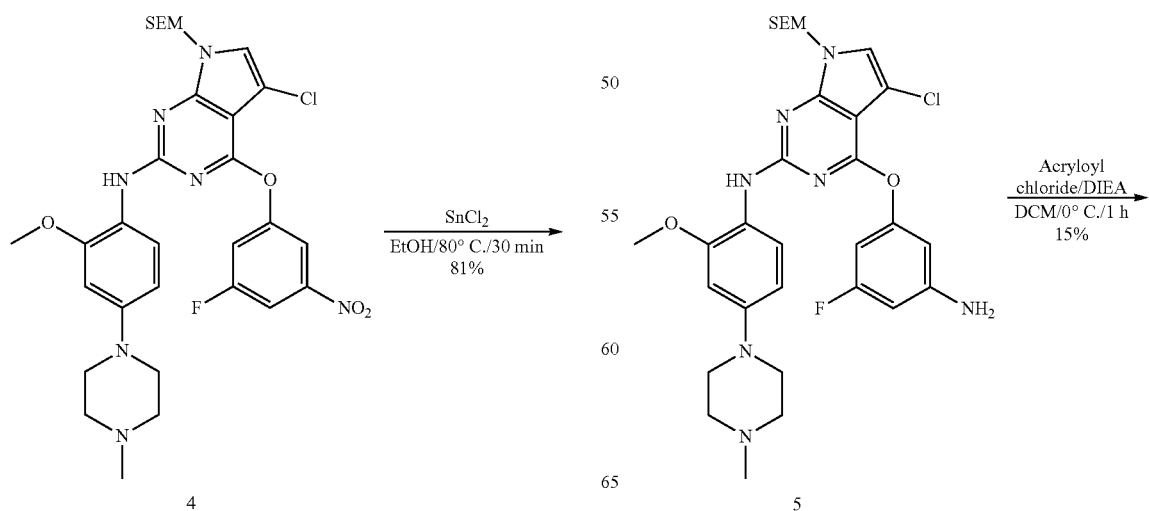

-continued

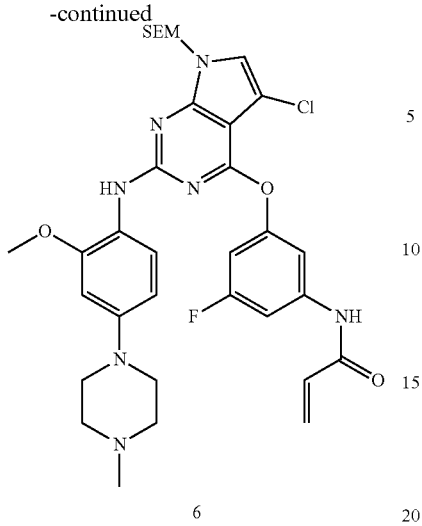

6

-continued

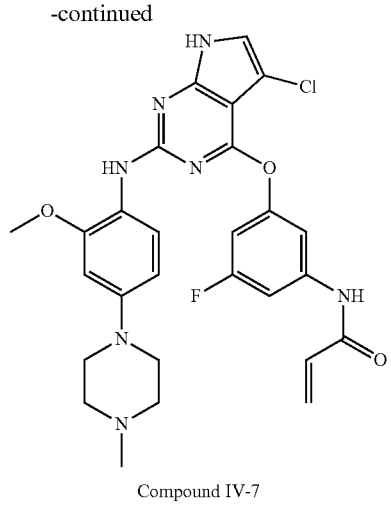

Compound IV-7

To a solution of 4-(3-amino-5-fluorophenoxy)-5-chloro-N-(2-methoxy-4-(4-methylpiperazin-1-yl)phenyl)-7-((2-(trimethylsilyl)ethoxy)methyl)-7H-pyrrolo[2,3-d]pyrimidin-2-amine (5, 0.18 g, 0.28 mmol) in DCM (20 mL) was added DIEA (0.05 mL, 0.281 mmol) at RT and stirred for 5 min. Acryloyl chloride (0.023 mL, 0.28 mL) in DCM (0.5 mL) was added drop wise at 0° C. and stirred at same temperature for 1 h. Reaction was monitored by TLC. After completion of the reaction, reaction mixture was quenched with aq. sodium bicarbonate solution, extracted with dichloromethane. Organic layer was dried over anhydrous sodium sulfate and evaporated under reduced pressure. Crude product was purified by prep TLC using 10% MeOH-DCM to afford N-(3-((5-chloro-2-((2-methoxy-4-(4-methylpiperazin-1-yl)phenyl)amino)-7-((2-(trimethylsilyl)ethoxy)methyl)-7H-pyrrolo[2,3-d]pyrimidin-4-yl)oxy)-5-fluorophenyl)acrylamide (6, 30 mg, 15%) as off-white solid. $^1$H NMR (400 MHz, CDCl$_3$): δ 8.00 (bs, 1H), 7.70-7.60 (d, 1H), 7.30 (s, 1H), 7.10 (s, 1H), 6.85-6.80 (d, 1H), 6.60 (s, 1H), 6.40-6.30 (m, 3H), 5.82-5.75 (t, 1H), 5.50 (s, 2H), 3.80 (s, 3H), 3.60-3.50 (t, 2H), 3.20-3.10 (m, 4H), 2.65-2.60 (m, 4H), 2.40 (s, 3H), 1.00-0.95 (t, 2H), 0.20 (s, 9H).

Step 5: Synthesis of N-(3-((5-chloro-2-((2-methoxy-4-(4-methylpiperazin-1-yl)phenyl)amino)-7H-pyrrolo[2,3-d]pyrimidin-4-yl)oxy)-5-fluorophenyl)acrylamide

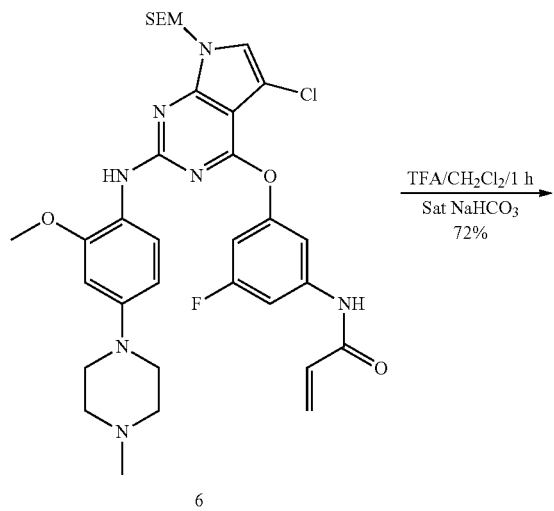

6

To a solution of N-(3-((5-chloro-2-((2-methoxy-4-(4-methylpiperazin-1-yl)phenyl)amino)-7-((2-(trimethylsilyl)ethoxy)methyl)-7H-pyrrolo[2,3-d]pyrimidin-4-yl)oxy)-5-fluorophenyl)acrylamide (6, 50 mg, 0.07 mmol) in DCM (5 mL) was added TFA (0.5 mL, 6.2 mmol) and stirred at RT for 1 h. Reaction was monitored by TLC. After completion of the reaction, reaction mixture was concentrated under reduced pressure, basified with aq. sodium bicarbonate solution, extracted with ethyl acetate. Organic layer was dried over anhydrous sodium sulfate and evaporated to dryness. Crude product was triturated with DCM, precipitated solid was filtered and dried to afford Compound IV-7 (29 mg, 72%). $^1$H NMR (400 MHz, CDCl$_3$): δ 8.87 (bs, 1H), 7.94-7.91 (d, 1H), 7.80-7.60 (d, 1H), 7.40 (s, 1H), 7.20 (s, 1H), 7.10 (s, 1H), 6.90-6.80 (d, 1H), 6.78 (s, 1H), 6.59-6.50 (d, 1H), 6.41 (s, 1H), 6.40-6.38 (d, 1H), 6.30-6.19 (m, 1H), 5.85-5.80 (d, 1H), 3.80 (s, 3H), 3.20-3.10 (m, 4H), 2.60-2.50 (m, 4H), 2.40 (s, 3H).

Example 9: Synthesis of Compound XII-3

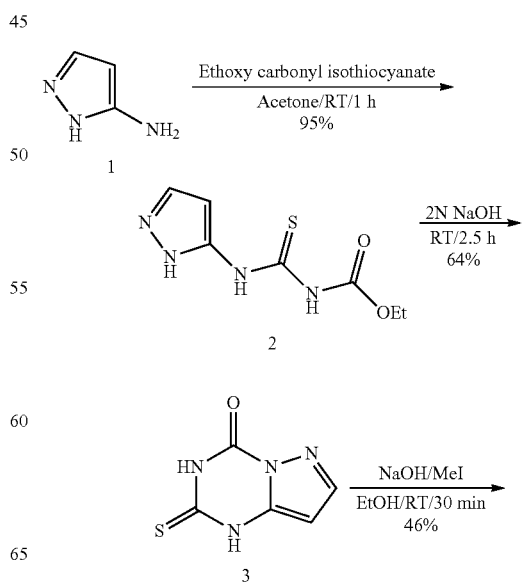

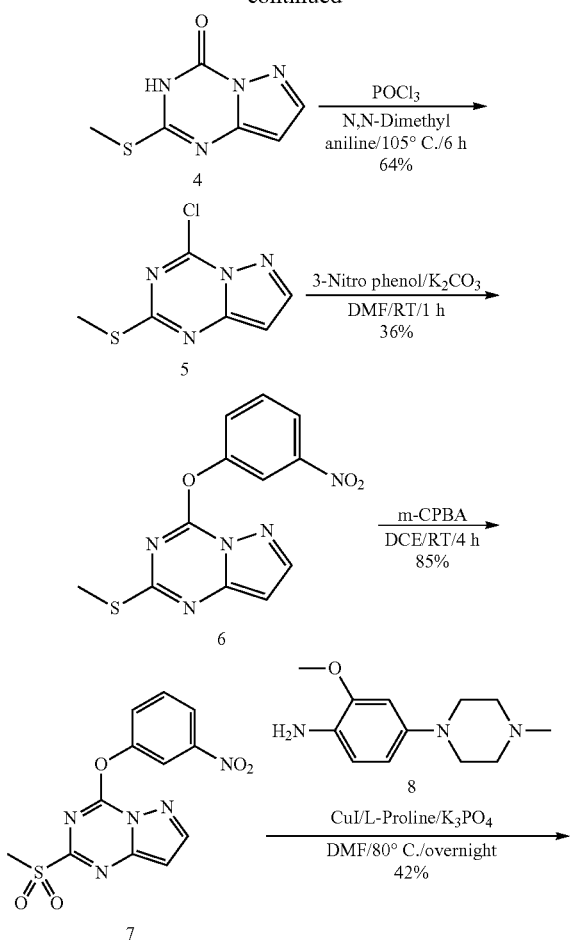

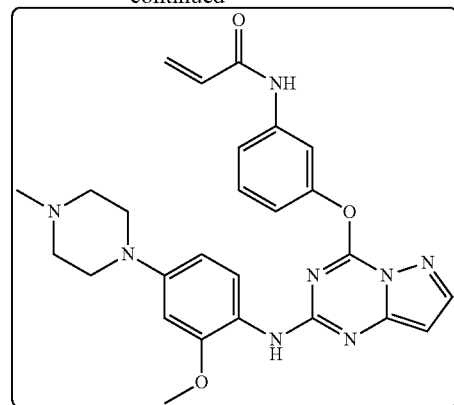

Compound XII-3

Step 1: Synthesis of ethyl 1H-pyrazol-5-yl carbamothioyl carbamate

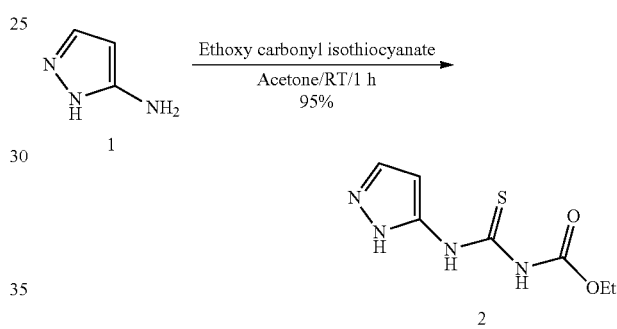

Ethoxy carbonyl isothiocyanate (1, 10 g, 70.76 mmol) was added to 3-amino pyrazole (6.3 g, 75.76 mmol) in acetone (100 mL) and stirred at RT for 1 h. Reaction was monitored by TLC. After completion of the reaction, 100 mL of ice water was added, solid precipitate was collected through filtration. Filtered solid was washed with water and dried to afford ethyl 1H-pyrazol-5-yl carbamothioyl carbamate (2, 15 g, 95%) and used as such for the next step.

Step 2: Synthesis of 2-thioxo-2,3-dihydropyrazolo [1,5-a][1,3,5]triazin-4(1H)-one

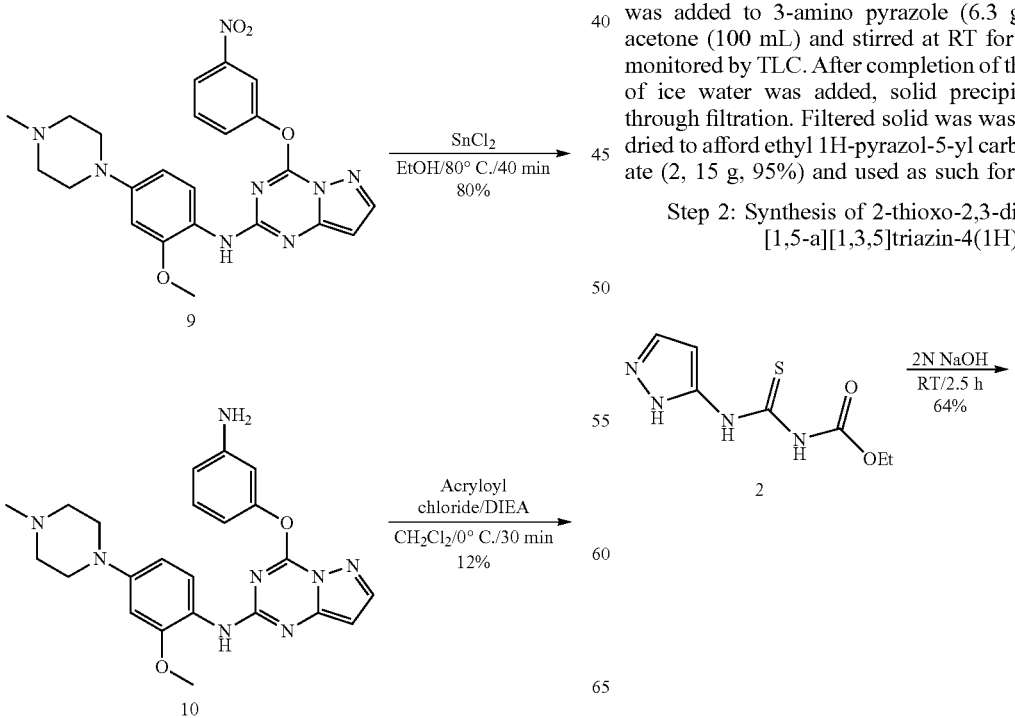

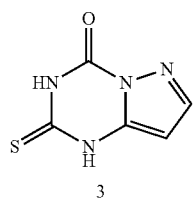

Ethyl 1H-pyrazol-5-yl carbamothioyl carbamate (2, 15 g, 70 mmol) was added to 2N NaOH solution (250 mL) and stirred at RT for 2 h. Reaction mixture was acidified with 2NH2SO4 and the resulting precipitate was collected by vacuum filtration, washed with water followed by diethyl ether and dried to afford 2-thioxo-2,3-dihydropyrazolo[1,5-a][1,3,5]triazin-4(1H)-one (3, 6 g, 64%). $^1$H NMR (400 MHz, DMSO): δ 7.83 (s, 1H), 5.85 (s, 1H).

Step 3: Synthesis of 2-(methylthio)pyrazolo[1,5-a][1,3,5]triazin-4(3H)-one

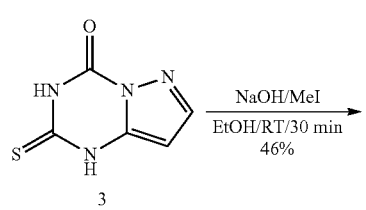

2N NaOH solution (20 mL) was added to a suspension of 2-thioxo-2,3-dihydropyrazolo[1,5-a][1,3,5]triazin-4(1H)-one (3, 6 g, 35.7 mmol) in ethanol (80 mL). Methyl iodide (6 g, 42.2 mmol) was added slowly at 0° C. and stirred RT for 30 min. Resulting precipitate was collected by vacuum filtration, suspended in water (100 mL) and acidified with 2NH2SO4, solution was stirred at 0° C. for 5 min and the new precipitate was collected by vacuum filtration, washed with cold water and then dried to afford 2-(methylthio)pyrazolo[1,5-a][1,3,5]triazin-4(3H)-one (4, 5 g, 46%). $^1$H NMR (400 MHz, DMSO): δ 7.95 (s, 1H), 6.35 (s, 1H), 2.50 (s, 3H).

Step 4: Synthesis of 4-chloro-2-(methylthio)pyrazolo[1,5-a][1,3,5]triazine

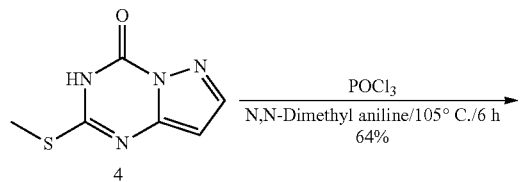

N,N-dimethyl aniline (0.36 mL) was added to a suspension of 2-(methylthio)pyrazolo[1,5-a][1,3,5]triazin-4(3H)-one (4, 1 g, 5.4 mmol) in POCl3 (15 mL) and stirred at 105° C. for 6 h. Reaction was monitored by TLC. After completion of the reaction, reaction mixture was concentrated under reduced pressure, diluted with water (100 mL) the resulting solid was collected by vacuum filtration, washed with cold water, hexane and dried to afford 4-chloro-2-(methylthio)pyrazolo[1,5-a][1,3,5]triazine (5, 0.7 g, 64%). $^1$H NMR (400 MHz, CDCl3): δ 8.18 (s, 1H), 6.50 (s, 1H), 2.60 (s, 3H).

Step 5: Synthesis of 2-(methylthio)-4-(3-nitrophenoxy)pyrazolo[1,5-a][1,3,5]triazine

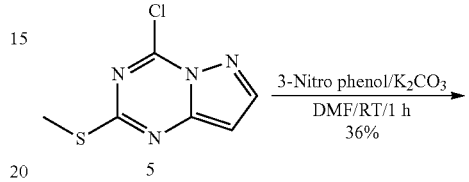

4-chloro-2-(methylthio)pyrazolo[1,5-a][1,3,5]triazine (0.45 g, 2.2 mmol), 3-nitro phenol (0.31 g, 2.2 mmol) and potassium carbonate (5, 0.625 g, 4.5 mmol) were taken in DMF (6 mL) and stirred at RT for 1 h. Reaction was monitored by TLC. After completion of the reaction, water was added and extracted with ethyl acetate. Organic layer was washed with brine, dried over anhydrous sodium sulfate and evaporated under reduced pressure to afford 2-(methylthio)-4-(3-nitrophenoxy)pyrazolo[1,5-a][1,3,5]triazine (6, 0.25 g, 36%). $^1$H NMR (400 MHz, DMSO): δ 8.50 (s, 1H), 8.35-8.20 (m, 2H), 8.05-7.95 (d, 1H), 7.85-7.80 (t, 1H), 6.60 (s, 1H), 2.43 (s, 3H).

Step 6: Synthesis of 2-(methylsulfonyl)-4-(3-nitrophenoxy)pyrazolo[1,5-a][1,3,5]triazine

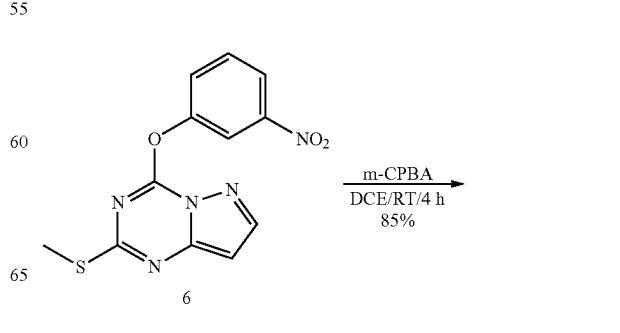

-continued

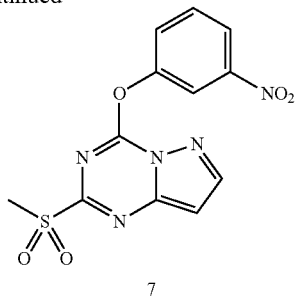

7 m-CPBA (1.1 g, 6.6 mmol) was added to 2-(methylthio)-4-(3-nitrophenoxy)pyrazolo[1,5-a][1,3,5]triazine (6, 0.5 g, 1.6 mmol) in DCE (10 mL) and stirred at RT for 4 h. Reaction was monitored by TLC. After completion of the reaction, solvent was evaporated under reduced pressure. Crude product was triturated with diethyl ether, filtered thru Buchner funnel and dried to afford 2-(methylsulfonyl)-4-(3-nitrophenoxy)pyrazolo[1,5-a][1,3,5]triazine (7, 0.47 g, 85%) as white solid. $^1$H NMR (400 MHz, CDCl$_3$): δ 8.45 (s, 1H), 8.38-8.30 (m, 2H), 7.86-7.83 (d, 1H), 7.80-7.70 (t, 1H), 7.00 (s, 1H), 3.25 (s, 3H).

Step 7: Synthesis of N-(2-methoxy-4-(4-methylpiperazin-1-yl)phenyl)-4-(3-nitrophenoxy)pyrazolo[1,5-a][1,3,5]triazin-2-amine

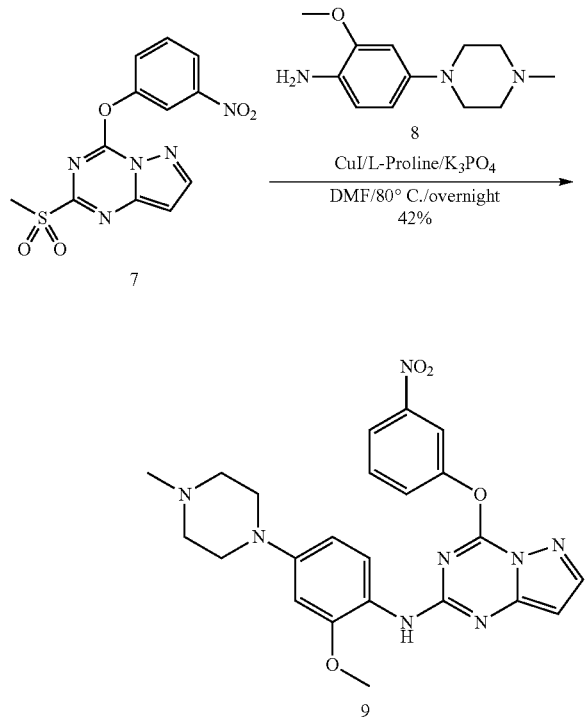

2-(methylsulfonyl)-4-(3-nitrophenoxy)pyrazolo[1,5-a][1,3,5]triazine (7, 0.25 g, 0.74 mmol), 2-methoxy-4-(4-methylpiperazin-1-yl)aniline (8, 0.164 g, 0.74 mmol), CuI (14 mg, 0.074 mmol), L-proline (17 mg, 0.14 mmol) and K$_3$PO$_4$ (0.474 g, 2.2 mmol) in DMF (5 mL) was stirred at 80° C. for overnight. Reaction was monitored by TLC and LCMS. After completion of the reaction, water was added and extracted with ethyl acetate. Organic layer was washed with brine, dried over anhydrous sodium sulfate and evaporated under reduced pressure. Crude product was purified by column chromatography using 3% MeOH-DCM to afford N-(2-methoxy-4-(4-methylpiperazin-1-yl)phenyl)-4-(3-nitrophenoxy)pyrazolo[1,5-a][1,3,5]triazin-2-amine (9, 0.15 g, 42%). $^1$H NMR (400 MHz, CD$_3$OD): δ 8.20-8.18 (m, 2H), 8.10 (s, 1H), 7.70-7.45 (m, 3H), 6.65 (s, 1H), 6.40-6.30 (d, 1H), 6.25 (s, 1H), 3.95 (s, 3H), 3.30-3.20 (t, 4H), 2.70-2.60 (t, 4H), 2.32 (s, 3H).

Step 8: Synthesis of 4-(3-aminophenoxy)-N-(2-methoxy-4-(4-methylpiperazin-1-yl)phenyl)pyrazolo[1,5-a][1,3,5]triazin-2-amine

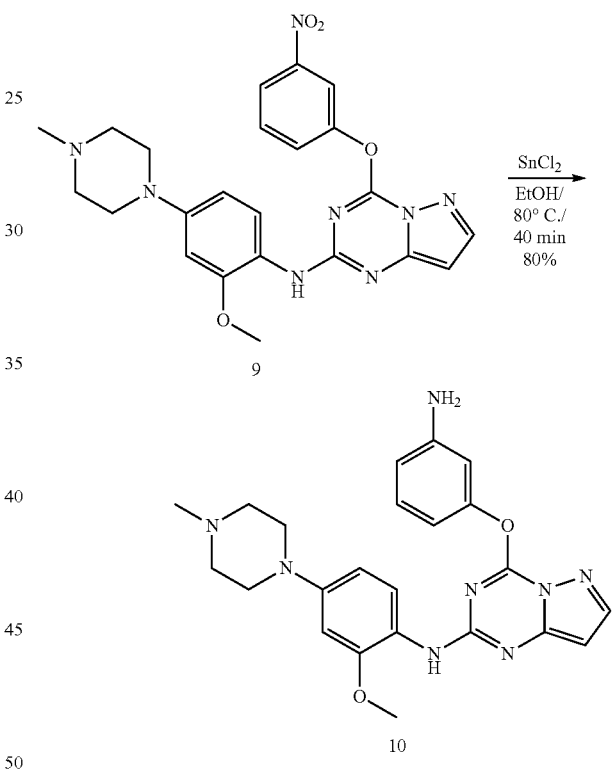

N-(2-methoxy-4-(4-methylpiperazin-1-yl)phenyl)-4-(3-nitrophenoxy)pyrazolo[1,5-a][1,3,5]triazin-2-amine (9, 0.1 g, 0.21 mmol) and stannous chloride (94 mg, 0.42 mmol) in 10 mL of ethanol was stirred at 80° C. for 40 min. Reaction was monitored by TLC and LCMS. After completion of the reaction, solvent was evaporated under reduced pressure, basified with aq. NaHCO3 solution, extracted with ethyl acetate. Organic layer was dried over anhydrous sodium sulfate and evaporated under reduced pressure to afford 4-(3-aminophenoxy)-N-(2-methoxy-4-(4-methylpiperazin-1-yl)phenyl)pyrazolo[1,5-a][1,3,5]triazin-2-amine (10, 75 mg, 80%) and used as such for the next step. $^1$H NMR (400 MHz, CDCl$_3$): δ 8.86 (s, 1H), 8.20-8.10 (d, 1H), 7.95 (s, 1H), 7.25-7.00 (t, 2H), 6.60-6.40 (m, 4H), 6.25 (s, 1H), 3.92 (s, 3H), 3.30-3.20 (m, 4H), 2.35-2.30 (m, 4H), 2.20 (s, 3H).

153

Step 9: Synthesis of N-(3-((2-((2-methoxy-4-(4-methylpiperazin-1-yl)phenyl)amino)pyrazolo[1,5-a][1,3,5]triazin-4-yl)oxy)phenyl)acrylamide

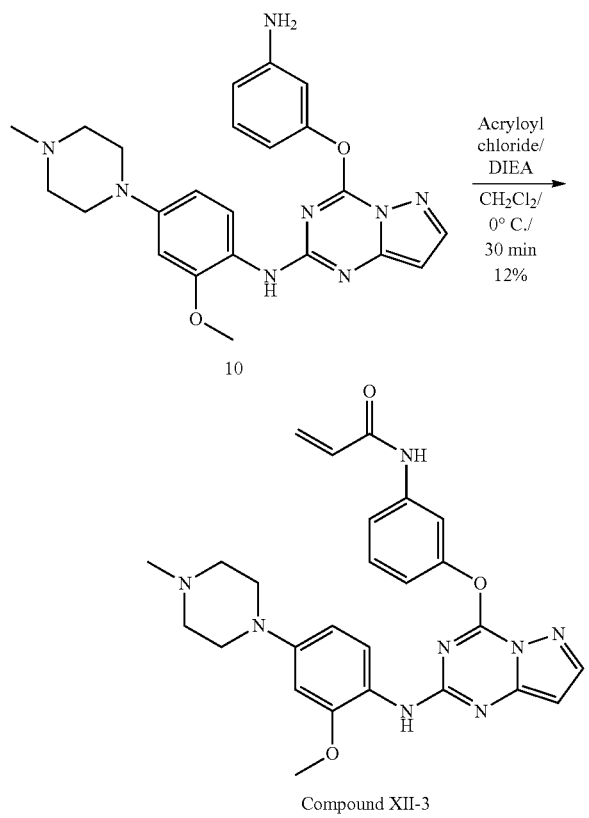

Compound XII-3

4-(3-aminophenoxy)-N-(2-methoxy-4-(4-methylpiperazin-1-yl)phenyl)pyrazolo[1,5-a][1,3,5]triazin-2-amine (10, 60 mg, 0.13 mmol) was taken in DCM (10 mL), DIEA (0.02 mL, 0.134 mmol) was added and stirred for 10 min at RT. Acryloyl chloride (0.01 mL, 0.134 mmol) in DCM (1 mL) was added drop wise at 0° C. and stirred at same temperature for 30 min. Reaction was monitored by TLC. After completion of the reaction, aq. NaHCO₃ solution was added. Organic layer was separated, dried over anhydrous sodium sulfate and concentrated under reduced pressure. Crude product was purified by prep TLC using 5% MeOH: DCM to afford N-(3-((2-((2-methoxy-4-(4-methylpiperazin-1-yl)phenyl)amino) pyrazolo[1,5-a][1,3,5]triazin-4-yl)oxy)phenyl)acrylamide (Compound XII-3, 8 mg, 12%). $^1$H NMR (400 MHz, CD₃OD): δ 8.10 (s, 1H), 7.75-7.70 (d, H), 7.65-7.55 (m, 2H), 7.45-7.40 (t, 1H), 7.00-6.95 (d, 1H), 6.67 (s, 1H), 6.50-6.30 (m, 3H), 6.28-6.25 (d, 1H), 6.18-6.10 (d, 1H), 5.80-5.75 (d, 1H), 5.55-5.45 (d, 1H), 3.95 (s, 3H), 3.25-3.18 (t, 4H), 2.65-2.60 (t, 4H), 2.38 (s, 3H).

Example 10: In Vitro Assays in EGFR mutant Ba/F3 cells

Activity of various compounds of the invention was determined in vitro in EGFR mutant Ba/F3 cells according to the procedures set forth in Example 1. The results are summarized in the table below.

154

| Compound | IC$_{50}$ (nM) in Ba/F3 Cells | |
|---|---|---|
| | EGFR Del 19/T790M | EGFR L858R/T790M |
| VIII-1 | 864 | 2164 |
| IV-1 | 435 | 688 |

The following are some illustrative embodiments of the invention:

1. A compound of Formula I:

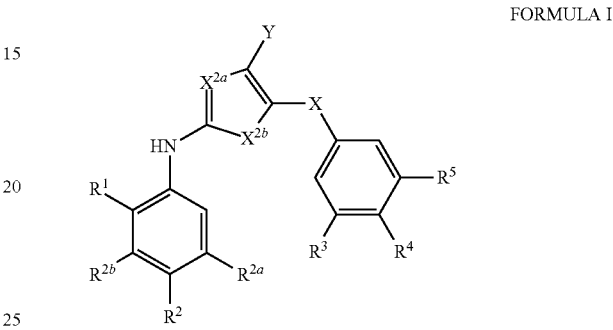

FORMULA I or a pharmaceutically acceptable salt or ester thereof, wherein:

X is oxygen, sulfur, carbonyl, —NR⁶, C₁-C₆ alkyl, or C₁-C₆ haloalkyl;

$X^{2a}$ is nitrogen, CH, or CR³⁰;

$X^{2b}$ is oxygen, sulfur, NH, or NR⁹;

Y is hydrogen, halogen, or C₁-C₆ alkyl;

each R¹ is independently C₁-C₆ alkyl, C₁-C₆ alkoxy, C₁-C₆ haloalkyl, or C₁-C₆ haloalkoxy;

(i) one of R², $R^{2a}$, and $R^{2b}$ is piperidine, pyrrolidine, piperazine, or morpholine that is optionally substituted with C₁-C₆ alkyl; or C₃-C₆ alkyl or C₃-C₆ cycloalkyl containing at least one nitrogen; and the other two of R², $R^{2a}$, and $R^{2b}$ are hydrogen or C₁-C₆ alkyl; or (ii) R² and one of $R^{2a}$ and $R^{2b}$ join to form a piperidine, pyrrolidine, or morpholine that is optionally substituted with C₁-C₆ alkyl; or C₃-C₆ cycloalkyl containing at least one nitrogen; and the other of $R^{2a}$ and $R^{2b}$ is hydrogen or C₁-C₆ alkyl;

one of R³, R⁴, and R⁵ is Z, and the other two of R³, R⁴, and R⁵ are hydrogen;

each R⁶ is independently hydrogen or C₁-C₆ alkyl;

R⁷ is hydrogen, C₁-C₆ alkyl, or C₂-C₆ alkenyl;

R⁸ is C₁-C₆ alkyl that is substituted with halogen, cyano, —C(O)R⁹, or —OC(O)R⁹; C₂-C₆ alkenyl that is optionally substituted with halogen or —NR⁹₂; C₂-C₆ alkynyl; C₃-C₆ cycloalkyl that is substituted with cyano or —C(O)R⁹; C₄-C₆ cycloalkenyl that is optionally substituted with halogen; or C₄-C₉ heterocycloalkenyl that is optionally substituted with halogen, C₁-C₆ alkyl, or carbonyl;

each R⁹ is independently C₁-C₆ alkyl;

R¹⁰ is hydrogen or C₁-C₆ alkyl;

R¹¹ is C₂-C₆ alkenyl;

R¹² is C₂-C₆ alkenyl substituted with cyano or —C(O)OR⁹;

R³⁰ is halogen or C₁-C₆ alkyl;

Z is C₂-C₆ alkenyl, C₂-C₆ alkynyl, C₃-C₆ cycloalkyl that is substituted with cyano or acetyl, —(CH₂)ₙNR⁷C(O)R⁸, —(CH₂)ₙC(O)(CH₂)ₙR⁸, —(CH₂)ₙOC(O)R⁸,

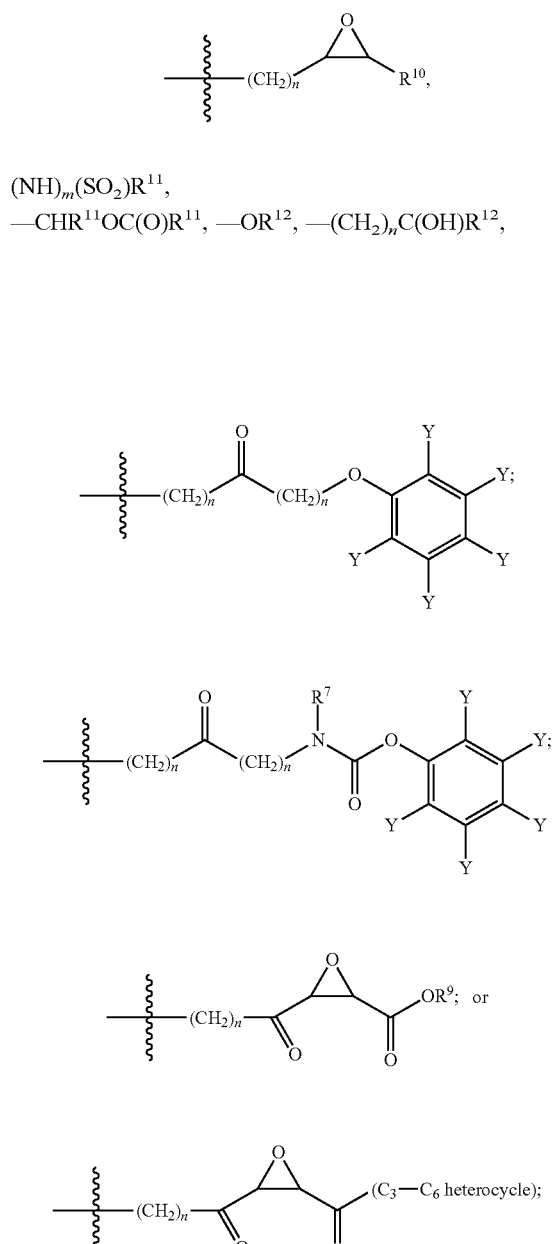

n is an integer from 0 to 6; and m is 0 or 1.

2. The compound of embodiment 1, wherein

X is oxygen;

Y is halogen;

$R^1$ is $C_1$-$C_6$ alkoxy;

$R^2$ is piperidine that is substituted at the N position with $C_1$-$C_6$ alkyl;

$R^{2a}$ and $R^{2b}$ are hydrogen;

one of $R^3$, $R^4$, and $R^5$ is Z, and the other two of $R^3$, $R^4$, and $R^5$ are hydrogen;

$R^7$ is hydrogen or $C_1$-$C_6$ alkyl; $R^8$ is $C_2$-$C_6$ alkenyl; and

Z is —$(CH_2)_nNR^7C(O)R^8$.

3. The compound of embodiment 1, wherein the compound of Formula I is:

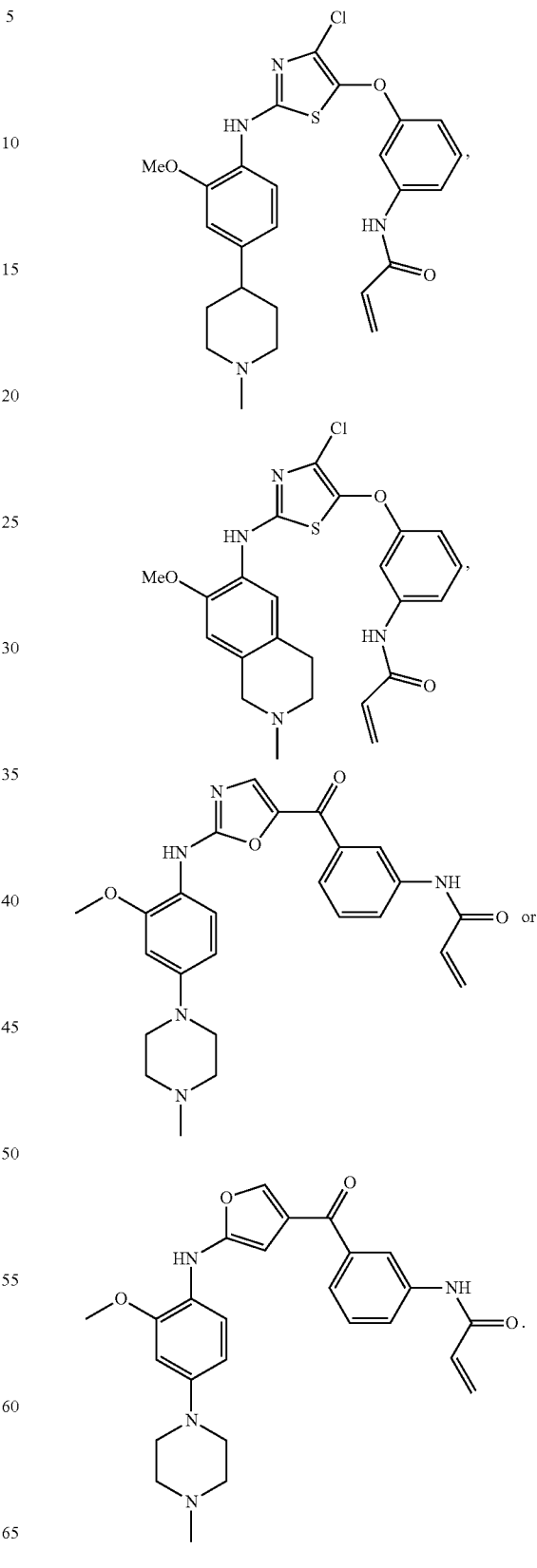

4. A compound of Formula II:

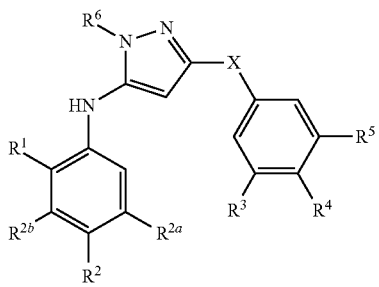
FORMULA II or a pharmaceutically acceptable salt or ester thereof, wherein:

X is oxygen, sulfur, carbonyl, —$NR^6$, $C_1$-$C_6$ alkyl, or $C_1$-$C_6$ haloalkyl;

Y is hydrogen, halogen, or $C_1$-$C_6$ alkyl;

each $R^1$ is independently $C_1$-$C_6$ alkyl, $C_1$-$C_6$ alkoxy, $C_1$-$C_6$ haloalkyl, or $C_1$-$C_6$ haloalkoxy;

(i) one of $R^2$, $R^{2a}$, and $R^{2b}$ is piperidine, pyrrolidine, piperazine, or morpholine that is optionally substituted with $C_1$-$C_6$ alkyl; or $C_3$-$C_6$ alkyl or $C_3$-$C_6$ cycloalkyl containing at least one nitrogen; and the other two of $R^2$, $R^{2a}$, and $R^{2b}$ are hydrogen or $C_1$-$C_6$ alkyl; or (ii) $R^2$ and one of $R^{2a}$ and $R^{2b}$ join to form a piperidine, pyrrolidine, or morpholine that is optionally substituted with $C_1$-$C_6$ alkyl; or $C_3$-$C_6$ cycloalkyl containing at least one nitrogen; and the other of $R^{2a}$ and $R^{2b}$ is hydrogen or $C_1$-$C_6$ alkyl;

one of $R^3$, $R^4$, and $R^5$ is Z, and the other two of $R^3$, $R^4$, and $R^5$ are hydrogen;

each $R^6$ is independently hydrogen or $C_1$-$C_6$ alkyl;

$R^7$ is hydrogen, $C_1$-$C_6$ alkyl, or $C_2$-$C_6$ alkenyl;

$R^8$ is $C_1$-$C_6$ alkyl that is substituted with halogen, cyano, —C(O)$R^9$, or —OC(O)$R^9$; $C_2$-$C_6$ alkenyl that is optionally substituted with halogen or —$NR^9{}_2$; $C_2$-$C_6$ alkynyl; $C_3$-$C_6$ cycloalkyl that is substituted with cyano or —C(O)$R^9$; $C_4$-$C_6$ cycloalkenyl that is optionally substituted with halogen; or $C_4$-$C_9$ heterocycloalkenyl that is optionally substituted with halogen, $C_1$-$C_6$ alkyl, or carbonyl;

each $R^9$ is independently $C_1$-$C_6$ alkyl;

$R^{10}$ is hydrogen or $C_1$-$C_6$ alkyl;

$R^{11}$ is $C_2$-$C_6$ alkenyl;

$R^{12}$ is $C_2$-$C_6$ alkenyl substituted with cyano or —C(O)$OR^9$;

$R^{30}$ is halogen or $C_1$-$C_6$ alkyl;

Z is $C_2$-$C_6$ alkenyl, $C_2$-$C_6$ alkynyl, $C_3$-$C_6$ cycloalkyl that is substituted with cyano or acetyl, —(CH$_2$)$_n$NR$^7$C(O)R$^8$, —(CH$_2$)$_n$C(O)(CH$_2$)$_n$R$^8$, —(CH$_2$)$_n$OC(O)R$^8$,

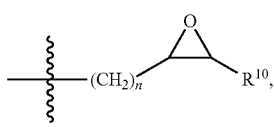

(NH)$_m$(SO$_2$)R$^{11}$,
—CHR$^{11}$OC(O)R$^{11}$, —OR$^{12}$, —(CH$_2$)$_n$C(OH)R$^{12}$,

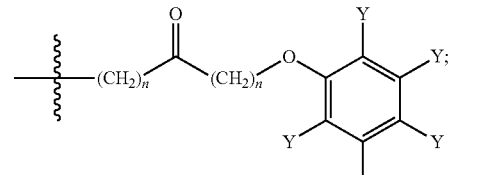

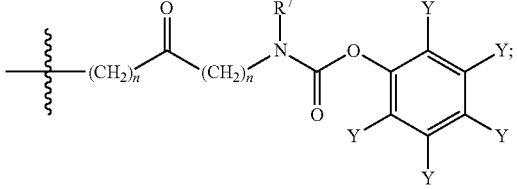

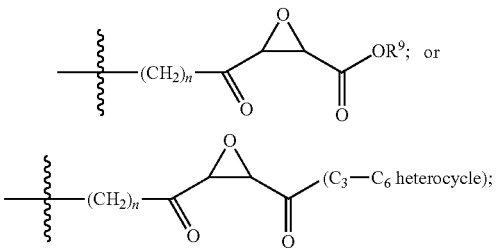

n is an integer from 0 to 6; and
m is 0 or 1.

5. The compound of embodiment 4, wherein:

X is oxygen;

Y is halogen;

$R^1$ is $C_1$-$C_6$ alkoxy;

$R^2$ is piperidine that is substituted at the N position with $C_1$-$C_6$ alkyl;

$R^{2a}$ and $R^{2b}$ are hydrogen;

one of $R^3$, $R^4$, and $R^5$ is Z, and the other two of $R^3$, $R^4$, and $R^5$ are hydrogen;

$R^7$ is hydrogen or $C_1$-$C_6$ alkyl; $R^8$ is $C_2$-$C_6$ alkenyl; and

Z is —(CH$_2$)$_n$NR$^7$C(O)R$^8$.

6. The compound of embodiment 4, wherein the compound of Formula II is:

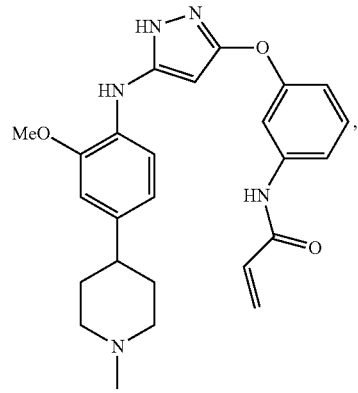

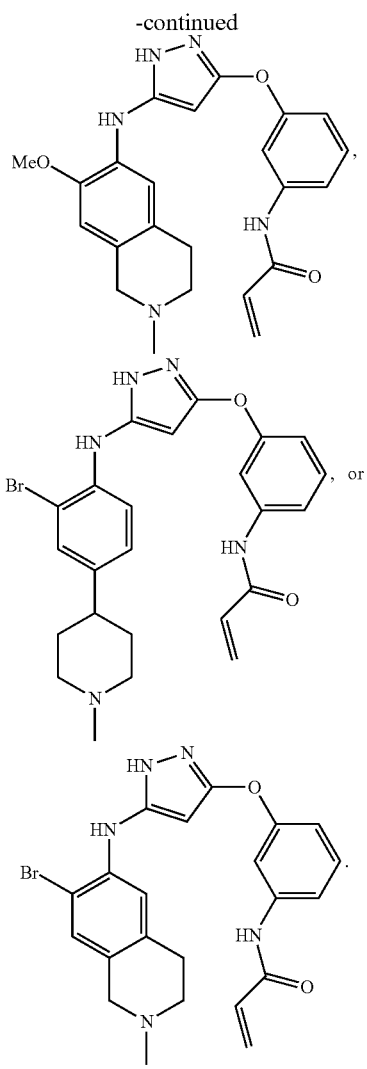

7. A compound of Formula III:

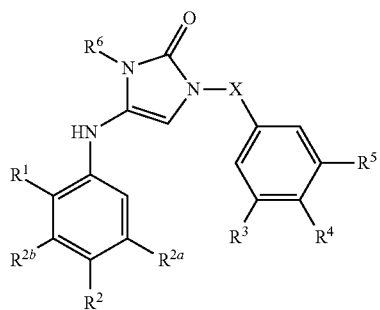

FORMULA III or a pharmaceutically acceptable salt or ester thereof, wherein:

X is oxygen, sulfur, carbonyl, —NR$^6$, C$_1$-C$_6$ alkyl, or C$_1$-C$_6$ haloalkyl;

Y is hydrogen, halogen, or C$_1$-C$_6$ alkyl;

each R$^1$ is independently C$_1$-C$_6$ alkyl, C$_1$-C$_6$ alkoxy, C$_1$-C$_6$ haloalkyl, or C$_1$-C$_6$ haloalkoxy;

(i) one of R$^2$, R$^{2a}$, and R$^{2b}$ is piperidine, pyrrolidine, piperazine, or morpholine that is optionally substituted with C$_1$-C$_6$ alkyl; or C$_3$-C$_6$ alkyl or C$_3$-C$_6$ cycloalkyl containing at least one nitrogen; and the other two of R$^2$, R$^{2a}$, and R$^{2b}$ are hydrogen or C$_1$-C$_6$ alkyl; or (ii) R$^2$ and one of R$^{2a}$ and R$^{2b}$ join to form a piperidine, pyrrolidine, or morpholine that is optionally substituted with C$_1$-C$_6$ alkyl; or C$_3$-C$_6$ cycloalkyl containing at least one nitrogen; and the other of R$^{2a}$ and R$^{2b}$ is hydrogen or C$_1$-C$_6$ alkyl;

one of R$^3$, R$^4$, and R$^5$ is Z, and the other two of R$^3$, R$^4$, and R$^5$ are hydrogen;

each R$^6$ is independently hydrogen or C$_1$-C$_6$ alkyl;

R$^7$ is hydrogen, C$_1$-C$_6$ alkyl, or C$_2$-C$_6$ alkenyl;

R$^8$ is C$_1$-C$_6$ alkyl that is substituted with halogen, cyano, —C(O)R$^9$, or —OC(O)R$^9$; C$_2$-C$_6$ alkenyl that is optionally substituted with halogen or —NR$^9{}_2$; C$_2$-C$_6$ alkynyl; C$_3$-C$_6$ cycloalkyl that is substituted with cyano or —C(O)R$^9$; C$_4$-C$_6$ cycloalkenyl that is optionally substituted with halogen; or C$_4$-C$_9$ heterocycloalkenyl that is optionally substituted with halogen, C$_1$-C$_6$ alkyl, or carbonyl;

each R$^9$ is independently C$_1$-C$_6$ alkyl;

R$^{10}$ is hydrogen or C$_1$-C$_6$ alkyl;

R$^{11}$ is C$_2$-C$_6$ alkenyl;

R$^{12}$ is C$_2$-C$_6$ alkenyl substituted with cyano or —C(O)OR$^9$;

Z is C$_2$-C$_6$ alkenyl, C$_2$-C$_6$ alkynyl, C$_3$-C$_6$ cycloalkyl that is substituted with cyano or acetyl,
—(CH$_2$)$_n$NR$^7$C(O)R$^8$, —(CH$_2$)$_n$C(O)(CH$_2$)$_n$R$^8$,
—(CH$_2$)$_n$OC(O)R$^8$,

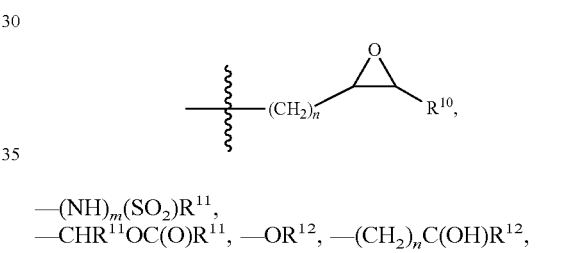

—(NH)$_m$(SO$_2$)R$^{11}$,
—CHR$^{11}$OC(O)R$^{11}$, —OR$^{12}$, —(CH$_2$)$_n$C(OH)R$^{12}$,

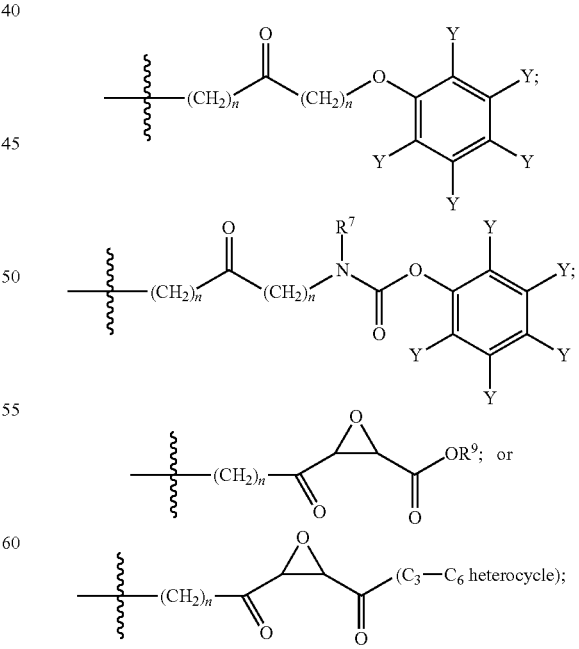

n is an integer from 0 to 6; and
m is 0 or 1.

8. The compound of embodiment 7, wherein:
X is $C_1$-$C_6$ alkyl;
$R^1$ is $C_1$-$C_6$ alkoxy;
$R^2$ is pyrrolidine that is substituted at the N position with $C_1$-$C_6$ alkyl;
$R^{2a}$ and $R^{2b}$ are hydrogen;
one of $R^3$, $R^4$, and $R^5$ is Z, and the other two of $R^3$, $R^4$, and $R^5$ are hydrogen;
$R^7$ is hydrogen or $C_1$-$C_6$ alkyl;
$R^8$ is $C_2$-$C_6$ alkenyl; and
Z is —$(CH_2)_n NR^7 C(O)R^8$.

9. The compound of embodiment 7, wherein the compound of Formula III is:

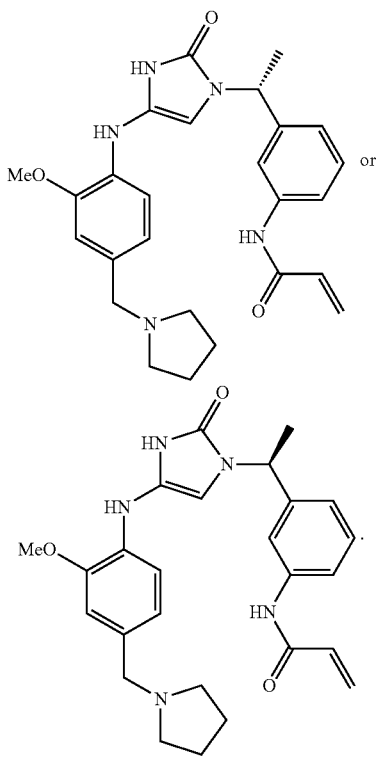

10. The compound of embodiment 1, 4, or 7, wherein X is oxygen, sulfur, carbonyl, NH, $NCH_3$, $CH_2$, $CF_2$, or $CH(CH_3)$.

11. The compound of embodiment 1, 4, or 7, wherein Y is hydrogen, fluorine, chlorine, or methyl.

12. The compound of embodiment 1, 4, or 7, wherein $R^1$ is —$CH_3$, —$CH_2CH_3$, —$OCH_3$, —$OCH_2CH_3$, or —$OCH_2(CH_3)_2$.

13. A compound of Formula IV:

FORMULA IV

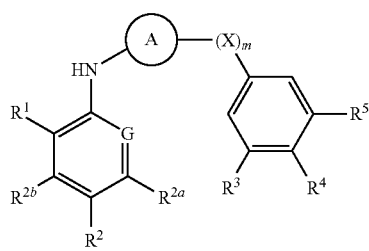

or a pharmaceutically acceptable salt or ester thereof, wherein:
X is oxygen, sulfur, carbonyl, —$NR^6$, $C_1$-$C_6$ alkyl, or $C_1$-$C_6$ haloalkyl;
$X^{2b}$ is oxygen, sulfur, NH, or $NR^{30}$;
each $R^1$ is independently $C_1$-$C_6$ alkyl, $C_1$-$C_6$ alkoxy, $C_1$-$C_6$ haloalkyl, or $C_1$-$C_6$ haloalkoxy;
(i) one of $R^2$, $R^{2a}$, and $R^{2b}$ is piperidine, pyrrolidine, piperazine, or morpholine that is optionally substituted with $C_1$-$C_6$ alkyl; or $C_3$-$C_6$ alkyl or $C_3$-$C_6$ cycloalkyl containing at least one nitrogen; and the other two of $R^2$, $R^{2a}$, and $R^{2b}$ are hydrogen or $C_1$-$C_6$ alkyl; or (ii) $R^2$ and one of $R^{2a}$ and $R^{2b}$ join to form a piperidine, pyrrolidine, or morpholine that is optionally substituted with $C_1$-$C_6$ alkyl; or $C_3$-$C_6$ cycloalkyl containing at least one nitrogen; and the other of $R^{2a}$ and $R^{2b}$ is hydrogen or $C_1$-$C_6$ alkyl;
one of $R^3$, $R^4$, and $R^5$ is Z, and the other two of $R^3$, $R^4$, and $R^5$ are hydrogen;
each $R^6$ is independently hydrogen or $C_1$-$C_6$ alkyl;
$R^7$ is hydrogen, $C_1$-$C_6$ alkyl, or $C_2$-$C_6$ alkenyl;
$R^8$ is $C_1$-$C_6$ alkyl that is substituted with halogen, cyano, —$C(O)R^9$, or —$OC(O)R^9$; $C_2$-$C_6$ alkenyl that is optionally substituted with halogen or —$NR^9_2$; $C_2$-$C_6$ alkynyl; $C_3$-$C_6$ cycloalkyl that is substituted with cyano or —$C(O)R^9$; $C_4$-$C_6$ cycloalkenyl that is optionally substituted with halogen; or $C_4$-$C_9$ heterocycloalkenyl that is optionally substituted with halogen, $C_1$-$C_6$ alkyl, or carbonyl;
each $R^9$ is independently $C_1$-$C_6$ alkyl;
$R^{10}$ is hydrogen or $C_1$-$C_6$ alkyl;
$R^{11}$ is $C_2$-$C_6$ alkenyl;
$R^{12}$ is $C_2$-$C_6$ alkenyl substituted with cyano or —$C(O)OR^9$;
$R^{30}$ is halogen or $C_1$-$C_6$ alkyl;
Z is $C_2$-$C_6$ alkenyl, $C_2$-$C_6$ alkynyl, $C_3$-$C_6$ cycloalkyl that is substituted with cyano or acetyl, —$(CH_2)_n NR^7 C(O)R^8$, —$(CH_2)_n C(O)(CH_2)_n R^8$, —$(CH_2)_n OC(O)R^8$,

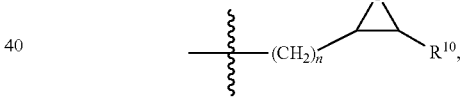

—$(NH)_m(SO_2)R^{11}$,
—$CHR^{11}OC(O)R^{11}$, —$OR^{12}$, —$(CH_2)_n C(OH)R^{12}$,

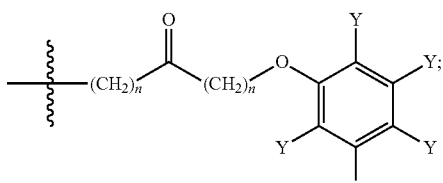

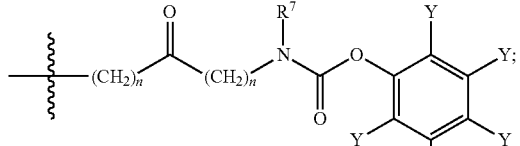

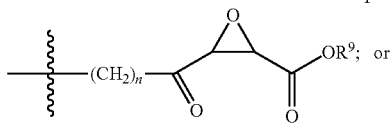

-continued

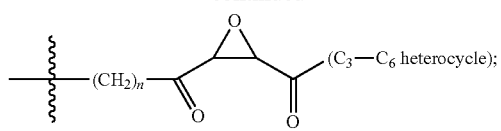

n is an integer from 0 to 6; and
m is 0 or 1;

Ⓐ is

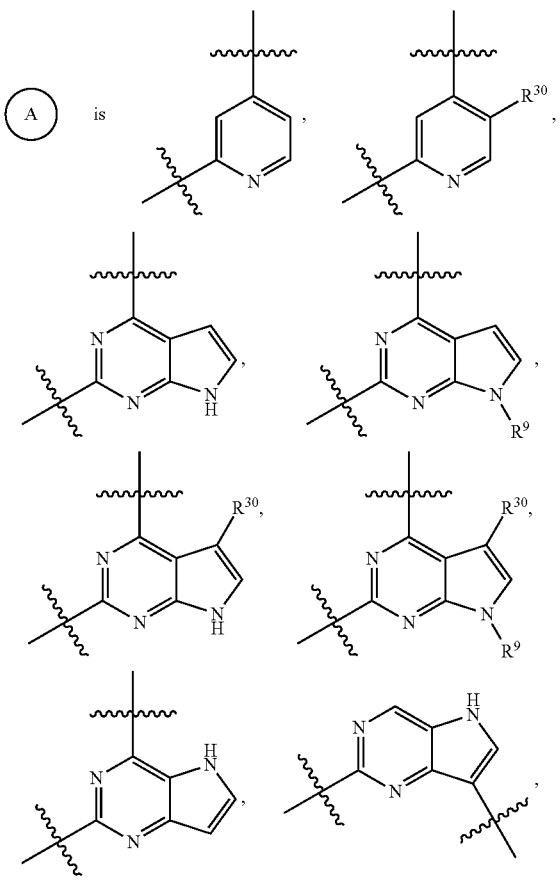

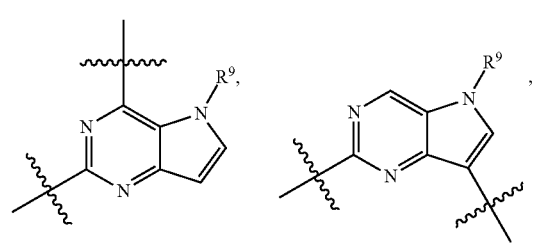

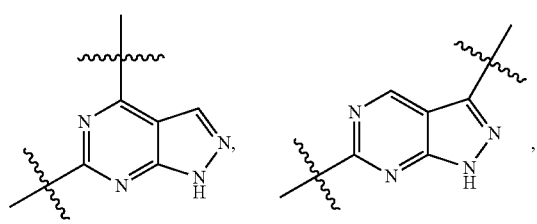

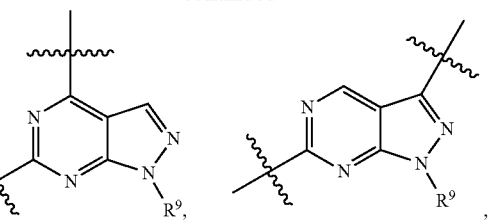

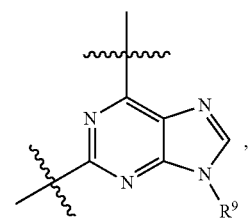

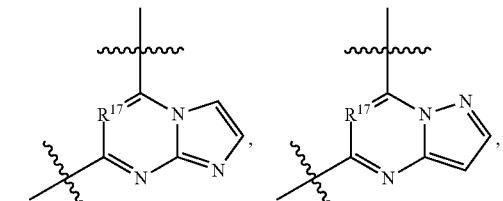

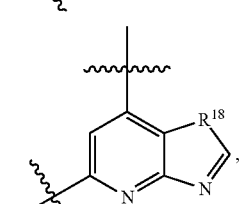

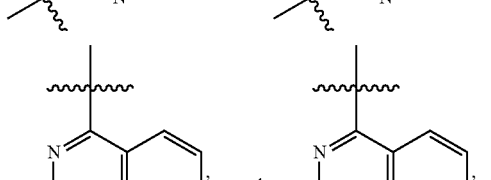

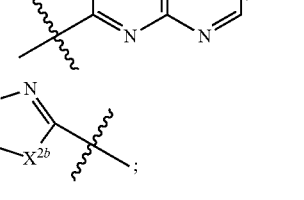

$R^{17}$ is N, CH, or $CR^{30}$;
$R^{18}$ is O or S; and
G is N, CH, or $CR^{30}$.

14. The compound of embodiment 13, wherein:
X is oxygen;
$R^1$ is $C_1$-$C_6$ alkoxy;
$R^2$ is piperazine that is substituted at the N position with $C_1$-$C_6$ alkyl;
$R^{2a}$ and $R^{2b}$ are hydrogen;
one of $R^3$, $R^4$, and $R^5$ is Z, and the other two of $R^3$, $R^4$, and $R^5$ are hydrogen;
$R^7$ is hydrogen or $C_1$-$C_6$ alkyl;
$R^8$ is $C_2$-$C_6$ alkenyl; and
Z is —$(CH_2)_n NR^7 C(O)R^8$.

15. A compound of Formula VI:

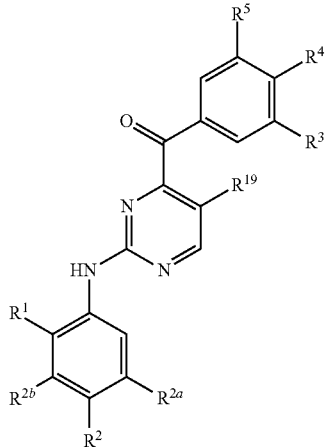

FORMULA VI or a pharmaceutically acceptable salt or ester thereof, wherein:

each $R^1$ is independently $C_1$-$C_6$ alkyl, $C_1$-$C_6$ alkoxy, $C_1$-$C_6$ haloalkyl, or $C_1$-$C_6$ haloalkoxy;

(i) one of $R^2$, $R^{2a}$, and $R^{2b}$ is piperidine, pyrrolidine, piperazine, or morpholine that is optionally substituted with $C_1$-$C_6$ alkyl; or $C_3$-$C_6$ alkyl or $C_3$-$C_6$ cycloalkyl containing at least one nitrogen; and the other two of $R^2$, $R^{2a}$, and $R^{2b}$ are hydrogen or $C_1$-$C_6$ alkyl; or (ii) $R^2$ and one of $R^{2a}$ and $R^{2b}$ join to form a piperidine, pyrrolidine, or morpholine that is optionally substituted with $C_1$-$C_6$ alkyl; or $C_3$-$C_6$ cycloalkyl containing at least one nitrogen; and the other of $R^{2a}$ and $R^{2b}$ is hydrogen or $C_1$-$C_6$ alkyl;

one of $R^3$, $R^4$, and $R^5$ is Z, and the other two of $R^3$, $R^4$, and $R^5$ are hydrogen;

each $R^6$ is independently hydrogen or $C_1$-$C_6$ alkyl;

$R^7$ is hydrogen, $C_1$-$C_6$ alkyl, or $C_2$-$C_6$ alkenyl;

$R^8$ is $C_1$-$C_6$ alkyl that is substituted with halogen, cyano, —C(O)$R^9$, or —OC(O)$R^9$; $C_2$-$C_6$ alkenyl that is optionally substituted with halogen or —NR$^9{}_2$; $C_2$-$C_6$ alkynyl; $C_3$-$C_6$ cycloalkyl that is substituted with cyano or —C(O)$R^9$; $C_4$-$C_6$ cycloalkenyl that is optionally substituted with halogen; or $C_4$-$C_9$ heterocycloalkenyl that is optionally substituted with halogen, $C_1$-$C_6$ alkyl, or carbonyl;

each $R^9$ is independently $C_1$-$C_6$ alkyl;

$R^{10}$ is hydrogen or $C_1$-$C_6$ alkyl;

$R^{11}$ is $C_2$-$C_6$ alkenyl;

$R^{12}$ is $C_2$-$C_6$ alkenyl substituted with cyano or —C(O)O$R^9$;

Z is $C_2$-$C_6$ alkenyl, $C_2$-$C_6$ alkynyl, $C_3$-$C_6$ cycloalkyl that is substituted with cyano or acetyl, —(CH$_2$)$_n$NR$^7$C(O)$R^8$, —(CH$_2$)$_n$C(O)(CH$_2$)$_n$R$^8$, —(CH$_2$)$_n$OC(O)R$^8$,

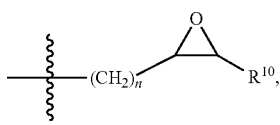

—(NH)$_m$(SO$_2$)R$^{11}$,
—CHR$^{11}$OC(O)R$^{11}$, —OR$^{12}$, —(CH$_2$)$_n$C(OH)R$^{12}$,

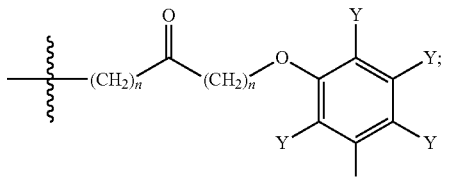

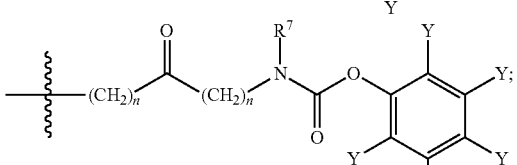

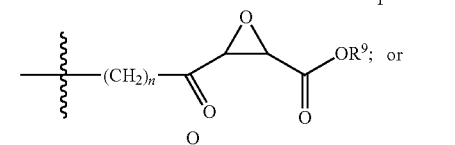

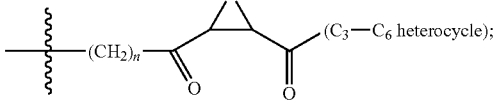

n is an integer from 0 to 6;
m is 0 or 1; and
$R^{19}$ is hydrogen, halogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, OH, NR$^6{}_2$, CN, N$_3$, or NO$_2$.

16. The compound of embodiment 15, wherein:
$R^1$ is $C_1$-$C_6$ alkoxy;
$R^2$ is piperazine that is substituted at the N position with $C_1$-$C_6$ alkyl;
$R^{2a}$ and $R^{2b}$ are hydrogen;
$R^{19}$ is halogen;
one of $R^3$, $R^4$, and $R^5$ is Z, and the other two of $R^3$, $R^4$, and $R^5$ are hydrogen;
$R^7$ is hydrogen or $C_1$-$C_6$ alkyl;
$R^8$ is $C_2$-$C_6$ alkenyl; and
Z is —(CH$_2$)$_n$NR$^7$C(O)R$^8$.

17. The compound of embodiment 15, wherein the compound of Formula VI is:

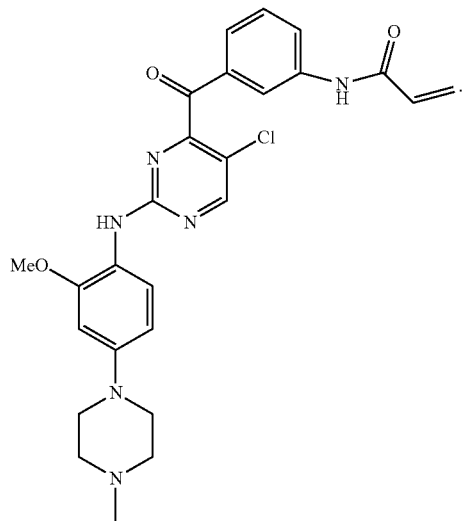 [SMILES: C=CC(=O)Nc1cccc(C(=O)c2nc(Nc3ccc(N4CCN(C)CC4)cc3OC)ncc2Cl)c1]

18. A compound of Formula VII:

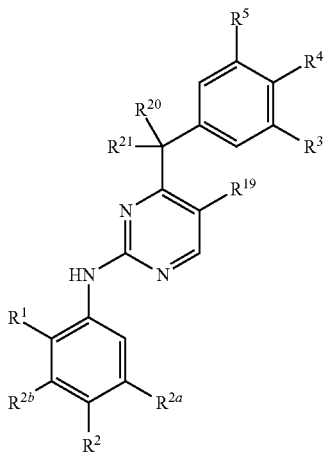

FORMULA VII

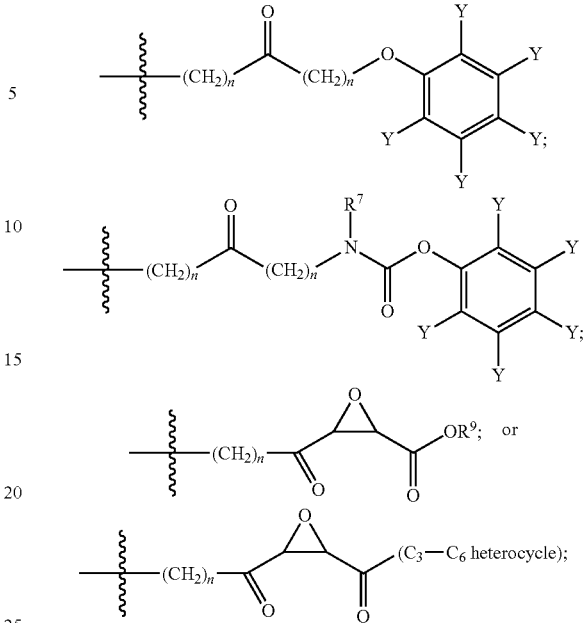

or a pharmaceutically acceptable salt or ester thereof, wherein:

each $R^1$ is independently $C_1$-$C_6$ alkyl, $C_1$-$C_6$ alkoxy, $C_1$-$C_6$ haloalkyl, or $C_1$-$C_6$ haloalkoxy;

(i) one of $R^2$, $R^{2a}$, and $R^{2b}$ is piperidine, pyrrolidine, piperazine, or morpholine that is optionally substituted with $C_1$-$C_6$ alkyl; or $C_3$-$C_6$ alkyl or $C_3$-$C_6$ cycloalkyl containing at least one nitrogen; and the other two of $R^2$, $R^{2a}$, and $R^{2b}$ are hydrogen or $C_1$-$C_6$ alkyl; or (ii) $R^2$ and one of $R^{2a}$ and $R^{2b}$ join to form a piperidine, pyrrolidine, or morpholine that is optionally substituted with $C_1$-$C_6$ alkyl; or $C_3$-$C_6$ cycloalkyl containing at least one nitrogen; and the other of $R^{2a}$ and $R^{2b}$ is hydrogen or $C_1$-$C_6$ alkyl;

one of $R^3$, $R^4$, and $R^5$ is Z, and the other two of $R^3$, $R^4$, and $R^5$ are hydrogen;

each $R^6$ is independently hydrogen or $C_1$-$C_6$ alkyl;

$R^7$ is hydrogen, $C_1$-$C_6$ alkyl, or $C_2$-$C_6$ alkenyl;

$R^8$ is $C_1$-$C_6$ alkyl that is substituted with halogen, cyano, —C(O)$R^9$, or —OC(O)$R^9$; $C_2$-$C_6$ alkenyl that is optionally substituted with halogen or —NR$^9_2$; $C_2$-$C_6$ alkynyl; $C_3$-$C_6$ cycloalkyl that is substituted with cyano or —C(O)$R^9$; $C_4$-$C_6$ cycloalkenyl that is optionally substituted with halogen; or $C_4$-$C_9$ heterocycloalkenyl that is optionally substituted with halogen, $C_1$-$C_6$ alkyl, or carbonyl;

each $R^9$ is independently $C_1$-$C_6$ alkyl;

$R^{10}$ is hydrogen or $C_1$-$C_6$ alkyl;

$R^{11}$ is $C_2$-$C_6$ alkenyl;

$R^{12}$ is $C_2$-$C_6$ alkenyl substituted with cyano or —C(O)O$R^9$;

Z is $C_2$-$C_6$ alkenyl, $C_2$-$C_6$ alkynyl, $C_3$-$C_6$ cycloalkyl that is substituted with cyano or acetyl, —(CH$_2$)$_n$NR$^7$C(O)R$^8$, —(CH$_2$)$_n$C(O)(CH$_2$)$_n$R$^8$, —(CH$_2$)$_n$OC(O)R$^8$,

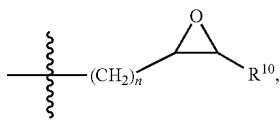

—(NH)$_m$(SO$_2$)R$^{11}$,
—CHR$^{11}$OC(O)R$^{11}$, —OR$^{12}$, —(CH$_2$)$_n$C(OH)R$^{12}$, n is an integer from 0 to 6;
m is 0 or 1; and $R^{19}$ is hydrogen, halogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, OH, NR$^6_2$, CN, N$_3$, or NO$_2$; and $R^{20}$ and $R^{21}$ are each independently hydrogen, halogen, $C_1$-$C_6$ alkyl, or $C_1$-$C_6$ haloalkyl, or $R^{20}$ and $R^{21}$ together form a $C_3$-$C_6$ cycloalkyl that is optionally substituted with halogen or $C_1$-$C_6$ alkyl, a $C_3$-$C_6$ cycloalkenyl that is optionally substituted with halogen or $C_1$-$C_6$ alkyl, or a $C_3$-$C_6$ heterocycle that is optionally substituted with halogen or $C_1$-$C_6$ alkyl.

19. The compound of embodiment 18, wherein:
$R^1$ is $C_1$-$C_6$ alkoxy;
$R^2$ is piperazine that is substituted at the N position with $C_1$-$C_6$ alkyl;
$R^{2a}$ and $R^{2b}$ are hydrogen;
$R^{19}$ is halogen;
one of $R^3$, $R^4$, and $R^5$ is Z, and the other two of $R^3$, $R^4$, and $R^5$ are hydrogen;
$R^7$ is hydrogen or $C_1$-$C_6$ alkyl;
$R^8$ is $C_2$-$C_6$ alkenyl;
Z is —(CH$_2$)$_n$NR$^7$C(O)R$^8$; and
$R^{20}$ and $R^{21}$ together form a $C_3$-$C_6$ cycloalkyl or $C_3$-$C_6$ cycloalkenyl.

20. A compound of Formula VIII:

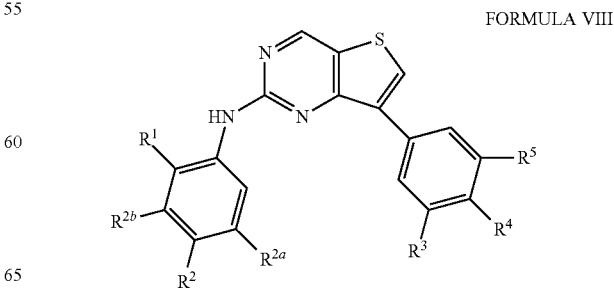

FORMULA VIII or a pharmaceutically acceptable salt or ester thereof, wherein:

X is oxygen, sulfur, carbonyl, —NR$^6$, C$_1$-C$_6$ alkyl, or C$_1$-C$_6$ haloalkyl;

Y is hydrogen, halogen, or C$_1$-C$_6$ alkyl;

each R$^1$ is independently C$_1$-C$_6$ alkyl, C$_1$-C$_6$ alkoxy, C$_1$-C$_6$ haloalkyl, or C$_1$-C$_6$ haloalkoxy;

(i) one of R$^2$, R$^{2a}$, and R$^{2b}$ is piperidine, pyrrolidine, or morpholine that is optionally substituted with C$_1$-C$_6$ alkyl; or C$_3$-C$_6$ alkyl or C$_3$-C$_6$ cycloalkyl containing at least one nitrogen; and the other two of R$^2$, R$^{2a}$, and R$^{2b}$ are hydrogen or C$_1$-C$_6$ alkyl; or (ii) R$^2$ and one of R$^{2a}$ and R$^{2b}$ join to form a piperidine, pyrrolidine, or morpholine that is optionally substituted with C$_1$-C$_6$ alkyl; or C$_3$-C$_6$ cycloalkyl containing at least one nitrogen; and the other of R$^{2a}$ and R$^{2b}$ is hydrogen or C$_1$-C$_6$ alkyl;

one of R$^3$, R$^4$, and R$^5$ is Z, and the other two of R$^3$, R$^4$, and R$^5$ are hydrogen;

each R$^6$ is independently hydrogen or C$_1$-C$_6$ alkyl;

R$^7$ is hydrogen, C$_1$-C$_6$ alkyl, or C$_2$-C$_6$ alkenyl;

R$^8$ is C$_1$-C$_6$ alkyl that is substituted with halogen, cyano, —C(O)R$^9$, or —OC(O)R$^9$; C$_2$-C$_6$ alkenyl that is optionally substituted with halogen or —NR$^9$$_2$; C$_2$-C$_6$ alkynyl; C$_3$-C$_6$ cycloalkyl that is substituted with cyano or —C(O)R$^9$; C$_4$-C$_6$ cycloalkenyl that is optionally substituted with halogen; or C$_4$-C$_9$ heterocycloalkenyl that is optionally substituted with halogen, C$_1$-C$_6$ alkyl, or carbonyl;

each R$^9$ is independently C$_1$-C$_6$ alkyl;

R$^{10}$ is hydrogen or C$_1$-C$_6$ alkyl;

R$^{11}$ is C$_2$-C$_6$ alkenyl;

R$^{12}$ is C$_2$-C$_6$ alkenyl substituted with cyano or —C(O)OR$^9$;

Z is C$_2$-C$_6$ alkenyl, C$_2$-C$_6$ alkynyl, C$_3$-C$_6$ cycloalkyl that is substituted with cyano or acetyl, —(CH$_2$)$_n$NR$^7$C(O)R$^8$, —(CH$_2$)$_n$C(O)(CH$_2$)$_n$R$^8$, —(CH$_2$)$_n$OC(O)R$^8$,

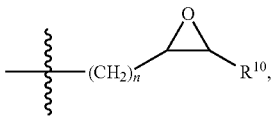

—(NH)$_m$(SO$_2$)R$^{11}$,
—CHR$^{11}$OC(O)R$^{11}$, —OR$^{12}$, —(CH$_2$)$_n$C(OH)R$^{12}$,

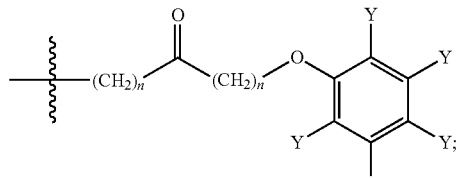

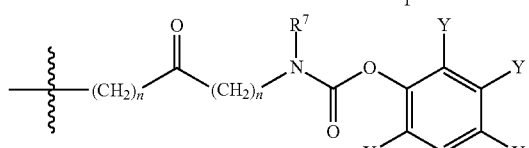

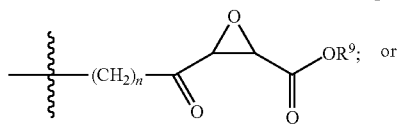

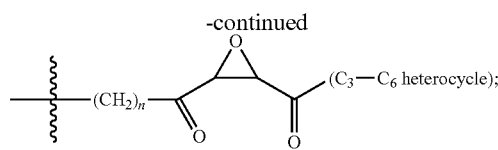

n is an integer from 0 to 6; and
m is 0 or 1.

21. The compound of embodiment 20, wherein:
R$^1$ is C$_1$-C$_6$ alkoxy;
R$^2$ is piperazine that is substituted at the N position with C$_1$-C$_6$ alkyl;
R$^{2a}$ and R$^{2b}$ are hydrogen;
one of R$^3$, R$^4$, and R$^5$ is Z, and the other two of R$^3$, R$^4$, and R$^5$ are hydrogen;
R$^7$ is hydrogen or C$_1$-C$_6$ alkyl;
R$^8$ is C$_2$-C$_6$ alkenyl; and
Z is —(CH$_2$)$_n$NR$^7$C(O)R$^8$.

22. The compound of embodiment 20, wherein the compound of Formula VIII is:

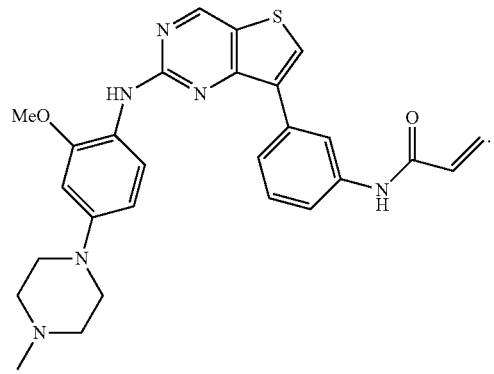 [SMILES: C=CC(=O)Nc1cccc(-c2csc3cnc(Nc4ccc(N5CCN(C)CC5)cc4OC)nc23)c1]

23. A compound of Formula IX:

FORMULA IX

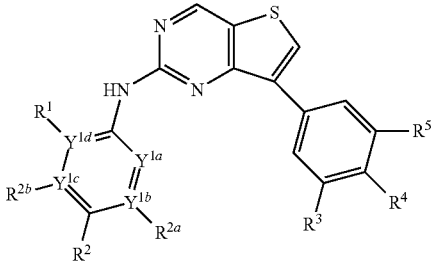

or a pharmaceutically acceptable salt or ester thereof, wherein:

X is oxygen, sulfur, carbonyl, —NR$^6$, C$_1$-C$_6$ alkyl, or C$_1$-C$_6$ haloalkyl;

Y is hydrogen, halogen, or C$_1$-C$_6$ alkyl;

each R$^1$ is independently C$_1$-C$_6$ alkyl, C$_1$-C$_6$ alkoxy, C$_1$-C$_6$ haloalkyl, or C$_1$-C$_6$ haloalkoxy;

(i) one of R$^2$, R$^{2a}$, and R$^{2b}$ is piperidine, pyrrolidine, piperazine, or morpholine that is optionally substituted with C$_1$-C$_6$ alkyl; or C$_3$-C$_6$ alkyl or C$_3$-C$_6$ cycloalkyl containing at least one nitrogen; and the other two of R$^2$, R$^{2a}$, and R$^{2b}$ are hydrogen or C$_1$-C$_6$ alkyl; or (ii) R$^2$ and one of R$^{2a}$ and $R^{2b}$ join to form a piperidine, pyrrolidine, or morpholine that is optionally substituted with $C_1$-$C_6$ alkyl; or $C_3$-$C_6$ cycloalkyl containing at least one nitrogen; and the other of $R^{2a}$ and $R^{2b}$ is hydrogen or $C_1$-$C_6$ alkyl;

one of $R^3$, $R^4$, and $R^5$ is Z, and the other two of $R^3$, $R^4$, and $R^5$ are hydrogen;

each $R^6$ is independently hydrogen or $C_1$-$C_6$ alkyl;

$R^7$ is hydrogen, $C_1$-$C_6$ alkyl, or $C_2$-$C_6$ alkenyl;

$R^8$ is $C_1$-$C_6$ alkyl that is substituted with halogen, cyano, —C(O)$R^9$, or —OC(O)$R^9$; $C_2$-$C_6$ alkenyl that is optionally substituted with halogen or —NR$^9{}_2$; $C_2$-$C_6$ alkynyl; $C_3$-$C_6$ cycloalkyl that is substituted with cyano or —C(O)$R^9$; $C_4$-$C_6$ cycloalkenyl that is optionally substituted with halogen; or $C_4$-$C_9$ heterocycloalkenyl that is optionally substituted with halogen, $C_1$-$C_6$ alkyl, or carbonyl;

each $R^9$ is independently $C_1$-$C_6$ alkyl;

$R^{10}$ is hydrogen or $C_1$-$C_6$ alkyl;

$R^{11}$ is $C_2$-$C_6$ alkenyl;

$R^{12}$ is $C_2$-$C_6$ alkenyl substituted with cyano or —C(O)OR$^9$;

Z is $C_2$-$C_6$ alkenyl, $C_2$-$C_6$ alkynyl, $C_3$-$C_6$ cycloalkyl that is substituted with cyano or acetyl, —(CH$_2$)$_n$NR$^7$C(O)R$^8$, —(CH$_2$)$_n$C(O)(CH$_2$)$_n$R$^8$, —(CH$_2$)$_n$OC(O)R$^8$,

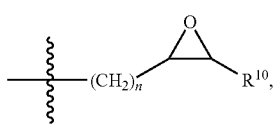

—(NH)$_m$(SO$_2$)R$^{11}$,
—CHR$^{11}$OC(O)R$^{11}$, —OR$^{12}$, —(CH$_2$)$_n$C(OH)R$^{12}$,

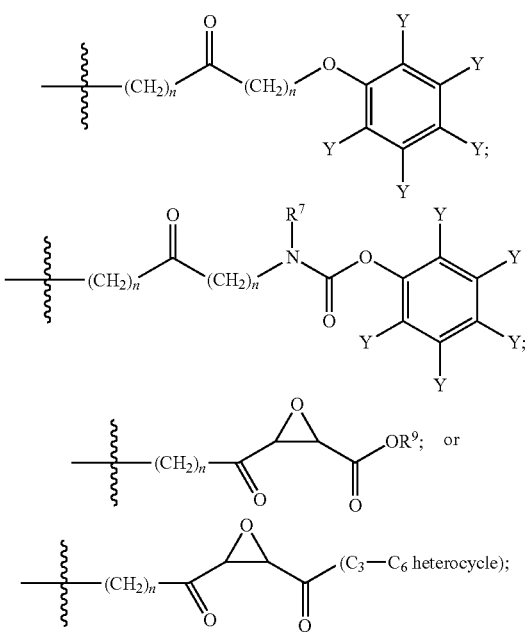

m is 0 or 1; and each of $Y^{1a}$, $Y^{1b}$, $Y^{1c}$, and $Y^{1d}$ is independently carbon or nitrogen, wherein at least one of $Y^{1a}$, $Y^{1b}$, $Y^{1c}$, and $Y^{1d}$ is nitrogen.

24. The compound of embodiment 23, wherein:
$R^1$ is $C_1$-$C_6$ alkoxy;
$R^2$ is piperazine that is substituted at the N position with $C_1$-$C_6$ alkyl;
$R^{2a}$ and $R^{2b}$ are hydrogen;
one of $R^3$, $R^4$, and $R^5$ is Z, and the other two of $R^3$, $R^4$, and $R^5$ are hydrogen;
$R^7$ is hydrogen or $C_1$-$C_6$ alkyl;
$R^8$ is $C_2$-$C_6$ alkenyl;
Z is —(CH$_2$)$_n$NR$^7$C(O)R$^8$;
one of $Y^{1a}$ and $Y^{1d}$ is nitrogen; and
$Y^{1b}$, $Y^{1c}$, and the other of $Y^{1a}$ and $Y^{1d}$ are carbon.

25. The compound of embodiment 23, wherein the compound of Formula IX is:

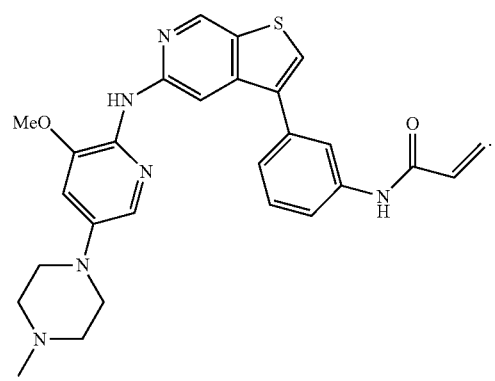 [SMILES: C=CC(=O)Nc1cccc(-c2csc3cnc(Nc4ncc(N5CCN(C)CC5)cc4OC)cc23)c1]

26. A compound of Formula XI:

FORMULA XI

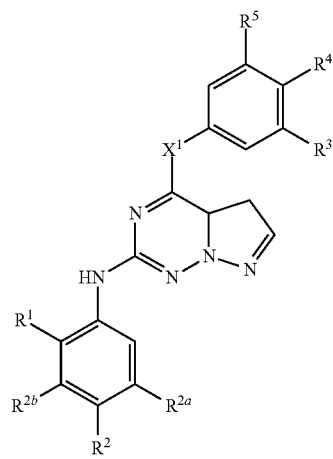

or a pharmaceutically acceptable salt or ester thereof, wherein:
each $R^1$ is independently $C_1$-$C_6$ alkyl, $C_1$-$C_6$ alkoxy, $C_1$-$C_6$ haloalkyl, or $C_1$-$C_6$ haloalkoxy;
(i) one of $R^2$, $R^{2a}$, and $R^{2b}$ is piperidine, pyrrolidine, piperazine, or morpholine that is optionally substituted with $C_1$-$C_6$ alkyl; or $C_3$-$C_6$ alkyl or $C_3$-$C_6$ cycloalkyl containing at least one nitrogen; and the other two of $R^2$, $R^{2a}$, and $R^{2b}$ are hydrogen or $C_1$-$C_6$ alkyl; or (ii) $R^2$ and one of $R^{2a}$ and $R^{2b}$ join to form a piperidine, pyrrolidine, or morpholine that is optionally substituted with $C_1$-$C_6$ alkyl; or $C_3$-$C_6$ cycloalkyl containing at least one nitrogen; and the other of $R^{2a}$ and $R^{2b}$ is hydrogen or $C_1$-$C_6$ alkyl;

one of R³, R⁴, and R⁵ is Z, and the other two of R³, R⁴, and R⁵ are hydrogen;

each R⁶ is independently hydrogen or C₁-C₆ alkyl;

R⁷ is hydrogen, C₁-C₆ alkyl, or C₂-C₆ alkenyl;

R⁸ is C₁-C₆ alkyl that is substituted with halogen, cyano, —C(O)R⁹, or —OC(O)R⁹; C₂-C₆ alkenyl that is optionally substituted with halogen or —NR⁹₂; C₂-C₆ alkynyl; C₃-C₆ cycloalkyl that is substituted with cyano or —C(O)R⁹; C₄-C₆ cycloalkenyl that is optionally substituted with halogen; or C₄-C₉ heterocycloalkenyl that is optionally substituted with halogen, C₁-C₆ alkyl, or carbonyl;

each R⁹ is independently C₁-C₆ alkyl;

R¹⁰ is hydrogen or C₁-C₆ alkyl;

R¹¹ is C₂-C₆ alkenyl;

R¹² is C₂-C₆ alkenyl substituted with cyano or —C(O)OR⁹;

Z is C₂-C₆ alkenyl, C₂-C₆ alkynyl, C₃-C₆ cycloalkyl that is substituted with cyano or acetyl, —(CH₂)ₙNR⁷C(O)R⁸, —(CH₂)ₙC(O)(CH₂)ₙR⁸, —(CH₂)ₙOC(O)R⁸,

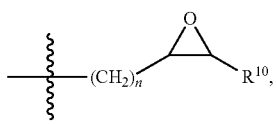

—(NH)ₘ(SO₂)R¹¹,
—CHR¹¹OC(O)R¹¹, —OR¹², —(CH₂)ₙC(OH)R¹²,

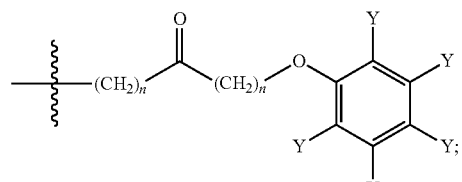

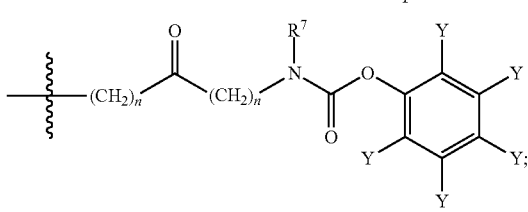

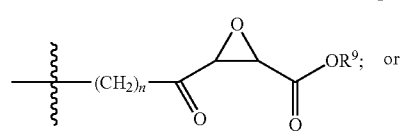

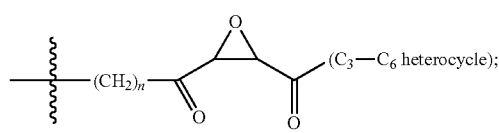

n is an integer from 0 to 6;

m is 0 or 1; and

X¹ is oxygen, sulfur, or —NR⁶.

27. A compound of Formula XII:

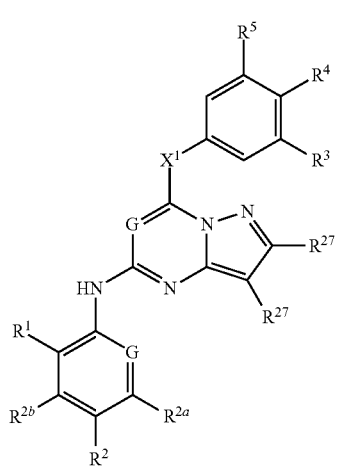

FORMULA XII each R¹ is independently C₁-C₆ alkyl, C₁-C₆ alkoxy, C₁-C₆ haloalkyl, or C₁-C₆ haloalkoxy;

(i) one of R², R²ᵃ, and R²ᵇ is piperidine, pyrrolidine, piperazine, or morpholine that is optionally substituted with C₁-C₆ alkyl; or C₃-C₆ alkyl or C₃-C₆ cycloalkyl containing at least one nitrogen; and the other two of R², R²ᵃ, and R²ᵇ are hydrogen or C₁-C₆ alkyl; or (ii) R² and one of R²ᵃ and R²ᵇ join to form a piperidine, pyrrolidine, or morpholine that is optionally substituted with C₁-C₆ alkyl; or C₃-C₆ cycloalkyl containing at least one nitrogen; and the other of R²ᵃ and R²ᵇ is hydrogen or C₁-C₆ alkyl;

one of R³, R⁴, and R⁵ is Z, and the other two of R³, R⁴, and R⁵ are hydrogen;

each R⁶ is independently hydrogen or C₁-C₆ alkyl;

R⁷ is hydrogen, C₁-C₆ alkyl, or C₂-C₆ alkenyl;

R⁸ is C₁-C₆ alkyl that is substituted with halogen, cyano, —C(O)R⁹, or —OC(O)R⁹; C₂-C₆ alkenyl that is optionally substituted with halogen or —NR⁹₂; C₂-C₆ alkynyl; C₃-C₆ cycloalkyl that is substituted with cyano or —C(O)R⁹; C₄-C₆ cycloalkenyl that is optionally substituted with halogen; or C₄-C₉ heterocycloalkenyl that is optionally substituted with halogen, C₁-C₆ alkyl, or carbonyl;

each R⁹ is independently C₁-C₆ alkyl;

R¹⁰ is hydrogen or C₁-C₆ alkyl;

R¹¹ is C₂-C₆ alkenyl;

R¹² is C₂-C₆ alkenyl substituted with cyano or —C(O)OR⁹;

Z is C₂-C₆ alkenyl, C₂-C₆ alkynyl, C₃-C₆ cycloalkyl that is substituted with cyano or acetyl, —(CH₂)ₙNR⁷C(O)R⁸, —(CH₂)ₙC(O)(CH₂)ₙR⁸, —(CH₂)ₙOC(O)R⁸,

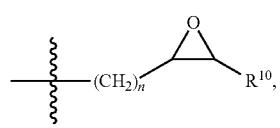

—(NH)ₘ(SO₂)R¹¹,
—CHR¹¹OC(O)R¹¹, —OR¹², —(CH₂)ₙC(OH)R¹²,

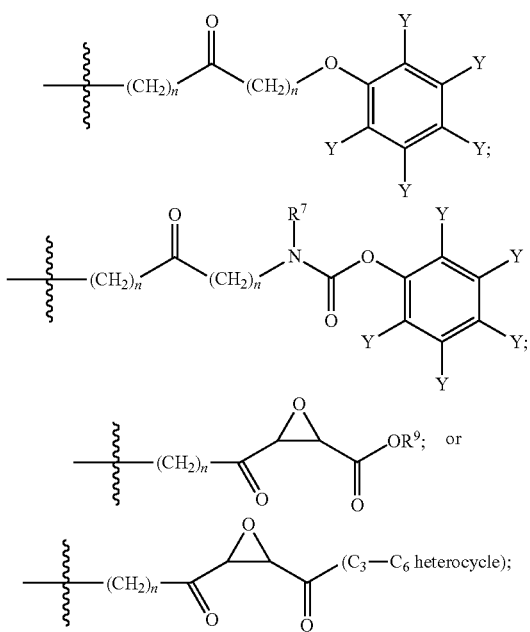

n is an integer from 0 to 6;
m is 0 or 1;
$X^1$ is oxygen, sulfur, or —$NR^6$;
each G is independently N, CH, or $CR^{30}$; and
each $R^{27}$ is independently hydrogen, halogen, $C_1$-$C_3$ alkyl, or $C_1$-$C_3$ alkoxy.

28. The compound of embodiment 1, 4, 7, 13, 15, 18, 20, 23, 26, or 27, wherein Z is —$(CH_2)_n NR^7 C(O)R^8$; $R^7$ is hydrogen; and $R^8$ is $C_2$-$C_6$ alkenyl.

29. The compound of embodiment 1, 4, 7, 13, 15, 18, 20, or 23, 26, or 27, wherein Z is

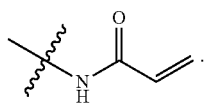 [SMILES: *NC(=O)C=C]

30. A compound of Formula V:

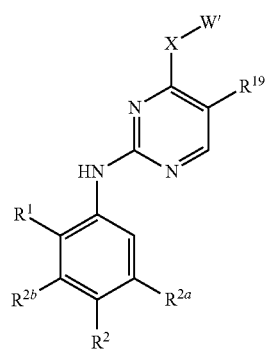

FORMULA V or a pharmaceutically acceptable salt or ester thereof, wherein:

X is oxygen, sulfur, carbonyl, —$NR^6$, $C_1$-$C_6$ alkyl, or $C_1$-$C_6$ haloalkyl;

each $R^1$ is independently $C_1$-$C_6$ alkyl, $C_1$-$C_6$ alkoxy, $C_1$-$C_6$ haloalkyl, or $C_1$-$C_6$ haloalkoxy;

(i) one of $R^2$, $R^{2a}$, and $R^{2b}$ is piperidine, pyrrolidine, piperazine, or morpholine that is optionally substituted with $C_1$-$C_6$ alkyl; or $C_3$-$C_6$ alkyl or $C_3$-$C_6$ cycloalkyl containing at least one nitrogen; and the other two of $R^2$, $R^{2a}$, and $R^{2b}$ are hydrogen or $C_1$-$C_6$ alkyl; or (ii) $R^2$ and one of $R^{2a}$ and $R^{2b}$ join to form a piperidine, pyrrolidine, or morpholine that is optionally substituted with $C_1$-$C_6$ alkyl; or $C_3$-$C_6$ cycloalkyl containing at least one nitrogen; and the other of $R^{2a}$ and $R^{2b}$ is hydrogen or $C_1$-$C_6$ alkyl;

each $R^6$ is independently hydrogen or $C_1$-$C_6$ alkyl;
each $R^{14}$ is independently sulfur, nitrogen, or oxygen;
$R^{16}$ is $C_2$-$C_6$ alkenyl that is optionally substituted with $NR^6_2$ or $C_2$-$C_6$ alkynyl;
$R^{25}$ is halogen;
$R^{26}$ is halogen, $C_1$-$C_6$ alkyl, or $C_1$-$C_6$ haloalkyl;

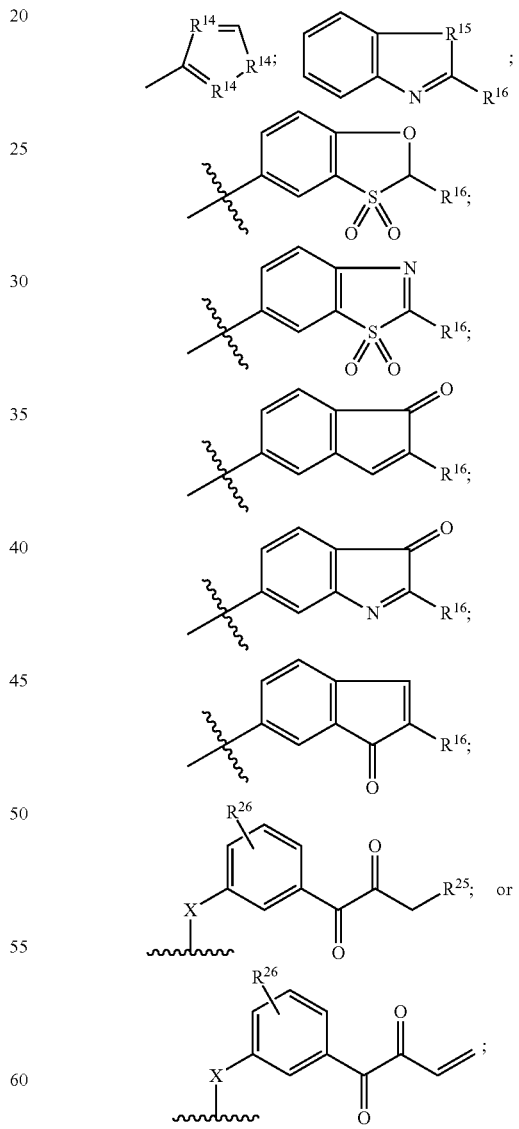

and $R^{19}$ is hydrogen, halogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, OH, $NR^6_2$, CN, $N_3$, or $NO_2$.

31. The compound of embodiment 30, wherein X is carbonyl; R is $C_1$-$C_6$ alkoxy; $R^2$ is piperazine that is substituted at the N position with $C_1$-$C_6$ alkyl; $R^{2a}$ and $R^{2b}$ are hydrogen; and $R^{19}$ is halogen.

32. A compound of Formula Ia:

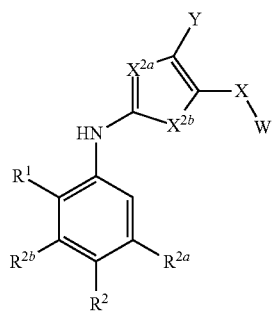

FORMULA Ia or a pharmaceutically acceptable salt or ester thereof, wherein:

X is oxygen, sulfur, carbonyl, —$NR^6$, $C_1$-$C_6$ alkyl, or $C_1$-$C_6$ haloalkyl;

$X^{2a}$ is nitrogen, CH, or $CR^{30}$;

$X^{2b}$ is oxygen, sulfur, NH, or $NR^9$;

Y is hydrogen, halogen, or $C_1$-$C_6$ alkyl;

each $R^1$ is independently $C_1$-$C_6$ alkyl, $C_1$-$C_6$ alkoxy, $C_1$-$C_6$ haloalkyl, or $C_1$-$C_6$ haloalkoxy;

(i) one of $R^2$, $R^{2a}$, and $R^{2b}$ is piperidine, pyrrolidine, piperazine, or morpholine that is optionally substituted with $C_1$-$C_6$ alkyl; or $C_3$-$C_6$ alkyl or $C_3$-$C_6$ cycloalkyl containing at least one nitrogen; and the other two of $R^2$, $R^{2a}$, and $R^{2b}$ are hydrogen or $C_1$-$C_6$ alkyl; or (ii) $R^2$ and one of $R^{2a}$ and $R^{2b}$ join to form a piperidine, pyrrolidine, or morpholine that is optionally substituted with $C_1$-$C_6$ alkyl; or $C_3$-$C_6$ cycloalkyl containing at least one nitrogen; and the other of $R^{2a}$ and $R^{2b}$ is hydrogen or $C_1$-$C_6$ alkyl;

each $R^6$ is independently hydrogen or $C_1$-$C_6$ alkyl;

W is

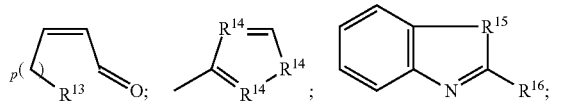

a benzene ring substituted with at least one of halogen, —$NO_2$, or cyano; a pyridine, pyrimidine, oxazole, isoxazole, thiazole, or isothiazole ring that is substituted with at least one of $C_2$-$C_6$ alkenyl, $C_2$-$C_6$ alkynyl, halogen, or cyano; an imidazole or pyrazole ring that is C-substituted with at least one of $C_2$-$C_6$ alkenyl, $C_2$-$C_6$ alkynyl, halogen, or cyano and that is optionally N-substituted with $C_1$-$C_6$ alkyl; a 3-oxobenzisothiazole that is optionally substituted with halogen or $C_1$-$C_6$ alkyl; a pyrrolidine that is N-substituted with acrylate or cyano;

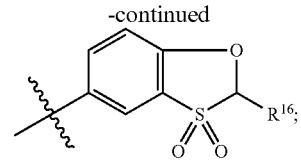

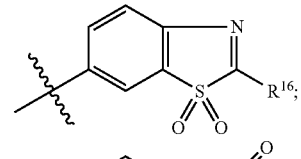

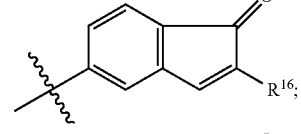

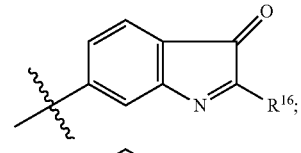

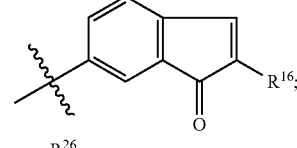

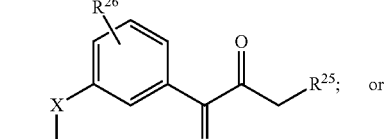

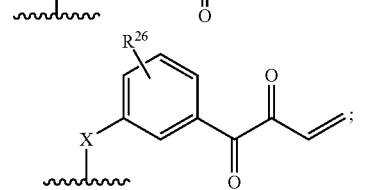

$R^{13}$ is carbon, nitrogen, or oxygen;

each $R^{14}$ is independently sulfur, nitrogen, or oxygen;

$R^{15}$ is oxygen or sulfur;

$R^{16}$ is $C_2$-$C_6$ alkenyl that is optionally substituted with $NR^6_2$ or $C_2$-$C_6$ alkynyl;

$R^{25}$ is halogen;

$R^{26}$ is halogen, $C_1$-$C_6$ alkyl, or $C_1$-$C_6$ haloalkyl;

$R^{30}$ is halogen or $C_1$-$C_6$ alkyl; and p is 1 or 2.

33. A compound of Formula IIa:

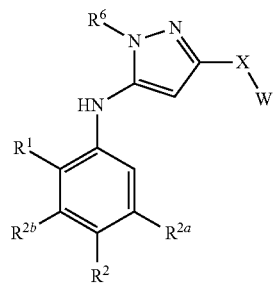

FORMULA IIa or a pharmaceutically acceptable salt or ester thereof, wherein:

X is oxygen, sulfur, carbonyl, —NR$^6$, C$_1$-C$_6$ alkyl, or C$_1$-C$_6$ haloalkyl;

Y is hydrogen, halogen, or C$_1$-C$_6$ alkyl;

each R$^1$ is independently C$_1$-C$_6$ alkyl, C$_1$-C$_6$ alkoxy, C$_1$-C$_6$ haloalkyl, or C$_1$-C$_6$ haloalkoxy;

(i) one of R$^2$, R$^{2a}$, and R$^{2b}$ is piperidine, pyrrolidine, piperazine, or morpholine that is optionally substituted with C$_1$-C$_6$ alkyl; or C$_3$-C$_6$ alkyl or C$_3$-C$_6$ cycloalkyl containing at least one nitrogen; and the other two of R$^2$, R$^{2a}$, and R$^{2b}$ are hydrogen or C$_1$-C$_6$ alkyl; or (ii) R$^2$ and one of R$^{2a}$ and R$^{2b}$ join to form a piperidine, pyrrolidine, or morpholine that is optionally substituted with C$_1$-C$_6$ alkyl; or C$_3$-C$_6$ cycloalkyl containing at least one nitrogen; and the other of R$^{2a}$ and R$^{2b}$ is hydrogen or C$_1$-C$_6$ alkyl;

each R$^6$ is independently hydrogen or C$_1$-C$_6$ alkyl;

W is

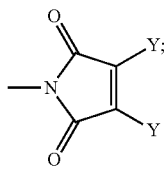

a benzene ring substituted with at least one of halogen, —NO$_2$, or cyano; a pyridine, pyrimidine, oxazole, isoxazole, thiazole, or isothiazole ring that is substituted with at least one of C$_2$-C$_6$ alkenyl, C$_2$-C$_6$ alkynyl, halogen, or cyano; an imidazole or pyrazole ring that is C-substituted with at least one of C$_2$-C$_6$ alkenyl, C$_2$-C$_6$ alkynyl, halogen, or cyano and that is optionally N-substituted with C$_1$-C$_6$ alkyl; a 3-oxobenzisothiazole that is optionally substituted with halogen or C$_1$-C$_6$ alkyl; a pyrrolidine that is N-substituted with acrylate or cyano;

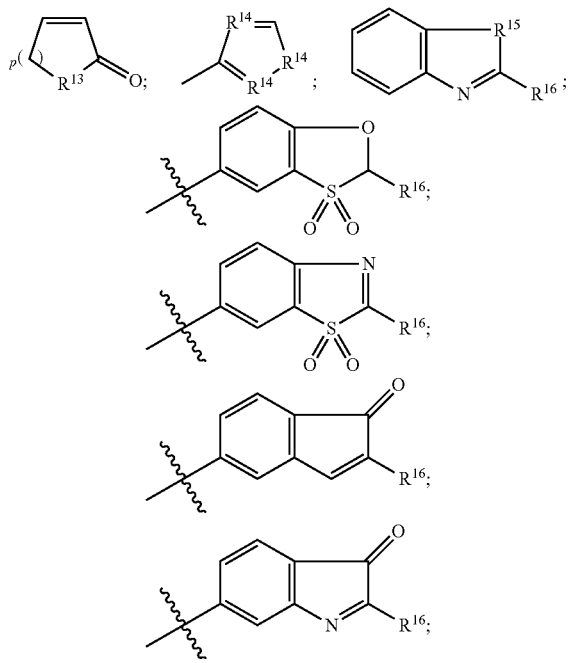

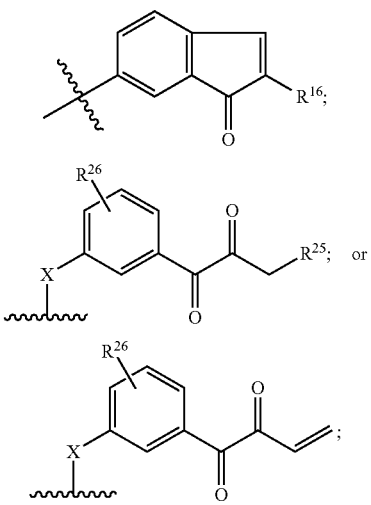

R$^{13}$ is carbon, nitrogen, or oxygen;

each R$^{14}$ is independently sulfur, nitrogen, or oxygen;

R$^{15}$ is oxygen or sulfur;

R$^{16}$ is C$_2$-C$_6$ alkenyl that is optionally substituted with NR$^6_2$ or C$_2$-C$_6$ alkynyl;

R$^{25}$ is halogen;

R$^{26}$ is halogen, C$_1$-C$_6$ alkyl, or C$_1$-C$_6$ haloalkyl; and p is 1 or 2.

34. A compound of Formula IIIa:

FORMULA IIIa

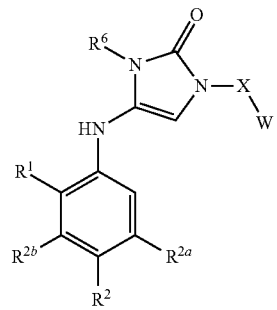

or a pharmaceutically acceptable salt or ester thereof, wherein:

X is oxygen, sulfur, carbonyl, —NR$^6$, C$_1$-C$_6$ alkyl, or C$_1$-C$_6$ haloalkyl;

Y is hydrogen, halogen, or C$_1$-C$_6$ alkyl;

each R$^1$ is independently C$_1$-C$_6$ alkyl, C$_1$-C$_6$ alkoxy, C$_1$-C$_6$ haloalkyl, or C$_1$-C$_6$ haloalkoxy;

(i) one of R$^2$, R$^{2a}$, and R$^{2b}$ is piperidine, pyrrolidine, piperazine, or morpholine that is optionally substituted with C$_1$-C$_6$ alkyl; or C$_3$-C$_6$ alkyl or C$_3$-C$_6$ cycloalkyl containing at least one nitrogen; and the other two of R$^2$, R$^{2a}$, and R$^{2b}$ are hydrogen or C$_1$-C$_6$ alkyl; or (ii) R$^2$ and one of R$^{2a}$ and R$^{2b}$ join to form a piperidine, pyrrolidine, or morpholine that is optionally substituted with $C_1$-$C_6$ alkyl; or $C_3$-$C_6$ cycloalkyl containing at least one nitrogen; and the other of $R^{2a}$ and $R^{2b}$ is hydrogen or $C_1$-$C_6$ alkyl;

each $R^6$ is independently hydrogen or $C_1$-$C_6$ alkyl;

W is

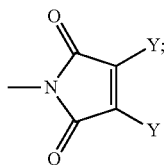

a benzene ring substituted with at least one of halogen, —$NO_2$, or cyano; a pyridine, pyrimidine, oxazole, isoxazole, thiazole, or isothiazole ring that is substituted with at least one of $C_2$-$C_6$ alkenyl, $C_2$-$C_6$ alkynyl, halogen, or cyano; an imidazole or pyrazole ring that is C-substituted with at least one of $C_2$-$C_6$ alkenyl, $C_2$-$C_6$ alkynyl, halogen, or cyano and that is optionally N-substituted with $C_1$-$C_6$ alkyl; a 3-oxobenzisothiazole that is optionally substituted with halogen or $C_1$-$C_6$ alkyl; a pyrrolidine that is N-substituted with acrylate or cyano;

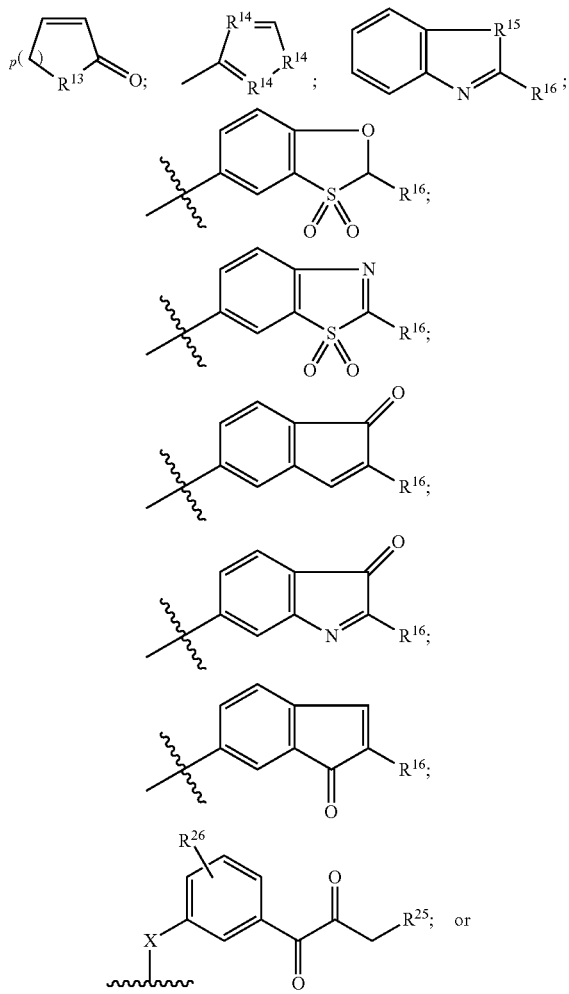

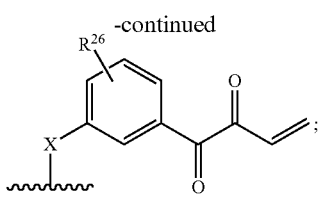

$R^{13}$ is carbon, nitrogen, or oxygen;

each $R^{14}$ is independently sulfur, nitrogen, or oxygen;

$R^{15}$ is oxygen or sulfur;

$R^{16}$ is $C_2$-$C_6$ alkenyl that is optionally substituted with $NR^6_2$ or $C_2$-$C_6$ alkynyl;

$R^{25}$ is halogen;

$R^{26}$ is halogen, $C_1$-$C_6$ alkyl, or $C_1$-$C_6$ haloalkyl; and p is 1 or 2.

35. A compound of Formula IVa:

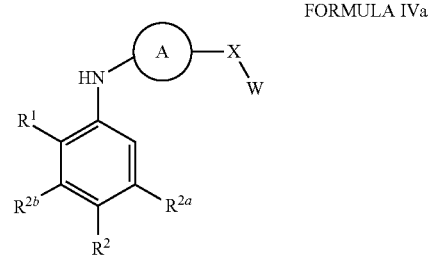

FORMULA IVa or a pharmaceutically acceptable salt or ester thereof, wherein:

X is oxygen, sulfur, carbonyl, —$NR^6$, $C_1$-$C_6$ alkyl, or $C_1$-$C_6$ haloalkyl;

$X^{2b}$ is oxygen, sulfur, NH, or $NR^9$;

Y is hydrogen, halogen, or $C_1$-$C_6$ alkyl;

each $R^1$ is independently $C_1$-$C_6$ alkyl, $C_1$-$C_6$ alkoxy, $C_1$-$C_6$ haloalkyl, or $C_1$-$C_6$ haloalkoxy;

(i) one of $R^2$, $R^{2a}$, and $R^{2b}$ is piperidine, pyrrolidine, piperazine, or morpholine that is optionally substituted with $C_1$-$C_6$ alkyl; or $C_3$-$C_6$ alkyl or $C_3$-$C_6$ cycloalkyl containing at least one nitrogen; and the other two of $R^2$, $R^{2a}$, and $R^{2b}$ are hydrogen or $C_1$-$C_6$ alkyl; or (ii) $R^2$ and one of $R^{2a}$ and $R^{2b}$ join to form a piperidine, pyrrolidine, or morpholine that is optionally substituted with $C_1$-$C_6$ alkyl; or $C_3$-$C_6$ cycloalkyl containing at least one nitrogen; and the other of $R^{2a}$ and $R^{2b}$ is hydrogen or $C_1$-$C_6$ alkyl;

each $R^6$ is independently hydrogen or $C_1$-$C_6$ alkyl;

each $R^9$ is independently $C_1$-$C_6$ alkyl;

W is

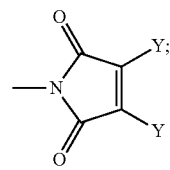

a benzene ring substituted with at least one of halogen, —$NO_2$, or cyano; a pyridine, pyrimidine, oxazole, isoxazole, thiazole, or isothiazole ring that is substituted with at least one of $C_2$-$C_6$ alkenyl, $C_2$-$C_6$ alkynyl, halogen, or cyano; an imidazole or pyrazole ring that is C-substituted with at least one of $C_2$-$C_6$ alkenyl, $C_2$-$C_6$ alkynyl, halogen, or cyano and that is optionally N-substituted with $C_1$-$C_6$ alkyl; a 3-oxobenzisothiazole that is optionally substituted with halogen or $C_1$-$C_6$ alkyl; a pyrrolidine that is N-substituted with acrylate or cyano;

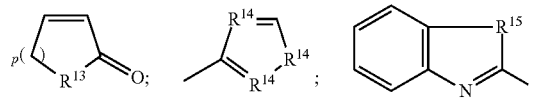

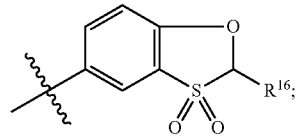

$R^{13}$ is carbon, nitrogen, or oxygen;

each $R^{14}$ is independently sulfur, nitrogen, or oxygen;

$R^{15}$ is oxygen or sulfur;

$R^{16}$ is $C_2$-$C_6$ alkenyl that is optionally substituted with $NR^6_2$ or $C_2$-$C_6$ alkynyl;

$R^{25}$ is halogen;

$R^{26}$ is halogen, $C_1$-$C_6$ alkyl, or $C_1$-$C_6$ haloalkyl;

$R^{30}$ is halogen or $C_1$-$C_6$ alkyl;

p is 1 or 2;

A is

-continued

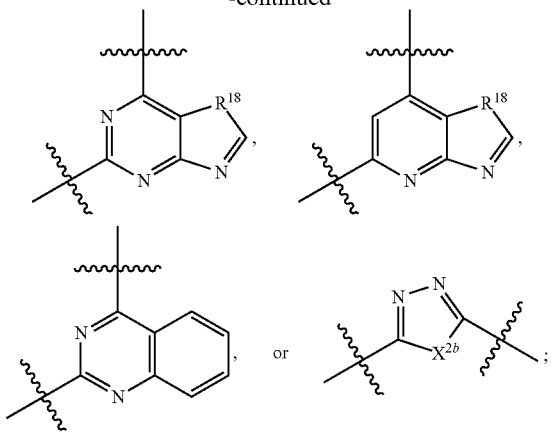

R¹⁷ is N, CH, or CR³⁰; and
R¹⁸ is O or S.

36. A compound of Formula VIa:

FORMULA VIa

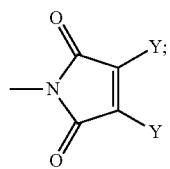

or a pharmaceutically acceptable salt or ester thereof, wherein:
X is oxygen, sulfur, carbonyl, —NR⁶, $C_1$-$C_6$ alkyl, or $C_1$-$C_6$ haloalkyl;
Y is hydrogen, halogen, or $C_1$-$C_6$ alkyl;
each R¹ is independently $C_1$-$C_6$ alkyl, $C_1$-$C_6$ alkoxy, $C_1$-$C_6$ haloalkyl, or $C_1$-$C_6$ haloalkoxy;
(i) one of R², R²ᵃ, and R²ᵇ is piperidine, pyrrolidine, piperazine, or morpholine that is optionally substituted with $C_1$-$C_6$ alkyl; or $C_3$-$C_6$ alkyl or $C_3$-$C_6$ cycloalkyl containing at least one nitrogen; and the other two of R², R²ᵃ, and R²ᵇ are hydrogen or $C_1$-$C_6$ alkyl; or (ii) R² and one of R²ᵃ and R²ᵇ join to form a piperidine, pyrrolidine, or morpholine that is optionally substituted with $C_1$-$C_6$ alkyl; or $C_3$-$C_6$ cycloalkyl containing at least one nitrogen; and the other of R²ᵃ and R²ᵇ is hydrogen or $C_1$-$C_6$ alkyl;
each R⁶ is independently hydrogen or $C_1$-$C_6$ alkyl;
W is a benzene ring substituted with at least one of halogen, —NO₂, or cyano; a pyridine, pyrimidine, oxazole, isoxazole, thiazole, or isothiazole ring that is substituted with at least one of $C_2$-$C_6$ alkenyl, $C_2$-$C_6$ alkynyl, halogen, or cyano; an imidazole or pyrazole ring that is C-substituted with at least one of $C_2$-$C_6$ alkenyl, $C_2$-$C_6$ alkynyl, halogen, or cyano and that is optionally N-substituted with $C_1$-$C_6$ alkyl; a 3-oxobenzisothiazole that is optionally substituted with halogen or $C_1$-$C_6$ alkyl; a pyrrolidine that is N-substituted with acrylate or cyano;

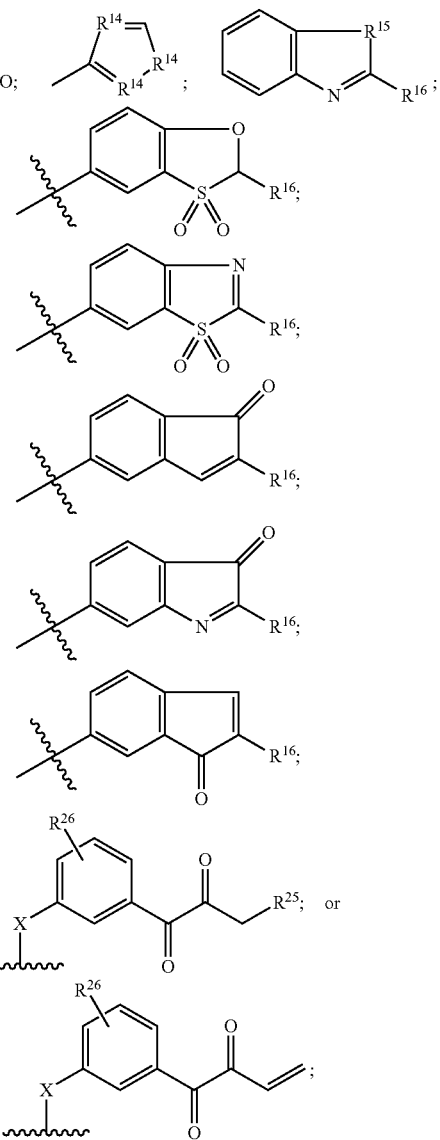

R¹³ is carbon, nitrogen, or oxygen;
each R¹⁴ is independently sulfur, nitrogen, or oxygen;
R¹⁵ is oxygen or sulfur;
R¹⁶ is $C_2$-$C_6$ alkenyl that is optionally substituted with NR⁶₂ or $C_2$-$C_6$ alkynyl;
R¹⁹ is hydrogen, halogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, OH, NR⁶₂, CN, N₃, or NO₂;
R²⁵ is halogen;
R²⁶ is halogen, $C_1$-$C_6$ alkyl, or $C_1$-$C_6$ haloalkyl; and
p is 1 or 2.

37. A compound of Formula VIIa:

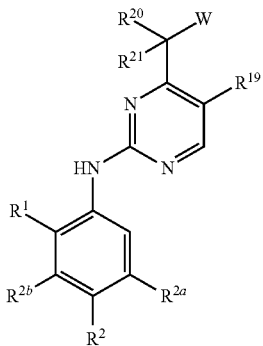

FORMULA VIIa or a pharmaceutically acceptable salt or ester thereof, wherein:

X is oxygen, sulfur, carbonyl, —NR$^6$, C$_1$-C$_6$ alkyl, or C$_1$-C$_6$ haloalkyl;

Y is hydrogen, halogen, or C$_1$-C$_6$ alkyl;

each R$^1$ is independently C$_1$-C$_6$ alkyl, C$_1$-C$_6$ alkoxy, C$_1$-C$_6$ haloalkyl, or C$_1$-C$_6$ haloalkoxy;

(i) one of R$^2$, R$^{2a}$, and R$^{2b}$ is piperidine, pyrrolidine, piperazine, or morpholine that is optionally substituted with C$_1$-C$_6$ alkyl; or C$_3$-C$_6$ alkyl or C$_3$-C$_6$ cycloalkyl containing at least one nitrogen; and the other two of R$^2$, R$^{2a}$, and R$^{2b}$ are hydrogen or C$_1$-C$_6$ alkyl; or (ii) R$^2$ and one of R$^{2a}$ and R$^{2b}$ join to form a piperidine, pyrrolidine, or morpholine that is optionally substituted with C$_1$-C$_6$ alkyl; or C$_3$-C$_6$ cycloalkyl containing at least one nitrogen; and the other of R$^{2a}$ and R$^{2b}$ is hydrogen or C$_1$-C$_6$ alkyl;

each R$^6$ is independently hydrogen or C$_1$-C$_6$ alkyl;

W is

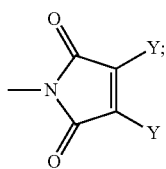

a benzene ring substituted with at least one of halogen, —NO$_2$, or cyano; a pyridine, pyrimidine, oxazole, isoxazole, thiazole, or isothiazole ring that is substituted with at least one of C$_2$-C$_6$ alkenyl, C$_2$-C$_6$ alkynyl, halogen, or cyano; an imidazole or pyrazole ring that is C-substituted with at least one of C$_2$-C$_6$ alkenyl, C$_2$-C$_6$ alkynyl, halogen, or cyano and that is optionally N-substituted with C$_1$-C$_6$ alkyl; a 3-oxobenzisothiazole that is optionally substituted with halogen or C$_1$-C$_6$ alkyl; a pyrrolidine that is N-substituted with acrylate or cyano;

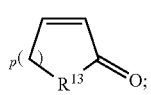 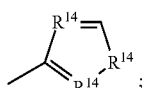 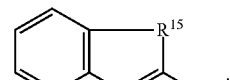

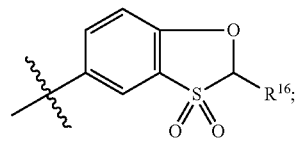

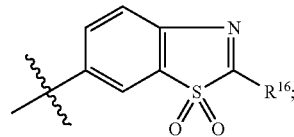

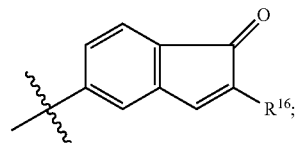

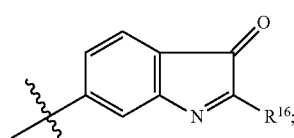

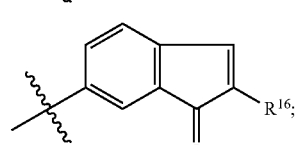

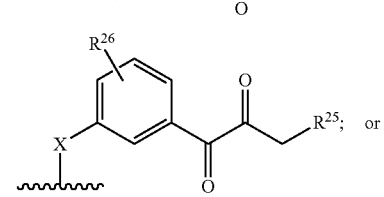

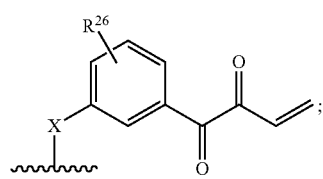

R$^{13}$ is carbon, nitrogen, or oxygen;

each R$^{14}$ is independently sulfur, nitrogen, or oxygen;

R$^{15}$ is oxygen or sulfur;

R$^{16}$ is C$_2$-C$_6$ alkenyl that is optionally substituted with NR$^6_2$ or C$_2$-C$_6$ alkynyl;

R$^{19}$ is hydrogen, halogen, C$_1$-C$_6$ alkyl, C$_1$-C$_6$ haloalkyl, C$_2$-C$_6$ alkenyl, C$_2$-C$_6$ haloalkenyl, C$_2$-C$_6$ alkynyl, C$_2$-C$_6$ haloalkynyl, OH, NR$^6_2$, CN, N$_3$, or NO$_2$;

R$^{20}$ and R$^{21}$ are each independently hydrogen, halogen, C$_1$-C$_6$ alkyl, or C$_1$-C$_6$ haloalkyl, or R$^{20}$ and R$^{21}$ together form a C$_3$-C$_6$ cycloalkyl that is optionally substituted with halogen or C$_1$-C$_6$ alkyl, a C$_3$-C$_6$ cycloalkenyl that is optionally substituted with halogen or C$_1$-C$_6$ alkyl, or a C$_3$-C$_6$ heterocycle that is optionally substituted with halogen or C$_1$-C$_6$ alkyl;

R$^{25}$ is halogen;

R$^{26}$ is halogen, C$_1$-C$_6$ alkyl, or C$_1$-C$_6$ haloalkyl; and p is 1 or 2.

38. A compound of Formula VIIIa:

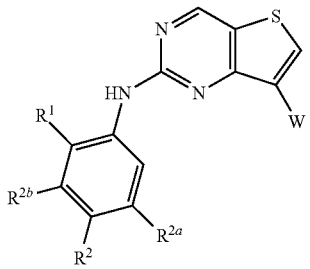

FORMULA VIIIa or a pharmaceutically acceptable salt or ester thereof, wherein:

X is oxygen, sulfur, carbonyl, —$NR^6$, $C_1$-$C_6$ alkyl, or $C_1$-$C_6$ haloalkyl;

Y is hydrogen, halogen, or $C_1$-$C_6$ alkyl;

each $R^1$ is independently $C_1$-$C_6$ alkyl, $C_1$-$C_6$ alkoxy, $C_1$-$C_6$ haloalkyl, or $C_1$-$C_6$ haloalkoxy;

(i) one of $R^2$, $R^{2a}$, and $R^{2b}$ is piperidine, pyrrolidine, piperazine, or morpholine that is optionally substituted with $C_1$-$C_6$ alkyl; or $C_3$-$C_6$ alkyl or $C_3$-$C_6$ cycloalkyl containing at least one nitrogen; and the other two of $R^2$, $R^{2a}$, and $R^{2b}$ are hydrogen or $C_1$-$C_6$ alkyl; or (ii) $R^2$ and one of $R^{2a}$ and $R^{2b}$ join to form a piperidine, pyrrolidine, or morpholine that is optionally substituted with $C_1$-$C_6$ alkyl; or $C_3$-$C_6$ cycloalkyl containing at least one nitrogen; and the other of $R^{2a}$ and $R^{2b}$ is hydrogen or $C_1$-$C_6$ alkyl;

each $R^6$ is independently hydrogen or $C_1$-$C_6$ alkyl;

W is

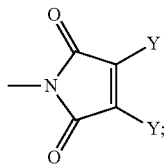

a benzene ring substituted with at least one of halogen, —$NO_2$, or cyano; a pyridine, pyrimidine, oxazole, isoxazole, thiazole, or isothiazole ring that is substituted with at least one of $C_2$-$C_6$ alkenyl, $C_2$-$C_6$ alkynyl, halogen, or cyano; an imidazole or pyrazole ring that is C-substituted with at least one of $C_2$-$C_6$ alkenyl, $C_2$-$C_6$ alkynyl, halogen, or cyano and that is optionally N-substituted with $C_1$-$C_6$ alkyl; a 3-oxobenzisothiazole that is optionally substituted with halogen or $C_1$-$C_6$ alkyl; a pyrrolidine that is N-substituted with acrylate or cyano;

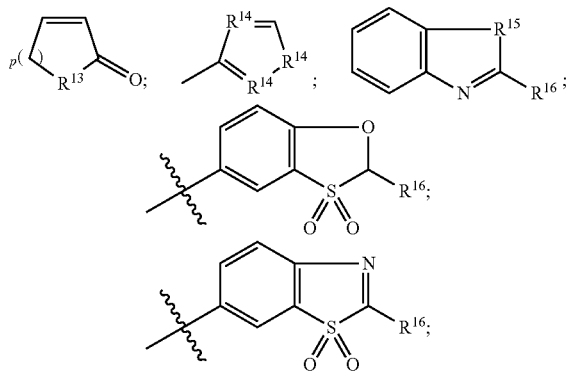

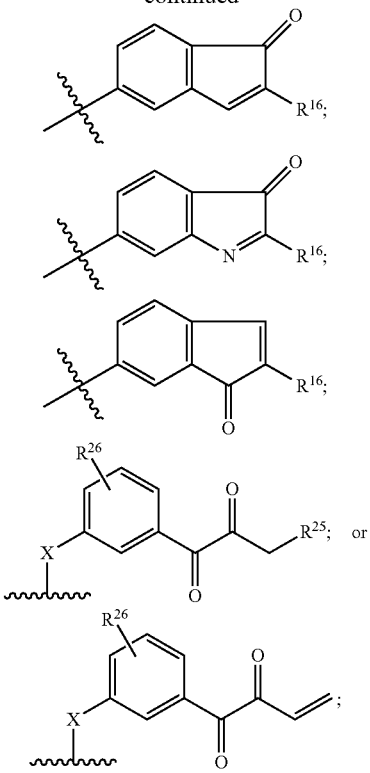

$R^{13}$ is carbon, nitrogen, or oxygen;

each $R^{14}$ is independently sulfur, nitrogen, or oxygen;

$R^{15}$ is oxygen or sulfur;

$R^{16}$ is $C_2$-$C_6$ alkenyl that is optionally substituted with $NR^6_2$ or $C_2$-$C_6$ alkynyl;

$R^{25}$ is halogen;

$R^{26}$ is halogen, $C_1$-$C_6$ alkyl, or $C_1$-$C_6$ haloalkyl; and p is 1 or 2.

39. A compound of Formula IXa:

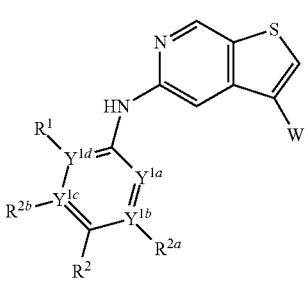

FORMULA IXa or a pharmaceutically acceptable salt or ester thereof, wherein:

X is oxygen, sulfur, carbonyl, —$NR^6$, $C_1$-$C_6$ alkyl, or $C_1$-$C_6$ haloalkyl;

Y is hydrogen, halogen, or $C_1$-$C_6$ alkyl;

each $R^1$ is independently $C_1$-$C_6$ alkyl, $C_1$-$C_6$ alkoxy, $C_1$-$C_6$ haloalkyl, or $C_1$-$C_6$ haloalkoxy;

(i) one of $R^2$, $R^{2a}$, and $R^{2b}$ is piperidine, pyrrolidine, piperazine, or morpholine that is optionally substituted with $C_1$-$C_6$ alkyl; or $C_3$-$C_6$ alkyl or $C_3$-$C_6$ cycloalkyl containing at least one nitrogen; and the other two of $R^2$, $R^{2a}$, and $R^{2b}$ are hydrogen or $C_1$-$C_6$ alkyl; or (ii) $R^2$ and one of $R^{2a}$ and $R^{2b}$ join to form a piperidine, pyrrolidine, or morpholine that is optionally substituted with $C_1$-$C_6$ alkyl; or $C_3$-$C_6$ cycloalkyl containing at least one nitrogen; and the other of $R^{2a}$ and $R^{2b}$ is hydrogen or $C_1$-$C_6$ alkyl;

each $R^6$ is independently hydrogen or $C_1$-$C_6$ alkyl;

W is

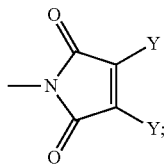

a benzene ring substituted with at least one of halogen, —$NO_2$, or cyano; a pyridine, pyrimidine, oxazole, isoxazole, thiazole, or isothiazole ring that is substituted with at least one of $C_2$-$C_6$ alkenyl, $C_2$-$C_6$ alkynyl, halogen, or cyano; an imidazole or pyrazole ring that is C-substituted with at least one of $C_2$-$C_6$ alkenyl, $C_2$-$C_6$ alkynyl, halogen, or cyano and that is optionally N-substituted with $C_1$-$C_6$ alkyl; a 3-oxobenzisothiazole that is optionally substituted with halogen or $C_1$-$C_6$ alkyl; a pyrrolidine that is N-substituted with acrylate or cyano;

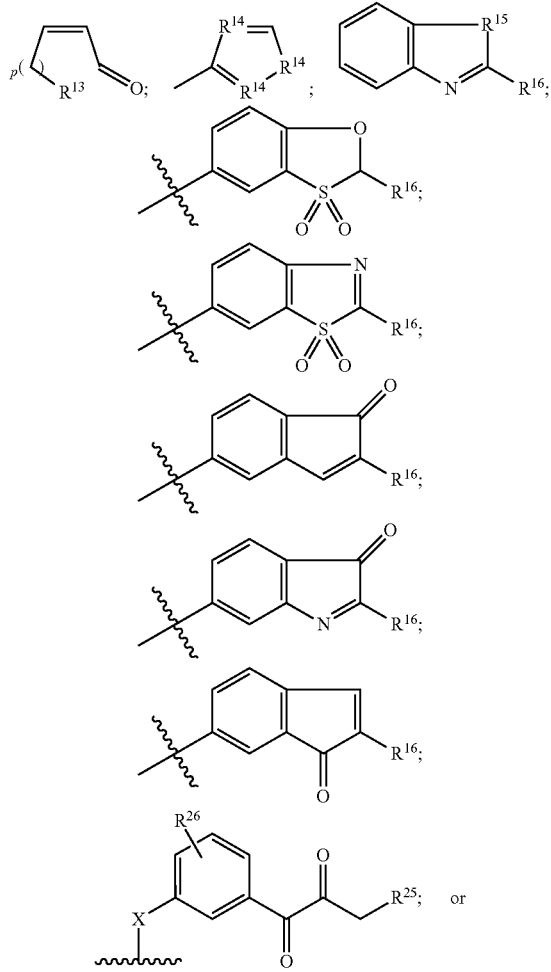

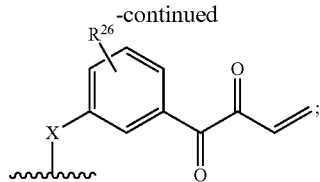

$R^{13}$ is carbon, nitrogen, or oxygen;
each $R^{14}$ is independently sulfur, nitrogen, or oxygen;
$R^{15}$ is oxygen or sulfur;
$R^{16}$ is $C_2$-$C_6$ alkenyl that is optionally substituted with $NR^6_2$ or $C_2$-$C_6$ alkynyl;
$R^{25}$ is halogen;
$R^{26}$ is halogen, $C_1$-$C_6$ alkyl, or $C_1$-$C_6$ haloalkyl;
p is 1 or 2; and
each of $Y^{1a}$, $Y^{1b}$, $Y^{1c}$, and $Y^{1d}$ is independently carbon or nitrogen, wherein at least one of $Y^{1a}$, $Y^{1b}$, $Y^{1c}$ and $Y^{1d}$ is nitrogen.

40. A compound of Formula XIa:

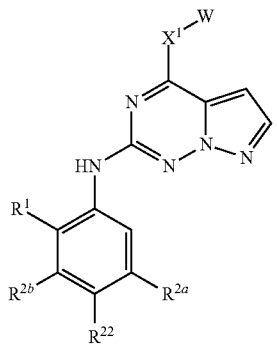

FORMULA XIa or a pharmaceutically acceptable salt or ester thereof, wherein:

each $R^1$ is independently $C_1$-$C_6$ alkyl, $C_1$-$C_6$ alkoxy, $C_1$-$C_6$ haloalkyl, or $C_1$-$C_6$ haloalkoxy;

(i) one of $R^2$, $R^{2a}$, and $R^{2b}$ is piperidine, pyrrolidine, piperazine, or morpholine that is optionally substituted with $C_1$-$C_6$ alkyl; or $C_3$-$C_6$ alkyl or $C_3$-$C_6$ cycloalkyl containing at least one nitrogen; and the other two of $R^2$, $R^{2a}$, and $R^{2b}$ are hydrogen or $C_1$-$C_6$ alkyl; or (ii) $R^2$ and one of $R^{2a}$ and $R^{2b}$ join to form a piperidine, pyrrolidine, or morpholine that is optionally substituted with $C_1$-$C_6$ alkyl; or $C_3$-$C_6$ cycloalkyl containing at least one nitrogen; and the other of $R^{2a}$ and $R^{2b}$ is hydrogen or $C_1$-$C_6$ alkyl;

each $R^6$ is independently hydrogen or $C_1$-$C_6$ alkyl;

W is

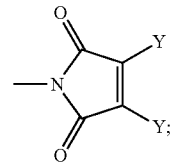

a benzene ring substituted with at least one of halogen, —$NO_2$, or cyano; a pyridine, pyrimidine, oxazole, isoxazole, thiazole, or isothiazole ring that is substituted with at least one of $C_2$-$C_6$ alkenyl, $C_2$-$C_6$ alkynyl, halogen, or cyano; an imidazole or pyrazole ring that is C-substituted with at least one of $C_2$-$C_6$ alkenyl, $C_2$-$C_6$ alkynyl, halogen, or cyano and that is optionally N-substituted with $C_1$-$C_6$ alkyl; a 3-oxobenzisothiazole that is optionally substituted with halogen or $C_1$-$C_6$ alkyl; a pyrrolidine that is N-substituted with acrylate or cyano;

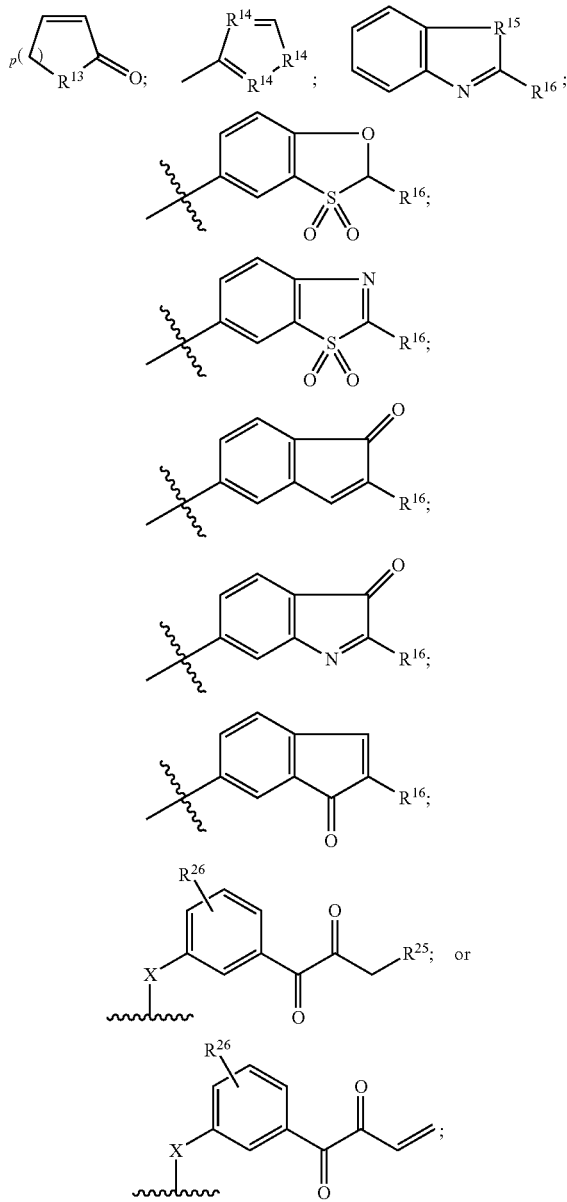

$R^{13}$ is carbon, nitrogen, or oxygen;

each $R^{14}$ is independently sulfur, nitrogen, or oxygen;

$R^{15}$ is oxygen or sulfur;

$R^{16}$ is $C_2$-$C_6$ alkenyl that is optionally substituted with $NR^6_2$ or $C_2$-$C_6$ alkynyl;

$R^{25}$ is halogen;

$R^{26}$ is halogen, $C_1$-$C_6$ alkyl, or $C_1$-$C_6$ haloalkyl;

p is 1 or 2; and $X^1$ is oxygen, sulfur, or —$NR^6$.

41. A compound of Formula XIIa:

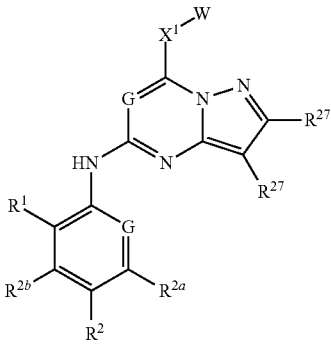

FORMULA XIIa or a pharmaceutically acceptable salt or ester thereof, wherein:

each $R^1$ is independently $C_1$-$C_6$ alkyl, $C_1$-$C_6$ alkoxy, $C_1$-$C_6$ haloalkyl, or $C_1$-$C_6$ haloalkoxy;

(i) one of $R^2$, $R^{2a}$, and $R^{2b}$ is piperidine, pyrrolidine, piperazine, or morpholine that is optionally substituted with $C_1$-$C_6$ alkyl; or $C_3$-$C_6$ alkyl or $C_3$-$C_6$ cycloalkyl containing at least one nitrogen; and the other two of $R^2$, $R^{2a}$, and $R^{2b}$ are hydrogen or $C_1$-$C_6$ alkyl; or (ii) $R^2$ and one of $R^{2a}$ and $R^{2b}$ join to form a piperidine, pyrrolidine, or morpholine that is optionally substituted with $C_1$-$C_6$ alkyl; or $C_3$-$C_6$ cycloalkyl containing at least one nitrogen; and the other of $R^{2a}$ and $R^{2b}$ is hydrogen or $C_1$-$C_6$ alkyl;

each $R^6$ is independently hydrogen or $C_1$-$C_6$ alkyl;

W is

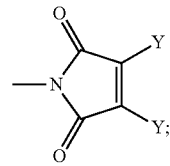

a benzene ring substituted with at least one of halogen, —$NO_2$, or cyano; a pyridine, pyrimidine, oxazole, isoxazole, thiazole, or isothiazole ring that is substituted with at least one of $C_2$-$C_6$ alkenyl, $C_2$-$C_6$ alkynyl, halogen, or cyano; an imidazole or pyrazole ring that is C-substituted with at least one of $C_2$-$C_6$ alkenyl, $C_2$-$C_6$ alkynyl, halogen, or cyano and that is optionally N-substituted with $C_1$-$C_6$ alkyl; a 3-oxobenzisothiazole that is optionally substituted with halogen or $C_1$-$C_6$ alkyl; a pyrrolidine that is N-substituted with acrylate or cyano;

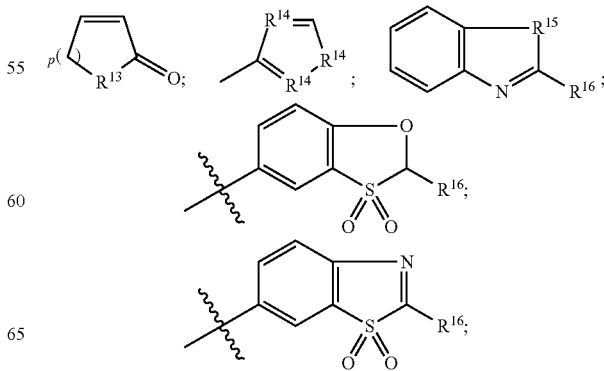

-continued

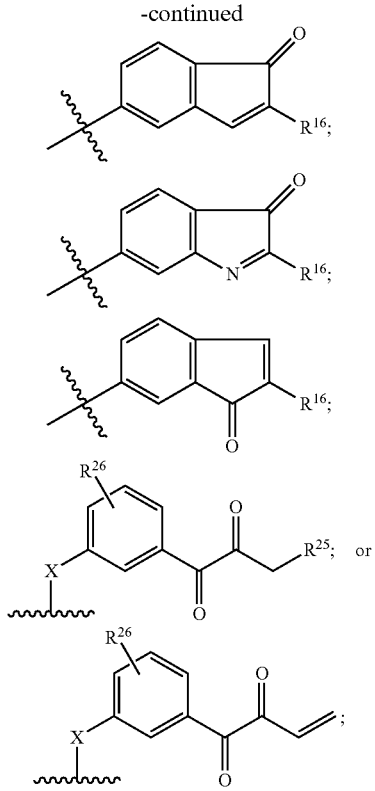

R[13] is carbon, nitrogen, or oxygen;
each R[14] is independently sulfur, nitrogen, or oxygen;
R[15] is oxygen or sulfur;
R[16] is $C_2$-$C_6$ alkenyl that is optionally substituted with NR[6]$_2$ or $C_2$-$C_6$ alkynyl;
R[25] is halogen;
R[26] is halogen, $C_1$-$C_6$ alkyl, or $C_1$-$C_6$ haloalkyl;
p is 1 or 2;
X[1] is oxygen, sulfur, or —NR[6];
each G is independently N, CH, or CR[30]; and
each R[27] is independently hydrogen, halogen, $C_1$-$C_3$ alkyl, or $C_1$-$C_3$ alkoxy.

42. A compound of Formula Ib:

FORMULA Ib

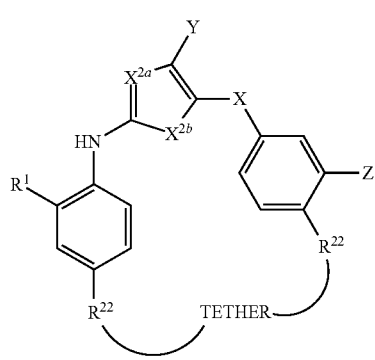

or a pharmaceutically acceptable salt or ester thereof, wherein:
X is oxygen, sulfur, carbonyl, —NR[6], $C_1$-$C_6$ alkyl, or $C_1$-$C_6$ haloalkyl;
X[2a] is nitrogen, CH, or CR[30];
X[2b] is oxygen, sulfur, NH, or NR[9];
Y is hydrogen, halogen, or $C_1$-$C_6$ alkyl;
each R[1] is independently $C_1$-$C_6$ alkyl, $C_1$-$C_6$ alkoxy, $C_1$-$C_6$ haloalkyl, or $C_1$-$C_6$ haloalkoxy;
each R[6] is independently hydrogen or $C_1$-$C_6$ alkyl;
R[7] is hydrogen, $C_1$-$C_6$ alkyl, or $C_2$-$C_6$ alkenyl;
R[8] is $C_1$-$C_6$ alkyl that is substituted with halogen, cyano, —C(O)R[9], or —OC(O)R[9]; $C_2$-$C_6$ alkenyl that is optionally substituted with halogen or —NR[9]$_2$; $C_2$-$C_6$ alkynyl; $C_3$-$C_6$ cycloalkyl that is substituted with cyano or —C(O)R[9]; $C_4$-$C_6$ cycloalkenyl that is optionally substituted with halogen; or $C_4$-$C_9$ heterocycloalkenyl that is optionally substituted with halogen, $C_1$-$C_6$ alkyl, or carbonyl;
each R[9] is independently $C_1$-$C_6$ alkyl;
R[10] is hydrogen or $C_1$-$C_6$ alkyl;
R[11] is $C_2$-$C_6$ alkenyl;
R[12] is $C_2$-$C_6$ alkenyl substituted with cyano or —C(O)OR[9];
R[30] is halogen or $C_1$-$C_6$ alkyl;
Z is $C_2$-$C_6$ alkenyl, $C_2$-$C_6$ alkynyl, $C_3$-$C_6$ cycloalkyl that is substituted with cyano or acetyl, —(CH$_2$)$_n$NR[7]C(O)R[8], —(CH$_2$)$_n$C(O)(CH$_2$)$_n$R[8], —(CH$_2$)$_n$OC(O)R[8],

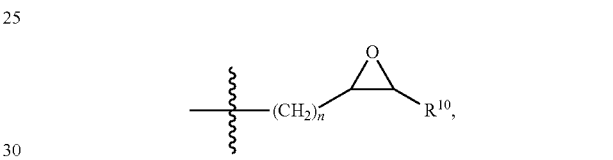

—(NH)$_m$(SO$_2$)R[11],
—CHR[11]OC(O)R[11], —OR[12], —(CH$_2$)$_n$C(OH)R[12],

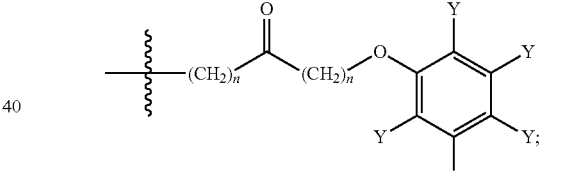

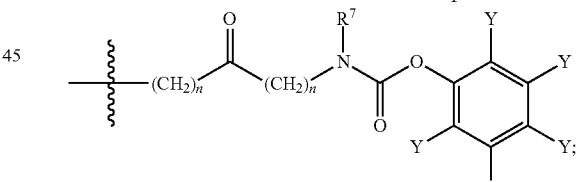

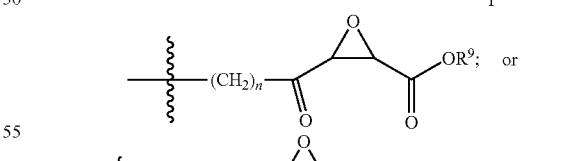

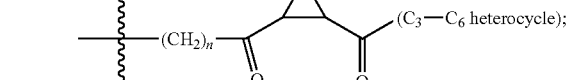

n is an integer from 0 to 6;
m is 0 or 1;
each R[22] is independently CH$_2$, CHR[1], CR[1]$_2$, sulfur, oxygen, carbonyl, or NR[6]; and TETHER is a group having 3-10 atoms selected from carbon, nitrogen, sulfur and oxygen.

43. A compound of Formula IIb:

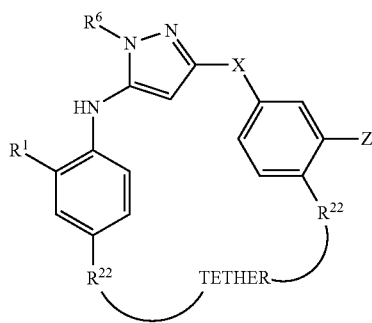

FORMULA IIb or a pharmaceutically acceptable salt or ester thereof, wherein:

X is oxygen, sulfur, carbonyl, —$NR^6$, $C_1$-$C_6$ alkyl, or $C_1$-$C_6$ haloalkyl;

each $R^1$ is independently $C_1$-$C_6$ alkyl, $C_1$-$C_6$ alkoxy, $C_1$-$C_6$ haloalkyl, or $C_1$-$C_6$ haloalkoxy;

each $R^6$ is independently hydrogen or $C_1$-$C_6$ alkyl;

$R^7$ is hydrogen, $C_1$-$C_6$ alkyl, or $C_2$-$C_6$ alkenyl;

$R^8$ is $C_1$-$C_6$ alkyl that is substituted with halogen, cyano, —$C(O)R^9$, or —$OC(O)R^9$; $C_2$-$C_6$ alkenyl that is optionally substituted with halogen or —$NR^9{}_2$; $C_2$-$C_6$ alkynyl; $C_3$-$C_6$ cycloalkyl that is substituted with cyano or —$C(O)R^9$; $C_4$-$C_6$ cycloalkenyl that is optionally substituted with halogen; or $C_4$-$C_9$ heterocycloalkenyl that is optionally substituted with halogen, $C_1$-$C_6$ alkyl, or carbonyl;

each $R^9$ is independently $C_1$-$C_6$ alkyl;

$R^{10}$ is hydrogen or $C_1$-$C_6$ alkyl;

$R^{11}$ is $C_2$-$C_6$ alkenyl;

$R^{12}$ is $C_2$-$C_6$ alkenyl substituted with cyano or —$C(O)OR^9$;

Z is $C_2$-$C_6$ alkenyl, $C_2$-$C_6$ alkynyl, $C_3$-$C_6$ cycloalkyl that is substituted with cyano or acetyl, —$(CH_2)_nNR^7C(O)R^8$, —$(CH_2)_nC(O)(CH_2)_nR^8$, —$(CH_2)_nOC(O)R^8$,

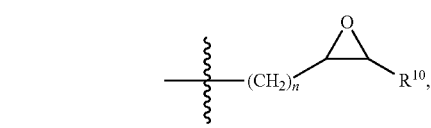

—$(NH)_m(SO_2)R^{11}$,
—$CHR^{11}OC(O)R^{11}$, —$OR^{12}$, —$(CH_2)_nC(OH)R^{12}$,

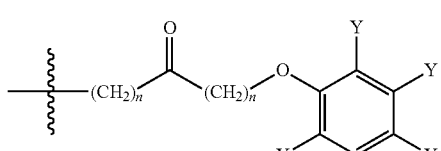

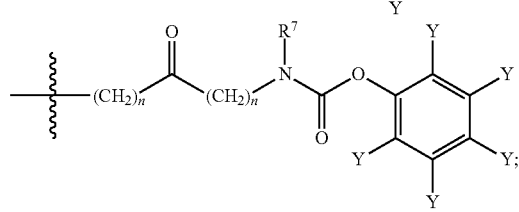

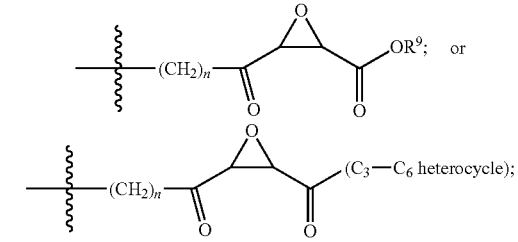

n is an integer from 0 to 6;

m is 0 or 1;

each $R^{22}$ is independently $CH_2$, $CHR^1$, $CR^1{}_2$, sulfur, oxygen, carbonyl, or $NR^6$; and TETHER is a group having 3-10 atoms selected from carbon, nitrogen, sulfur and oxygen.

44. A compound of Formula IIIb:

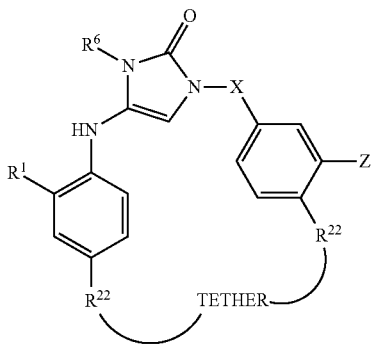

FORMULA IIIb or a pharmaceutically acceptable salt or ester thereof, wherein:

X is oxygen, sulfur, carbonyl, —$NR^6$, $C_1$-$C_6$ alkyl, or $C_1$-$C_6$ haloalkyl;

each $R^1$ is independently $C_1$-$C_6$ alkyl, $C_1$-$C_6$ alkoxy, $C_1$-$C_6$ haloalkyl, or $C_1$-$C_6$ haloalkoxy;

each $R^6$ is independently hydrogen or $C_1$-$C_6$ alkyl;

$R^7$ is hydrogen, $C_1$-$C_6$ alkyl, or $C_2$-$C_6$ alkenyl;

$R^8$ is $C_1$-$C_6$ alkyl that is substituted with halogen, cyano, —$C(O)R^9$, or —$OC(O)R^9$; $C_2$-$C_6$ alkenyl that is optionally substituted with halogen or —$NR^9{}_2$; $C_2$-$C_6$ alkynyl; $C_3$-$C_6$ cycloalkyl that is substituted with cyano or —$C(O)R^9$; $C_4$-$C_6$ cycloalkenyl that is optionally substituted with halogen; or $C_4$-$C_9$ heterocycloalkenyl that is optionally substituted with halogen, $C_1$-$C_6$ alkyl, or carbonyl;

each $R^9$ is independently $C_1$-$C_6$ alkyl;

$R^{10}$ is hydrogen or $C_1$-$C_6$ alkyl;

$R^{11}$ is $C_2$-$C_6$ alkenyl;

$R^{12}$ is $C_2$-$C_6$ alkenyl substituted with cyano or —$C(O)OR^9$;

Z is $C_2$-$C_6$ alkenyl, $C_2$-$C_6$ alkynyl, $C_3$-$C_6$ cycloalkyl that is substituted with cyano or acetyl, —$(CH_2)_nNR^7C(O)R^8$, —$(CH_2)_nC(O)(CH_2)_nR^8$, —$(CH_2)_nOC(O)R^8$,

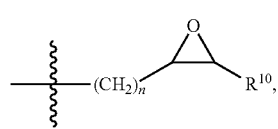

—(NH)$_m$(SO$_2$)R$^{11}$,
—CHR$^{11}$OC(O)R$^{11}$, —OR$^{12}$, —(CH$_2$)$_n$C(OH)R$^{12}$,

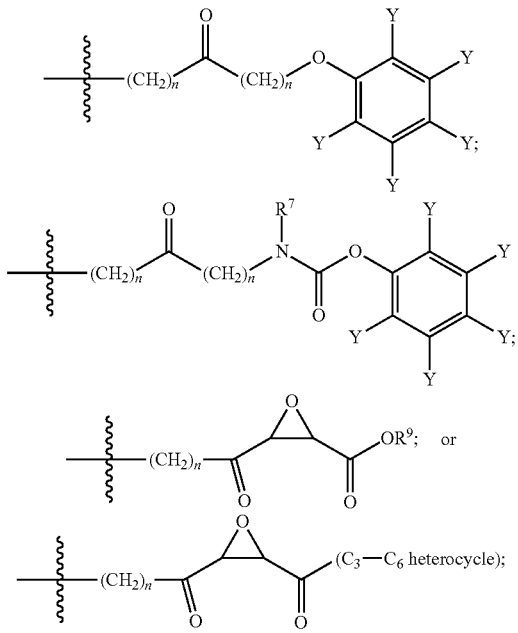

n is an integer from 0 to 6;
m is 0 or 1;
each R$^{22}$ is independently CH$_2$, CHR$^1$, CR$^1{}_2$, sulfur, oxygen, carbonyl, or NR$^6$; and TETHER is a group having 3-10 atoms selected from carbon, nitrogen, sulfur and oxygen.

45. A compound of Formula IVb:

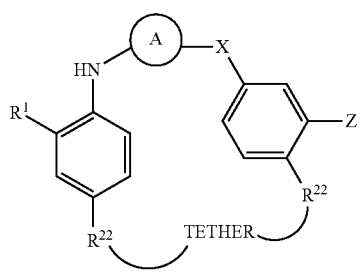

FORMULA IVb or a pharmaceutically acceptable salt or ester thereof, wherein:

X is oxygen, sulfur, carbonyl, —NR$^6$, C$_1$-C$_6$ alkyl, or C$_1$-C$_6$ haloalkyl;

X$^{2b}$ is oxygen, sulfur, NH, or NR$^9$;

each R$^1$ is independently C$_1$-C$_6$ alkyl, C$_1$-C$_6$ alkoxy, C$_1$-C$_6$ haloalkyl, or C$_1$-C$_6$ haloalkoxy;

each R$^6$ is independently hydrogen or C$_1$-C$_6$ alkyl;

R$^7$ is hydrogen, C$_1$-C$_6$ alkyl, or C$_2$-C$_6$ alkenyl;

R$^8$ is C$_1$-C$_6$ alkyl that is substituted with halogen, cyano, —C(O)R$^9$, or —OC(O)R$^9$; C$_2$-C$_6$ alkenyl that is optionally substituted with halogen or —NR$^9{}_2$; C$_2$-C$_6$ alkynyl; C$_3$-C$_6$ cycloalkyl that is substituted with cyano or —C(O)R$^9$; C$_4$-C$_6$ cycloalkenyl that is optionally substituted with halogen; or C$_4$-C$_9$ heterocycloalkenyl that is optionally substituted with halogen, C$_1$-C$_6$ alkyl, or carbonyl;

each R$^9$ is independently C$_1$-C$_6$ alkyl;

R$^{10}$ is hydrogen or C$_1$-C$_6$ alkyl;

R$^{11}$ is C$_2$-C$_6$ alkenyl;

R$^{12}$ is C$_2$-C$_6$ alkenyl substituted with cyano or —C(O)OR$^9$;

R$^{30}$ is halogen or C$_1$-C$_6$ alkyl;

Z is C$_2$-C$_6$ alkenyl, C$_2$-C$_6$ alkynyl, C$_3$-C$_6$ cycloalkyl that is substituted with cyano or acetyl, —(CH$_2$)$_n$NR$^7$C(O)R$^8$, —(CH$_2$)$_n$C(O)(CH$_2$)$_n$R$^8$, —(CH$_2$)$_n$OC(O)R$^8$,

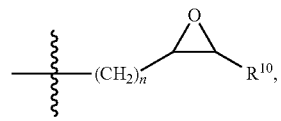

—(NH)$_m$(SO$_2$)R$^{11}$,
—CHR$^{11}$OC(O)R$^{11}$, —OR$^{12}$, —(CH$_2$)$_n$C(OH)R$^{12}$,

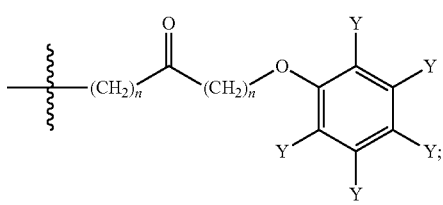

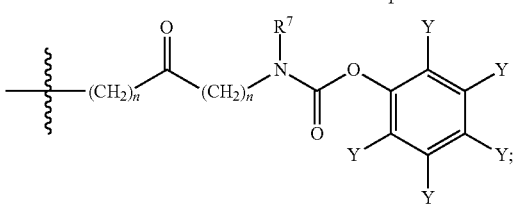

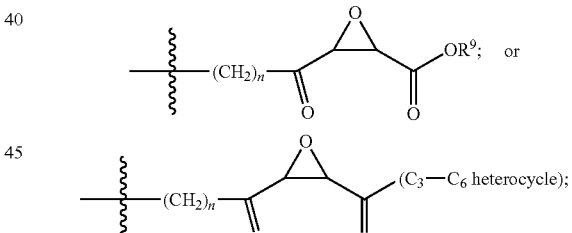

n is an integer from 0 to 6;
m is 0 or 1;
each R$^{22}$ is independently CH$_2$, CHR$^1$, CR$^1{}_2$, sulfur, oxygen, carbonyl, or NR$^6$; TETHER is a group having 3-10 atoms selected from carbon, nitrogen, sulfur and oxygen;

A is 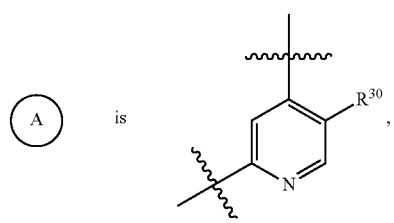

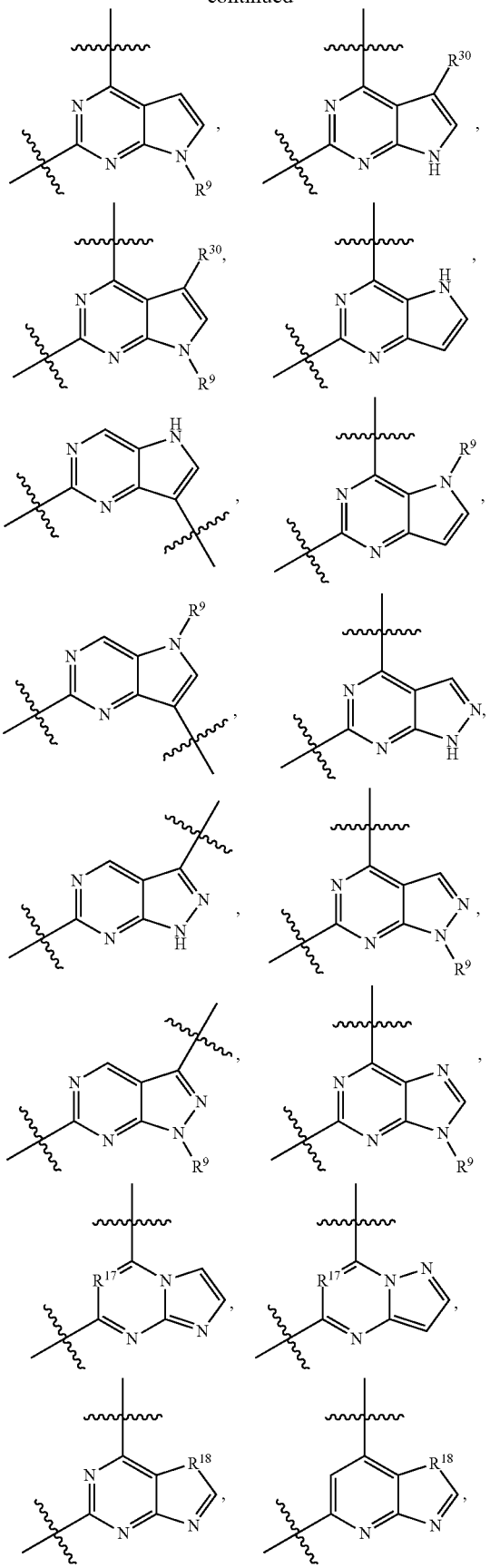

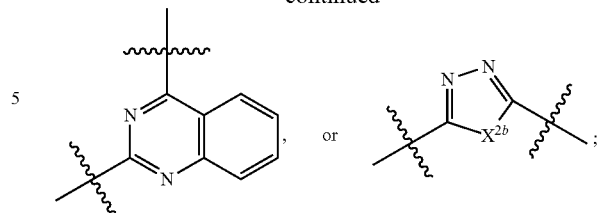

$R^{17}$ is N or CH; and
$R^{18}$ is O or S.

46. A compound of Formula VIb:

FORMULA VIb

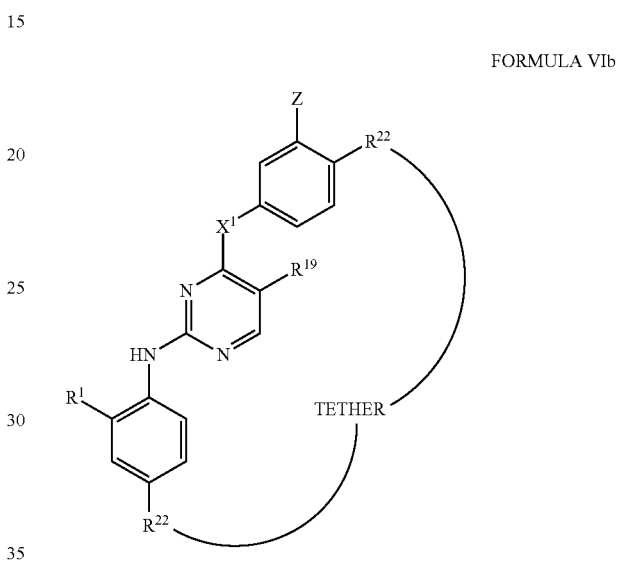

or a pharmaceutically acceptable salt or ester thereof, wherein:

X is oxygen, sulfur, carbonyl, —$NR^6$, $C_1$-$C_6$ alkyl, or $C_1$-$C_6$ haloalkyl;

each $R^1$ is independently $C_1$-$C_6$ alkyl, $C_1$-$C_6$ alkoxy, $C_1$-$C_6$ haloalkyl, or $C_1$-$C_6$ haloalkoxy;

each $R^6$ is independently hydrogen or $C_1$-$C_6$ alkyl;

$R^7$ is hydrogen, $C_1$-$C_6$ alkyl, or $C_2$-$C_6$ alkenyl;

$R^8$ is $C_1$-$C_6$ alkyl that is substituted with halogen, cyano, —C(O)$R^9$, or —OC(O)$R^9$; $C_2$-$C_6$ alkenyl that is optionally substituted with halogen or —$NR^9_2$; $C_2$-$C_6$ alkynyl; $C_3$-$C_6$ cycloalkyl that is substituted with cyano or —C(O)$R^9$; $C_4$-$C_6$ cycloalkenyl that is optionally substituted with halogen; or $C_4$-$C_9$ heterocycloalkenyl that is optionally substituted with halogen, $C_1$-$C_6$ alkyl, or carbonyl;

each $R^9$ is independently $C_1$-$C_6$ alkyl;

$R^{10}$ is hydrogen or $C_1$-$C_6$ alkyl;

$R^{11}$ is $C_2$-$C_6$ alkenyl;

$R^{12}$ is $C_2$-$C_6$ alkenyl substituted with cyano or —C(O)O$R^9$;

Z is $C_2$-$C_6$ alkenyl, $C_2$-$C_6$ alkynyl, $C_3$-$C_6$ cycloalkyl that is substituted with cyano or acetyl, —$(CH_2)_n NR^7 C(O)R^8$, —$(CH_2)_n C(O)(CH_2)_n R^8$, —$(CH_2)_n OC(O)R^8$,

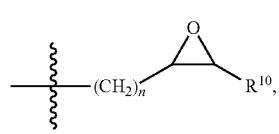

—(NH)$_m$(SO$_2$)R$^{11}$,
—CHR$^{11}$OC(O)R$^{11}$, —OR$^{12}$, —(CH$_2$)$_n$C(OH)R$^{12}$,

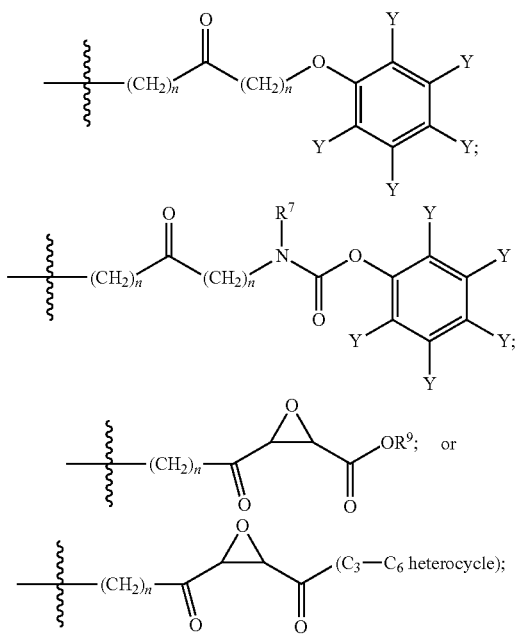

n is an integer from 0 to 6;
m is 0 or 1;
each R$^{22}$ is independently CH$_2$, CHR$^1$, CR$^1$$_2$, sulfur, oxygen, carbonyl, or NR$^6$; TETHER is a group having 3-10 atoms selected from carbon, nitrogen, sulfur and oxygen; and
R$^{19}$ is hydrogen, halogen, C$_1$-C$_6$ alkyl, C$_1$-C$_6$ haloalkyl, C$_2$-C$_6$ alkenyl, C$_2$-C$_6$ haloalkenyl, C$_2$-C$_6$ alkynyl, C$_2$-C$_6$ haloalkynyl, OH, NR$^6$$_2$, CN, N$_3$, or NO$_2$.

47. A compound of Formula VIIb:

FORMULA VIIb

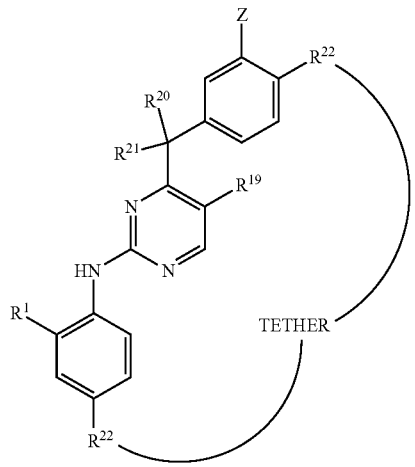

or a pharmaceutically acceptable salt or ester thereof, wherein:
X is oxygen, sulfur, carbonyl, —NR$^6$, C$_1$-C$_6$ alkyl, or C$_1$-C$_6$ haloalkyl;
each R$^1$ is independently C$_1$-C$_6$ alkyl, C$_1$-C$_6$ alkoxy, C$_1$-C$_6$ haloalkyl, or C$_1$-C$_6$ haloalkoxy;

each R$^6$ is independently hydrogen or C$_1$-C$_6$ alkyl;
R$^7$ is hydrogen, C$_1$-C$_6$ alkyl, or C$_2$-C$_6$ alkenyl;
R$^8$ is C$_1$-C$_6$ alkyl that is substituted with halogen, cyano, —C(O)R$^9$, or —OC(O)R$^9$; C$_2$-C$_6$ alkenyl that is optionally substituted with halogen or —NR$^9$$_2$; C$_2$-C$_6$ alkynyl; C$_3$-C$_6$ cycloalkyl that is substituted with cyano or —C(O)R$^9$; C$_4$-C$_6$ cycloalkenyl that is optionally substituted with halogen; or C$_4$-C$_9$ heterocycloalkenyl that is optionally substituted with halogen, C$_1$-C$_6$ alkyl, or carbonyl;
each R$^9$ is independently C$_1$-C$_6$ alkyl;
R$^{10}$ is hydrogen or C$_1$-C$_6$ alkyl;
R$^{11}$ is C$_2$-C$_6$ alkenyl;
R$^{12}$ is C$_2$-C$_6$ alkenyl substituted with cyano or —C(O)OR$^9$;
Z is C$_2$-C$_6$ alkenyl, C$_2$-C$_6$ alkynyl, C$_3$-C$_6$ cycloalkyl that is substituted with cyano or acetyl, —(CH$_2$)$_n$NR$^7$C(O)R$^8$, —(CH$_2$)$_n$C(O)(CH$_2$)$_n$R$^8$, —(CH$_2$)$_n$OC(O)R$^8$,

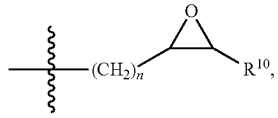

—(NH)$_m$(SO$_2$)R$^{11}$,
—CHR$^{11}$OC(O)R$^{11}$, —OR$^{12}$, —(CH$_2$)$_n$C(OH)R$^{12}$,

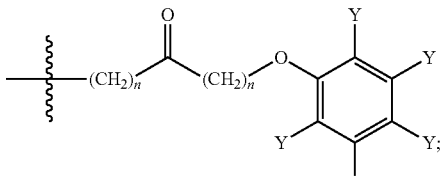

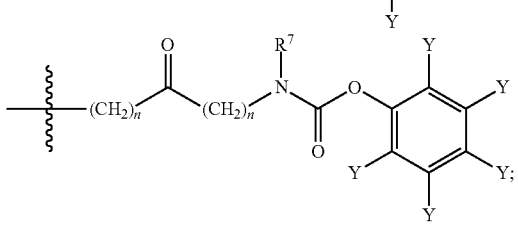

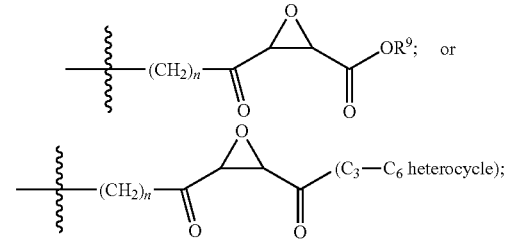

n is an integer from 0 to 6;
m is 0 or 1;
each R$^{22}$ is independently CH$_2$, CHR$^1$, CR$^1$$_2$, sulfur, oxygen, carbonyl, or NR$^6$; TETHER is a group having 3-10 atoms selected from carbon, nitrogen, sulfur and oxygen;
R$^{19}$ is hydrogen, halogen, C$_1$-C$_6$ alkyl, C$_1$-C$_6$ haloalkyl, C$_2$-C$_6$ alkenyl, C$_2$-C$_6$ haloalkenyl, C$_2$-C$_6$ alkynyl, C$_2$-C$_6$ haloalkynyl, OH, NR$^6$$_2$, CN, N$_3$, or NO$_2$; and
R$^{20}$ and R$^{21}$ are each independently hydrogen, halogen, C$_1$-C$_6$ alkyl, or C$_1$-C$_6$ haloalkyl, or R$^{20}$ and R$^{21}$ together form a C$_3$-C$_6$ cycloalkyl that is optionally substituted with halogen or C$_1$-C$_6$ alkyl, a C$_3$-C$_6$ cycloalkenyl that is optionally substituted with halogen or $C_1$-$C_6$ alkyl, or a $C_3$-$C_6$ heterocycle that is optionally substituted with halogen or $C_1$-$C_6$ alkyl.

48. A compound of Formula VIIIb:

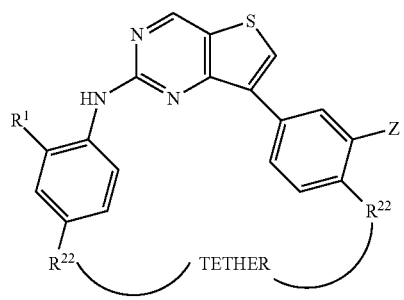

FORMULA VIIIb or a pharmaceutically acceptable salt or ester thereof, wherein:

X is oxygen, sulfur, carbonyl, —$NR^6$, $C_1$-$C_6$ alkyl, or $C_1$-$C_6$ haloalkyl;

each $R^1$ is independently $C_1$-$C_6$ alkyl, $C_1$-$C_6$ alkoxy, $C_1$-$C_6$ haloalkyl, or $C_1$-$C_6$ haloalkoxy;

each $R^6$ is independently hydrogen or $C_1$-$C_6$ alkyl;

$R^7$ is hydrogen, $C_1$-$C_6$ alkyl, or $C_2$-$C_6$ alkenyl;

$R^8$ is $C_1$-$C_6$ alkyl that is substituted with halogen, cyano, —C(O)$R^9$, or —OC(O)$R^9$; $C_2$-$C_6$ alkenyl that is optionally substituted with halogen or —$NR^9{}_2$; $C_2$-$C_6$ alkynyl; $C_3$-$C_6$ cycloalkyl that is substituted with cyano or —C(O)$R^9$; $C_4$-$C_6$ cycloalkenyl that is optionally substituted with halogen; or $C_4$-$C_9$ heterocycloalkenyl that is optionally substituted with halogen, $C_1$-$C_6$ alkyl, or carbonyl;

each $R^9$ is independently $C_1$-$C_6$ alkyl;

$R^{10}$ is hydrogen or $C_1$-$C_6$ alkyl;

$R^{11}$ is $C_2$-$C_6$ alkenyl;

$R^{12}$ is $C_2$-$C_6$ alkenyl substituted with cyano or —C(O)$OR^9$;

Z is $C_2$-$C_6$ alkenyl, $C_2$-$C_6$ alkynyl, $C_3$-$C_6$ cycloalkyl that is substituted with cyano or acetyl, —$(CH_2)_nNR^7C(O)R^8$, —$(CH_2)_nC(O)(CH_2)_nR^8$, —$(CH_2)_nOC(O)R^8$,

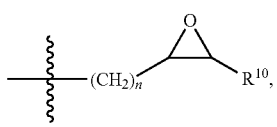

—$(NH)_m(SO_2)R^{11}$,
—$CHR^{11}OC(O)R^{11}$, —$OR^{12}$, —$(CH_2)_nC(OH)R^{12}$,

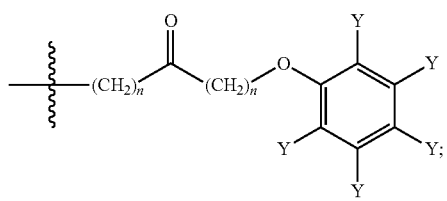

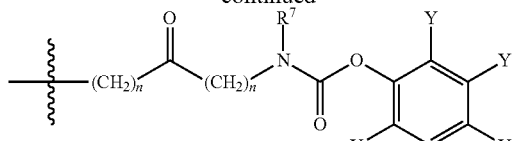

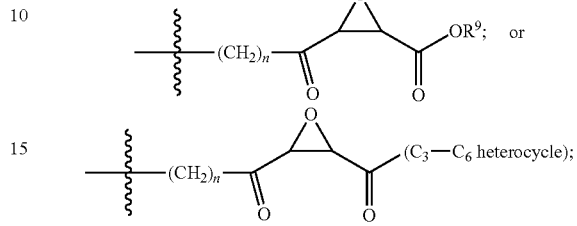

n is an integer from 0 to 6;

m is 0 or 1;

each $R^{22}$ is independently $CH_2$, $CHR^1$, $CR^1{}_2$, sulfur, oxygen, carbonyl, or $NR^6$; and TETHER is a group having 3-10 atoms selected from carbon, nitrogen, sulfur and oxygen.

49. A compound of Formula IXb:

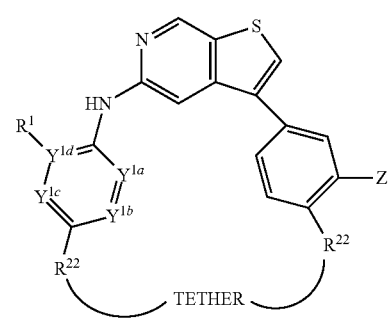

FORMULA IXb or a pharmaceutically acceptable salt or ester thereof, wherein:

X is oxygen, sulfur, carbonyl, —$NR^6$, $C_1$-$C_6$ alkyl, or $C_1$-$C_6$ haloalkyl;

each $R^1$ is independently $C_1$-$C_6$ alkyl, $C_1$-$C_6$ alkoxy, $C_1$-$C_6$ haloalkyl, or $C_1$-$C_6$ haloalkoxy;

each $R^6$ is independently hydrogen or $C_1$-$C_6$ alkyl;

$R^7$ is hydrogen, $C_1$-$C_6$ alkyl, or $C_2$-$C_6$ alkenyl;

$R^8$ is $C_1$-$C_6$ alkyl that is substituted with halogen, cyano, —C(O)$R^9$, or —OC(O)$R^9$; $C_2$-$C_6$ alkenyl that is optionally substituted with halogen or —$NR^9{}_2$; $C_2$-$C_6$ alkynyl; $C_3$-$C_6$ cycloalkyl that is substituted with cyano or —C(O)$R^9$; $C_4$-$C_6$ cycloalkenyl that is optionally substituted with halogen; or $C_4$-$C_9$ heterocycloalkenyl that is optionally substituted with halogen, $C_1$-$C_6$ alkyl, or carbonyl;

each $R^9$ is independently $C_1$-$C_6$ alkyl;

$R^{10}$ is hydrogen or $C_1$-$C_6$ alkyl;

$R^{11}$ is $C_2$-$C_6$ alkenyl;

$R^{12}$ is $C_2$-$C_6$ alkenyl substituted with cyano or —C(O)$OR^9$;

Z is $C_2$-$C_6$ alkenyl, $C_2$-$C_6$ alkynyl, $C_3$-$C_6$ cycloalkyl that is substituted with cyano or acetyl, —$(CH_2)_nNR^7C(O)R^8$, —$(CH_2)_nC(O)(CH_2)_nR^8$, —$(CH_2)_nOC(O)R^8$,

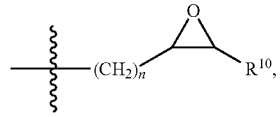

—(NH)$_m$(SO$_2$)R$^{11}$,
—CHR$^{11}$OC(O)R$^{11}$, —OR$^{12}$, —(CH$_2$)$_n$C(OH)R$^{12}$,

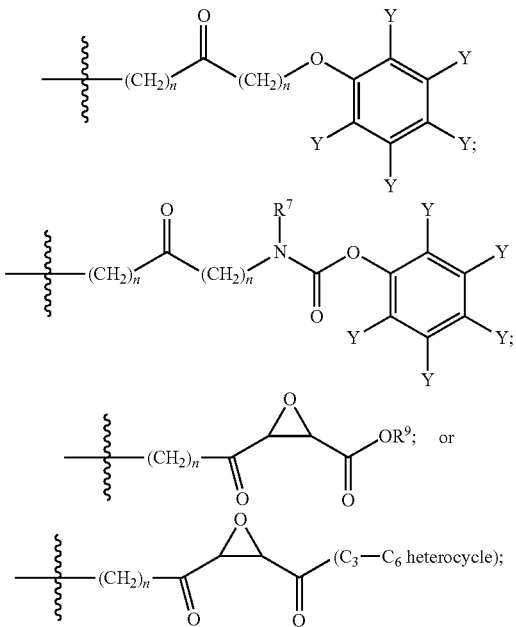

n is an integer from 0 to 6;
m is 0 or 1;
each R$^{22}$ is independently CH$_2$, CHR$^1$, CR$^1_2$, sulfur, oxygen, carbonyl, or NR$^6$; TETHER is a group having 3-10 atoms selected from carbon, nitrogen, sulfur and oxygen; and
each of Y$^{1a}$, Y$^{1b}$, Y$^{1c}$, and Y$^{1d}$ is independently carbon or nitrogen, wherein at least one of Y$^{1a}$, Y$^{1b}$, Y$^{1c}$, and Y$^{1d}$ is nitrogen.

50. A compound of Formula Xb:

FORMULA Xb

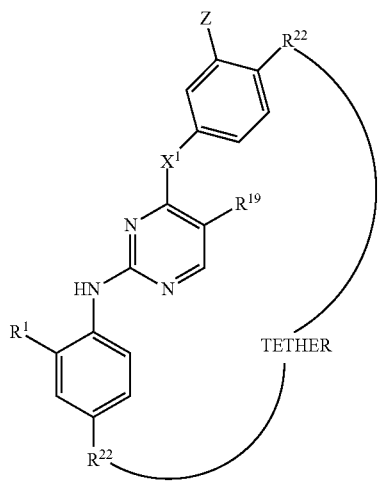

or a pharmaceutically acceptable salt or ester thereof, wherein:
X' is oxygen, sulfur, or —NR$^6$;
each R$^1$ is independently C$_1$-C$_6$ alkyl, C$_1$-C$_6$ alkoxy, C$_1$-C$_6$ haloalkyl, or C$_1$-C$_6$ haloalkoxy;

each R$^6$ is independently hydrogen or C$_1$-C$_6$ alkyl;
R$^7$ is hydrogen, C$_1$-C$_6$ alkyl, or C$_2$-C$_6$ alkenyl;
R$^8$ is C$_1$-C$_6$ alkyl that is substituted with halogen, cyano, —C(O)R$^9$, or —OC(O)R$^9$; C$_2$-C$_6$ alkenyl that is optionally substituted with halogen or —NR$^9_2$; C$_2$-C$_6$ alkynyl; C$_3$-C$_6$ cycloalkyl that is substituted with cyano or —C(O)R$^9$; C$_4$-C$_6$ cycloalkenyl that is optionally substituted with halogen; or C$_4$-C$_9$ heterocycloalkenyl that is optionally substituted with halogen, C$_1$-C$_6$ alkyl, or carbonyl;
each R$^9$ is independently C$_1$-C$_6$ alkyl;
R$^{10}$ is hydrogen or C$_1$-C$_6$ alkyl;
R$^{11}$ is C$_2$-C$_6$ alkenyl;
R$^{12}$ is C$_2$-C$_6$ alkenyl substituted with cyano or —C(O)OR$^9$;
Z is C$_2$-C$_6$ alkenyl, C$_2$-C$_6$ alkynyl, C$_3$-C$_6$ cycloalkyl that is substituted with cyano or acetyl, —(CH$_2$)$_n$NR$^7$C(O)R$^8$, —(CH$_2$)$_n$C(O)(CH$_2$)$_n$R$^8$, —(CH$_2$)$_n$OC(O)R$^8$,

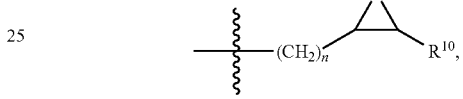

—(NH)$_m$(SO$_2$)R$^{11}$,
—CHR$^{11}$OC(O)R$^{11}$, —OR$^{12}$, —(CH$_2$)$_n$C(OH)R$^{12}$,

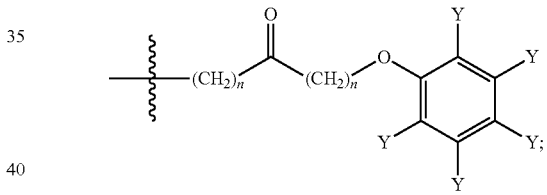

n is an integer from 0 to 6;
m is 0 or 1;
each R$^{22}$ is independently CH$_2$, CHR$^1$, CR$^1_2$, sulfur, oxygen, carbonyl, or NR$^6$; and TETHER is a group having 3-10 atoms selected from carbon, nitrogen, sulfur and oxygen.

51. A compound of Formula XIb:

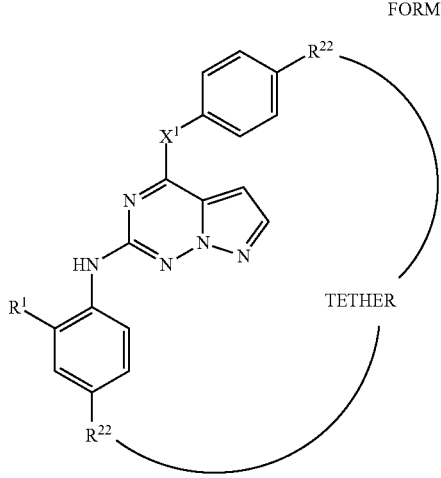

FORMULA XIb or a pharmaceutically acceptable salt or ester thereof, wherein:

each $R^1$ is independently $C_1$-$C_6$ alkyl, $C_1$-$C_6$ alkoxy, $C_1$-$C_6$ haloalkyl, or $C_1$-$C_6$ haloalkoxy;

each $R^6$ is independently hydrogen or $C_1$-$C_6$ alkyl;

$R^7$ is hydrogen, $C_1$-$C_6$ alkyl, or $C_2$-$C_6$ alkenyl;

$R^8$ is $C_1$-$C_6$ alkyl that is substituted with halogen, cyano, —C(O)$R^9$, or —OC(O)$R^9$; $C_2$-$C_6$ alkenyl that is optionally substituted with halogen or —$NR^9{}_2$; $C_2$-$C_6$ alkynyl; $C_3$-$C_6$ cycloalkyl that is substituted with cyano or —C(O)$R^9$; $C_4$-$C_6$ cycloalkenyl that is optionally substituted with halogen; or $C_4$-$C_9$ heterocycloalkenyl that is optionally substituted with halogen, $C_1$-$C_6$ alkyl, or carbonyl;

each $R^9$ is independently $C_1$-$C_6$ alkyl;

$R^{10}$ is hydrogen or $C_1$-$C_6$ alkyl;

$R^{11}$ is $C_2$-$C_6$ alkenyl;

$R^{12}$ is $C_2$-$C_6$ alkenyl substituted with cyano or —C(O)$OR^9$;

Z is $C_2$-$C_6$ alkenyl, $C_2$-$C_6$ alkynyl, $C_3$-$C_6$ cycloalkyl that is substituted with cyano or acetyl, —(CH$_2$)$_n$NR$^7$C(O)R$^8$, —(CH$_2$)$_n$C(O)(CH$_2$)$_n$R$^8$, —(CH$_2$)$_n$OC(O)R$^8$,

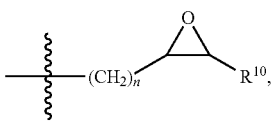

(NH)$_m$(SO$_2$)R$^{11}$, —CHR$^{11}$OC(O)R$^{11}$, —OR$^{12}$, —(CH$_2$)$_n$C(OH)R$^{12}$,

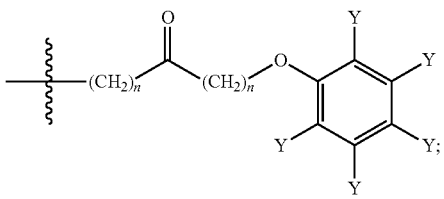

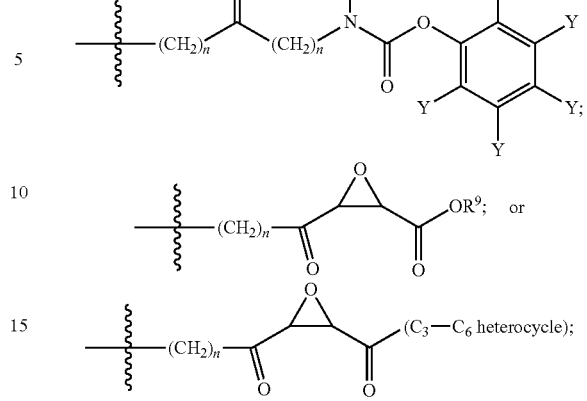

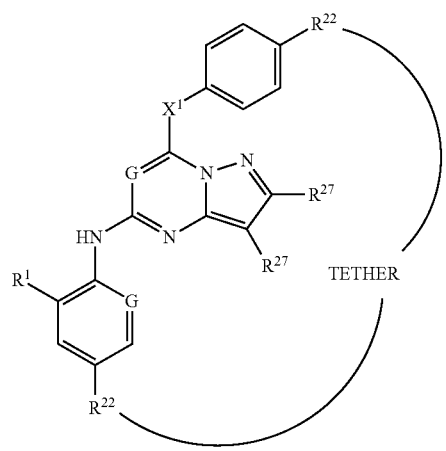

n is an integer from 0 to 6;
m is 0 or 1;
each $R^{22}$ is independently CH$_2$, CHR$^1$, CR$^1{}_2$, sulfur, oxygen, carbonyl, or NR$^6$;
$X^1$ is oxygen, sulfur, or —NR$^6$; and
TETHER is a group having 3-10 atoms selected from carbon, nitrogen, sulfur and oxygen.

52. A compound of Formula XIIb:

or a pharmaceutically acceptable salt or ester thereof, wherein:

each $R^1$ is independently $C_1$-$C_6$ alkyl, $C_1$-$C_6$ alkoxy, $C_1$-$C_6$ haloalkyl, or $C_1$-$C_6$ haloalkoxy;

each $R^6$ is independently hydrogen or $C_1$-$C_6$ alkyl;

$R^7$ is hydrogen, $C_1$-$C_6$ alkyl, or $C_2$-$C_6$ alkenyl;

$R^8$ is $C_1$-$C_6$ alkyl that is substituted with halogen, cyano, —C(O)$R^9$, or —OC(O)$R^9$; $C_2$-$C_6$ alkenyl that is optionally substituted with halogen or —$NR^9{}_2$; $C_2$-$C_6$ alkynyl; $C_3$-$C_6$ cycloalkyl that is substituted with cyano or —C(O)$R^9$; $C_4$-$C_6$ cycloalkenyl that is optionally substituted with halogen; or $C_4$-$C_9$ heterocycloalkenyl that is optionally substituted with halogen, $C_1$-$C_6$ alkyl, or carbonyl;

each $R^9$ is independently $C_1$-$C_6$ alkyl;

$R^{10}$ is hydrogen or $C_1$-$C_6$ alkyl;

$R^{11}$ is $C_2$-$C_6$ alkenyl;

$R^{12}$ is $C_2$-$C_6$ alkenyl substituted with cyano or —C(O)$OR^9$;

Z is $C_2$-$C_6$ alkenyl, $C_2$-$C_6$ alkynyl, $C_3$-$C_6$ cycloalkyl that is substituted with cyano or acetyl, —(CH$_2$)$_n$NR$^7$C(O)R$^8$, —(CH$_2$)$_n$C(O)(CH$_2$)$_n$R$^8$, —(CH$_2$)$_n$OC(O)R$^8$,

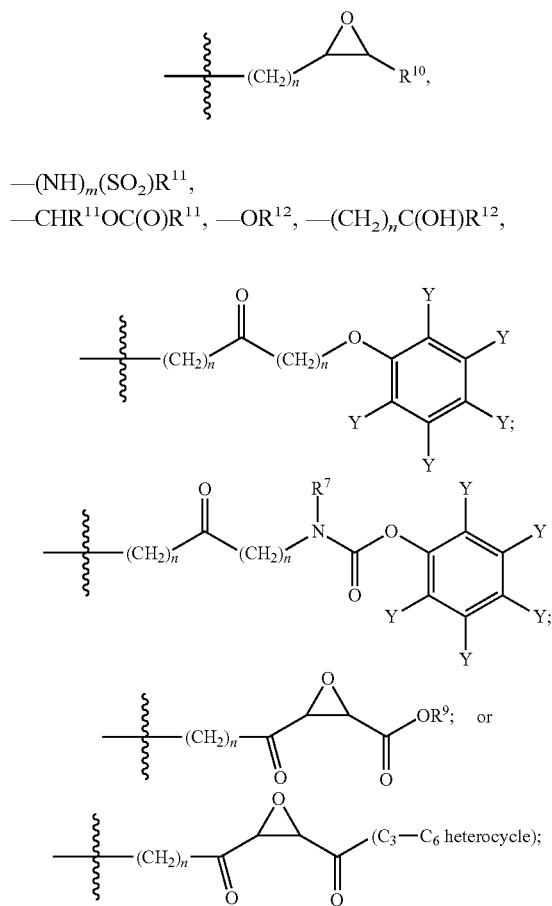

—(NH)$_m$(SO$_2$)R$^{11}$,
—CHR$^{11}$OC(O)R$^{11}$, —OR$^{12}$, —(CH$_2$)$_n$C(OH)R$^{12}$, n is an integer from 0 to 6;

m is 0 or 1;

each R$^{22}$ is independently CH$_2$, CHR$^1$, CR$^1{}_2$, sulfur, oxygen, carbonyl, or NR$^6$;

X$^1$ is oxygen, sulfur, or —NR$^6$;

each G is independently N or CH or CR$^{30}$;

each R$^{27}$ is independently hydrogen, halogen, C$_1$-C$_3$ alkyl, or C$_1$-C$_3$ alkoxy; and TETHER is a group having 3-10 atoms selected from carbon, nitrogen, sulfur and oxygen.

53. The compound of any one of embodiments 38 to 52, wherein the R$^{22}$-TETHER-R$^{22}$ moiety is:

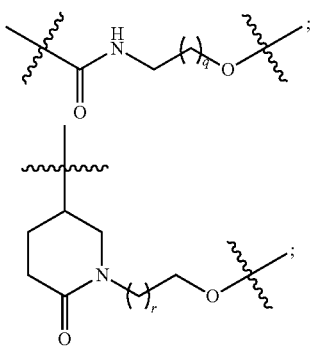

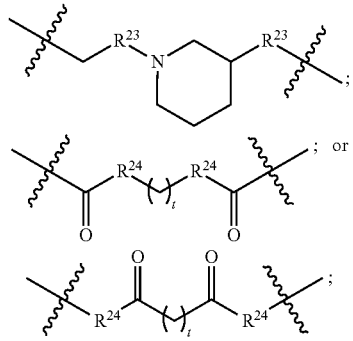

wherein:
q is 0, 1, 2, 3, or 4;
r is 1, 2, 3, or 4;
t is 2, 3, or 4;
each R$^{23}$ is independently oxygen, sulfur, NR$^6$, or CR$^1{}_2$; and
each R$^{24}$ is independently oxygen, sulfur, or NR$^6$.

54. A pharmaceutical composition comprising a compound of any one of embodiments 1 to 53 and a pharmaceutically acceptable excipient.

55. A method for inhibiting a kinase, comprising contacting the kinase with an effective amount of a compound of any one of embodiments 1 to 53.

56. The method of embodiment 55, wherein the kinase comprises a cysteine residue.

57. The method of embodiment 55, wherein the kinase is EGFR.

58. The method of embodiment 56, wherein the cysteine residue is located in or near the position equivalent to Cys 797 in EGFR.

59. The method of embodiment 55, wherein the kinase comprises EGFR, Jak3, Blk, Bmx, Btk, HER2 (ErbB2), HER4 (ErbB4), Itk, Tec, or Txk.

60. The method of embodiment 57, wherein the EGFR is a mutant EGFR.

61. The method of embodiment 60, wherein the EGFR mutation comprises G719S, G719C, G719A, L858R, L861Q, an exon 19 deletion mutation or an exon 20 insertion mutation.

62. The method of embodiment 61, wherein the EGFR mutation further comprises an EGFR T790M, T854A or D761Y resistance mutation.

63. A method of inhibiting EGFR in a subject in need thereof, comprising administering to the subject an effective amount of a compound of any one of embodiments 1 to 53.

64. The method of embodiment 63, wherein the EGFR is a Her-kinase.

65. The method of embodiment 63, wherein the subject is a human.

66. A method for treating or preventing a disease that is mediated by a kinase comprising administering an effective amount of a compound of any one of embodiments 1 to 53 to a subject in need thereof.

67. The method of embodiment 66, wherein the kinase comprises a cysteine residue.

68. The method of embodiment 67, wherein the cysteine residue is located in or near the position equivalent to Cys 797 in EGFR.

69. The method of embodiment 66, wherein the kinase is EGFR, Jak3, Blk, Bmx, Btk, HER2 (ErbB2), HER4 (ErbB4), Itk, Tec, or Txk.

70. The method of embodiment 66, wherein the kinase is EGFR.

71. The method of embodiment 70, wherein the EGFR is a Her-kinase.

72. The method of embodiment 66, wherein the disease comprises a cancer or a proliferation disease.

73. The method of embodiment 72, wherein the cancer or proliferation disease comprises lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or a solid tumor.

74. The method of embodiment 66, wherein the disease comprises inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoisosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamus cell and/or basal cell cancers, prostate cancer, renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, peripheral neuropathy, or Canine B-Cell Lymphoma.

75. The method of embodiment 66, wherein the disease comprises inflammation, arthritis, rheumatoid arthritis, spondylarthropathies, gouty arthritis, osteoarthritis, juvenile arthritis, and other arthritic conditions, systemic lupus erthematosus (SLE), skin-related conditions, psoriasis, eczema, dermatitis, pain, pulmonary disorders, lung inflammation, adult respiratory distress syndrome, pulmonary sarcoisosis, asthma, chronic pulmonary inflammatory disease, and chronic obstructive pulmonary disease (COPD), cardiovascular disease, arteriosclerosis, myocardial infarction, a post-myocardial infarction indication, congestive heart failure, cardiac reperfusion injury, inflammatory bowel disease, Crohn's disease, gastritis, irritable bowel syndrome, leukemia, or lymphoma.

76. The method of embodiment 66, wherein the subject is a human.

77. A method for treating or preventing a disease resistant to an EGFR targeted therapy in a subject in need thereof, comprising administering to the subject an effective amount of a compound of any one of embodiments 1 to 53.

78. The method of embodiment 77, wherein the EGFR targeted therapy comprises treatment with gefitinib, erlotinib, lapatinib, XL-647, HKI-272, BIBW2992, AV-412, CI-1033, PF00299804, BMS 690514, cetuximab, panitumumab, zalutumumab, nimotuzumab, or matuzumab.

79. The method of embodiment 77, wherein the disease is mediated by an EGFR having a mutation.

80. The method of embodiment 79, wherein the EGFR mutation comprises an EGFR T790M, T854A or D761Y resistance mutation.

81. The method of embodiment 77, wherein the disease comprises cancer.

82. The method of embodiment 81, wherein the cancer comprises lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemia, lymphoma, myeloma, or a solid tumor.

83. The method of embodiment 77, wherein the subject is a human.

84. A method for treating or preventing an EGFR activated disease in a subject in need thereof, comprising administering to the subject an effective amount of a compound of any one of embodiments 1 to 53.

85. The method of embodiment 84, wherein the EGFR activation comprises a mutation of EGFR, amplification of EGFR, expression of EGFR, ligand mediated activation of EGFR, or a combination of any thereof.

86. The method of embodiment 85, wherein the mutation of EGFR comprises G719S, G719C, G719A, L858R, L861Q, an exon 19 deletion mutation or an exon 20 insertion mutation.

87. The method of embodiment 84, wherein the disease comprises lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemia, lymphoma, myeloma, or a solid tumor.

88. The method of embodiment 84, wherein the subject is identified as being in need of EGFR inhibition for the treatment of cancer.

89. The method of embodiment 84, wherein the subject is a human.

90. A method for treating or preventing an ERBB2 activated disease in a subject in need thereof, comprising administering to the subject an effective amount of a compound of any one of embodiments 1 to 53.

91. The method of embodiment 90, wherein the ERBB2 activation comprises a mutation of ERBB2, expression of ERBB2, amplification of ERBB2, or a combination thereof.
92. The method of embodiment 91, wherein the mutation comprises a mutation in exon 20 of ERBB2.
93. The method of embodiment 90, wherein the disease comprises lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemia, lymphoma, myeloma, or a solid tumor.
94. The method of embodiment 90, wherein the subject is identified as being in need of ERBB2 inhibition for the treatment of the cancer.
95. The method of embodiment 90, wherein the subject is a human.
96. A method for preventing resistance to gefitinib or erlotinib in a subject in need thereof, comprising administering to the subject an effective amount of a compound of any one of embodiments 1 to 53.
97. The method of embodiment 96, wherein the subject has a cancer.
98. The method of embodiment 97, wherein the cancer comprises lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemia, lymphomas, myeloma, or a solid tumor.
99. The method of embodiment 96, wherein the subject is a human.
100. A kit comprising a compound of any one of embodiments 1 to 53 and instructions for use of the compound in treating a disease or disorder in a subject in need thereof.
101. The kit of embodiment 100, wherein the disease or disorder comprises a cancer or a proliferative disorder.

What is claimed is:
1. A compound of Formula IV:

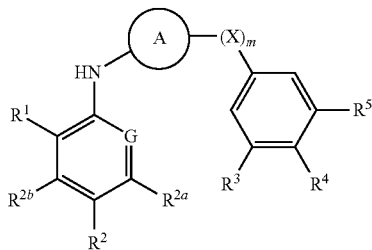

FORMULA IV or a pharmaceutically acceptable salt thereof, wherein:
X is carbonyl;
$X^{26}$ is sulfur;
each $R^1$ is independently $C_1$-$C_6$ alkyl, $C_1$-$C_6$ alkoxy, $C_1$-$C_6$ haloalkyl, or $C_1$-$C_6$ haloalkoxy;
$R^2$ is piperidine, pyrrolidine, piperazine, or morpholine that is optionally substituted with $C_1$-$C_6$ alkyl; or $C_3$-$C_6$ alkyl or $C_3$-$C_6$ cycloalkyl containing at least one nitrogen; and $R^{2a}$, and $R^{2b}$ are hydrogen or $C_1$-$C_6$ alkyl;
one of $R^3$, $R^4$, and $R^5$ is Z, and the other two of $R^3$, $R^4$, and $R^5$ are hydrogen;
each $R^6$ is independently hydrogen or $C_1$-$C_6$ alkyl;

$R^7$ is hydrogen, $C_1$-$C_6$ alkyl, or $C_2$-$C_6$ alkenyl;
$R^8$ is $C_1$-$C_6$ alkyl that is substituted with halogen, cyano, —C(O)$R^9$, or —OC(O)$R^9$; $C_2$-$C_6$ alkenyl that is optionally substituted with halogen or —NR$^9{}_2$; $C_2$-$C_6$ alkynyl; $C_3$-$C_6$ cycloalkyl that is substituted with cyano or —C(O)$R^9$; $C_4$-$C_6$ cycloalkenyl that is optionally substituted with halogen; or $C_4$-$C_9$ heterocycloalkenyl that is optionally substituted with halogen, $C_1$-$C_6$ alkyl, or carbonyl;
each $R^9$ is independently $C_1$-$C_6$ alkyl;
$R^{10}$ is hydrogen or $C_1$-$C_6$ alkyl;
$R^{11}$ is $C_2$-$C_6$ alkenyl;
$R^{12}$ is $C_2$-$C_6$ alkenyl substituted with cyano or —C(O)OR$^9$;
$R^{30}$ is halogen or $C_1$-$C_6$ alkyl;
Z is $C_2$-$C_6$ alkenyl, $C_2$-$C_6$ alkynyl, $C_3$-$C_6$ cycloalkyl that is substituted with cyano or acetyl, —(CH$_2$)$_n$NR$^7$C(O)R$^8$, —(CH$_2$)$_n$C(O)(CH$_2$)$_n$R$^8$, —(CH$_2$)$_n$OC(O)R$^8$, (NH)$_m$(SO$_2$)R$^{11}$,
—CHR$^{11}$OC(O)R$^{11}$, —OR$^{12}$,

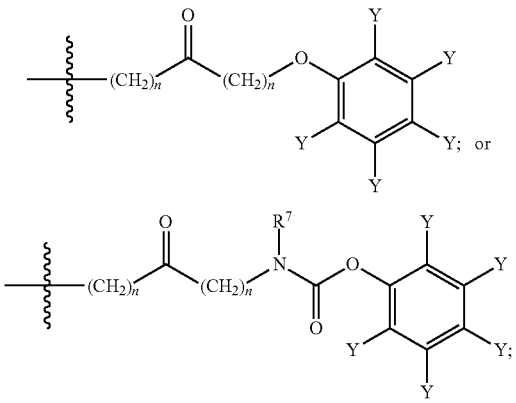

n is an integer from 0 to 6; and
m is 0 or 1;

A is

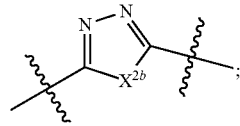

$R^{17}$ is N, CH, or CR$^{30}$;
$R^{18}$ is O or S; and
G is N, CH, or CR$^{30}$.
2. The compound of claim 1, wherein Z is —(CH$_2$)$_n$NR$^7$C(O)R$^8$; $R^7$ is hydrogen; and $R^8$ is $C_2$-$C_6$ alkenyl.

3. The compound of claim 1, wherein Z is

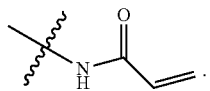 [SMILES: *NC(=O)C=C]

4. The compound of claim 1, wherein:
X is carbonyl;
$R^1$ is $C_1$-$C_6$ alkoxy;
$R^2$ is piperazine that is substituted at the N position with $C_1$-$C_6$ alkyl;
$R^{2a}$ and $R^{2b}$ are hydrogen;
one of $R^3$, $R^4$, and $R^5$ is Z, and the other two of $R^3$, $R^4$, and $R^5$ are hydrogen;
$R^7$ is hydrogen or $C_1$-$C_6$ alkyl;
$R^8$ is $C_2$-$C_6$ alkenyl; and
Z is —$(CH_2)_n NR^7 C(O)R^8$.

5. The compound of claim 1, wherein the compound has the formula:

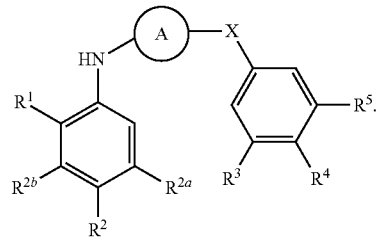

6. The compound of claim 1, wherein the compound has the formula:

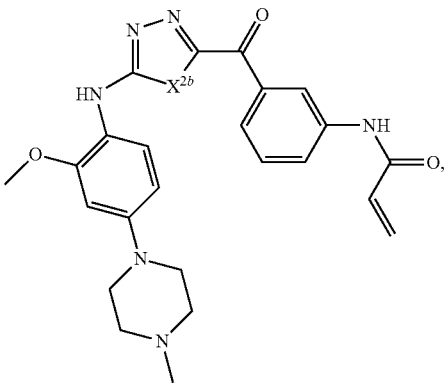

or a pharmaceutically acceptable salt thereof.

7. A pharmaceutical composition comprising the compound of claim 1 and a pharmaceutically acceptable excipient.

8. A kit comprising the compound of claim 1 and instructions for use of the compound in treating breast cancer in a subject in need thereof.

9. A method for inhibiting a mutant EGFR kinase, comprising contacting the kinase with an effective amount of the compound of claim 1.

10. The method of claim 9, wherein the EGFR mutation comprises G719S, G719C, G719A, L858R, L861Q, an exon 19 deletion mutation or an exon 20 insertion mutation.

11. The method of claim 10, wherein the EGFR mutation further comprises an EGFR T790M, T854A or D761Y resistance mutation.

* * * * *